US011779657B2

(12) United States Patent
Burnett et al.

(10) Patent No.: US 11,779,657 B2
(45) Date of Patent: Oct. 10, 2023

(54) COMPOSITIONS AND METHODS FOR MITOCHONDRIAL GENOME EDITING

(71) Applicants: City of Hope, Duarte, CA (US); The Regents of the University of California, Oakland, CA (US)

(72) Inventors: John Burnett, Chatsworth, CA (US); Anh Pham, Chatsworth, CA (US)

(73) Assignees: City of Hope, Duarte, CA (US); The Regents of the University of California, Oakland, CA (US)

(*) Notice: Subject to any disclaimer, the term of this patent is extended or adjusted under 35 U.S.C. 154(b) by 789 days.

(21) Appl. No.: 16/307,128

(22) PCT Filed: Jun. 9, 2017

(86) PCT No.: PCT/US2017/036821
§ 371 (c)(1),
(2) Date: Dec. 4, 2018

(87) PCT Pub. No.: WO2017/222834
PCT Pub. Date: Dec. 28, 2017

(65) Prior Publication Data
US 2019/0290780 A1    Sep. 26, 2019

Related U.S. Application Data

(60) Provisional application No. 62/348,262, filed on Jun. 10, 2016.

(51) Int. Cl.
| | |
|---|---|
| *A61K 48/00* | (2006.01) |
| *C12N 15/86* | (2006.01) |
| *C12N 15/52* | (2006.01) |
| *A61K 9/51* | (2006.01) |
| *C12N 15/113* | (2010.01) |
| *C12N 9/22* | (2006.01) |
| *C12N 15/10* | (2006.01) |
| *C12N 15/88* | (2006.01) |

(52) U.S. Cl.
CPC ............ *A61K 48/0058* (2013.01); *A61K 9/51* (2013.01); *A61K 48/0066* (2013.01); *A61K 48/0091* (2013.01); *C12N 9/22* (2013.01); *C12N 15/102* (2013.01); *C12N 15/113* (2013.01); *C12N 15/1137* (2013.01); *C12N 15/52* (2013.01); *C12N 15/86* (2013.01); *C07K 2319/07* (2013.01); *C12N 15/88* (2013.01); *C12N 2310/20* (2017.05); *C12N 2310/3517* (2013.01); *C12N 2310/3519* (2013.01); *C12N 2330/51* (2013.01); *C12N 2710/10343* (2013.01); *C12N 2740/16043* (2013.01); *C12N 2750/14143* (2013.01); *C12Y 109/03001* (2013.01); *C12Y 301/27007* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 3,991,776 | A | 11/1976 | Duffy |
| 4,076,779 | A | 2/1978 | Skriletz |
| 4,093,709 | A | 6/1978 | Choi et al. |
| 4,118,470 | A | 10/1978 | Casey et al. |
| 4,131,648 | A | 12/1978 | Choi et al. |
| 4,138,344 | A | 2/1979 | Choi et al. |
| 4,293,539 | A | 10/1981 | Ludwig et al. |
| 4,603,044 | A | 7/1986 | Geho et al. |
| 4,675,189 | A | 6/1987 | Kent et al. |
| 5,034,506 | A | 7/1991 | Summerton et al. |
| 5,143,854 | A | 9/1992 | Pirrung et al. |
| 5,235,033 | A | 8/1993 | Summerton et al. |
| 9,139,628 | B2 | 9/2015 | Minczuk et al. |
| 2005/0019923 | A1 | 1/2005 | Uchegbu et al. |
| 2008/0267903 | A1 | 10/2008 | Uchegbu et al. |
| 2015/0259684 | A1 | 9/2015 | Church et al. |
| 2015/0361450 | A1 | 12/2015 | Tarassov et al. |
| 2016/0138008 | A1 | 5/2016 | Doudna et al. |

FOREIGN PATENT DOCUMENTS

| | | |
|---|---|---|
| CN | 105602935 A | 5/2016 |
| CN | 105602993 A | 5/2016 |
| WO | WO-96/17958 A1 | 6/1996 |
| WO | WO-2014/085830 A2 | 6/2014 |
| WO | WO-2014/085830 A3 | 6/2014 |
| WO | WO-2015/071474 A2 | 5/2015 |
| WO | WO-2015/071474 A3 | 5/2015 |
| WO | WO-2015/071474 A9 | 5/2015 |
| WO | WO-2015/089419 A2 | 6/2015 |
| WO | WO-2015/089419 A3 | 6/2015 |
| WO | WO-2015/089419 A9 | 6/2015 |

(Continued)

OTHER PUBLICATIONS

Jo, et al. (2015) "Efficient Mitochondrial Genome Editing by CRISPR/Cas9", BioMed Research International, (no journal, no volume) Article ID 30716, 10 pages long. (Year: 2015).*
Wang, et al. (2012) "Correcting human mitochondrial mutations with targeting RNA import", Proceedings of the National Academy of Science, USA, 109(13): 4840-45. (Year: 2012).*
Kahn, et al. (2015) "Mitochondrial disorders: Challenges in diagnosis & treatment", Indian Journal of Medical Research, 141: 13-26. (Year: 2015).*
Slone and Huang (2020) "The special considerations of gene therapy for mitochondrial diseases", Nature: Genomic Medicine, 5: article 7, 7 pages. (Year: 2020).*

(Continued)

*Primary Examiner* — Robert M Kelly
(74) *Attorney, Agent, or Firm* — Mintz, Levin, Cohn, Ferris, Glovsky and Popeo, P.C.

(57) ABSTRACT

Compositions and methods for mitochondria genome editing are provided. Also provided are methods for treating mitochondrial disorders by the disclosed compositions.

18 Claims, 15 Drawing Sheets

Specification includes a Sequence Listing.

(56) References Cited

FOREIGN PATENT DOCUMENTS

| WO | WO-2016/073433 A1 | 5/2016 |
|---|---|---|
| WO | WO-2016/073990 A2 | 5/2016 |
| WO | WO-2016/073990 A3 | 5/2016 |

OTHER PUBLICATIONS

Alexeyev. M. et al. (May 2013). "The maintenance of mitochondrial DNA integrity—critical analysis and update," *Cold Spring Harb Perspect Biol* 5(5):a012641.
Bacman, S.R. et al. (Sep. 2013, e-published Aug. 4, 2013). "Specific elimination of mutant mitochondrial genomes in patient-derived cells by mitoTALENs," *Nat Med* 19(9):1111-1113.
Baracca, A. et al. (May 2005). "Severe impairment of complex I-driven adenosine triphosphate synthesis in leber hereditary optic neuropathy cybrids," *Arch Neurol* 62(5):730-736.
Bayona-Bafaluy, M.P. et al. (Oct. 2005), e-published Sep. 22, 2005). "Rapid directional shift of mitochondrial DNA heteroplasmy in animal tissues by a mitochondrially targeted restriction endonuclease," *PNAS USA* 102(40:14392-14397.
Berqkvist, A. et al. (Apr. 2010, e-published Jan. 15, 2010). "Gene expression profiling—Clusters of possibilities," *Methods* 50(4):323-335.
Bettinger, T. et al. (Apr. 2001). Recent developments in RNA-based strategies for cancer gene therapy. *Curr Opin Mol Ther* 3(2):116-124.
Brandon, M.C. et al. (Jan. 1, 2005). "MITOMAP: a human mitochondrial genome database—2004 update," *Nucleic Acids Res* 33(Database issue):D611-613.
Bristow, E.A. et al. (Jun. 2002). "The distribution of mitochondrial activity in relation to optic nerve structure," *Arch Ophthalmol* 120(6):791-796.
Bu, X.D. et al. (Sep. 15, 1991). "X chromosome-linked and mitochondrial gene control of Leber hereditary optic neuropathy: evidence from segregation analysis for dependence on X chromosome inactivation," *PNAS USA* 88(18):8198-8202.
Burnett, J.C. et al. (Jan. 2009, e-published Jan. 9, 2009). "Control of stochastic gene expression by host factors at the HIV promoter," *PLoS Pathog* 5(1):e1000260.
Burnett, J.C. et al. (Jan. 27, 2012). "RNA-based therapeutics: current progress and future prospects," *Chem Biol* 19(1):60-71.
Carelli, V. et al. (Jan. 2004). "Mitochondrial dysfunction as a cause of optic neuropathies," *Prog Retin Eye Res* 23(1):53-89.
Chen, J.D. et al. (Sep. 1991). "X-chromosomal gene in Leber hereditary optic neuroretinopathy," *Am J Hum Genet* 49(3):692-693.
Coelho, T. et al. (Aug. 29, 2013). "Safety and efficacy of RNAi therapy for transthyretin amyloidosis," *N Engl J Med* 369(9):819-829.
Comte, C. et al. (Jan. 7, 2013, e-published Oct. 18, 2012). "Mitochondrial targeting of recombinant RNAs modulates the level of a heteroplasmic mutation in human mitochondrial DNA associated with Kearns Sayre Syndrome," *Nucleic Acids Res* 41(1):418-433.
Deuse, T. et al. (Jan. 8, 2015, e-published Nov. 20, 2014). "SCNT-derived ESCs with mismatched mitochondria trigger an immune response in allogeneic hosts," *Cell Stem Cell* 16(1):33-38.
Erickson, R.P. et al. (May 1972). "Leber's optic atrophy, a possible example of maternal inheritance," *Am J Hum Genet* 24(3):348-349.
Fodor, S.P. et al. (Feb. 15, 1991). "Light-directed, spatially addressable parallel chemical synthesis," *Science* 251(4995):767-773.
Folmes, C.D. et al. (Jul. 2013). "Disease-causing mitochondrial heteroplasmy segregated within induced pluripotent stem cell clones derived from a patient with MELAS," *Stem Cells* 31(7):1298-1308.
Fu, Y. et al. (Mar. 2014, e-published Jan. 26, 2014). "Improving CRISPR-Cas nuclease specificity using truncated guide RNAs," *Nat Biotechnol* 32(3)279-284.
Gammage, P.A. et al. (Apr. 2014, e-published Feb. 24, 2014). "Mitochondrially targeted ZFNs for selective degradation of pathogenic mitochondrial genomes bearing large-scale deletions or point mutations," *EMBO Mol Med* 6(4):458-466.
Giordano, C. et al. (Jan. 2011, e-published Oct. 13, 2010). "Oestrogens ameliorate mitochondrial dysfunction in Leber's hereditary optic neuropathy," *Brain* 134(Pt 1):220-234.
Hashimoto, M. et al. (Oct. 2015, e-published Jul. 10, 2015). "MitoTALEN: a General Approach to Reduce Mutant mtDNA Loads and Restore Oxidative Phosphorylation Function in Mitochondrial Diseases," *Mol Ther* 23(10):1592-1599.
Howell, N. et al. (Jul. 1994). "MitoTALEN: a General Approach to Reduce Mutant mtDNA Loads and Restore Oxidative Phosphorylation Function in Mitochondrial Diseases," *Am J Hum Genet* 55(1):203-206.
Hsu, P.D. et al. (Jun. 5, 2014). "Development and applications of CRISPR-Cas9 for genome engineering," *Cell* 157(6):1262-1278.
Hudson, G. et al. (Dec. 2005, e-published Oct. 11, 2005). "Identification of an X-chromosomal locus and haplotype modulating the phenotype of a mitochondrial DNA disorder," *Am J Hum Genet* 77(6):1086-1091.
Huoponen, K. et al. (Jun. 1991). "A new mtDNA mutation associated with Leber hereditary optic neuroretinopathy," *Am J Hum Genet* 48(6):1147-1153.
Huoponen, K. (Jul. 2001). "Leber hereditary optic neuropathy: clinical and molecular genetic findings," *Neurogenetics* 3(3):119-125.
International Search Report dated Sep. 25, 2017, for PCT Application No. PCT/US2017/036821, filed Jun. 9, 2017, 5 pages.
Ji Y. et al. (Mar. 11, 2010). "Evaluation of the X-linked modifier loci for Leber hereditary optic neuropathy with the G11778A mutation in Chinese," *Mol Vis* 16:416-424.
Jinek, M. et al. (Aug. 17, 2012, e-published Jun. 28, 2012). "A programmable dual-RNA-guided DNA endonuclease in adaptive bacterial immunity," *Science* 337(6096):816-821.
Jo, A. et al. (2015, e-published Sep. 10, 2015). "Efficient Mitochondrial Genome Editing by CRISPR/Cas9," *Biomed Res Int* 2015:305716.
Johnston, M. et al. (Feb. 26, 1998). "Gene chips: array of hope for understanding gene regulation," *Curr Biol* 8(5):R171-174.
Journal of Polymer Science: Polymer Letters Edition (1980). "Preparation of Polyacetals by the Relaxation of Divinyl Ethers and Polyols," 18:293-297.
Kazak, L. et al. (Oct. 2012, e-published Sep. 20, 2012). "Minimizing the damage: repair pathways keep mitochondrial DNA intact," *Nat Rev Mol Cell Biol* 13(10):659-671.
Kern, S. et al. (Jul. 1997). "Direct hybridization of large-insert genomic clones on high-density gridded cDNA filter arrays," *Biotechniques* 23(1):120-124.
King, M.P. et al. (Oct. 27, 1989). "Human cells lacking mtDNA: repopulation with exogenous mitochondria by complementation," *Science* 246(4929):500-503.
Kirches, F. (Mar. 2011). "LHON: Mitochondrial Mutations and More," *Curr Genomics* 12(1):44-54.
Kleinstiver, B.P. et al. (Jul. 23, 2015, e-published Jun. 22, 2015). "Engineered CRISPR-Cas9 nucleases with altered PAM specificities," *Nature* 523(7561):481-485.
Kleinstiver, B.P. et al. (Jan. 28, 2016, e-published Jan. 6, 2016). "High-fidelity CRISPR-Cas9 nucleases with no detectable genome-wide off-target effects," *Nature* 529(7587):490-495.
Koilkonda, R.D. et al. (2011, e-published Dec. 26, 2010). "Leber's Hereditary Optic Neuropathy-Gene Therapy: From Benchtopto Bedside," *J Ophthalmol* 2011:179412.
Koilkonda, R.D. et al. (Apr. 1, 2014). "Safety and effects of the vector for the Leber hereditary optic neuropathy gene therapy clinical trial," *JAMA Ophthalmol* 132(4):409-420.
Kolesnikova, O. et al. (May 2010, e-published Mar. 26, 2010). "Selection of RNA aptamers imported into yeast and human mitochondria," *RNA* 16(5):926-941.
Konermann, S. et al. (Jan. 29, 2015, e-published Dec. 10, 2014). "Genome-scale transcriptional activation by an engineered CRISPR-Cas9 complex," *Nature* 517(7536):583-588.
Li, Y. et al. (Jan. 2011). "Prophylactic, therapeutic and immune enhancement effect of liposome-encapsulated PolyICLC on highly pathogenic H5N1 influenza infection," *J Gene Med* 13(1):60-72.

(56) References Cited

OTHER PUBLICATIONS

Lightowlers, R.N. et al. (Sep. 25, 2015, e-published Sep. 24, 2015). "Mutations causing mitochondrial disease: What is new and what challenges remain?" Science 349(6255):1494-1499.
Little, S.R. et al. (Jun. 29, 2004, e-published Jun. 21, 2004). "Poly-β amino ester-containing microparticles enhance the activity of nonviral genetic vaccines," PNAS USA 101(26):9534-9539.
Lu D. et al. (Dec. 1994). "Optimization of methods to achieve mRNA-mediated transfection of tumor cells in vitro and in vivo employing cationic liposome vectors," Cancer Gene Ther 1(4):245-252.
Ma, H. et al. (Aug. 2015, e-published Jul. 15, 2015). "Metabolic rescue in pluripotent cells from patients with mtDNA disease," Nature 524(7564):234-238.
Makarova, K.S. et al. (Nov. 2015, e-published Sep. 28, 2015). "An updated evolutionary classification of CRISPR-Cas systems," Nat Rev Microbiol 13(11):722-736.
McNamara, M.A. et al. (2015, e-published Nov. 19, 2015). "RNA-Based Vaccines in Cancer Immunotherapy," J Immunol Res 2015:794528.
Meyerson, C. et al. (Jun. 26, 2015). "RNA-Based Vaccines in Cancer Immunotherapy," Clin Ophthalmol 9:1165-1176.
Minczuk, M. et al. (Feb. 2010, e-published Feb. 4, 2010). "Construction and testing of engineered zinc-finger proteins for sequence-specific modification of mtDNA," Nat Protoc 52):342-356.
Oostra, R.J. et al. (Apr. 1996). "No evidence for 'skewed' inactivation of the X-chromosome as cause of Leber's hereditary optic neuropathy in female carriers," Hum Genet 97(4):500-505.
Pan, B.X. et al. (Nov. 9, 2012). "Mathematically modeling the involvement of axons in Leber's hereditary optic neuropathy," Invest Ophthalmol Vis Sci 53(12):7608-7617.
Phillips, N.R. et al. (Jan. 27, 2014). "Simultaneous quantification of mitochondrial DNA copy number and deletion ratio: a multiplex real-time PCR assay," Sci Rep 4:3887.
Phua, K.K. et al. (Mar. 28, 2013, e-published Jan. 7, 2013). "Transfection efficiency and transgene expression kinetics of mRNA delivered in naked and nanoparticle format," J Control Release 166(3):227-233.
Phua, K.K. et al. (Jun. 4, 2014). "Intranasal mRNA nanoparticle vaccination induces prophylactic and therapeutic anti-tumor immunity," Sci Rep 4:5128.
Phua, K.K. et al. (Jul. 21, 2014). "Messenger RNA (mRNA) nanoparticle tumour vaccination," Nanoscale 6(14):7715-7729.
Pichon, C. et al. (2013). "Mannosylated and histidylated LPR technology for vaccination with tumor antigen mRNA," Methods Mol Biol 969:247-274.
Pisano,A. et al. (Dec. 15, 2015, e-published Sep. 26, 2015). "Targeting estrogen receptor β as preventive therapeutic strategy for Leber's hereditary optic neuropathy," Hum Mol Genet 24(24):6921-6931.
Ran, F.A. et al. (Apr. 9, 2015, e-published Apr. 1, 2015). "In vivo genome editing using Staphylococcus aureus Cas9," Nature 520(7546):186-191.
Rana, M. et al. (Nov. 2000). "An out-of-frame cytochrome b gene deletion from a patient with parkinsonism is associated with impaired complex III assembly and an increase in free radical production," Ann Neurol 48(5):774-781.
Reddy, P. et al. (Apr. 23, 2015). "Selective elimination of mitochondrial mutations in the germline by genome editing," Cell 161(3):459-469.
Sadun, A.A. et al. (Aug. 2003). "Extensive investigation of a large Brazilian pedigree of 11778/haplogroup J Leber hereditary optic neuropathy," Am J Ophthalmol 136(2):231-238.
Sadun, A.A. et al. (Mar. 2012). "Effect of EPI-743 on the clinical course of the mitochondrial disease Leber hereditary optic neuropathy," Arch Neurol 69(3):331-338.
Sadun, A.A. et al. (2000). "Leber's hereditary optic neuropathy differentially affects smaller axons in the optic nerve," Trans Am Ophthalmol Soc 98:223-232; discussion 232-235.

Sayour, E.J. et al. (2015). "Bridging infection disease vaccines with cancer immunotherapy: a role for targeted RNA based immunotherapeutics," Journal for Immunotherapy of Cancer 3:13.
Schneider, A. (2011). "Mitochondrial tRNA import and its consequences for mitochondrial translation," Annu Rev Biochem 80:1033-1053.
Schoeler, S. et al. (Mar. 2007, e-published Dec. 12, 2006). "Glutathione depletion in antioxidant defense of differentiated NT2-LHON cybrids," Neurobiol Dis 25(3):536-544.
Schummer, M. et al. (Dec. 1997). "Inexpensive handheld device for the construction of high-density nucleic acid arrays," Biotechniques 23(6):1087-1092.
Schwartz, S.D. et al. (Feb. 7, 2015, e-published Oct. 15, 2014). "Human embryonic stem cell-derived retinal pigment epithelium in patients with age-related macular degeneration and Stargardt's macular dystrophy: follow-up of two open-label phase ½ studies," Lancet 385(9967):509-516.
Schwendener, R.A. et al. (Nov. 2014). "Liposomes as vaccine delivery systems: a review of the recent advances," Ther Adv Vaccines 2(6):159-182.
Slaymaker, I.M. et al. (Jan. 1, 2016, e-published Dec. 1, 2015). "Rationally engineered Cas9 nucleases with improved specificity," Science 31(6268):84-88.
Smirnov, A. et al. (Apr. 2008, e-published Feb. 26, 2008). "Two distinct structural elements of 5S rRNA are needed for its import into human mitochondria," RNA 14(4):749-759.
Song, W.K. et al. (May 12, 2015, e-published Apr. 30, 2015). "Two distinct structural elements of 5S rRNA are needed for its import into human mitochondria, " Stem Cell Reports 4(5):860-872.
Su, X. et al. (Jun. 6, 2011, e-published Apr. 1, 2011). "In vitro and in vivo mRNA delivery using lipid-enveloped pH-responsive polymer nanoparticles" Mol Pharm 8(3):774-787.
Tabernero, J. et al. (Apr. 2013, e-published Jan. 28, 2013). "First-in-humans trial of an RNA interference therapeutic targeting VEGF and KSP in cancer patients with liver involvement," Cancer Discov 3(4):406-417.
Tachibana, M. et al. (Sep. 2009, e-published Aug. 26, 2009). "Mitochondrial gene replacement in primate offspring and embryonic stem cells," Nature 462(7262):367-372.
Takahashi, M. et al. (2015). "Aptamer-siRNA chimeras for HIV," Adv Exp Med Biol 848:211-234.
Tanaka, T. et al. (Feb. 10, 2015). "Generation of retinal ganglion cells with functional axons from human induced pluripotent stem cells," Sci Rep 5:8344.
Tonin, Y. et al. (May 9, 2014, e-published Apr. 1, 2014). "Modeling of antigenomic therapy of mitochondrial diseases by mitochondrially addressed RNA targeting a pathogenic point mutation in mitochondrial DNA," J Biol Chem 289(19):13323-13334.
Vierbuchen, T. et al. (Feb. 25, 2010, e-published Jan. 27, 2010). "Direct conversion of fibroblasts to functional neurons by defined factors," Nature 463(7284):1035-1041.
Wallace, D.C. et al. (Dec. 9, 1988). "Mitochondrial DNA mutation associated with Leber's hereditary optic neuropathy," Science 242(4884):1427-1430.
Wang, G. et al. (Aug. 6, 2010). "PNPASE regulates RNA import into mitochondria," Cell 142(3):456-467.
Wasungu, L. et al. (Nov. 28, 2006, e-published Jun. 28, 2006). "Cationic lipids, lipoplexes and intracellular delivery of genes," J Control Release 116(2):255-264.
Wolf, A.R. et al. (May 8, 2014, e-published Apr. 18, 2014). "Functional genomic analysis of human mitochondrial RNA processing," Cell Rep 7(3):918-931.
Written Opinion dated Sep. 25, 2017, for PCT Application No. PCT/US2017/036821, filed Jun. 9, 2017, 9 pages.
Yu-Wai-Man, P. et al. (Mar. 2011, e-published Nov. 26, 2010). "Mitochondrial optic neuropathies—disease mechanisms and therapeutic strategies," Prog Retin Eye Res 30(2):81-114.
Zanna, C. et al. (Oct. 2005). "Caspase-independent death of Leber's hereditary optic neuropathy cybrids is driven by energetic failure and mediated by AIF and Endonuclease G.," Apoptosis 10(5):997-1007.
Zelenka, J. et al. (Apr. 2014, e-published Feb. 23, 2014). "Import of desired nucleic acid sequences using addressing motif of mitochondrial

(56) References Cited

OTHER PUBLICATIONS ribosomal 5S-rRNA for fluorescent in vivo hybridization of mitochondrial DNA and RNA," *J Bioenerg Biomembr* 46(2):147-156.

Zetsche, B. et al. (Oct. 22, 2015, e-published Sep. 25, 2015). "Cpf1 is a single RNA-guided endonuclease of a class 2 CRISPR-Cas system," Cell 163(3):759-771.

Zhang, Y. et al. (Jun. 5, 2013). "Rapid single-step induction of functional neurons from human pluripotent stem cells," *Neuron* 78(5):785-798.

Zhou, J. et al. (Apr. 2013, e-published Mar. 6, 2013). "Dual functional BAFF receptor aptamers inhibit ligand-induced proliferation and deliver siRNAs to NHL cells," *Nucleic Acids Res* 41(7):4266-4283.

Zhou, J. et al. (Mar. 19, 2015, e-published Mar. 5, 2015). "Cell-specific RNA aptamer against human CCR5 specifically targets HIV-1 susceptible cells and inhibits HIV-1 infectivity," *Chem Biol* 22(3):379-390.

Zuris, J.A. et al. (Jan. 2015, e-published Oct. 30, 2014). "Cationic lipid-mediated delivery of proteins enables efficient protein-based genome editing in vitro and in vivo" *Nat Biotechnol* 33(1):73-80.

\* cited by examiner

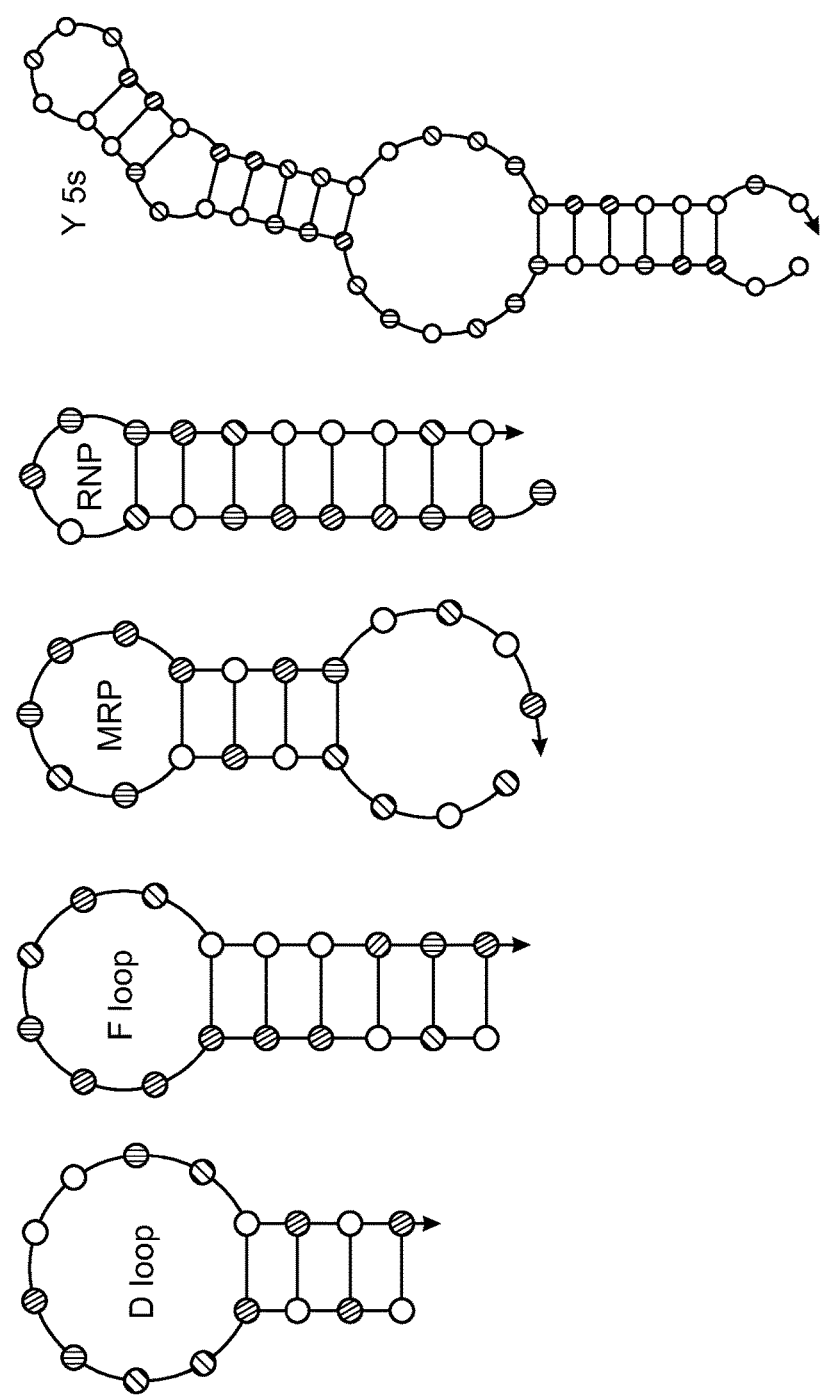
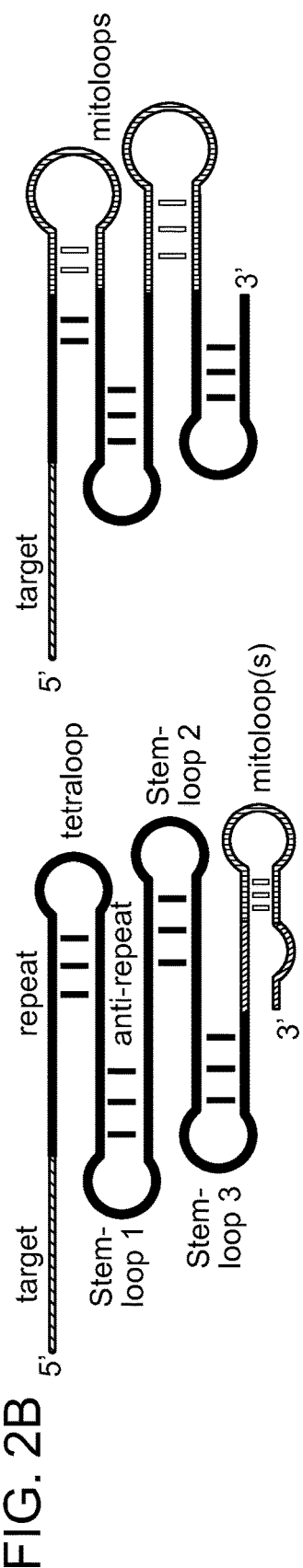
FIG. 2A
FIG. 2B

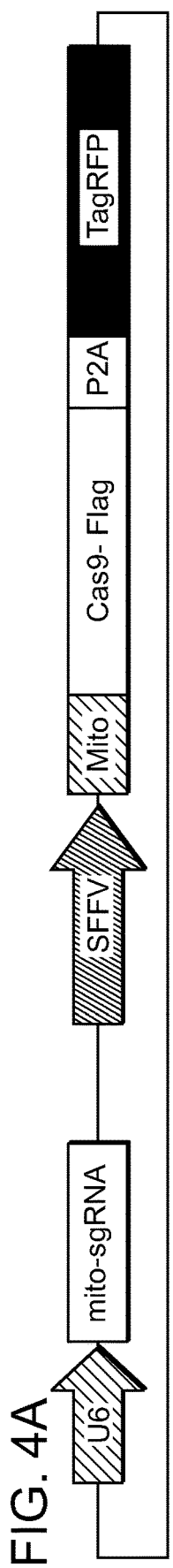
FIG. 4A
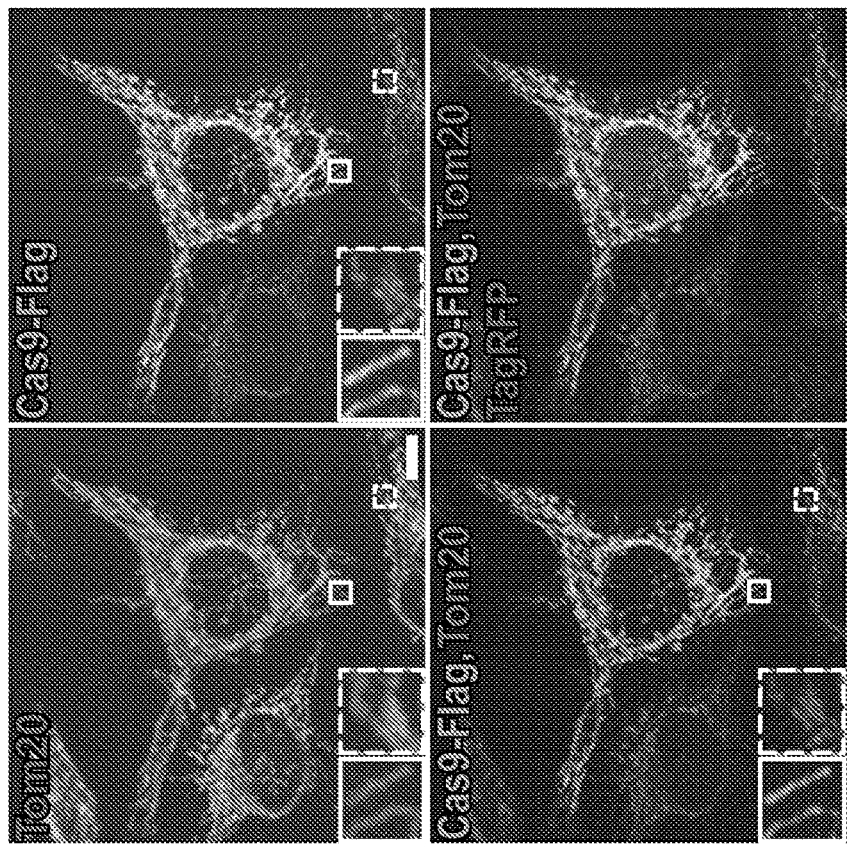
FIG. 4B
FIG. 4C

|  | CytB/Bactin | |
|---|---|---|
|  | Mean | SD |
| Mock | 1.00 | 0.20 |
| sgRNA ctrl | 1.01 | 0.18 |
| LF | 0.91 | 0.15 |
| LD | 0.63 | 1.07 |
| LDF | 1.04 | 0.19 |
| zDF | 0.92 | 0.20 |
| G5S | 0.68 | 0.24 |
| RNP | 0.67 | 0.21 |
| MRP | 0.89 | 0.15 |

|  | ND1-int/HBB | | | ND1-5'/HBB | | |
| --- | --- | --- | --- | --- | --- | --- |
|  | Mean | Upper Limit | Lower Limit | Mean | Upper Limit | Lower Limit |
| sgRNA ctrl | 1.69 | 1.18 | 2.41 | 1.91 | 1.29 | 2.81 |
| LF | 1.04 | 0.85 | 1.27 | 1.35 | 1.15 | 1.60 |
| LD | 1.04 | 0.49 | 2.23 | 0.71 | 0.33 | 1.52 |
| LDF | 1.09 | 0.73 | 1.62 | 1.41 | 0.96 | 2.07 |
| zDF | 0.21 | 0.17 | 0.25 | 0.27 | 0.22 | 0.32 |
| G5S | 0.45 | 0.30 | 0.66 | 0.62 | 0.41 | 0.93 |
| RNP | 0.60 | 0.51 | 0.70 | 0.76 | 0.62 | 0.91 |
| MRP | 0.35 | 0.29 | 0.44 | 0.44 | 0.35 | 0.55 |

SEQUENCE LISTING

```
<160> NUMBER OF SEQ ID NOS: 125

<210> SEQ ID NO 1
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 1

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu
            20                  25

<210> SEQ ID NO 2
<211> LENGTH: 87
<212> TYPE: DNA
<213> ORGANISM: Artificial Sequence
<220> FEATURE:
<223> OTHER INFORMATION: synthetic polynucleotide

<400> SEQUENCE: 2
atgtccgtcc tgacgccgct gctgctgcgg ggcttgacag gctcggcccg gcggctccca      60
gtgccgcgcg ccaagatcca ttcgttg                                         87

<210> SEQ ID NO 3
<211> LENGTH: 16
<212> TYPE: DNA
<213> ORGANISM: Artificial Sequence
<220> FEATURE:
<223> OTHER INFORMATION: synthetic polynucleotide

<400> SEQUENCE: 3
gcgcaatcgg tagcgc                                                     16

<210> SEQ ID NO 4
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 4 gagccccta cagggctc                                                    18

<210> SEQ ID NO 5
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 5
```

-continued agaagcgtat cccgctgagc                                           20

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
tctccctgag cttcagggag                                           20

<210> SEQ ID NO 7
<211> LENGTH: 46
<212> TYPE: DNA
<213> ORGANISM: Artificial Sequence
<220> FEATURE:
<223> OTHER INFORMATION: synthetic polynucleotide

<400> SEQUENCE: 7
ggcctggtta gtacttggat gggagaccgc caaggaatac cgggtg              46

<210> SEQ ID NO 8
<211> LENGTH: 85
<212> TYPE: DNA
<213> ORGANISM: Artificial Sequence
<220> FEATURE:
<223> OTHER INFORMATION: synthetic polynucleotide

<400> SEQUENCE: 8
ccaatgaccc caatacgcaa aattaacccc ctaataaaac taaccactca ttcatcgacc    60
tccccacccc atccaacatc tccgc                                         85

<210> SEQ ID NO 9
<211> LENGTH: 46
<212> TYPE: DNA
<213> ORGANISM: Artificial Sequence
<220> FEATURE:
<223> OTHER INFORMATION: synthetic polynucleotide

<400> SEQUENCE: 9
cagggtttgt taagatggca gggcccggta atcgcataaa acttaa                46

<210> SEQ ID NO 10
<211> LENGTH: 56
<212> TYPE: DNA
<213> ORGANISM: Artificial Sequence
<220> FEATURE:
<223> OTHER INFORMATION: synthetic polynucleotide

<400> SEQUENCE: 10
cccggtaatc gcataaaact taaaacctta cagtcagagg ttcaattcct cttctt     56

<210> SEQ ID NO 11
<211> LENGTH: 65
<212> TYPE: DNA
<213> ORGANISM: Artificial Sequence
<220> FEATURE:
<223> OTHER INFORMATION: synthetic polynucleotide

<400> SEQUENCE: 11
gcattaacct tttaagttaa agattaagag agccaacacc tctctacagt gaaatgcccc    60
aacta                                                                65

<210> SEQ ID NO 12
<211> LENGTH: 63
<212> TYPE: DNA
<213> ORGANISM: Artificial Sequence
<220> FEATURE:
<223> OTHER INFORMATION: synthetic polynucleotide

<400> SEQUENCE: 12 cctttaagt taaagattaa gagaaccaac acctctctac agtgaaatgc cccaactaaa    60
tac                                                                 63

<210> SEQ ID NO 13
<211> LENGTH: 63
<212> TYPE: DNA
<213> ORGANISM: Artificial Sequence
<220> FEATURE:
<223> OTHER INFORMATION: synthetic polynucleotide

<400> SEQUENCE: 13
ccatcagcct actcattcaa ccaatagccc gggccgtacg cctaaccgct aacattactg    60
cag                                                                 63

<210> SEQ ID NO 14
<211> LENGTH: 63
<212> TYPE: DNA
<213> ORGANISM: Artificial Sequence
<220> FEATURE:
<223> OTHER INFORMATION: synthetic polynucleotide

<400> SEQUENCE: 14
ccatcagcct actcattcaa ccaatagccc cggccgtacg cctaaccgct aacattactg    60
cag                                                                 63

<210> SEQ ID NO 15
<211> LENGTH: 53
<212> TYPE: DNA
<213> ORGANISM: Artificial Sequence
<220> FEATURE:
<223> OTHER INFORMATION: synthetic polynucleotide

<400> SEQUENCE: 15
gggctactac aaccctcgc tgacaccata aaactcttca ccaaagagcc cct            53

<210> SEQ ID NO 16
<211> LENGTH: 76
<212> TYPE: DNA
<213> ORGANISM: Artificial Sequence
<220> FEATURE:
<223> OTHER INFORMATION: synthetic polynucleotide

<400> SEQUENCE: 16
gcctagcaaa ctcaaactac gaacgcactc acagtcacat cataatcctc tctcaaggac    60
ttcaaactct actccc                                                   76

<210> SEQ ID NO 17
<211> LENGTH: 68
<212> TYPE: DNA
<213> ORGANISM: Artificial Sequence
<220> FEATURE:
<223> OTHER INFORMATION: synthetic polynucleotide

<400> SEQUENCE: 17
gccatcgctg tagtatatcc aaagacaacc accattcccc ctaaataaat taaaaaaact    60

```
attaaacc                                                              68

<210> SEQ ID NO 18
<211> LENGTH: 66
<212> TYPE: DNA
<213> ORGANISM: Artificial Sequence
<220> FEATURE:
<223> OTHER INFORMATION: synthetic polynucleotide

<400> SEQUENCE: 18
attctcgcac ggactacaac cacgaccaat gatacgaaaa accatcgttg tatttcaact    60
acaaga                                                                66

<210> SEQ ID NO 19
<211> LENGTH: 44
<212> TYPE: DNA
<213> ORGANISM: Artificial Sequence
<220> FEATURE:
<223> OTHER INFORMATION: synthetic polynucleotide

<400> SEQUENCE: 19 ccccctacgca tttatataga ggagacaagt cgtaacatgg taag                    44

<210> SEQ ID NO 20
<211> LENGTH: 61
<212> TYPE: DNA
<213> ORGANISM: Artificial Sequence
<220> FEATURE:
<223> OTHER INFORMATION: synthetic polynucleotide

<400> SEQUENCE: 20
gactaccaca actcaacggc tacatagaaa aacccacccc ttacgagtgc ggcttcgacc    60
c                                                                     61

<210> SEQ ID NO 21
<211> LENGTH: 69
<212> TYPE: DNA
<213> ORGANISM: Artificial Sequence
<220> FEATURE:
<223> OTHER INFORMATION: synthetic polynucleotide

<400> SEQUENCE: 21 cccccttacga gtgcggcttc gaccctatac ccccgcccg cgtcccttc tccataaaat     60 tcttcttag                                                             69

<210> SEQ ID NO 22
<211> LENGTH: 70
<212> TYPE: DNA
<213> ORGANISM: Artificial Sequence
<220> FEATURE:
<223> OTHER INFORMATION: synthetic polynucleotide

<400> SEQUENCE: 22
gaaatgatct gctgcagtgc tctgagccct aagattcatc tttctttca ccgtaggtgg     60 cctgactggc                                                            70

<210> SEQ ID NO 23
<211> LENGTH: 87
<212> TYPE: DNA
<213> ORGANISM: Artificial Sequence
<220> FEATURE:
<223> OTHER INFORMATION: synthetic polynucleotide
```

<400> SEQUENCE: 23

```
gttggaacca ttcaaaacag catagcaagt taaataagg ctagtccgtt atcaacttga    60
aaaagtggca ccgagtcggt gcttttt                                      87
```

<210> SEQ ID NO 24
<211> LENGTH: 1367
<212> TYPE: PRT
<213> ORGANISM: Streptococcus pyogenes

<400> SEQUENCE: 24

```
Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350
```

```
Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765
```

```
Thr Gln Lys Gly Gln Lys Asn Ser Arg Glu Arg Met Lys Arg Ile Glu
770                 775                 780

Glu Gly Ile Lys Glu Leu Gly Ser Gln Ile Leu Lys Glu His Pro Val
    785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
```

```
              1175                1180                1185

Val Lys Lys Asp Leu Ile Ile Lys Leu Pro Lys Tyr Ser Leu Phe
        1190                1195                1200

Glu Leu Glu Asn Gly Arg Lys Arg Met Leu Ala Ser Ala Gly Glu
        1205                1210                1215

Leu Gln Lys Gly Asn Glu Leu Ala Leu Pro Ser Lys Tyr Val Asn
        1220                1225                1230

Phe Leu Tyr Leu Ala Ser His Tyr Glu Lys Leu Lys Gly Ser Pro
        1235                1240                1245

Glu Asp Asn Glu Gln Lys Gln Leu Phe Val Glu Gln His Lys His
        1250                1255                1260

Tyr Leu Asp Glu Ile Ile Glu Gln Ile Ser Glu Phe Ser Lys Arg
        1265                1270                1275

Val Ile Leu Ala Asp Ala Asn Leu Asp Lys Val Leu Ser Ala Tyr
        1280                1285                1290

Asn Lys His Arg Asp Lys Pro Ile Arg Glu Gln Ala Glu Asn Ile
        1295                1300                1305

Ile His Leu Phe Thr Leu Thr Asn Leu Gly Ala Pro Ala Ala Phe
        1310                1315                1320

Lys Tyr Phe Asp Thr Thr Ile Asp Arg Lys Arg Tyr Thr Ser Thr
        1325                1330                1335

Lys Glu Val Leu Asp Ala Thr Leu Ile His Gln Ser Ile Thr Gly
        1340                1345                1350

Leu Tyr Glu Thr Arg Ile Asp Leu Ser Gln Leu Gly Gly Asp
        1355                1360                1365

<210> SEQ ID NO 25
<211> LENGTH: 1306
<212> TYPE: PRT
<213> ORGANISM: Artificial Sequence
<220> FEATURE:
<223> OTHER INFORMATION: synthetic polypeptide

<400> SEQUENCE: 25

Thr Gln Phe Glu Gly Phe Thr Asn Leu Tyr Gln Val Ser Lys Thr Leu
1               5                   10                  15

Arg Phe Glu Leu Ile Pro Gln Gly Lys Thr Leu Lys His Ile Gln Glu
            20                  25                  30

Gln Gly Phe Ile Glu Glu Asp Lys Ala Arg Asn Asp His Tyr Lys Glu
        35                  40                  45

Leu Lys Pro Ile Ile Asp Arg Ile Tyr Lys Thr Tyr Ala Asp Gln Cys
    50                  55                  60

Leu Gln Leu Val Gln Leu Asp Trp Glu Asn Leu Ser Ala Ala Ile Asp
65                  70                  75                  80

Ser Tyr Arg Lys Glu Lys Thr Glu Glu Thr Arg Asn Ala Leu Ile Glu
                85                  90                  95

Glu Gln Ala Thr Tyr Arg Asn Ala Ile His Asp Tyr Phe Ile Gly Arg
            100                 105                 110

Thr Asp Asn Leu Thr Asp Ala Ile Asn Lys Arg His Ala Glu Ile Tyr
        115                 120                 125

Lys Gly Leu Phe Lys Ala Glu Leu Phe Asn Gly Lys Val Leu Lys Gln
    130                 135                 140

Leu Gly Thr Val Thr Thr Thr Glu His Glu Asn Ala Leu Leu Arg Ser
145                 150                 155                 160

Phe Asp Lys Phe Thr Thr Tyr Phe Ser Gly Phe Tyr Glu Asn Arg Lys
```

```
                    165                 170                 175
Asn Val Phe Ser Ala Glu Asp Ile Ser Thr Ala Ile Pro His Arg Ile
                180                 185                 190
Val Gln Asp Asn Phe Pro Lys Phe Lys Glu Asn Cys His Ile Phe Thr
                195                 200                 205
Arg Leu Ile Thr Ala Val Pro Ser Leu Arg Glu His Phe Glu Asn Val
            210                 215                 220
Lys Lys Ala Ile Gly Ile Phe Val Ser Thr Ser Ile Glu Glu Val Phe
225                 230                 235                 240
Ser Phe Pro Phe Tyr Asn Gln Leu Leu Thr Gln Thr Gln Ile Asp Leu
                245                 250                 255
Tyr Asn Gln Leu Leu Gly Gly Ile Ser Arg Glu Ala Gly Thr Glu Lys
            260                 265                 270
Ile Lys Gly Leu Asn Glu Val Leu Asn Leu Ala Ile Gln Lys Asn Asp
            275                 280                 285
Glu Thr Ala His Ile Ile Ala Ser Leu Pro His Arg Phe Ile Pro Leu
        290                 295                 300
Phe Lys Gln Ile Leu Ser Asp Arg Asn Thr Leu Ser Phe Ile Leu Glu
305                 310                 315                 320
Glu Phe Lys Ser Asp Glu Glu Val Ile Gln Ser Phe Cys Lys Tyr Lys
                325                 330                 335
Thr Leu Leu Arg Asn Glu Asn Val Leu Glu Thr Ala Glu Ala Leu Phe
                340                 345                 350
Asn Glu Leu Asn Ser Ile Asp Leu Thr His Ile Phe Ile Ser His Lys
                355                 360                 365
Lys Leu Glu Thr Ile Ser Ser Ala Leu Cys Asp His Trp Asp Thr Leu
        370                 375                 380
Arg Asn Ala Leu Tyr Glu Arg Arg Ile Ser Glu Leu Thr Gly Lys Ile
385                 390                 395                 400
Thr Lys Ser Ala Lys Glu Lys Val Gln Arg Ser Leu Lys His Glu Asp
                405                 410                 415
Ile Asn Leu Gln Glu Ile Ile Ser Ala Ala Gly Lys Glu Leu Ser Glu
                420                 425                 430
Ala Phe Lys Gln Lys Thr Ser Glu Ile Leu Ser His Ala His Ala Ala
            435                 440                 445
Leu Asp Gln Pro Leu Pro Thr Thr Leu Lys Lys Gln Glu Glu Lys Glu
        450                 455                 460
Ile Leu Lys Ser Gln Leu Asp Ser Leu Leu Gly Leu Tyr His Leu Leu
465                 470                 475                 480
Asp Trp Phe Ala Val Asp Glu Ser Asn Glu Val Asp Pro Glu Phe Ser
                485                 490                 495
Ala Arg Leu Thr Gly Ile Lys Leu Glu Met Glu Pro Ser Leu Ser Phe
                500                 505                 510
Tyr Asn Lys Ala Arg Asn Tyr Ala Thr Lys Lys Pro Tyr Ser Val Glu
            515                 520                 525
Lys Phe Lys Leu Asn Phe Gln Met Pro Thr Leu Ala Ser Gly Trp Asp
        530                 535                 540
Val Asn Lys Glu Lys Asn Asn Gly Ala Ile Leu Phe Val Lys Asn Gly
545                 550                 555                 560
Leu Tyr Tyr Leu Gly Ile Met Pro Lys Gln Lys Gly Arg Tyr Lys Ala
                565                 570                 575
Leu Ser Phe Glu Pro Thr Glu Lys Thr Ser Glu Gly Phe Asp Lys Met
                580                 585                 590
```

```
Tyr Tyr Asp Tyr Phe Pro Asp Ala Ala Lys Met Ile Pro Lys Cys Ser
        595             600                 605

Thr Gln Leu Lys Ala Val Thr Ala His Phe Gln Thr His Thr Thr Pro
610             615                 620

Ile Leu Leu Ser Asn Asn Phe Ile Glu Pro Leu Glu Ile Thr Lys Glu
625             630                 635                     640

Ile Tyr Asp Leu Asn Asn Pro Glu Lys Glu Pro Lys Lys Phe Gln Thr
            645                 650                 655

Ala Tyr Ala Lys Lys Thr Gly Asp Gln Lys Gly Tyr Arg Glu Ala Leu
            660                 665                 670

Cys Lys Trp Ile Asp Phe Thr Arg Asp Phe Leu Ser Lys Tyr Thr Lys
            675                 680                 685

Thr Thr Ser Ile Asp Leu Ser Ser Leu Arg Pro Ser Ser Gln Tyr Lys
        690                 695                 700

Asp Leu Gly Glu Tyr Tyr Ala Glu Leu Asn Pro Leu Leu Tyr His Ile
705                 710                 715                 720

Ser Phe Gln Arg Ile Ala Glu Lys Glu Ile Met Asp Ala Val Glu Thr
                725                 730                 735

Gly Lys Leu Tyr Leu Phe Gln Ile Tyr Asn Lys Asp Phe Ala Lys Gly
            740                 745                 750

His His Gly Lys Pro Asn Leu His Thr Leu Tyr Trp Thr Gly Leu Phe
        755                 760                 765

Ser Pro Glu Asn Leu Ala Lys Thr Ser Ile Lys Leu Asn Gly Gln Ala
770                 775                 780

Glu Leu Phe Tyr Arg Pro Lys Ser Arg Met Lys Arg Met Ala His Arg
785                 790                 795                 800

Leu Gly Glu Lys Met Leu Asn Lys Lys Leu Lys Asp Gln Lys Thr Pro
                805                 810                 815

Ile Pro Asp Thr Leu Tyr Gln Glu Leu Tyr Asp Tyr Val Asn His Arg
                820                 825                 830

Leu Ser His Asp Leu Ser Asp Glu Ala Arg Ala Leu Leu Pro Asn Val
        835                 840                 845

Ile Thr Lys Glu Val Ser His Glu Ile Ile Lys Asp Arg Arg Phe Thr
        850                 855                 860

Ser Asp Lys Phe Phe Phe His Val Pro Ile Thr Leu Asn Tyr Gln Ala
865                 870                 875                 880

Ala Asn Ser Pro Ser Lys Phe Asn Gln Arg Val Asn Ala Tyr Leu Lys
            885                 890                 895

Glu His Pro Glu Thr Pro Ile Ile Gly Ile Asp Arg Gly Glu Arg Asn
            900                 905                 910

Leu Ile Tyr Ile Thr Val Ile Asp Ser Thr Gly Lys Ile Leu Glu Gln
            915                 920                 925

Arg Ser Leu Asn Thr Ile Gln Gln Phe Asp Tyr Gln Lys Lys Leu Asp
930                 935                 940

Asn Arg Glu Lys Glu Arg Val Ala Ala Arg Gln Ala Trp Ser Val Val
945                 950                 955                 960

Gly Thr Ile Lys Asp Leu Lys Gln Gly Tyr Leu Ser Gln Val Ile His
                965                 970                 975

Glu Ile Val Asp Leu Met Ile His Tyr Gln Ala Val Val Val Leu Glu
            980                 985                 990

Asn Leu Asn Phe Gly Phe Lys Ser  Lys Arg Thr Gly Ile  Ala Glu Lys
            995                1000                1005
```

```
Ala Val Tyr Gln Gln Phe Glu Lys Met Leu Ile Asp Lys Leu Asn
    1010                1015                1020

Cys Leu Val Leu Lys Asp Tyr Pro Ala Glu Lys Val Gly Gly Val
    1025                1030                1035

Leu Asn Pro Tyr Gln Leu Thr Asp Gln Phe Thr Ser Phe Ala Lys
    1040                1045                1050

Met Gly Thr Gln Ser Gly Phe Leu Phe Tyr Val Pro Ala Pro Tyr
    1055                1060                1065

Thr Ser Lys Ile Asp Pro Leu Thr Gly Phe Val Asp Pro Phe Val
    1070                1075                1080

Trp Lys Thr Ile Lys Asn His Glu Ser Arg Lys His Phe Leu Glu
    1085                1090                1095

Gly Phe Asp Phe Leu His Tyr Asp Val Lys Thr Gly Asp Phe Ile
    1100                1105                1110

Leu His Phe Lys Met Asn Arg Asn Leu Ser Phe Gln Arg Gly Leu
    1115                1120                1125

Pro Gly Phe Met Pro Ala Trp Asp Ile Val Phe Glu Lys Asn Glu
    1130                1135                1140

Thr Gln Phe Asp Ala Lys Gly Thr Pro Phe Ile Ala Gly Lys Arg
    1145                1150                1155

Ile Val Pro Val Ile Glu Asn His Arg Phe Thr Gly Arg Tyr Arg
    1160                1165                1170

Asp Leu Tyr Pro Ala Asn Glu Leu Ile Ala Leu Leu Glu Glu Lys
    1175                1180                1185

Gly Ile Val Phe Arg Asp Gly Ser Asn Ile Leu Pro Lys Leu Leu
    1190                1195                1200

Glu Asn Asp Asp Ser His Ala Ile Asp Thr Met Val Ala Leu Ile
    1205                1210                1215

Arg Ser Val Leu Gln Met Arg Asn Ser Asn Ala Ala Thr Gly Glu
    1220                1225                1230

Asp Tyr Ile Asn Ser Pro Val Arg Asp Leu Asn Gly Val Cys Phe
    1235                1240                1245

Asp Ser Arg Phe Gln Asn Pro Glu Trp Pro Met Asp Ala Asp Ala
    1250                1255                1260

Asn Gly Ala Tyr His Ile Ala Leu Lys Gly Gln Leu Leu Leu Asn
    1265                1270                1275

His Leu Lys Glu Ser Lys Asp Leu Lys Leu Gln Asn Gly Ile Ser
    1280                1285                1290

Asn Gln Asp Trp Leu Ala Tyr Ile Gln Glu Leu Arg Asn
    1295                1300                1305

<210> SEQ ID NO 26
<211> LENGTH: 1052
<212> TYPE: PRT
<213> ORGANISM: Staphylococcus aureus

<400> SEQUENCE: 26

Lys Arg Asn Tyr Ile Leu Gly Leu Asp Ile Gly Ile Thr Ser Val Gly
1               5                   10                  15

Tyr Gly Ile Ile Asp Tyr Glu Thr Arg Asp Val Ile Asp Ala Gly Val
                20                  25                  30

Arg Leu Phe Lys Glu Ala Asn Val Glu Asn Asn Glu Gly Arg Arg Ser
            35                  40                  45

Lys Arg Gly Ala Arg Arg Leu Lys Arg Arg Arg Arg His Arg Ile Gln
        50                  55                  60
```

```
Arg Val Lys Lys Leu Leu Phe Asp Tyr Asn Leu Leu Thr Asp His Ser
 65                  70                  75                  80

Glu Leu Ser Gly Ile Asn Pro Tyr Glu Ala Arg Val Lys Gly Leu Ser
                 85                  90                  95

Gln Lys Leu Ser Glu Glu Phe Ser Ala Ala Leu Leu His Leu Ala
            100                 105                 110

Lys Arg Arg Gly Val His Asn Val Asn Glu Val Glu Glu Asp Thr Gly
            115                 120                 125

Asn Glu Leu Ser Thr Arg Glu Gln Ile Ser Arg Asn Ser Lys Ala Leu
130                 135                 140

Glu Glu Lys Tyr Val Ala Glu Leu Gln Leu Glu Arg Leu Lys Lys Asp
145                 150                 155                 160

Gly Glu Val Arg Gly Ser Ile Asn Arg Phe Lys Thr Ser Asp Tyr Val
                165                 170                 175

Lys Glu Ala Lys Gln Leu Leu Lys Val Gln Lys Ala Tyr His Gln Leu
                180                 185                 190

Asp Gln Ser Phe Ile Asp Thr Tyr Ile Asp Leu Leu Glu Thr Arg Arg
            195                 200                 205

Thr Tyr Tyr Glu Gly Pro Gly Glu Gly Ser Pro Phe Gly Trp Lys Asp
210                 215                 220

Ile Lys Glu Trp Tyr Glu Met Leu Met Gly His Cys Thr Tyr Phe Pro
225                 230                 235                 240

Glu Glu Leu Arg Ser Val Lys Tyr Ala Tyr Asn Ala Asp Leu Tyr Asn
                245                 250                 255

Ala Leu Asn Asp Leu Asn Asn Leu Val Ile Thr Arg Asp Glu Asn Glu
            260                 265                 270

Lys Leu Glu Tyr Tyr Glu Lys Phe Gln Ile Ile Glu Asn Val Phe Lys
            275                 280                 285

Gln Lys Lys Lys Pro Thr Leu Lys Gln Ile Ala Lys Glu Ile Leu Val
290                 295                 300

Asn Glu Glu Asp Ile Lys Gly Tyr Arg Val Thr Ser Thr Gly Lys Pro
305                 310                 315                 320

Glu Phe Thr Asn Leu Lys Val Tyr His Asp Ile Lys Asp Ile Thr Ala
                325                 330                 335

Arg Lys Glu Ile Ile Glu Asn Ala Glu Leu Leu Asp Gln Ile Ala Lys
            340                 345                 350

Ile Leu Thr Ile Tyr Gln Ser Ser Glu Asp Ile Gln Glu Glu Leu Thr
            355                 360                 365

Asn Leu Asn Ser Glu Leu Thr Gln Glu Glu Ile Glu Gln Ile Ser Asn
370                 375                 380

Leu Lys Gly Tyr Thr Gly Thr His Asn Leu Ser Leu Lys Ala Ile Asn
385                 390                 395                 400

Leu Ile Leu Asp Glu Leu Trp His Thr Asn Asp Asn Gln Ile Ala Ile
                405                 410                 415

Phe Asn Arg Leu Lys Leu Val Pro Lys Val Asp Leu Ser Gln Gln
            420                 425                 430

Lys Glu Ile Pro Thr Thr Leu Val Asp Asp Phe Ile Leu Ser Pro Val
            435                 440                 445

Val Lys Arg Ser Phe Ile Gln Ser Ile Lys Val Ile Asn Ala Ile Ile
    450                 455                 460

Lys Lys Tyr Gly Leu Pro Asn Asp Ile Ile Ile Glu Leu Ala Arg Glu
465                 470                 475                 480
```

```
Lys Asn Ser Lys Asp Ala Gln Lys Met Ile Asn Glu Met Gln Lys Arg
                485                 490                 495

Asn Arg Gln Thr Asn Glu Arg Ile Glu Glu Ile Ile Arg Thr Thr Gly
            500                 505                 510

Lys Glu Asn Ala Lys Tyr Leu Ile Glu Lys Ile Lys Leu His Asp Met
            515                 520                 525

Gln Glu Gly Lys Cys Leu Tyr Ser Leu Glu Ala Ile Pro Leu Glu Asp
            530                 535                 540

Leu Leu Asn Asn Pro Phe Asn Tyr Glu Val Asp His Ile Ile Pro Arg
545                 550                 555                 560

Ser Val Ser Phe Asp Asn Ser Phe Asn Asn Lys Val Leu Val Lys Gln
                565                 570                 575

Glu Glu Asn Ser Lys Lys Gly Asn Arg Thr Pro Phe Gln Tyr Leu Ser
            580                 585                 590

Ser Ser Asp Ser Lys Ile Ser Tyr Glu Thr Phe Lys Lys His Ile Leu
            595                 600                 605

Asn Leu Ala Lys Gly Lys Gly Arg Ile Ser Lys Thr Lys Lys Glu Tyr
            610                 615                 620

Leu Leu Glu Glu Arg Asp Ile Asn Arg Phe Ser Val Gln Lys Asp Phe
625                 630                 635                 640

Ile Asn Arg Asn Leu Val Asp Thr Arg Tyr Ala Thr Arg Gly Leu Met
                645                 650                 655

Asn Leu Leu Arg Ser Tyr Phe Arg Val Asn Asn Leu Asp Val Lys Val
            660                 665                 670

Lys Ser Ile Asn Gly Gly Phe Thr Ser Phe Leu Arg Arg Lys Trp Lys
            675                 680                 685

Phe Lys Lys Glu Arg Asn Lys Gly Tyr Lys His His Ala Glu Asp Ala
            690                 695                 700

Leu Ile Ile Ala Asn Ala Asp Phe Ile Phe Lys Glu Trp Lys Lys Leu
705                 710                 715                 720

Asp Lys Ala Lys Lys Val Met Glu Asn Gln Met Phe Glu Glu Lys Gln
                725                 730                 735

Ala Glu Ser Met Pro Glu Ile Glu Thr Glu Gln Glu Tyr Lys Glu Ile
            740                 745                 750

Phe Ile Thr Pro His Gln Ile Lys His Ile Lys Asp Phe Lys Asp Tyr
            755                 760                 765

Lys Tyr Ser His Arg Val Asp Lys Lys Pro Asn Arg Glu Leu Ile Asn
            770                 775                 780

Asp Thr Leu Tyr Ser Thr Arg Lys Asp Asp Lys Gly Asn Thr Leu Ile
785                 790                 795                 800

Val Asn Asn Leu Asn Gly Leu Tyr Asp Lys Asp Asn Asp Lys Leu Lys
                805                 810                 815

Lys Leu Ile Asn Lys Ser Pro Glu Lys Leu Leu Met Tyr His His Asp
            820                 825                 830

Pro Gln Thr Tyr Gln Lys Leu Lys Leu Ile Met Glu Gln Tyr Gly Asp
            835                 840                 845

Glu Lys Asn Pro Leu Tyr Lys Tyr Tyr Glu Glu Thr Gly Asn Tyr Leu
            850                 855                 860

Thr Lys Tyr Ser Lys Lys Asp Asn Gly Pro Val Ile Lys Lys Ile Lys
865                 870                 875                 880

Tyr Tyr Gly Asn Lys Leu Asn Ala His Leu Asp Ile Thr Asp Asp Tyr
                885                 890                 895

Pro Asn Ser Arg Asn Lys Val Val Lys Leu Ser Leu Lys Pro Tyr Arg
```

```
                900             905             910
Phe Asp Val Tyr Leu Asp Asn Gly Val Tyr Lys Phe Val Thr Val Lys
            915             920             925

Asn Leu Asp Val Ile Lys Lys Glu Asn Tyr Tyr Glu Val Asn Ser Lys
        930             935             940

Cys Tyr Glu Glu Ala Lys Lys Leu Lys Lys Ile Ser Asn Gln Ala Glu
945             950             955             960

Phe Ile Ala Ser Phe Tyr Asn Asn Asp Leu Ile Lys Ile Asn Gly Glu
            965             970             975

Leu Tyr Arg Val Ile Gly Val Asn Asn Asp Leu Leu Asn Arg Ile Glu
            980             985             990

Val Asn Met Ile Asp Ile Thr Tyr Arg Glu Tyr Leu Glu Asn Met Asn
        995             1000            1005

Asp Lys Arg Pro Pro Arg Ile Ile Lys Thr Ile Ala Ser Lys Thr
    1010            1015            1020

Gln Ser Ile Lys Lys Tyr Ser Thr Asp Ile Leu Gly Asn Leu Tyr
    1025            1030            1035

Glu Val Lys Ser Lys Lys His Pro Gln Ile Ile Lys Lys Gly
    1040            1045            1050

<210> SEQ ID NO 27
<211> LENGTH: 1367
<212> TYPE: PRT
<213> ORGANISM: Artificial Sequence
<220> FEATURE:
<223> OTHER INFORMATION: synthetic polypeptide

<400> SEQUENCE: 27

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
```

-continued

```
            210                 215                 220
Ile Ala Gln Leu Pro Gly Glu Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
                260                 265                 270

Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
            290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
            450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640
```

```
Leu Phe Asp Asp Lys Val Met Lys Gln Leu Lys Arg Arg Tyr Thr
            645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050
```

```
Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Val Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Gln Tyr Arg Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 28
<211> LENGTH: 1367
<212> TYPE: PRT
<213> ORGANISM: Artificial Sequence
<220> FEATURE:
<223> OTHER INFORMATION: synthetic polypeptide

<400> SEQUENCE: 28

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30
```

Val Leu Gly Asn Thr Asp Arg His Ser Ile Lys Lys Asn Leu Ile Gly
         35                  40                  45

Ala Leu Leu Phe Asp Ser Gly Glu Thr Ala Glu Ala Thr Arg Leu Lys
 50                  55                  60

Arg Thr Ala Arg Arg Tyr Thr Arg Arg Lys Asn Arg Ile Cys Tyr
 65                  70                  75                  80

Leu Gln Glu Ile Phe Ser Asn Glu Met Ala Lys Val Asp Asp Ser Phe
                 85                  90                  95

Phe His Arg Leu Glu Glu Ser Phe Leu Val Glu Asp Lys Lys His
                 100                 105                 110

Glu Arg His Pro Ile Phe Gly Asn Ile Val Asp Glu Val Ala Tyr His
                 115                 120                 125

Glu Lys Tyr Pro Thr Ile Tyr His Leu Arg Lys Lys Leu Val Asp Ser
 130                 135                 140

Thr Asp Lys Ala Asp Leu Arg Leu Ile Tyr Leu Ala Leu Ala His Met
 145                 150                 155                 160

Ile Lys Phe Arg Gly His Phe Leu Ile Glu Gly Asp Leu Asn Pro Asp
                 165                 170                 175

Asn Ser Asp Val Asp Lys Leu Phe Ile Gln Leu Val Gln Thr Tyr Asn
                 180                 185                 190

Gln Leu Phe Glu Glu Asn Pro Ile Asn Ala Ser Gly Val Asp Ala Lys
                 195                 200                 205

Ala Ile Leu Ser Ala Arg Leu Ser Lys Ser Arg Arg Leu Glu Asn Leu
 210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                 245                 250                 255

Leu Ala Glu Asp Ala Lys Leu Gln Leu Ser Lys Asp Thr Tyr Asp Asp
                 260                 265                 270

Asp Leu Asp Asn Leu Leu Ala Gln Ile Gly Asp Gln Tyr Ala Asp Leu
                 275                 280                 285

Phe Leu Ala Ala Lys Asn Leu Ser Asp Ala Ile Leu Leu Ser Asp Ile
 290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                 325                 330                 335

Leu Val Arg Gln Gln Leu Pro Glu Lys Tyr Lys Glu Ile Phe Phe Asp
                 340                 345                 350

Gln Ser Lys Asn Gly Tyr Ala Gly Tyr Ile Asp Gly Gly Ala Ser Gln
                 355                 360                 365

Glu Glu Phe Tyr Lys Phe Ile Lys Pro Ile Leu Glu Lys Met Asp Gly
                 370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                 405                 410                 415

Glu Leu His Ala Ile Leu Arg Arg Gln Glu Asp Phe Tyr Pro Phe Leu
                 420                 425                 430

Lys Asp Asn Arg Glu Lys Ile Glu Lys Ile Leu Thr Phe Arg Ile Pro
                 435                 440                 445

Tyr Tyr Val Gly Pro Leu Ala Arg Gly Asn Ser Arg Phe Ala Trp Met

```
                450                 455                 460
Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
            690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880
```

-continued

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr
            1025                1030                1035

Ser Asn Ile Met Asn Phe Phe Lys Thr Glu Ile Thr Leu Ala Asn
            1040                1045                1050

Gly Glu Ile Arg Lys Arg Pro Leu Ile Glu Thr Asn Gly Glu Thr
            1055                1060                1065

Gly Glu Ile Val Trp Asp Lys Gly Arg Asp Phe Ala Thr Val Arg
            1070                1075                1080

Lys Val Leu Ser Met Pro Gln Val Asn Ile Val Lys Lys Thr Glu
            1085                1090                1095

Val Gln Thr Gly Gly Phe Ser Lys Glu Ser Ile Leu Pro Lys Arg
            1100                1105                1110

Asn Ser Asp Lys Leu Ile Ala Arg Lys Lys Asp Trp Asp Pro Lys
            1115                1120                1125

Lys Tyr Gly Gly Phe Val Ser Pro Thr Val Ala Tyr Ser Val Leu
            1130                1135                1140

Val Val Ala Lys Val Glu Lys Gly Lys Ser Lys Lys Leu Lys Ser
            1145                1150                1155

Val Lys Glu Leu Leu Gly Ile Thr Ile Met Glu Arg Ser Ser Phe
            1160                1165                1170

Glu Lys Asn Pro Ile Asp Phe Leu Glu Ala Lys Gly Tyr Lys Glu
            1175                1180                1185

Val Lys Lys Asp Leu Ile Ile Lys Leu Pro Lys Tyr Ser Leu Phe
            1190                1195                1200

Glu Leu Glu Asn Gly Arg Lys Arg Met Leu Ala Ser Ala Arg Glu
            1205                1210                1215

Leu Gln Lys Gly Asn Glu Leu Ala Leu Pro Ser Lys Tyr Val Asn
            1220                1225                1230

Phe Leu Tyr Leu Ala Ser His Tyr Glu Lys Leu Lys Gly Ser Pro
            1235                1240                1245

Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg
            1265                1270                1275

```
Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Asn Leu Gly Ala Pro Ala Ala Phe
    1310                1315                1320

Lys Tyr Phe Asp Thr Thr Ile Asp Arg Lys Glu Tyr Arg Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 29
<211> LENGTH: 1367
<212> TYPE: PRT
<213> ORGANISM: Artificial Sequence
<220> FEATURE:
<223> OTHER INFORMATION: synthetic polypeptide

<400> SEQUENCE: 29

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270
```

```
Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
            290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
            370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
            435                 440                 445

Tyr Tyr Val Gly Pro Leu Ala Arg Gly Asn Ser Arg Phe Ala Trp Met
            450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
            530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
            610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
```

```
                690               695               700
Glu Asp Ile Gln Lys Ala Gln Val Ser Gly Gln Gly Asp Ser Leu His
705               710               715               720

Glu His Ile Ala Asn Leu Ala Gly Ser Pro Ala Ile Lys Lys Gly Ile
                725               730               735

Leu Gln Thr Val Lys Val Val Asp Glu Leu Val Lys Val Met Gly Arg
                740               745               750

His Lys Pro Glu Asn Ile Val Ile Glu Met Ala Arg Glu Asn Gln Thr
        755               760               765

Thr Gln Lys Gly Gln Lys Asn Ser Arg Glu Arg Met Lys Arg Ile Glu
        770               775               780

Glu Gly Ile Lys Glu Leu Gly Ser Gln Ile Leu Lys Glu His Pro Val
785               790               795               800

Glu Asn Thr Gln Leu Gln Asn Glu Lys Leu Tyr Leu Tyr Tyr Leu Gln
                805               810               815

Asn Gly Arg Asp Met Tyr Val Asp Gln Glu Leu Asp Ile Asn Arg Leu
                820               825               830

Ser Asp Tyr Asp Val Asp His Ile Val Pro Gln Ser Phe Leu Lys Asp
        835               840               845

Asp Ser Ile Asp Asn Lys Val Leu Thr Arg Ser Asp Lys Asn Arg Gly
        850               855               860

Lys Ser Asp Asn Val Pro Ser Glu Glu Val Val Lys Lys Met Lys Asn
865               870               875               880

Tyr Trp Arg Gln Leu Leu Asn Ala Lys Leu Ile Thr Gln Arg Lys Phe
                885               890               895

Asp Asn Leu Thr Lys Ala Glu Arg Gly Gly Leu Ser Glu Leu Asp Lys
                900               905               910

Ala Gly Phe Ile Lys Arg Gln Leu Val Glu Thr Arg Gln Ile Thr Lys
                915               920               925

His Val Ala Gln Ile Leu Asp Ser Arg Met Asn Thr Lys Tyr Asp Glu
        930               935               940

Asn Asp Lys Leu Ile Arg Glu Val Lys Val Ile Thr Leu Lys Ser Lys
945               950               955               960

Leu Val Ser Asp Phe Arg Lys Asp Phe Gln Phe Tyr Lys Val Arg Glu
                965               970               975

Ile Asn Asn Tyr His His Ala His Asp Ala Tyr Leu Asn Ala Val Val
                980               985               990

Gly Thr Ala Leu Ile Lys Lys Tyr Pro Lys Leu Glu Ser Glu Phe Val
                995               1000              1005

Tyr Gly Asp Tyr Lys Val Tyr Asp Val Arg Lys Met Ile Ala Lys
        1010              1015              1020

Ser Glu Gln Glu Ile Gly Lys Ala Thr Ala Lys Tyr Phe Phe Tyr
        1025              1030              1035

Ser Asn Ile Met Asn Phe Phe Lys Thr Glu Ile Thr Leu Ala Asn
        1040              1045              1050

Gly Glu Ile Arg Lys Arg Pro Leu Ile Glu Thr Asn Gly Glu Thr
        1055              1060              1065

Gly Glu Ile Val Trp Asp Lys Gly Arg Asp Phe Ala Thr Val Arg
        1070              1075              1080

Lys Val Leu Ser Met Pro Gln Val Asn Ile Val Lys Lys Thr Glu
        1085              1090              1095

Val Gln Thr Gly Gly Phe Ser Lys Glu Ser Ile Leu Pro Lys Arg
        1100              1105              1110
```

Asn Ser Asp Lys Leu Ile Ala Arg Lys Lys Asp Trp Asp Pro Lys
1115                1120                1125

Lys Tyr Gly Gly Phe Glu Ser Pro Thr Val Ala Tyr Ser Val Leu
      1130                1135                1140

Val Val Ala Lys Val Glu Lys Gly Lys Ser Lys Lys Leu Lys Ser
   1145                1150                1155

Val Lys Glu Leu Leu Gly Ile Thr Ile Met Glu Arg Ser Ser Phe
  1160                1165                1170

Glu Lys Asn Pro Ile Asp Phe Leu Glu Ala Lys Gly Tyr Lys Glu
  1175                1180                1185

Val Lys Lys Asp Leu Ile Ile Lys Leu Pro Lys Tyr Ser Leu Phe
  1190                1195                1200

Glu Leu Glu Asn Gly Arg Lys Arg Met Leu Ala Ser Ala Gly Glu
  1205                1210                1215

Leu Gln Lys Gly Asn Glu Leu Ala Leu Pro Ser Lys Tyr Val Asn
  1220                1225                1230

Phe Leu Tyr Leu Ala Ser His Tyr Glu Lys Leu Lys Gly Ser Pro
  1235                1240                1245

Glu Asp Asn Glu Gln Lys Gln Leu Phe Val Glu Gln His Lys His
  1250                1255                1260

Tyr Leu Asp Glu Ile Ile Glu Gln Ile Ser Glu Phe Ser Lys Arg
  1265                1270                1275

Val Ile Leu Ala Asp Ala Asn Leu Asp Lys Val Leu Ser Ala Tyr
  1280                1285                1290

Asn Lys His Arg Asp Lys Pro Ile Arg Glu Gln Ala Glu Asn Ile
  1295                1300                1305

Ile His Leu Phe Thr Leu Thr Asn Leu Gly Ala Pro Ala Ala Phe
  1310                1315                1320

Lys Tyr Phe Asp Thr Thr Ile Asp Arg Lys Arg Tyr Thr Ser Thr
  1325                1330                1335

Lys Glu Val Leu Asp Ala Thr Leu Ile His Gln Ser Ile Thr Gly
  1340                1345                1350

Leu Tyr Glu Thr Arg Ile Asp Leu Ser Gln Leu Gly Gly Asp
  1355                1360                1365

<210> SEQ ID NO 30
<211> LENGTH: 1367
<212> TYPE: PRT
<213> ORGANISM: Artificial Sequence
<220> FEATURE:
<223> OTHER INFORMATION: synthetic polypeptide

<400> SEQUENCE: 30

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

```
Phe His Arg Leu Glu Glu Ser Phe Leu Val Glu Glu Asp Lys Lys His
                100                 105                 110

Glu Arg His Pro Ile Phe Gly Asn Ile Val Asp Glu Val Ala Tyr His
                115                 120                 125

Glu Lys Tyr Pro Thr Ile Tyr His Leu Arg Lys Lys Leu Val Asp Ser
            130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
                180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
        210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
        290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
        370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
        450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510
```

```
Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
        530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
            565                 570                 575

Val Glu Ile Ser Gly Val Glu Asp Arg Phe Asn Ala Ser Leu Gly Thr
        580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
        610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
            645                 650                 655

Gly Trp Gly Arg Leu Ser Arg Lys Leu Ile Asn Gly Ile Arg Asp Lys
        660                 665                 670

Gln Ser Gly Lys Thr Ile Leu Asp Phe Leu Lys Ser Asp Gly Phe Ala
    675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
            725                 730                 735

Leu Gln Thr Val Lys Val Val Asp Glu Leu Val Lys Val Met Gly Arg
        740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
        820                 825                 830

Ser Asp Tyr Asp Val Asp His Ile Val Pro Gln Ser Phe Leu Ala Asp
            835                 840                 845

Asp Ser Ile Asp Asn Lys Val Leu Thr Arg Ser Asp Lys Asn Arg Gly
        850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
        900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
```

```
                930              935              940
Asn Asp Lys Leu Ile Arg Glu Val Lys Val Ile Thr Leu Lys Ser Lys
945              950              955              960
Leu Val Ser Asp Phe Arg Lys Asp Phe Gln Phe Tyr Lys Val Arg Glu
                965              970              975
Ile Asn Asn Tyr His His Ala His Asp Ala Tyr Leu Asn Ala Val Val
            980              985              990
Gly Thr Ala Leu Ile Lys Lys Tyr Pro Ala Leu Glu Ser Glu Phe Val
        995              1000             1005
Tyr Gly Asp Tyr Lys Val Tyr Asp Val Arg Lys Met Ile Ala Lys
    1010             1015             1020
Ser Glu Gln Glu Ile Gly Lys Ala Thr Ala Lys Tyr Phe Phe Tyr
    1025             1030             1035
Ser Asn Ile Met Asn Phe Phe Lys Thr Glu Ile Thr Leu Ala Asn
    1040             1045             1050
Gly Glu Ile Arg Lys Ala Pro Leu Ile Glu Thr Asn Gly Glu Thr
    1055             1060             1065
Gly Glu Ile Val Trp Asp Lys Gly Arg Asp Phe Ala Thr Val Arg
    1070             1075             1080
Lys Val Leu Ser Met Pro Gln Val Asn Ile Val Lys Lys Thr Glu
    1085             1090             1095
Val Gln Thr Gly Gly Phe Ser Lys Glu Ser Ile Leu Pro Lys Arg
    1100             1105             1110
Asn Ser Asp Lys Leu Ile Ala Arg Lys Lys Asp Trp Asp Pro Lys
    1115             1120             1125
Lys Tyr Gly Gly Phe Asp Ser Pro Thr Val Ala Tyr Ser Val Leu
    1130             1135             1140
Val Val Ala Lys Val Glu Lys Gly Lys Ser Lys Lys Leu Lys Ser
    1145             1150             1155
Val Lys Glu Leu Leu Gly Ile Thr Ile Met Glu Arg Ser Ser Phe
    1160             1165             1170
Glu Lys Asn Pro Ile Asp Phe Leu Glu Ala Lys Gly Tyr Lys Glu
    1175             1180             1185
Val Lys Lys Asp Leu Ile Ile Lys Leu Pro Lys Tyr Ser Leu Phe
    1190             1195             1200
Glu Leu Glu Asn Gly Arg Lys Arg Met Leu Ala Ser Ala Gly Glu
    1205             1210             1215
Leu Gln Lys Gly Asn Glu Leu Ala Leu Pro Ser Lys Tyr Val Asn
    1220             1225             1230
Phe Leu Tyr Leu Ala Ser His Tyr Glu Lys Leu Lys Gly Ser Pro
    1235             1240             1245
Glu Asp Asn Glu Gln Lys Gln Leu Phe Val Glu Gln His Lys His
    1250             1255             1260
Tyr Leu Asp Glu Ile Ile Glu Gln Ile Ser Glu Phe Ser Lys Arg
    1265             1270             1275
Val Ile Leu Ala Asp Ala Asn Leu Asp Lys Val Leu Ser Ala Tyr
    1280             1285             1290
Asn Lys His Arg Asp Lys Pro Ile Arg Glu Gln Ala Glu Asn Ile
    1295             1300             1305
Ile His Leu Phe Thr Leu Thr Asn Leu Gly Ala Pro Ala Ala Phe
    1310             1315             1320
Lys Tyr Phe Asp Thr Thr Ile Asp Arg Lys Arg Tyr Thr Ser Thr
    1325             1330             1335
```

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 31
<211> LENGTH: 1367
<212> TYPE: PRT
<213> ORGANISM: Artificial Sequence
<220> FEATURE:
<223> OTHER INFORMATION: synthetic polypeptide

<400> SEQUENCE: 31

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
            85                  90                  95

Phe His Arg Leu Glu Glu Ser Phe Leu Val Glu Glu Asp Lys Lys His
        100                 105                 110

Glu Arg His Pro Ile Phe Gly Asn Ile Val Asp Glu Val Ala Tyr His
    115                 120                 125

Glu Lys Tyr Pro Thr Ile Tyr His Leu Arg Lys Lys Leu Val Asp Ser
130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
            165                 170                 175

Asn Ser Asp Val Asp Lys Leu Phe Ile Gln Leu Val Gln Thr Tyr Asn
        180                 185                 190

Gln Leu Phe Glu Glu Asn Pro Ile Asn Ala Ser Gly Val Asp Ala Lys
    195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
            245                 250                 255

Leu Ala Glu Asp Ala Lys Leu Gln Leu Ser Lys Asp Thr Tyr Asp Asp
        260                 265                 270

Asp Leu Asp Asn Leu Leu Ala Gln Ile Gly Asp Gln Tyr Ala Asp Leu
    275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
            325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
                355                 360                 365

Glu Glu Phe Tyr Lys Phe Ile Lys Pro Ile Leu Glu Lys Met Asp Gly
    370                 375                 380

Thr Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
                435                 440                 445

Tyr Tyr Val Gly Pro Leu Ala Arg Gly Asn Ser Arg Phe Ala Trp Met
                450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Ala
                485                 490                 495

Phe Asp Lys Asn Leu Pro Asn Glu Lys Val Leu Pro Lys His Ser Leu
                500                 505                 510

Leu Tyr Glu Tyr Phe Thr Val Tyr Asn Glu Leu Thr Lys Val Lys Tyr
                515                 520                 525

Val Thr Glu Gly Met Arg Lys Pro Ala Phe Leu Ser Gly Glu Gln Lys
                530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
                595                 600                 605

Glu Glu Asn Glu Asp Ile Leu Glu Asp Ile Val Leu Thr Leu Thr Leu
                610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Ala Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
                675                 680                 685

Asn Arg Asn Phe Met Ala Leu Ile His Asp Asp Ser Leu Thr Phe Lys
                690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
                740                 745                 750

```
His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Ala Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
```

-continued

```
                      1160                1165                1170

Glu  Lys  Asn  Pro  Ile  Asp  Phe  Leu  Glu  Ala  Lys  Gly  Tyr  Lys  Glu
              1175                1180                1185

Val  Lys  Lys  Asp  Leu  Ile  Ile  Lys  Leu  Pro  Lys  Tyr  Ser  Leu  Phe
         1190                1195                1200

Glu  Leu  Glu  Asn  Gly  Arg  Lys  Arg  Met  Leu  Ala  Ser  Ala  Gly  Glu
    1205                1210                1215

Leu  Gln  Lys  Gly  Asn  Glu  Leu  Ala  Leu  Pro  Ser  Lys  Tyr  Val  Asn
    1220                1225                1230

Phe  Leu  Tyr  Leu  Ala  Ser  His  Tyr  Glu  Lys  Leu  Lys  Gly  Ser  Pro
    1235                1240                1245

Glu  Asp  Asn  Glu  Gln  Lys  Gln  Leu  Phe  Val  Glu  Gln  His  Lys  His
    1250                1255                1260

Tyr  Leu  Asp  Glu  Ile  Ile  Glu  Gln  Ile  Ser  Glu  Phe  Ser  Lys  Arg
    1265                1270                1275

Val  Ile  Leu  Ala  Asp  Ala  Asn  Leu  Asp  Lys  Val  Leu  Ser  Ala  Tyr
    1280                1285                1290

Asn  Lys  His  Arg  Asp  Lys  Pro  Ile  Arg  Glu  Gln  Ala  Glu  Asn  Ile
    1295                1300                1305

Ile  His  Leu  Phe  Thr  Leu  Thr  Asn  Leu  Gly  Ala  Pro  Ala  Ala  Phe
    1310                1315                1320

Lys  Tyr  Phe  Asp  Thr  Thr  Ile  Asp  Arg  Lys  Arg  Tyr  Thr  Ser  Thr
    1325                1330                1335

Lys  Glu  Val  Leu  Asp  Ala  Thr  Leu  Ile  His  Gln  Ser  Ile  Thr  Gly
    1340                1345                1350

Leu  Tyr  Glu  Thr  Arg  Ile  Asp  Leu  Ser  Gln  Leu  Gly  Gly  Asp
    1355                1360                1365
```

<210> SEQ ID NO 32
<211> LENGTH: 4101
<212> TYPE: DNA
<213> ORGANISM: Artificial Sequence
<220> FEATURE:
<223> OTHER INFORMATION: synthetic polynucleotide

<400> SEQUENCE: 32

```
gacaagaagt acagcatcgg cctggacatc ggcaccaact ctgtgggctg ggccgtgatc    60
accgacgagt acaaggtgcc cagcaagaaa ttcaaggtgc tgggcaacac cgaccggcac   120
agcatcaaga gaaacctgat cggagccctg ctgttcgaca gcggcgaaac agccgaggcc   180
acccggctga gagaaccgc cagaagaaga taccaccaga ggaagaaccg gatctgctat   240
ctgcaagaga tcttcagcaa cgagatggcc aaggtggacg acagcttctt ccacagactg   300
gaagagtcct tcctggtgga agaggataag aagcacgagc ggcaccccat cttcggcaac   360
atcgtggacg aggtggccta ccacgagaag taccccacca tctaccacct gagaaagaaa   420
ctggtggaca gcaccgacaa ggccgacctg cggctgatct atctggccct ggcccacatg   480
atcaagttcc ggggccactt cctgatcgag ggcgacctga accccgacaa cagcgacgtg   540
gacaagctgt tcatccagct ggtgcagacc tacaaccagc tgttcgagga aaaccccatc   600
aacgccagcg gcgtggacgc caaggccatc ctgtctgcca gactgagcaa gagcagacgg   660
ctggaaaatc tgatcgccca gctgcccggc gagaagaaga tggcctgttc ggaaacctg    720
attgccctga gctgggcct gaccccgaac ttcaagagca cttcgacct ggccgaggat     780
gccaaactgc agctgagcaa ggacacctac gacgacgacc tggacaacct gctggcccag   840
```

```
atcggcgacc agtacgccga cctgtttctg gccgccaaga acctgtccga cgccatcctg    900
ctgagcgaca tcctgagagt gaacaccgag atcaccaagg cccccctgag cgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttacccca ttcctgaagg acaaccggga aaagatcgag   1320
aagatcctga ccttccgcat ccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgacctttta agaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280
gaaatggcca gagagaacca gaccacccag aagggacaga agaacagccg cgagagaatg   2340
aagcggatcg aagagggcat caaagagctg ggcagccaga tcctgaaaga acacccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact ttttcaagac cgagattacc ctggccaacg gcgagatccg gaagcggcct   3180
ctgatcgaga caaacggcga aaccggggag atcgtgtggg ataagggccg ggattttgcc   3240
```

```
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagcccac cgtggcctat    3420 tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca caagcaccg ggataagccc    3900 atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccacccctgat ccaccagagc atcaccggcc tgtacgagac acggatcgac    4080
ctgtctcagc tgggaggcga c                                              4101

<210> SEQ ID NO 33
<211> LENGTH: 3966
<212> TYPE: DNA
<213> ORGANISM: Artificial Sequence
<220> FEATURE:
<223> OTHER INFORMATION: synthetic polynucleotide

<400> SEQUENCE: 33
acacagttcg agggctttac caacctgtat caggtgagca agacactgcg gtttgagctg      60
atcccacagg gcaagaccct gaagcacatc caggagcagg gcttcatcga ggaggacaag     120
gcccgcaatg atcactacaa ggagctgaag cccatcatcg atcggatcta caagacctat     180
gccgaccagt gcctgcagct ggtgcagctg gattgggaga acctgagcgc cgccatcgac     240
tcctatagaa aggagaaaac cgaggagaca aggaacgccc tgatcgagga gcaggccaca     300
tatcgcaatg ccatccacga ctacttcatc ggccggacag acaacctgac cgatgccatc     360
aataagagac acgccgagat ctacaagggc ctgttcaagg ccgagctgtt taatggcaag     420
gtgctgaagc agctgggcac cgtgaccaca accgagcacg agaacgccct gctgcggagc     480
ttcgacaagt ttacaaccta cttctccggc ttttatgaga acaggaagaa cgtgttcagc     540
gccgaggata tcagcacagc catcccacac cgcatcgtgc aggacaactt ccccaagttt     600
aaggagaatt gtcacatctt cacacgcctg atcaccgccg tgcccagcct gcgggagcac     660
tttgagaacg tgaagaaggc catcggcatc ttcgtgagca cctccatcga ggaggtgttt     720
tccttccctt tttataacca gctgctgaca cagacccaga tcgacctgta taaccagctg     780
ctgggaggaa tctctcggga ggcaggcacc gagaagatca agggcctgaa cgaggtgctg     840
aatctggcca tccagaagaa tgatgagaca gcccacatca tcgcctccct gccacacaga     900
ttcatccccc tgtttaagca gatcctgtcc gataggaaca ccctgtcttt catcctggag     960
gagtttaaga gcgacgagga agtgatccag tccttctgca gtacaagac actgctgaga    1020 aacgagaacg tgctggagac agccgaggcc ctgtttaacg agctgaacag catcgacctg    1080
acacacatct tcatcagcca caagaagctg gagacaatca gcagcgccct gtgcgaccac    1140
```

-continued

| | |
|---|---|
| tgggatacac tgaggaatgc cctgtatgag cggagaatct ccgagctgac aggcaagatc | 1200 |
| accaagtctg ccaaggagaa ggtgcagcgc agcctgaagc acgaggatat caacctgcag | 1260 |
| gagatcatct ctgccgcagg caaggagctg agcgaggcct tcaagcagaa aaccagcgag | 1320 |
| atcctgtccc acgcacacgc cgccctggat cagccactgc ctacaaccct gaagaagcag | 1380 |
| gaggagaagg agatcctgaa gtctcagctg gacagcctgc tgggcctgta ccacctgctg | 1440 |
| gactggtttg ccgtggatga gtccaacgag gtggaccccg agttctctgc ccggctgacc | 1500 |
| ggcatcaagc tggagatgga gccttctctg agcttctaca caaggccag aaattatgcc | 1560 |
| accaagaagc cctactccgt ggagaagttc aagctgaact ttcagatgcc tacactggcc | 1620 |
| tctggctggg acgtgaataa ggagaagaac aatggcgcca tcctgtttgt gaagaacggc | 1680 |
| ctgtactatc tgggcatcat gccaaagcag aagggcaggt ataaggccct gagcttcgag | 1740 |
| cccacagaga aaccagcga gggctttgat aagatgtact atgactactt ccctgatgcc | 1800 |
| gccaagatga tcccaaagtg cagcacccag ctgaaggccg tgacagccca ctttcagacc | 1860 |
| cacacaaccc ccatcctgct gtccaacaat ttcatcgagc tctggagat cacaaaggag | 1920 |
| atctacgacc tgaacaatcc tgagaaggag ccaaagaagt ttcagacagc ctacgccaag | 1980 |
| aaaaccggcg accagaaggg ctacagagag ccctgtgca gtggatcga cttcacaagg | 2040 |
| gattttctgt ccaagtatac caagacaacc tctatcgatc tgtctagcct gcggccatcc | 2100 |
| tctcagtata aggacctggg cgagtactat gccgagctga tcccctgct gtaccacatc | 2160 |
| agcttccaga gaatcgccga gaaggagatc atggatgccg tggagacagg caagctgtac | 2220 |
| ctgttccaga tctataacaa ggactttgcc aagggccacc acggcaagcc taatctgcac | 2280 |
| acactgtatt ggaccggcct gttttctcca gagaacctgg ccaagacaag catcaagctg | 2340 |
| aatggccagg ccgagctgtt ctaccgccct aagtccagga tgaagaggat ggcacaccgg | 2400 |
| ctgggagaga agatgctgaa caagaagctg aaggatcaga aaaccccaat ccccgacacc | 2460 |
| ctgtaccagg agctgtacga ctatgtgaat cacagactgt cccacgacct gtctgatgag | 2520 |
| gccagggccc tgctgcccaa cgtgatcacc aaggaggtgt ctcacgagat catcaaggat | 2580 |
| aggcgcttta ccagcgacaa gttctttttc cacgtgccta tcacactgaa ctatcaggcc | 2640 |
| gccaattccc catctaagtt caaccagagg gtgaatgcct acctgaagga gcaccccgag | 2700 |
| acacctatca tcggcatcga tcggggcgag agaaacctga tctatatcac agtgatcgac | 2760 |
| tccaccggca agatcctgga gcagcggagc ctgaacacca tccagcagtt tgattaccag | 2820 |
| aagaagctgg acaacaggga gaaggagagg gtggcagcaa ggcaggcctg gtctgtggtg | 2880 |
| ggcacaatca aggatctgaa gcagggctat ctgagccagg tcatccacga gatcgtggac | 2940 |
| ctgatgatcc actaccaggc cgtggtggtg ctggagaacc tgaatttcgg ctttaagagc | 3000 |
| aagaggaccg gcatcgccga gaaggccgtg taccagcagt tcgagaagat gctgatcgat | 3060 |
| aagctgaatt gcctggtgct gaaggactat ccagcagaga agtgggagg cgtgctgaac | 3120 |
| ccataccagc tgacagacca gttcacctcc tttgccaaga tgggcaccca gtctggcttc | 3180 |
| ctgttttacg tgcctgcccc atatacatct aagatcgatc ccctgaccgg cttcgtggac | 3240 |
| cccttcgtgt ggaaaaccat caagaatcac gagagccgca agcacttcct ggagggcttc | 3300 |
| gactttctgc actacgacgt gaaaaccggc gacttcatcc tgcactttaa gatgaacaga | 3360 |
| aatctgtcct tccagagggg cctgccggc tttatgcctg catgggatat cgtgttcgag | 3420 |
| aagaacgaga cacagtttga cgccaagggc acccctttca tcgccggcaa gagaatcgtg | 3480 |
| ccagtgatcg agaatcacag attcaccggc agataccggg acctgtatcc tgccaacgag | 3540 |

-continued

| | |
|---|---|
| ctgatcgccc tgctggagga gaagggcatc gtgttcaggg atggctccaa catcctgcca | 3600 |
| aagctgctgg agaatgacga ttctcacgcc atcgacacca tggtggccct gatccgcagc | 3660 |
| gtgctgcaga tgcggaactc caatgccgcc acaggcgagg actatatcaa cagccccgtg | 3720 |
| cgcgatctga tggcgtgtgt cttcgactcc cggtttcaga acccagagtg gcccatggac | 3780 |
| gccgatgcca atggcgccta ccacatcgcc ctgaagggcc agctgctgct gaatcacctg | 3840 |
| aaggagagca aggatctgaa gctgcagaac ggcatctcca atcaggactg gctggcctac | 3900 |
| atccaggagc tgcgcaacaa aaggccggcg ccacgaaaa aggccggcca ggcaaaaaag | 3960 |
| aaaaag | 3966 |

<210> SEQ ID NO 34
<211> LENGTH: 3156
<212> TYPE: DNA
<213> ORGANISM: Artificial Sequence
<220> FEATURE:
<223> OTHER INFORMATION: synthetic polynucleotide

<400> SEQUENCE: 34

| | |
|---|---|
| aagcggaact acatcctggg cctggacatc ggcatcacca gcgtgggcta cggcatcatc | 60 |
| gactacgaga cacgggacgt gatcgatgcc ggcgtgcggc tgttcaaaga ggccaacgtg | 120 |
| gaaaacaacg agggcaggcg gagcaagaga ggcgccagaa ggctgaagcg gcggaggcgg | 180 |
| catagaatcc agagagtgaa gaagctgctg ttcgactaca acctgctgac cgaccacagc | 240 |
| gagctgagcg gcatcaaccc ctacgaggcc agagtgaagg gcctgagcca gaagctgagc | 300 |
| gaggaagagt tctctgccgc cctgctgcac ctggccaaga gaagaggcgt gcacaacgtg | 360 |
| aacgaggtgg aagaggacac cggcaacgag ctgtccacca gagagcagat cagccggaac | 420 |
| agcaaggccc tggaagagaa atacgtggcc gaactgcagc tggaacggct gaagaaagac | 480 |
| ggcgaagtgc ggggcagcat caacagattc aagaccagcg actacgtgaa agaagccaaa | 540 |
| cagctgctga aggtgcagaa ggcctaccac cagctggacc agagcttcat cgacacctac | 600 |
| atcgacctgc tggaaacccg gcggacctac tatgagggac ctggcgaggg cagccccttc | 660 |
| ggctggaagg acatcaaaga atggtacgag atgctgatgg ccactgcac ctacttcccc | 720 |
| gaggaactgc ggagcgtgaa gtacgcctac aacgccgacc tgtacaacgc cctgaacgac | 780 |
| ctgaacaatc tcgtgatcac cagggacgag aacgagaagc tggaatatta cgagaagttc | 840 |
| cagatcatcg agaacgtgtt caagcagaag aagaagccca ccctgaagca gatcgccaaa | 900 |
| gaaatcctcg tgaacgaaga ggatattaag ggctacagag tgaccagcac cggcaagccc | 960 |
| gagttcacca acctgaaggt gtaccacgac atcaaggaca ttaccgcccg gaaagagatt | 1020 |
| attgagaacg ccgagctgct ggatcagatt gccaagatcc tgaccatcta ccagagcagc | 1080 |
| gaggacatcc aggaagaact gaccaatctg aactccgagc tgacccagga agagatcgag | 1140 |
| cagatctcta atctgaaggg ctataccggc acccacaacc tgagcctgaa ggccatcaac | 1200 |
| ctgatcctgg acgagctgtg gcacaccaac gacaaccaga tcgctatctt caaccggctg | 1260 |
| aagctggtgc ccaagaaggt ggacctgtcc cagcagaaag atccccac cacccctggtg | 1320 |
| gacgacttca tcctgagccc cgtcgtgaag agaagcttca tccagagcat caaagtgatc | 1380 |
| aacgccatca tcaagaagta cggcctgccc aacgacatca ttatcgagct ggcccgcgag | 1440 |
| aagaactcca aggacgccca gaaaatgatc aacgagatgc agaagcggaa ccggcagacc | 1500 |
| aacgagcgga tcgaggaaat catccggacc accggcaaag agaacgccaa gtacctgatc | 1560 |

```
gagaagatca agctgcacga catgcaggaa ggcaagtgcc tgtacagcct ggaagccatc   1620
cctctggaag atctgctgaa caacccttc aactatgagg tggaccacat catccccaga    1680
agcgtgtcct tcgacaacag cttcaacaac aaggtgctcg tgaagcagga agaaaacagc   1740
aagaagggca accggacccc attccagtac ctgagcagca gcgacagcaa gatcagctac   1800
gaaaccttca agaagcacat cctgaatctg gccaagggca agggcagaat cagcaagacc   1860
aagaaagagt atctgctgga agaacgggac atcaacaggt tctccgtgca gaaagacttc   1920
atcaaccgga acctggtgga taccagatac gccaccagag gcctgatgaa cctgctgcgg   1980
agctacttca gagtgaacaa cctggacgtg aaagtgaagt ccatcaatgg cggcttcacc   2040
agctttctgc ggcggaagtg gaagtttaag aaagagcgga caaggggta caagcaccac    2100 gccgaggacg ccctgatcat tgccaacgcc gatttcatct tcaaagagtg gaagaaactg   2160
gacaaggcca aaaagtgat ggaaaccag atgttcgagg aaaagcaggc cgagagcatg     2220
cccgagatcg aaaccgagca ggagtacaaa gagatcttca tcacccccca ccagatcaag   2280
cacattaagg acttcaagga ctacaagtac agccaccggg tggacaagaa gcctaataga   2340
gagctgatta cgacaccct gtactccacc cggaaggacg acaagggcaa caccctgatc    2400
gtgaacaatc tgaacggcct gtacgacaag gacaatgaca agctgaaaaa gctgatcaac   2460
aagagccccg aaaagctgct gatgtaccac cacgaccccc agacctacca gaaactgaag   2520
ctgattatgg aacagtacgg cgacgagaag aatccctgt acaagtacta cgaggaaacc    2580
gggaactacc tgaccaagta ctccaaaaag gacaacggcc ccgtgatcaa gaagattaag   2640
tattacggca caaactgaa cgcccatctg gacatcaccg acgactacc caacagcaga    2700 aacaaggtcg tgaagctgtc cctgaagccc tacagattcg acgtgtacct ggacaatggc   2760
gtgtacaagt tcgtgaccgt gaagaatctg gatgtgatca aaaaagaaaa ctactacgaa   2820
gtgaatagca agtgctatga ggaagctaag aagctgaaga gatcagcaa ccaggccgag    2880 tttatcgcct ccttctacaa caacgatctg atcaagatca cggcgagct gtatagagtg    2940 atcggcgtga caacgacct gctgaaccgg atcgaagtga acatgatcga catcacctac   3000
cgcgagtacc tggaaaaacat gaacgacaag aggcccccca ggatcattaa gacaatcgcc   3060
tccaagaccc agagcattaa gaagtacagc acagacattc tgggcaacct gtatgaagtg    3120
aaatctaaga gcacctca gatcatcaaa aagggc                               3156
```

<210> SEQ ID NO 35
<211> LENGTH: 4101
<212> TYPE: DNA
<213> ORGANISM: Artificial Sequence
<220> FEATURE:
<223> OTHER INFORMATION: synthetic polynucleotide

<400> SEQUENCE: 35

```
gataaaaagt attctattgg tttagacatc ggcactaatt ccgttggatg ggctgtcata     60
accgatgaat acaaagtacc ttcaaagaaa tttaaggtgt tggggaacac agaccgtcat    120
tcgattaaaa agaatcttat cggtgccctc ctattcgata gtggcgaaac ggcagaggcg    180
actcgcctga acgaaccgc tcggagaagg tatacgtc gcaagaaccg aatatgttac       240
ttacaagaaa ttttagcaa tgagatggcc aaagttgacg attctttctt tcaccgtttg    300
gaagagtcct tccttgtcga agaggacaag aaacatgaac ggcacccat ctttggaaac    360 atagtagatg aggtggcata tcatgaaaag tacccaacga tttatcacct cagaaaaaag   420
ctagttgact caactgataa agcggacctg aggttaatct acttggctct tgcccatatg   480
```

```
ataaagttcc gtgggcactt tctcattgag ggtgatctaa atccggacaa ctcggatgtc    540
gacaaactgt tcatccagtt agtacaaacc tataatcagt tgtttgaaga aaccctata     600 aatgcaagtg gcgtggatgc gaaggctatt cttagcgccc gcctctctaa atcccgacgg    660
ctagaaaacc tgatcgcaca attacccgga gagaagaaaa atgggttgtt cggtaaacctt   720 atagcgctct cactaggcct gacaccaaat tttaagtcga acttcgactt agctgaagat    780
gccaaattgc agcttagtaa ggacacgtac gatgacgatc tcgacaatct actggcacaa    840
attggagatc agtatgcgga cttattttg gctgccaaaa accttagcga tgcaatcctc     900
ctatctgaca tactgagagt taatactgag attaccaagg cgccgttatc cgcttcaatg    960
atcaaaaggt acgatgaaca tcaccaagac ttgacacttc tcaaggccct agtccgtcag   1020
caactgcctg agaaatataa ggaaatattc tttgatcagt cgaaaaacgg gtacgcaggt   1080
tatattgacg gcggagcgag tcaagaggaa ttctacaagt ttatcaaacc catattagag   1140
aagatggatg gacggaaga gttgcttgta aaactcaatc gcgaagatct actgcgaaag    1200
cagcggactt tcgacaacgg tagcattcca catcaaatcc acttaggcga attgcatgct   1260
atacttagaa ggcaggagga tttttatccg ttcctcaaag acaatcgtga aaagattgag   1320
aaaatcctaa cctttcgcat accttactat gtgggacccc tggcccgagg gaactctcgg   1380
ttcgcatgga tgacaagaaa gtccgaagaa acgattactc catggaattt tgaggaagtt   1440
gtcgataaag gtgcgtcagc tcaatcgttc atcgagagga tgaccaactt tgacaagaat   1500
ttaccgaacg aaaaagtatt gcctaagcac agtttacttt acgagtattt cacagtgtac   1560
aatgaactca cgaaagttaa gtatgtcact gagggcatgc gtaaacccgc ctttctaagc   1620
ggagaacaga agaaagcaat agtagatctg ttattcaaga ccaaccgcaa agtgacagtt   1680
aagcaattga agaggacta cttaagaaaa attgaatgct tcgattctgt cgagatctcc    1740
ggggtagaag atcgatttaa tgcgtcactt ggtacgtatc atgacctcct aaagataatt   1800
aaagataagg acttcctgga taacgaagag aatgaagata tcttagaaga tatagtgttg   1860
actcttaccc tctttgaaga tcgggaaatg attgaggaaa gactaaaaac atacgctcac   1920
ctgttcgacg ataaggttat gaaacagtta aagaggcgtc gctatacggg ctggggacga   1980
ttgtcgcgga aacttatcaa cgggataaga gacaagcaaa gtggtaaaac tattctcgat   2040
tttctaaaga gcgacggctt cgccaatagg aactttatgc agctgatcca tgatgactct   2100
ttaaccttca aagaggatat acaaaaggca caggtttccg gacaagggga ctcattgcac   2160
gaacatattg cgaatcttgc tggttcgcca gccatcaaaa agggcatact ccagacagtc   2220
aaagtagtgg atgagctagt taaggtcatg ggacgtcaca aaccggaaaa cattgtaatc   2280
gagatggcac gcgaaaatca aacgactcag aagggggcaaa aaacagtcg agagcggatg   2340 aagagaatag aagagggtat taaagaactg ggcagccaga tcttaaagga gcatcctgtg   2400
gaaaataccc aattgcagaa cgagaaactt tacctctatt acctacaaaa tggaagggac   2460
atgtatgttg atcaggaact ggacataaac cgtttatctg attacgacgt cgatcacatt   2520
gtaccccaat cctttttgaa ggacgattca atcgacaata aagtgcttac acgctcggat   2580
aagaaccgag ggaaaagtga caatgttcca agcgaggaag tcgtaaagaa atgaagaac    2640 tattggcggc agctcctaaa tgcgaaactg ataacgcaaa gaaagttcga taacttaact   2700
aaagctgaga ggggtggctt gtctgaactt gacaaggccg gatttattaa acgtcagctc   2760
gtggaaaccc gccaaatcac aaagcatgtt gcacagatac tagattcccg aatgaatacg   2820
```

```
aaatacgacg agaacgataa gctgattcgg gaagtcaaag taatcacttt aaagtcaaaa    2880
ttggtgtcgg acttcagaaa ggattttcaa ttctataaag ttagggagat aaataactac    2940
caccatgcgc acgacgctta tcttaatgcc gtcgtaggga ccgcactcat taagaaatac    3000
ccgaagctag aaagtgagtt tgtgtatggt gattacaaag tttatgacgt ccgtaagatg    3060
atcgcgaaaa gcgaacagga gataggcaag gctacagcca aatacttctt ttattctaac    3120
attatgaatt tctttaagac ggaaatcact ctggcaaacg gagagatacg caaacgacct    3180
ttaattgaaa ccaatgggga gacaggtgaa atcgtatggg ataagggccg ggacttcgcg    3240
acggtgagaa aagttttgtc catgccccaa gtcaacatag taaagaaaac tgaggtgcag    3300
accggagggt tttcaaagga atcgattctt ccaaaaagga atagtgataa gctcatcgct    3360
cgtaaaaagg actgggaccc gaaaaagtac ggtggcttcg tgagccctac agttgcctat    3420
tctgtcctag tagtggcaaa agttgagaag ggaaaatcca agaaactgaa gtcagtcaaa    3480
gaattattgg ggataacgat tatggagcgc tcgtcttttg aaaagaaccc catcgacttc    3540
cttgaggcga aaggttacaa ggaagtaaaa aaggatctca taattaaact accaaagtat    3600
agtctgtttg agttagaaaa tggccgaaaa cggatgttgg ctagcgccgg agagcttcaa    3660
aaggggaacg aactcgcact accgtctaaa tacgtgaatt tcctgtattt agcgtcccat    3720
tacgagaagt tgaaaggttc acctgaagat aacgaacaga agcaacttttt gttgagcag    3780
cacaaacatt atctcgacga aatcatagag caaatttcgg aattcagtaa gagagtcatc    3840
ctagctgatg ccaatctgga caaagtatta agcgcataca acaagcacag ggataaaccc    3900
atacgtgagc aggcggaaaa tattatccat ttgtttactc ttaccaacct cggcgctcca    3960
gccgcattca gtattttga cacaacgata gatcgcaaac agtacagatc taccaaggag    4020
gtgctagacg cgacactgat tcaccaatcc atcacgggat tatatgaaac tcggatagat    4080
ttgtcacagc ttgggggtga c                                              4101

<210> SEQ ID NO 36
<211> LENGTH: 4101
<212> TYPE: DNA
<213> ORGANISM: Artificial Sequence
<220> FEATURE:
<223> OTHER INFORMATION: synthetic polynucleotide

<400> SEQUENCE: 36
gataaaaagt attctattgg tttagacatc ggcactaatt ccgttggatg ggctgtcata     60
accgatgaat acaaagtacc ttcaaagaaa tttaaggtgt tggggaacac agaccgtcat    120
tcgattaaaa agaatcttat cggtgccctc ctattcgata gtggcgaaac ggcagaggcg    180
actcgcctga acgaaccgc tcggagaagg tatacacgtc gcaagaaccg aatatgttac    240
ttacaagaaa ttttttagcaa tgagatggcc aaagttgacg attctttctt tcaccgtttg    300
gaagagtcct tccttgtcga gaggacaag aaacatgaac ggcacccat ctttggaaac     360
atagtagatg aggtggcata tcatgaaaag tacccaacga tttatcacct cagaaaaaag    420
ctagttgact caactgataa agcggacctg aggttaatct acttggctct tgcccatatg    480
ataaagttcc gtgggcactt tctcattgag ggtgatctaa atccggacaa ctcggatgtc    540
gacaaactgt tcatccagtt agtacaaacc tataatcagt tgtttgaaga gaaccctata    600
aatgcaagtg gcgtggatgc gaaggctatt cttagcgccc gcctctctaa atcccgacgg    660
ctagaaaacc tgatcgcaca attacccgga gagaagaaaa atgggttgtt cggtaacctt    720
atagcgctct cactaggcct gacaccaaat tttaagtcga acttcgactt agctgaagat    780
```

```
gccaaattgc agcttagtaa ggacacgtac gatgacgatc tcgacaatct actggcacaa    840
attggagatc agtatgcgga cttattttg gctgccaaaa accttagcga tgcaatcctc     900
ctatctgaca tactgagagt taatactgag attaccaagg cgccgttatc cgcttcaatg    960
atcaaaaggt acgatgaaca tcaccaagac ttgacacttc tcaaggccct agtccgtcag    1020
caactgcctg agaaatataa ggaaatattc tttgatcagt cgaaaaacgg gtacgcaggt    1080
tatattgacg gcggagcgag tcaagaggaa ttctacaagt ttatcaaacc catattagag    1140
aagatggatg ggacggaaga gttgcttgta aaactcaatc gcgaagatct actgcgaaag    1200
cagcggactt tcgacaacgg tagcattcca catcaaatcc acttaggcga attgcatgct    1260
atacttagaa ggcaggagga tttttatccg ttcctcaaag acaatcgtga aaagattgag    1320
aaaatcctaa cctttcgcat accttactat gtgggacccc tggcccgagg gaactctcgg    1380
ttcgcatgga tgacaagaaa gtccgaagaa acgattactc catggaattt tgaggaagtt    1440
gtcgataaag gtgcgtcagc tcaatcgttc atcgagagga tgaccaactt tgacaagaat    1500
ttaccgaacg aaaaagtatt gcctaagcac agtttacttt acgagtattt cacagtgtac    1560
aatgaactca cgaaagttaa gtatgtcact gagggcatgc gtaaacccgc ctttctaagc    1620
ggagaacaga agaaagcaat agtagatctg ttattcaaga ccaaccgcaa agtgacagtt    1680
aagcaattga agaggactac ctttaagaaa attgaatgct tcgattctgt cgagatctcc    1740
ggggtagaag atcgatttaa tgcgtcactt ggtacgtatc atgacctcct aaagataatt    1800
aaagataagg acttcctgga taacgaagag aatgaagata tcttagaaga tatagtgttg    1860
actcttaccc tctttgaaga tcgggaaatg attgaggaaa gactaaaaac atacgctcac    1920
ctgttcgacg ataaggttat gaaacagtta aagaggcgtc gctatacggg ctggggacga    1980
ttgtcgcgga aacttatcaa cgggataaga gacaagcaaa gtggtaaaac tattctcgat    2040
tttctaaaga gcgacggctt cgccaatagg aactttatgc agctgatcca tgatgactct    2100
ttaaccttca agaggatat acaaaaggca caggtttccg gacaagggga ctcattgcac    2160
gaacatattg cgaatcttgc tggttcgcca gccatcaaaa agggcatact ccagacagtc    2220
aaagtagtgg atgagctagt taaggtcatg ggacgtcaca accggaaaaa cattgtaatc    2280
gagatggcac gcgaaaatca aacgactcag aaggggcaaa aaacagtcg agagcggatg    2340 aagagaatag aagagggtat taagaactg ggcagccaga tcttaaagga gcatcctgtg    2400 gaaaatacc aattgcagaa cgagaaactt tacctctatt acctacaaaa tggaagggac    2460
atgtatgttg atcaggaact ggacataaac cgtttatctg attacgacgt cgatcacatt    2520
gtaccccaat ccttttgaa ggacgattca atcgacaata agtgcttac acgctcggat    2580 aagaaccgag ggaaaagtga caatgttcca agcgaggaag tcgtaaagaa atgaagaac    2640 tattggcggc agctcctaaa tgcgaaactg ataacgcaaa gaaagttcga taacttaact    2700
aaagctgaga ggggtggctt gtctgaactt gacaaggccg gatttattaa acgtcagctc    2760
gtggaaaccc gccaaatcac aaagcatgtt gcacagatac tagattcccg aatgaatacg    2820
aaatacgacg agaacgataa gctgattcgg gaagtcaaag taatcacttt aaagtcaaaa    2880
ttggtgtcgg acttcagaaa ggattttcaa ttctataaag ttagggagat aaataactac    2940
caccatgcgc acgacgctta tcttaatgcc gtcgtaggga ccgcactcat taagaaatac    3000
ccgaagctag aaagtgagtt tgtgtatggt gattacaaag tttatgacgt ccgtaagatg    3060
atcgcgaaaa gcgaacagga gataggcaag gctacagcca atacttcttt ttattctaac    3120
```

```
attatgaatt tctttaagac ggaaatcact ctggcaaacg gagagatacg caaacgacct    3180
ttaattgaaa ccaatgggga gacaggtgaa atcgtatggg ataagggccg ggacttcgcg    3240
acggtgagaa aagttttgtc catgccccaa gtcaacatag taaagaaaac tgaggtgcag    3300
accggagggt tttcaaagga atcgattctt ccaaaaagga atagtgataa gctcatcgct    3360
cgtaaaaagg actgggaccc gaaaaagtac ggtggcttcg tgagccctac agttgcctat    3420
tctgtcctag tagtggcaaa agttgagaag ggaaaatcca agaaactgaa gtcagtcaaa    3480
gaattattgg ggataacgat tatggagcgc tcgtcttttg aaaagaaccc catcgacttc    3540
cttgaggcga aaggttacaa ggaagtaaaa aaggatctca taattaaact accaaagtat    3600
agtctgtttg agttagaaaa tggccgaaaa cggatgttgg ctagcgccag agagcttcaa    3660
aaggggaacg aactcgcact accgtctaaa tacgtgaatt tcctgtattt agcgtcccat    3720
tacgagaagt tgaaaggttc acctgaagat aacgaacaga agcaacttt tgttgagcag     3780 cacaaacatt atctcgacga aatcatagag caaatttcgg aattcagtaa gagagtcatc    3840
ctagctgatg ccaatctgga caaagtatta agcgcataca caagcacag ggataaaccc     3900 atacgtgagc aggcggaaaa tattatccat ttgtttactc ttaccaacct cggcgctcca    3960
gccgcattca gtattttga cacaacgata gatcgcaaag agtacagatc taccaaggag     4020
gtgctagacg cgacactgat tcaccaatcc atcacgggat tatatgaaac tcggatagat    4080
ttgtcacagc ttgggggtga c                                              4101

<210> SEQ ID NO 37
<211> LENGTH: 4101
<212> TYPE: DNA
<213> ORGANISM: Artificial Sequence
<220> FEATURE:
<223> OTHER INFORMATION: synthetic polynucleotide

<400> SEQUENCE: 37
gataaaaagt attctattgg tttagacatc ggcactaatt ccgttggatg ggctgtcata      60
accgatgaat acaaagtacc ttcaaagaaa tttaaggtgt tggggaacac agaccgtcat     120
tcgattaaaa agaatcttat cggtgccctc ctattcgata gtggcgaaac ggcagaggcg     180
actcgcctga aacgaaccgc tcggagaagg tatacacgtc gcaagaaccg aatatgttac     240
ttacaagaaa ttttttagcaa tgagatggcc aaagttgacg attctttctt tcaccgtttg     300
gaagagtcct tccttgtcga agaggacaag aaacatgaac ggcacccat ctttggaaac     360 atagtagatg aggtggcata tcatgaaaag tacccaacga tttatcacct cagaaaaaag    420
ctagttgact caactgataa agcggacctg aggttaatct acttggctct tgcccatatg    480
ataaagttcc gtgggcactt tctcattgag ggtgatctaa atccgacaa ctcggatgtc     540 gacaaactgt tcatccagtt agtacaaacc tataatcagt gtgtttgaaga gaaccctata    600 aatgcaagtg gcgtggatgc gaaggctatt cttagcgccc gcctctctaa atcccgacgg    660
ctagaaaacc tgatcgcaca attacccgga gagaagaaaa atgggttgtt cggtaacctt    720
atagcgctct cactaggcct gacaccaaat tttaagtcga acttcgactt agctgaagat    780
gccaaattgc agcttagtaa ggacacgtac gatgacgatc tcgacaatct actggcacaa    840
attggagatc agtatgcgga cttatttttg gctgccaaaa accttagcga tgcaatcctc    900
ctatctgaca tactgagagt taatactgag attaccaagg cgccgttatc cgcttcaatg    960
atcaaaaggt acgatgaaca tcaccaagac ttgacactc tcaaggccct agtccgtcag    1020
caactgcctg agaaatataa ggaaatattc tttgatcagt cgaaaaacgg gtacgcaggt    1080
```

| | |
|---|---|
| tatattgacg gcggagcgag tcaagaggaa ttctacaagt ttatcaaacc catattagag | 1140 |
| aagatggatg ggacggaaga gttgcttgta aaactcaatc gcgaagatct actgcgaaag | 1200 |
| cagcggactt tcgacaacgg tagcattcca catcaaatcc acttaggcga attgcatgct | 1260 |
| atacttagaa ggcaggagga tttttatccg ttcctcaaag acaatcgtga aaagattgag | 1320 |
| aaaatcctaa cctttcgcat accttactat gtgggacccc tggcccgagg gaactctcgg | 1380 |
| ttcgcatgga tgacaagaaa gtccgaagaa acgattactc catggaattt tgaggaagtt | 1440 |
| gtcgataaag gtgcgtcagc tcaatcgttc atcgagagga tgaccaactt tgacaagaat | 1500 |
| ttaccgaacg aaaaagtatt gcctaagcac agtttacttt acgagtattt cacagtgtac | 1560 |
| aatgaactca cgaaagttaa gtatgtcact gagggcatgc gtaaaccgc ctttctaagc | 1620 |
| ggagaacaga agaaagcaat agtagatctg ttattcaaga ccaaccgcaa agtgacagtt | 1680 |
| aagcaattga agaggacta ctttaagaaa attgaatgct tcgattctgt cgagatctcc | 1740 |
| ggggtagaag atcgatttaa tgcgtcactt ggtacgtatc atgacctcct aaagataatt | 1800 |
| aaagataagg acttcctgga taacgaagag aatgaagata tcttagaaga tatagtgttg | 1860 |
| actcttaccc tctttgaaga tcgggaaatg attgaggaaa gactaaaaac atacgctcac | 1920 |
| ctgttcgacg ataaggttat gaaacagtta aagaggcgtc gctatacggg ctggggacga | 1980 |
| ttgtcgcgga aacttatcaa cgggataaga gacaagcaaa gtggtaaaac tattctcgat | 2040 |
| tttctaaaga gcgacggctt cgccaatagg aactttatgc agctgatcca tgatgactct | 2100 |
| ttaaccttca aagaggatat acaaaaggca caggtttccg gacaagggga ctcattgcac | 2160 |
| gaacatattg cgaatcttgc tggttcgcca gccatcaaaa agggcatact ccagacagtc | 2220 |
| aaagtagtgg atgagctagt taaggtcatg ggacgtcaca aaccggaaaa cattgtaatc | 2280 |
| gagatggcac gcgaaaatca aacgactcag aagggggcaaa aaacagtcg agagcggatg | 2340 |
| aagagaatag aagagggtat taagaactg ggcagccaga tcttaaagga gcatcctgtg | 2400 |
| gaaaatacc aattgcagaa cgagaaactt tacctctatt acctacaaaa tggaagggac | 2460 |
| atgtatgttg atcaggaact ggacataaac cgtttatctg attacgacgt cgatcacatt | 2520 |
| gtaccccaat cctttttgaa ggacgattca atcgacaata aagtgcttac acgctcggat | 2580 |
| aagaaccgag ggaaaagtga caatgttcca agcgaggaag tcgtaaagaa aatgaagaac | 2640 |
| tattggcggc agctcctaaa tgcgaaactg ataacgcaaa gaaagttcga taacttaact | 2700 |
| aaagctgaga ggggtggctt gtctgaactt gacaaggccg gatttattaa acgtcagctc | 2760 |
| gtggaaaccc gccaaatcac aaagcatgtt gcacagatac tagattcccg aatgaatacg | 2820 |
| aaatacgacg agaacgataa gctgattcgg gaagtcaaag taatcacttt aaagtcaaaa | 2880 |
| ttggtgtcgg acttcagaaa ggattttcaa ttctataaag ttagggagat aaataactac | 2940 |
| caccatgcgc acgacgctta tcttaatgcc gtcgtaggga ccgcactcat taagaaatac | 3000 |
| ccgaagctag aaagtgagtt tgtgtatggt gattacaaag tttatgacgt ccgtaagatg | 3060 |
| atcgcgaaaa gcgaacagga gataggcaag gctacagcca atacttctt ttattctaac | 3120 |
| attatgaatt tctttaagac ggaaatcact ctggcaaacg gagagatacg caaacgacct | 3180 |
| ttaattgaaa ccaatgggga gacaggtgaa atcgtatggg ataagggccg ggacttcgcg | 3240 |
| acggtgagaa aagttttgtc catgccccaa gtcaacatag taaagaaaac tgaggtgcag | 3300 |
| accgagggt tttcaaagga atcgattctt ccaaaaagga atagtgataa gctcatcgct | 3360 |
| cgtaaaaagg actgggaccc gaaaaagtac ggtggcttcg agagccctac agttgcctat | 3420 |

```
tctgtcctag tagtggcaaa agttgagaag ggaaaatcca agaaactgaa gtcagtcaaa    3480
gaattattgg ggataacgat tatgagcgc tcgtcttttg aaaagaaccc catcgacttc    3540
cttgaggcga aaggttacaa ggaagtaaaa aaggatctca taattaaact accaaagtat    3600
agtctgtttg agttagaaaa tggccgaaaa cggatgttgg ctagcgccgg agagcttcaa    3660
aaggggaacg aactcgcact accgtctaaa tacgtgaatt tcctgtattt agcgtcccat    3720
tacgagaagt tgaaaggttc acctgaagat aacgaacaga agcaacttt tgttgagcag    3780 cacaaacatt atctcgacga aatcatagag caaatttcgg aattcagtaa gagagtcatc    3840
ctagctgatg ccaatctgga caaagtatta agcgcataca acaagcacag ggataaaccc    3900
atacgtgagc aggcggaaaa tattatccat ttgtttactc ttaccaacct cggcgctcca    3960
gccgcattca agtattttga cacaacgata gatcgcaaac gatacacttc taccaaggag    4020
gtgctagacg cgacactgat tcaccaatcc atcacgggat tatatgaaac tcggatagat    4080
ttgtcacagc ttgggggtga c                                              4101
```

<210> SEQ ID NO 38
<211> LENGTH: 4149
<212> TYPE: DNA
<213> ORGANISM: Artificial Sequence
<220> FEATURE:
<223> OTHER INFORMATION: synthetic polynucleotide

<400> SEQUENCE: 38

```
gacaagaagt acagcatcgg cctggacatc ggcaccaact ctgtgggctg gccgtgatc      60 accgacgagt acaaggtgcc cagcaagaaa ttcaaggtgc tgggcaacac cgaccggcac    120
agcatcaaga gaacctgat cggagccctg ctgttcgaca cggcgaaac agccgaggcc     180 acccggctga gagaaccgc cagaagaaga tacaccagac ggaagaaccg gatctgctat    240
ctgcaagaga tcttcagcaa cgagatggcc aaggtggacg acagcttctt ccacagactg    300
gaagagtcct tcctggtgga agaggataag agcacgagc ggcacccat cttcggcaac     360 atcgtggacg aggtggccta ccacgagaag taccccacca tctaccacct gagaaagaaa    420
ctggtggaca gcaccgacaa ggccgacctg cggctgatct atctggccct ggcccacatg    480
atcaagttcc ggggccactt cctgatcgag ggcgacctga ccccgacaa cagcgacgtg    540 gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga tggcctgtt cggaaacctg    720 attgccctga gcctgggcct gaccccaac ttcaagagca acttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg    960 atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
```

```
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga agaggactac cttcaagaaa tcgagtgct tcgactccgt ggaaatctcc    1740
ggcgtggaag atcggttcaa cgcctccctg ggcacatacc acgatctgct gaaaattatc   1800
aaggacaagg acttcctgga caatgaggaa acgaggaca ttctggaaga tatcgtgctg    1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctta aagaggacat ccagaaagcc caggtgtccg gccagggcga tagcctgcac    2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc    2280 gaaatggcca gagagaacca gaccacccag aagggacaga gaacagccg cgagagaatg    2340 aagcggatcg aagagggcat caaagagctg ggcagccaga tcctgaaaga cacccgtg     2400 gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctggc ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctgcgctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact ttttcaagac cgagattacc ctggccaacg gcgagatccg gaaggcgcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga cagcgataa gctgatcgcc    3360 agaaagaagg actgggaccc taagaagtac ggcggcttcg acagccccac cgtggcctat   3420
tctgtgctgg tggtggccaa agtggaaaag ggcaagtcca agaaactgaa gagtgtgaaa   3480
gagctgctgg gatcaccat catggaaaga agcagcttcg agaagaatcc catcgacttt   3540
ctggaagcca agggctacaa agaagtgaaa aaggacctga tcatcaagct gcctaagtac   3600
tccctgttcg agctggaaaa cggccggaag agaatgctgg cctctgccgg cgaactgcag   3660
aagggaaacg aactggccct gccctccaaa tatgtgaact tcctgtacct ggccagccac   3720
```

```
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca caagcaccg ggataagccc    3900 atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga caaaaggccg gcggccacga aaaggccgg ccaggcaaaa    4140 aagaaaaag                                                           4149

<210> SEQ ID NO 39
<211> LENGTH: 4101
<212> TYPE: DNA
<213> ORGANISM: Artificial Sequence
<220> FEATURE:
<223> OTHER INFORMATION: synthetic polynucleotide

<400> SEQUENCE: 39
gataaaaagt attctattgg tttagacatc ggcactaatt ccgttggatg ggctgtcata      60
accgatgaat acaaagtacc ttcaaagaaa tttaaggtgt tggggaacac agaccgtcat     120
tcgattaaaa agaatcttat cggtgccctc ctattcgata gtggcgaaac ggcagaggcg     180
actcgcctga acgaaccgc tcggagaagg tatacacgtc gcaagaaccg aatatgttac     240
ttacaagaaa ttttttagcaa tgagatggcc aaagttgacg attctttctt tcaccgtttg     300
gaagagtcct tccttgtcga gaggacaag aaacatgaac ggcacccat ctttggaaac      360 atagtagatg aggtggcata tcatgaaaag tacccaacga tttatcacct cagaaaaaag     420
ctagttgact caactgataa agcggacctg aggttaatct acttggctct tgcccatatg     480
ataaagttcc gtgggcactt tctcattgag ggtgatctaa atccggacaa ctcggatgtc     540
gacaaactgt tcatccagtt agtacaaacc tataatcagt gtttgaaga aaccc tata     600 aatgcaagtg gcgtggatgc gaaggctatt cttagcgccc gcctctctaa atccgacgg      660 ctagaaaacc tgatcgcaca attacccgga gagaagaaaa atgggttgtt cggtaacctt     720
atagcgctct cactaggcct gacaccaaat tttaagtcga acttcgactt agctgaagat     780
gccaaattgc agcttagtaa ggacacgtac gatgacgatc tcgacaatct actggcacaa     840
attggagatc agtatgcgga cttattttttg gctgccaaaa accttagcga tgcaatcctc     900
ctatctgaca tactgagagt taatactgag attaccaagg cgccgttatc cgcttcaatg     960 atcaaaggt acgatgaaca tcaccaagac ttgacacttc tcaaggccct agtccgtcag    1020
caactgcctg agaaatataa ggaaatattc tttgatcagt cgaaaaacgg gtacgcaggt    1080
tatattgacg gcggagcgag tcaagaggaa ttctacaagt ttatcaaacc catattagag    1140
aagatggatg gaacgaaga gttgcttgta aaactcaatc gcgaagatct actgcgaaag    1200
cagcggactt tcgacaacgg tagcattcca catcaaatcc acttaggcga attgcatgct    1260
atacttagaa ggcaggagga ttttttatccg ttcctcaaag acaatcgtga aaagattgag    1320
aaaatcctaa cctttcgcat acctactat gtgggacccc tggcccgagg gaactctcgg    1380
ttcgcatgga tgacaagaaa gtccgaagaa acgattactc cctggaattt tgaggaagtt    1440
gtcgataaag gtgcgtcagc tcaatcgttc atcgagagga tgaccgcctt tgacaagaat    1500
ttaccgaacg aaaaagtatt gcctaagcac agttttactt acgagtattt cacagtgtac    1560
aatgaactca cgaaagttaa gtatgtcact gagggcatgc gtaaacccgc ctttctaagc    1620
```

```
ggagaacaga agaaagcaat agtagatctg ttattcaaga ccaaccgcaa agtgacagtt   1680
aagcaattga agaggactac ctttaagaaa attgaatgct tcgattctgt cgagatctcc   1740
ggggtagaag atcgatttaa tgcgtcactt ggtacgtatc atgacctcct aaagataatt   1800
aaagataagg acttcctgga taacgaagag aatgaagata tcttagaaga tatagtgttg   1860
actcttaccc tctttgaaga tcgggaaatg attgaggaaa gactaaaaac atacgctcac   1920
ctgttcgacg ataaggttat gaaacagtta aagaggcgtc gctatacggg ctggggagcc   1980
ttgtcgcgga aacttatcaa cgggataaga gacaagcaaa gtggtaaaac tattctcgat   2040
tttctaaaga gcgacggctt cgccaatagg aactttatgg ccctgatcca tgatgactct   2100
ttaaccttca aagaggatat acaaaaggca caggtttccg acaagggga ctcattgcac    2160 gaacatattg cgaatcttgc tggttcgcca gccatcaaaa agggcatact ccagacagtc   2220
aaagtagtgg atgagctagt taaggtcatg ggacgtcaca accggaaaaa cattgtaatc   2280
gagatggcac gcgaaaatca aacgactcag aaggggcaaa aaacagtcg agagcggatg    2340 aagagaatag aagagggtat taaagaactg gcagccagat cttaaagga gcatcctgtg    2400 gaaaataccc aattgcagaa cgagaaactt tacctctatt acctacaaaa tggaagggac   2460
atgtatgttg atcaggaact ggacataaac cgtttatctg attacgacgt cgatcacatt   2520
gtaccccaat ccttttgaa ggacgattca atcgacaata aagtgcttac acgctcggat    2580
aagaaccgag ggaaaagtga caatgttcca agcgaggaag tcgtaaagaa aatgaagaac   2640
tattggcggc agctcctaaa tgcgaaactg ataacgcaaa gaaagttcga taacttaact   2700
aaagctgaga ggggtggctt gtctgaactt gacaaggccg gatttattaa acgtcagctc   2760
gtggaaaccc gcgccatcac aaagcatgtt gcccagatac tagattcccg aatgaatacg   2820
aaatacgacg agaacgataa gctgattcgg gaagtcaaag taatcacttt aaagtcaaaa   2880
ttggtgtcgg acttcagaaa ggattttcaa ttctataaag ttagggagat aaataactac   2940
caccatgcgc acgacgctta tcttaatgcc gtcgtaggga ccgcactcat taagaaatac   3000
ccgaagctag aaagtgagtt tgtgtatggt gattacaaag tttatgacgt ccgtaagatg   3060
atcgcgaaaa gcgaacagga gataggcaag gctacagcca aatacttctt ttattctaac   3120
attatgaatt tctttaagac ggaaatcact ctggcaaacg gagagatacg caaacgacct   3180
ttaattgaaa ccaatgggga gacaggtgaa atcgtatggg ataagggccg ggacttcgcg   3240
acggtgagaa aagttttgtc catgccccaa gtcaacatag taaagaaaac tgaggtgcag   3300
accggagggt tttcaaagga atcgattctt ccaaaaagga atagtgataa gctcatcgct   3360
cgtaaaaagg actgggaccc gaaaaagtac ggtggcttcg atagccctac agttgcctat   3420
tctgtcctag tagtggcaaa agttgagaag ggaaaatcca agaaactgaa gtcagtcaaa   3480
gaattattgg ggataacgat tatggagcgc tcgtcttttg aaaagaaccc catcgacttc   3540
cttgaggcga aaggttacaa ggaagtaaaa aaggatctca taattaaact accaaagtat   3600
agtctgtttg agttagaaaa tggccgaaaa cggatgttgg ctagcgccgg agagcttcaa   3660
aaggggaacg aactcgcact accgtctaaa tacgtgaatt tcctgtattt agcgtcccat   3720
tacgagaagt tgaaaggttc acctgaagat aacgaacaga agcaactttt tgttgagcag   3780
cacaaacatt atctcgacga aatcatagag caaatttcgg aattcagtaa gagagtcatc   3840
ctagctgatg ccaatctgga caaagtatta agcgcataca acaagcacag ggataaaccc   3900
atacgtgagc aggcggaaaa tattatccat ttgtttactc ttaccaacct cggcgctcca   3960
```

```
gccgcattca agtatttga cacaacgata gatcgcaaac gatacacttc taccaaggag      4020
gtgctagacg cgacactgat tcaccaatcc atcacgggat tatatgaaac tcggatagat     4080
ttgtcacagc ttgggggtga c                                               4101

<210> SEQ ID NO 40
<211> LENGTH: 106
<212> TYPE: DNA
<213> ORGANISM: Artificial Sequence
<220> FEATURE:
<223> OTHER INFORMATION: synthetic polynucleotide

<400> SEQUENCE: 40
gttttagagc tagaaatagc aagttaaaat aaggctagtc cgttatcaac ttgaaaaagt       60
ggcaccgagt cggtgcggga gcgcaatcgg tagcgcttcc cttttt                    106

<210> SEQ ID NO 41
<211> LENGTH: 108
<212> TYPE: DNA
<213> ORGANISM: Artificial Sequence
<220> FEATURE:
<223> OTHER INFORMATION: synthetic polynucleotide

<400> SEQUENCE: 41
gttttagagc tagaaatagc aagttaaaat aaggctagtc cgttatcaac ttgaaaaagt       60
ggcaccgagt cggtgcggga gagcccccta cagggctctt ccctttt                   108

<210> SEQ ID NO 42
<211> LENGTH: 124
<212> TYPE: DNA
<213> ORGANISM: Artificial Sequence
<220> FEATURE:
<223> OTHER INFORMATION: synthetic polynucleotide

<400> SEQUENCE: 42
gttttagagc tagaaatagc aagttaaaat aaggctagtc cgttatcaac ttgaaaaagt       60
ggcaccgagt cggtgcggga gcgcaatcgg tagcgcgagc cccctacagg gctcttccct     120
tttt                                                                  124

<210> SEQ ID NO 43
<211> LENGTH: 123
<212> TYPE: DNA
<213> ORGANISM: Artificial Sequence
<220> FEATURE:
<223> OTHER INFORMATION: synthetic polynucleotide

<400> SEQUENCE: 43
gttttagagc taggccgcgc aatcggtagc gcggcctagc aagttaaaat aaggctagtc       60
cgttatcaac ttggccgagc cccctacagg gctcggccaa gtggcaccga gtcggtgctt     120
ttt                                                                   123

<210> SEQ ID NO 44
<211> LENGTH: 110
<212> TYPE: DNA
<213> ORGANISM: Artificial Sequence
<220> FEATURE:
<223> OTHER INFORMATION: synthetic polynucleotide

<400> SEQUENCE: 44
gttttagagc tagaaatagc aagttaaaat aaggctagtc cgttatcaac ttgaaaaagt       60
ggcaccgagt cggtgcggga tctccctgag cttcagggag ttccctttt                 110
```

<210> SEQ ID NO 45
<211> LENGTH: 110
<212> TYPE: DNA
<213> ORGANISM: Artificial Sequence
<220> FEATURE:
<223> OTHER INFORMATION: synthetic polynucleotide

<400> SEQUENCE: 45
gttttagagc tagaaatagc aagttaaaat aaggctagtc cgttatcaac ttgaaaaagt    60
ggcaccgagt cggtgcggga agaagcgtat cccgctgagc ttccctttt                110

<210> SEQ ID NO 46
<211> LENGTH: 136
<212> TYPE: DNA
<213> ORGANISM: Artificial Sequence
<220> FEATURE:
<223> OTHER INFORMATION: synthetic polynucleotide

<400> SEQUENCE: 46
gttttagagc tagaaatagc aagttaaaat aaggctagtc cgttatcaac ttgaaaaagt    60
ggcaccgagt cggtgcggga ggcctggtta gtacttggat gggagaccgc caaggaatac   120
cgggtgttcc cttttt                                                    136

<210> SEQ ID NO 47
<211> LENGTH: 42
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (21)..(42)
<223> OTHER INFORMATION: n is a, c, g, or t

<400> SEQUENCE: 47
taatttctac tcttgtagat nnnnnnnnnn nnnnnnnnnn nn                        42

<210> SEQ ID NO 48
<211> LENGTH: 99
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(23)
<223> OTHER INFORMATION: n is a, c, g, or t

<400> SEQUENCE: 48
nnnnnnnnnn nnnnnnnnnn nnngttttag tactctggaa acagaatcta ctaaacaag     60 gcaaaatgcc gtgtttatct cgtcaacttg ttggcgaga                            99

<210> SEQ ID NO 49
<211> LENGTH: 75
<212> TYPE: DNA
<213> ORGANISM: Artificial Sequence
<220> FEATURE:
<223> OTHER INFORMATION: synthetic polynucleotide

<400> SEQUENCE: 49
ggtcccatgg tgtaatggtt agcactctgg actctgaatc cagcgatccg agttcaaatc    60
tcggtgggac ctcca                                                      75

<210> SEQ ID NO 50
<211> LENGTH: 75
<212> TYPE: DNA
<213> ORGANISM: Artificial Sequence
<220> FEATURE:
<223> OTHER INFORMATION: synthetic polynucleotide

<400> SEQUENCE: 50

```
ggtcccatgg tgtaatggtg agcactctgg actctgaatc cagcgatccg agttcaaatc    60
tcggtgggac ctcca                                                     75
```

<210> SEQ ID NO 51
<211> LENGTH: 75
<212> TYPE: DNA
<213> ORGANISM: Artificial Sequence
<220> FEATURE:
<223> OTHER INFORMATION: synthetic polynucleotide

<400> SEQUENCE: 51

```
ggtcccatgg tgtaatggtt agcactctgg actttgaatc cagcgatccg agttcaaatc    60
tcggtgggac ctcca                                                     75
```

<210> SEQ ID NO 52
<211> LENGTH: 75
<212> TYPE: DNA
<213> ORGANISM: Artificial Sequence
<220> FEATURE:
<223> OTHER INFORMATION: synthetic polynucleotide

<400> SEQUENCE: 52

```
ggtcccatgg tgtaatggtg agcactctgg actttgaatc cagcgatccg agttcaaatc    60
tcggtgggac ctcca                                                     75
```

<210> SEQ ID NO 53
<211> LENGTH: 75
<212> TYPE: DNA
<213> ORGANISM: Artificial Sequence
<220> FEATURE:
<223> OTHER INFORMATION: synthetic polynucleotide

<400> SEQUENCE: 53

```
ggttccatgg tgtaatggtg agcactctgg actctgaatc cagcgatccg agttcgagtc    60
tcggtggaac ctcca                                                     75
```

<210> SEQ ID NO 54
<211> LENGTH: 472
<212> TYPE: DNA
<213> ORGANISM: Artificial Sequence
<220> FEATURE:
<223> OTHER INFORMATION: synthetic polynucleotide

<400> SEQUENCE: 54

```
ggctacggct gaccgttttt tgtggtgtac tccgtgccat catgtccgtc ctgacgccgc    60
tgctgctgcg gggcttgaca ggctcggccc ggcggctccc agtgccgcgc gccaagatcc   120
attcgttgcc gccggagggg aagcttggga tcatggaatt ggccgttggg cttacctcct   180
gcttcgtgac cttcctcctg ccagcgggct ggatcctgtc acacctggag acctacagga   240
ggccagagtg aagggggtccg ttctgtccct cacactgtga cctgaccagc cccaccggcc   300
catcctggtc atgttactgc atttgtggcc ggctcccct ggatcatgtc attcaattcc    360
agtcacctct tctgcaatca tgacctcttg atgtctccat ggtgacctcc ttgggggtca   420
```
ctgaccctgc ttggtggggt cccccttgta acaataaatc tatttaaact tt    472

<210> SEQ ID NO 55
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 55
gagtggttag ttttattagg    20

<210> SEQ ID NO 56
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 56
aatgagtggt tagttttatt a    21

<210> SEQ ID NO 57
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 57
cagggtttgt taagatggca    20

<210> SEQ ID NO 58
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 58
acagggtttg ttaagatggc    20

<210> SEQ ID NO 59
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 59
gaattgaacc tctgactgta    20

<210> SEQ ID NO 60
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 60
acttaaaacc ttacagtcag    20

<210> SEQ ID NO 61
<211> LENGTH: 20
<212> TYPE: DNA

```
<213> ORGANISM: Artificial Sequence
<220> FEATURE:
<223> OTHER INFORMATION: synthetic polynucleotide

<400> SEQUENCE: 61
cttttaagtt aaagattaag                                              20

<210> SEQ ID NO 62
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 62
tttaagttaa agattaagag                                              20

<210> SEQ ID NO 63
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 63
tggggcattt cactgtagag                                              20

<210> SEQ ID NO 64
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 64
tagttggggc atttcactgt                                              20

<210> SEQ ID NO 65
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 65
aggcgtacgg cccgggctat                                              20

<210> SEQ ID NO 66
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 66
tactcattca accaatagcc                                              20

<210> SEQ ID NO 67
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 67
agcggttagg cgtacggccc                                              20
```

<210> SEQ ID NO 68
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 68
ggcgtacggc ccgggctatt gg                                    22

<210> SEQ ID NO 69
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 69
aggcgtacgg ccggggctat                                       20

<210> SEQ ID NO 70
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 70
ttagcggtta ggcgtacggc                                       20

<210> SEQ ID NO 71
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 71
agcggttagg cgtacggccg                                       20

<210> SEQ ID NO 72
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 72
gcgtacggcc ggggctattg g                                     21

<210> SEQ ID NO 73
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 73
gagttttatg gtgtcagcga                                       20

<210> SEQ ID NO 74
<211> LENGTH: 22
<212> TYPE: DNA
<213> ORGANISM: Artificial Sequence
<220> FEATURE:

<223> OTHER INFORMATION: synthetic polynucleotide

<400> SEQUENCE: 74
gaagagtttt atggtgtcag cg                                         22

<210> SEQ ID NO 75
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 75
gtgaagagtt ttatggtgtc agc                                        23

<210> SEQ ID NO 76
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 76
tggtgtcagc gaagggttgt agt                                        23

<210> SEQ ID NO 77
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 77
gtgaagagtt ttatggtgtc                                            20

<210> SEQ ID NO 78
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 78
gagagaggat tatgatgtga ct                                         22

<210> SEQ ID NO 79
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 79
cacatcataa tcctctctca                                            20

<210> SEQ ID NO 80
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 80
gattatgatg tgactgtgag                                            20

```
<210> SEQ ID NO 81
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 81
gaggattatg atgtgactg                                                   19

<210> SEQ ID NO 82
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 82
tttaatttat ttaggggggaa                                                 20

<210> SEQ ID NO 83
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 83
aatttattta gggggaatgg                                                  20

<210> SEQ ID NO 84
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 84
gggggaatgg tggttgtctt                                                  20

<210> SEQ ID NO 85
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 85 taggggggaat ggtggttgtc t                                               21

<210> SEQ ID NO 86
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 86
atttatttag ggggaatggt ggt                                              23

<210> SEQ ID NO 87
<211> LENGTH: 23
<212> TYPE: DNA
<213> ORGANISM: Artificial Sequence
<220> FEATURE:
<223> OTHER INFORMATION: synthetic polynucleotide
```

```
<400> SEQUENCE: 87
gggggaatgg tggttgtctt tgg                                                 23

<210> SEQ ID NO 88
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 88
tttaatttat ttaggggggaa tgg                                                23

<210> SEQ ID NO 89
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 89
acgatggttt ttcgtatcat                                                     20

<210> SEQ ID NO 90
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 90
gtatcattgg tcgtggttgt agt                                                 23

<210> SEQ ID NO 91
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 91
tcgtatcatt ggtcgtggtt gta                                                 23

<210> SEQ ID NO 92
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 92
gtttttcgta tcattggtcg                                                     20

<210> SEQ ID NO 93
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 93
cccctacgca tttatataga                                                     20

<210> SEQ ID NO 94
<211> LENGTH: 20
```

```
<212> TYPE: DNA
<213> ORGANISM: Artificial Sequence
<220> FEATURE:
<223> OTHER INFORMATION: synthetic polynucleotide

<400> SEQUENCE: 94
agaggagaca agtcgtaaca                                              20

<210> SEQ ID NO 95
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 95
tgtctcctct atataaatgc gt                                           22

<210> SEQ ID NO 96
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 96
tatagaggag acaagtcgta aca                                          23

<210> SEQ ID NO 97
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 97
aaacccaccc cttacgagtg                                              20

<210> SEQ ID NO 98
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 98
aagccgcact cgtaaggggt                                              20

<210> SEQ ID NO 99
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 99
catagaaaaa cccacccctt                                              20

<210> SEQ ID NO 100
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 100
```
ggacgcgggc gggggggtata 20

<210> SEQ ID NO 101
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 101
gagaaaggga cgcgggcggg 20

<210> SEQ ID NO 102
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 102
gaaagggacg cggcgggggg gta 23

<210> SEQ ID NO 103
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 103
gaaaagaaag atgaatctt 19

<210> SEQ ID NO 104
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 104
aagatgaatc ttagggctc 19

<210> SEQ ID NO 105
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 105
gatgaatctt agggctcag 19

<210> SEQ ID NO 106
<211> LENGTH: 76
<212> TYPE: DNA
<213> ORGANISM: Artificial Sequence
<220> FEATURE:
<223> OTHER INFORMATION: synthetic polynucleotide

<400> SEQUENCE: 106
gttttagagc tagaaatagc aagttaaaat aaggctagtc cgttatcaac ttgaaaaagt 60
ggcaccgagt cggtgc 76

<210> SEQ ID NO 107
<211> LENGTH: 76

```
<212> TYPE: DNA
<213> ORGANISM: Artificial Sequence
<220> FEATURE:
<223> OTHER INFORMATION: synthetic polynucleotide

<400> SEQUENCE: 107
gttttagtac tctggaaaca gaatctacta aaacaaggca aaatgccgtg tttatctcgt    60
caacttgttg gcgaga                                                    76

<210> SEQ ID NO 108
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 108
taatttctac tcttgtagat                                                20

<210> SEQ ID NO 109
<211> LENGTH: 56
<212> TYPE: DNA
<213> ORGANISM: Artificial Sequence
<220> FEATURE:
<223> OTHER INFORMATION: synthetic polynucleotide

<400> SEQUENCE: 109
gtcgtatcca gtgcgaatac ctcggaccct gcactggata cgaccggact agcctt        56

<210> SEQ ID NO 110
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 110
tacctcggac cctgcactgg                                                20

<210> SEQ ID NO 111
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 111
ggttagtttt attagggttt tagagc                                         26

<210> SEQ ID NO 112
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 112
agcaagttaa aataaggcta gtccggtcgt                                     30

<210> SEQ ID NO 113
<211> LENGTH: 27
<212> TYPE: DNA
<213> ORGANISM: Artificial Sequence
<220> FEATURE:
<223> OTHER INFORMATION: synthetic polynucleotide
```

<400> SEQUENCE: 113
gcctatatta cggatcattt ctctact 27

<210> SEQ ID NO 114
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 114
gcctatgaag gctgttgcta tagt 24

<210> SEQ ID NO 115
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 115
acctgactga ctacctcatg aagatcctca ccga 34

<210> SEQ ID NO 116
<211> LENGTH: 36
<212> TYPE: DNA
<213> ORGANISM: Artificial Sequence
<220> FEATURE:
<223> OTHER INFORMATION: synthetic polynucleotide

<400> SEQUENCE: 116
ggagctggaa gcagccgtgg ccatctcttg ctcgaa 36

<210> SEQ ID NO 117
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 117
cctgaaacat cggcattatc ctcctgct 28

<210> SEQ ID NO 118
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 118
agcgggaaat cgtgcgtgac atta 24

<210> SEQ ID NO 119
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 119
ccctaaaacc cgccacatct 20

<210> SEQ ID NO 120
<211> LENGTH: 22

```
<212> TYPE: DNA
<213> ORGANISM: Artificial Sequence
<220> FEATURE:
<223> OTHER INFORMATION: synthetic polynucleotide

<400> SEQUENCE: 120
gagcgatggt gagagctaag gt                                              22

<210> SEQ ID NO 121
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 121
aacataccca tggccaacct                                                 20

<210> SEQ ID NO 122
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 122
agcgaagggt tgtagtagcc c                                               21

<210> SEQ ID NO 123
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 123
gaagagccaa ggacaggtac                                                 20

<210> SEQ ID NO 124
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 124
caacttcatc cacgttcacc                                                 20

<210> SEQ ID NO 125
<211> LENGTH: 11948
<212> TYPE: DNA
<213> ORGANISM: Artificial Sequence
<220> FEATURE:
<223> OTHER INFORMATION: synthetic polynucleotide

<400> SEQUENCE: 125
ttaatgtagt cttatgcaat actcttgtag tcttgcaaca tggtaacgat gagttagcaa      60
catgccttac aaggagagaa aaagcaccgt gcatgccgat tggtggaagt aaggtggtac     120
gatcgtgcct tattaggaag gcaacagacg ggtctgacat ggattggacg aaccactgaa     180
ttgccgcatt gcagagatat tgtatttaag tgcctagctc gatacataaa cgggtctctc     240
tggttagacc agatctgagc ctgggagctc tctggctaac tagggaaccc actgcttaag     300
cctcaataaa gcttgccttg agtgcttcaa gtagtgtgtg cccgtctgtt gtgtgactct     360
```

```
ggtaactaga gatccctcag acccttttag tcagtgtgga aaatctctag cagtggcgcc    420
cgaacaggga cttgaaagcg aaagggaaac cagaggagct ctctcgacgc aggactcggc    480
ttgctgaagc gcgcacggca agaggcgagg ggcggcgact ggtgagtacg ccaaaaattt    540
tgactagcgg aggctagaag gagagagatg ggtgcgagag cgtcagtatt aagcggggga    600
gaattagatc gcgatgggaa aaaattcggt taaggccagg gggaagaaa aaatataaat     660
taaaacatat agtatgggca agcagggagc tagaacgatt cgcagttaat cctggcctgt    720
tagaaacatc agaaggctgt agacaaatac tgggacagct acaaccatcc cttcagacag    780
gatcagaaga acttagatca ttatataata cagtagcaac cctctattgt gtgcatcaaa    840
ggatagagat aaaagacacc aaggaagctt tagacaagat agaggaagag caaaacaaaa    900
gtaagaccac cgcacagcaa gcggccgctg atcttcagac ctggaggagg agatatgagg    960
gacaattgga gaagtgaatt atataaatat aaagtagtaa aaattgaacc attaggagta    1020
gcacccacca aggcaaagag aagagtggtg cagagagaaa aaagagcagt gggaatagga    1080
gctttgttcc ttgggttctt gggagcagca ggaagcacta tgggcgcagc gtcaatgacg    1140
ctgacggtac aggccagaca attattgtct ggtatagtgc agcagcagaa caatttgctg    1200
agggctattg aggcgcaaca gcatctgttg caactcacag tctggggcat caagcagctc    1260
caggcaagaa tcctggctgt ggaaagatac ctaaaggatc aacagctcct ggggatttgg    1320
ggttgctctg gaaaactcat ttgcaccact gctgtgcctt ggaatgctag ttggagtaat    1380
aaatctctgg aacagatttg gaatcacacg acctggatgg agtgggacag agaaattaac    1440
aattacacaa gcttaataca ctccttaatt gaagaatcgc aaaaccagca agaaaagaat    1500
gaacaagaat tattggaatt agataaatgg gcaagtttgt ggaattggtt taacataaca    1560
aattggctgt ggtatataaa attattcata atgatagtag gaggcttggt aggtttaaga    1620
atagtttttg ctgtactttc tatagtgaat agagttaggc agggatattc accattatcg    1680
tttcagaccc acctcccaac cccgagggga cccagagagg ccctatttcc catgattcct    1740
tcatatttgc atatacgata caaggctgtt agagagataa ttagaattaa tttgactgta    1800
aacacaaaga tattagtaca aaatacgtga cgtagaaagt aataaatttct tgggtagttt    1860
gcagttttaa aattatgttt taaaatggac tatcatatgc ttaccgtaac ttgaaagtat    1920
ttcgatttct tggctttata tatccttgtgg aaaggacgaa acaccggaga cggcggccgc    1980
cgtctctgtt ttagagctag aaatagcaag ttaaaataag gctagtccgt tatcaacttg    2040
aaaaagtggc accgagtcgg tgccaccggc cgcaggtggg atcccacctg ccatggtttt    2100
ttgaattcta gatcttgaga caaatggcag tattcatcca caatttttaaa agaaaagggg    2160
ggattggggg gtacagtgca ggggaaagaa tagtagacat aatagcaaca gacatacaaa    2220
ctaaagaatt acaaaaacaa attacaaaaa ttcaaaattt tcgggtttat tacagggaca    2280
gcagagatcc actttggcgc cggctcgagc gagctgcagt aacgccattt tgcaaggcat    2340
ggaaaaatac caaaccaaga atagagaagt tcagatcaag ggcgggtaca tgaaaatagc    2400
taacgttggg ccaaacagga tatctgcggt gagcagtttc ggccccggcc ggggccaag    2460
aacagatggt caccgcagtt tcggcccccgg cccgaggcca agaacagatg gtccccagat    2520
atggcccaac cctcagcagt ttcttaagac ccatcagatg tttccaggct ccccaagga    2580
cctgaaatga ccctgcgcct tatttgaatt aaccaatcag cctgcttctc gcttctgttc    2640
gcgcgcttct gcttcccgag ctctataaaa gagctcacaa cccctcactc ggcgcgccag    2700
tcctccgaca gactgagtcg gatcaactag tgccaccatg tccgtcctga cgccgctgct    2760
```

```
gctgcgggc  ttgacaggct  cggcccggcg  gctcccagtg  ccgcgcgcca  agatccattc    2820
gttggatccg  gacaagaagt  acagcatcgg  cctggacatc  ggcaccaact  ctgtgggctg    2880
ggccgtgatc  accgacgagt  acaaggtgcc  cagcaagaaa  ttcaaggtgc  tgggcaacac    2940
cgaccggcac  agcatcaaga  agaacctgat  cggagccctg  ctgttcgaca  gcggcgaaac    3000
agccgaggcc  acccggctga  agagaaccgc  cagaagaaga  tacaccagac  ggaagaaccg    3060
gatctgctat  ctgcaagaga  tcttcagcaa  cgagatggcc  aaggtggacg  acagcttctt    3120
ccacagactg  gaagagtcct  tcctggtgga  agaggataag  aagcacgagc  ggcaccccat    3180
cttcggcaac  atcgtggacg  aggtggccta  ccacgagaag  tacccaccca  tctaccacct    3240
gagaaagaaa  ctggtggaca  gcaccgacaa  ggccgacctg  cggctgatct  atctggccct    3300
ggcccacatg  atcaagttcc  ggggccactt  cctgatcgag  ggcgacctga  accccgacaa    3360
cagcgacgtg  gacaagctgt  tcatccagct  ggtgcagacc  tacaaccagc  tgttcgagga    3420
aaacccaatc  aacgccagcg  gcgtggacgc  caaggccatc  ctgtctgcca  gactgagcaa    3480
gagcagacgg  ctggaaaatc  tgatcgccca  gctgcccggc  gagaagaaga  atggcctgtt    3540
cggaaacctg  attgccctga  gcctgggcct  gacccccaac  ttcaagagca  acttcgacct    3600
ggccgaggat  gccaaactgc  agctgagcaa  ggacacctac  gacgacgacc  tggacaacct    3660
gctggcccag  atcggcgacc  agtacgccga  cctgtttctg  gccgccaaga  acctgtccga    3720
cgccatcctg  ctgagcgaca  tcctgagagt  gaacaccgag  atcaccaagg  cccccctgag    3780
cgcctctatg  atcaagagat  acgacgagca  ccaccaggac  ctgaccctgc  tgaaagctct    3840
cgtgcggcag  cagctgcctg  agaagtacaa  agagattttc  ttcgaccaga  gcaagaacgg    3900
ctacgccggc  tacattgacg  gcggagccag  ccaggaagag  ttctacaagt  tcatcaagcc    3960
catcctggaa  aagatggacg  gcaccgagga  actgctcgtg  aagctgaaca  gagaggacct    4020
gctgcggaag  cagcggacct  tcgacaacgg  cagcatcccc  caccagatcc  acctgggaga    4080
gctgcacgcc  attctgcggc  ggcaggaaga  ttttaccca  ttcctgaagg  acaacgggga    4140
aaagatcgag  aagatcctga  ccttccgcat  cccctactac  gtgggccctc  tggccagggg    4200
aaacagcaga  ttcgcctgga  tgaccagaaa  gagcgaggaa  accatcaccc  cctggaactt    4260
cgaggaagtg  gtggacaagg  gcgcttccgc  ccagagcttc  atcgagcgga  tgaccaactt    4320
cgataagaac  ctgcccaacg  agaaggtgct  gcccaagcac  agcctgctgt  acgagtactt    4380
caccgtgtat  aacgagctga  ccaaagtgaa  atacgtgacc  gagggaatga  gaaagcccgc    4440
cttcctgagc  ggcgagcaga  aaaaggccat  cgtggacctg  ctgttcaaga  ccaaccggaa    4500
agtgaccgtg  aagcagctga  aagaggacta  cttcaagaaa  atcgagtgct  tcgactccgt    4560
ggaaatctcc  ggcgtggaag  atcggttcaa  cgcctccctg  gcacatacc  acgatctgct    4620 gaaaattatc  aaggacaagg  acttcctgga  caatgaggaa  aacgaggaca  ttctggaaga    4680
tatcgtgctg  accctgacac  tgtttgagga  cagagagatg  atcgaggaac  ggctgaaaac    4740
ctatgcccac  ctgttcgacg  acaaagtgat  gaagcagctg  aagcggcgga  gatacaccgg    4800
ctggggcagg  ctgagccgga  agctgatcaa  cggcatccgg  gacaagcagt  ccggcaagac    4860
aatcctggat  ttcctgaagt  ccgacggctt  cgccaacaga  aacttcatgc  agctgatcca    4920
cgacgacagc  ctgacctta  aagaggacat  ccagaaagcc  caggtgtccg  gccagggcga    4980
tagcctgcac  gagcacattg  ccaatctggc  cggcagcccc  gccattaaga  agggcatcct    5040
gcagacagtg  aaggtggtgg  acgagctcgt  gaaagtgatg  ggccggcaca  gcccggaaa    5100
```

```
catcgtgatc gaaatggcca gagagaacca gaccacccag aagggacaga agaacagccg    5160
cgagagaatg aagcggatcg aagagggcat caaagagctg ggcagccaga tcctgaaaga    5220 acacccegtg gaaaacaccc agctgcagaa cgagaagctg tacctgtact acctgcagaa    5280
tgggcgggat atgtacgtgg accaggaact ggacatcaac cggctgtccg actacgatgt    5340
ggaccatatc gtgcctcaga gctttctgaa ggacgactcc atcgacaaca aggtgctgac    5400
cagaagcgac aagaaccggg gcaagagcga acgtgccc tccgaagagg tcgtgaagaa     5460
gatgaagaac tactggcggc agctgctgaa cgccaagctg attacccaga gaaagttcga    5520
caatctgacc aaggccgaga gaggcggcct gagcgaactg gataaggccg gcttcatcaa    5580
gagacagctg gtggaaaccc ggcagatcac aaagcacgtg gcacagatcc tggactcccg    5640
gatgaacact aagtacgacg agaatgacaa gctgatccgg gaagtgaaag tgatcaccct    5700
gaagtccaag ctggtgtccg atttccggaa ggatttccag ttttacaaag tgcgcgagat    5760
caacaactac caccacgccc acgacgccta cctgaacgcc gtcgtgggaa ccgccctgat    5820
caaaaagtac cctaagctgg aaagcgagtt cgtgtacggc gactacaagg tgtacgacgt    5880
gcggaagatg atcgccaaga gcgagcagga aatcggcaag gctaccgcca agtacttctt    5940
ctacagcaac atcatgaact ttttcaagac cgagattacc ctggccaacg gcgagatccg    6000
gaagcggcct ctgatcgaga caaacggcga accggggag atcgtgtggg ataagggccg     6060
ggattttgcc accgtgcgga aagtgctgag catgccccaa gtgaatatcg tgaaaaagac    6120
cgaggtgcag acaggcggct cagcaaaga gtctatcctg cccaagagga acagcgataa     6180
gctgatcgcc agaaagaagg actgggaccc taagaagtac ggcggcttcg acagccccac    6240
cgtggcctat tctgtgctgg tggtggccaa agtggaaaag ggcaagtcca gaaaactgaa    6300
gagtgtgaaa gagctgctgg ggatcaccat catggaaaga agcagcttcg agaagaatcc    6360
catcgacttt ctggaagcca agggctacaa agaagtgaaa aaggacctga tcatcaagct    6420
gcctaagtac tccctgttcg agctggaaaa cggccggaag agaatgctgg cctctgccgg    6480
cgaactgcag aagggaaacg aactggccct gccctccaaa tatgtgaact tcctgtacct    6540
ggccagccac tatgagaagc tgaagggctc ccccgaggat aatgagcaga acagctgtt     6600 tgtggaacag cacaagcact acctggacga gatcatcgag cagatcagcg agttctccaa    6660
gagagtgatc ctggccgacg ctaatctgga caaagtgctg tccgcctaca acaagcaccg    6720
ggataagccc atcagagagc aggccgagaa tatcatccac ctgtttaccc tgaccaatct    6780
gggagcccct gccgccttca gtactttga caccaccatc gaccggaaga ggtacaccag    6840
caccaaagag gtgctggacg ccaccctgat ccaccagagc atcaccggcc tgtacgagac    6900
acggatcgac ctgtctcagc tgggaggcga cgctagcgac tataaggacc acgacgagga    6960
ctacaaggat catgatattg attacaaaga cgatgacgat aagcctagcg gcagcggcgc    7020
caccaacttc agcctgctga agcaggccgg cgacgtggag gagaacccg gcccatggt     7080 gtctaagggc gaagagctga ttaaggagaa catgcacatg aagctgtata tggagggcac    7140
cgtgaacaac caccacttca gtgcacatc gagggcgaa ggcaagccct acgagggcac     7200
ccagaccatg agaatcaagg tggtcgaggg cggccctctc cccttcgcct tcgacatcct    7260
ggctaccagc ttcatgtacg gcagcagaac cttcatcaac cacacccagg gcatccccga    7320
cttctttaag cagtccttcc ctgagggctt cacatgggag agagtcacca catacgaaga    7380
cgggggcgtg ctgaccgcta cccaggacac cagcctccag gacggctgcc tcatctacaa    7440
cgtcaagatc agaggggtga acttcccatc caacggccct gtgatgcaga agaaaacact    7500
```

```
cggctgggag gccaacaccg agatgctgta ccccgctgac ggcggcctgg aaggcagaag    7560
cgacatggcc ctgaagctcg tgggcggggg ccacctgatc tgcaacttca agaccacata    7620
cagatccaag aaacccgcta agaacctcaa gatgcccggc gtctactatg tggaccacag    7680
actggaaaga atcaaggagg ccgacaaaga gacctacgtc gagcagcacg aggtggctgt    7740
ggccagatac tgcgacctcc ctagcaaact ggggcacaaa cttaattgaa cgcgttaagt    7800
cgacaatcaa cctctggatt acaaaatttg tgaaagattg actggtattc ttaactatgt    7860
tgctcctttt acgctatgtg gatacgctgc tttaatgcct ttgtatcatg ctattgcttc    7920
ccgtatggct ttcattttct cctccttgta taaatcctgg ttgctgtctc tttatgagga    7980
gttgtggccc gttgtcaggc aacgtggcgt ggtgtgcact gtgtttgctg acgcaacccc    8040
cactggttgg ggcattgcca ccacctgtca gctccttttcc gggactttcg ctttccccct    8100
ccctattgcc acggcggaac tcatcgccgc ctgccttgcc cgctgctgga caggggctcg    8160
gctgttgggc actgacaatt ccgtggtgtt gtcggggaaa tcatcgtcct ttccttggct    8220
gctcgcctgt gttgccacct ggattctgcg cgggacgtcc ttctgctacg tcccttcggc    8280
cctcaatcca gcggaccttc cttcccgcgg cctgctgccg gtctctgcggc ctcttccgcg    8340 tcttcgcctt cgccctcaga cgagtcggat ctcccttttgg gccgcctccc cgcgtcgact    8400
ttaagaccaa tgacttacaa ggcagctgta gatcttagcc actttttaaa agaaaagggg    8460
ggactggaag ggctaattca ctcccaacga agacaagatc tgcttttttgc ttgtactggg    8520 tctctctggt tagaccagat ctgagcctgg gagctctctg gctaactagg gaacccactg    8580
cttaagcctc aataaagctt gccttgagtg cttcaagtag tgtgtgcccg tctgttgtgt    8640
gactctggta actagagatc cctcagaccc ttttagtcag tgtggaaaat ctctagcagt    8700
acgtatagta gttcatgtca tcttattatt cagtatttat aacttgcaaa gaaatgaata    8760
tcagagagtg agaggaactt gtttattgca gcttataatg gttacaaata aagcaatagc    8820
atcacaaatt tcacaaataa agcatttttt tcactgcatt ctagttgtgg tttgtccaaa    8880
ctcatcaatg tatcttatca tgtctggctc tagctatccc gccccctaact ccgcccatcc    8940 cgcccctaac tccgcccagt tccgcccatt ctccgcccca tggctgacta attttttta    9000 tttatgcaga ggccgaggcc gcctcggcct ctgagctatt ccagaagtag tgaggaggct    9060 ttttttggagg cctaggacg tacccaattc gccctatagt gagtcgtatt acgcgcgctc    9120
actggccgtc gttttacaac gtcgtgactg ggaaaaccct ggcgttaccc aacttaatcg    9180
ccttgcagca catccccctt tcgccagctg gcgtaatagc gaagaggccc gcaccgatcg    9240
cccttcccaa cagttgcgca gcctgaatgg cgaatgggac gcgccctgta gcggcgcatt    9300
aagcgcggcg ggtgtggtgg ttacgcgcag cgtgaccgct acacttgcca gcgccctagc    9360
gcccgctcct ttcgctttct tcccttcctt tctcgccacg ttcgccggct ttccccgtca    9420
agctctaaat cggggctccc tttagggtt ccgatttagt gctttacggc acctcgaccc    9480
caaaaaactt gattagggtg atggttcacg tagtgggcca tcgccctgat agacggtttt    9540
tcgccctttg acgttggagt ccacgttctt taatagtgga ctcttgttcc aaactggaac    9600
aacactcaac cctatctcgg tctattcttt tgatttataa gggattttgc cgatttcggc    9660
ctattggtta aaaaatgagc tgatttaaca aaaatttaac gcgaatttta acaaaatatt    9720
aacgcttaca atttaggtgg cacttttcgg ggaaatgtgc gcggaacccc tatttgttta    9780 ttttttctaaa tacattcaaa tatgtatccg ctcatgagac aataaccctg ataaatgctt    9840
```

```
caataatatt gaaaaaggaa gagtatgagt attcaacatt tccgtgtcgc ccttattccc    9900 tttttttgcgg catttttgcct tcctgttttt gctcacccag aaacgctggt gaaagtaaaa    9960
gatgctgaag atcagttggg tgcacgagtg ggttacatcg aactggatct caacagcggt   10020
aagatccttg agagttttcg ccccgaagaa cgttttccaa tgatgagcac ttttaaagtt   10080
ctgctatgtg gcgcggtatt atcccgtatt gacgccgggc aagagcaact cggtcgccgc   10140
atacactatt ctcagaatga cttggttgag tactcaccag tcacagaaaa gcatcttacg   10200
gatggcatga cagtaagaga attatgcagt gctgccataa ccatgagtga taacactgcg   10260
gccaacttac ttctgacaac gatcggagga ccgaaggagc taaccgcttt tttgcacaac   10320
atgggggatc atgtaactcg ccttgatcgt tgggaaccgg agctgaatga agccatacca   10380
aacgacgagc gtgacaccac gatgcctgta gcaatggcaa caacgttgcg caaactatta   10440
actggcgaac tacttactct agcttcccgg caacaattaa tagactggat ggaggcggat   10500
aaagttgcag gaccacttct gcgctcggcc cttccggctg gctggtttat tgctgataaa   10560
tctggagccg gtgagcgtgg gtctcgcggt atcattgcag cactggggcc agatggtaag   10620
ccctcccgta tcgtagttat ctacacgacg gggagtcagg caactatgga tgaacgaaat   10680
agacagatcg ctgagatagg tgcctcactg attaagcatt ggtaactgtc agaccaagtt   10740
tactcatata tactttagat tgatttaaaa cttcattttt aatttaaaag gatctaggtg   10800
aagatccttt ttgataatct catgaccaaa atcccttaac gtgagttttc gttccactga   10860
gcgtcagacc ccgtagaaaa gatcaaagga tcttcttgag atcctttttt tctgcgcgta   10920
atctgctgct tgcaaacaaa aaaaccaccg ctaccagcgg tggtttgttt gccggatcaa   10980
gagctaccaa ctctttttcc gaaggtaact ggcttcagca gagcgcagat accaaatact   11040
gttcttctag tgtagccgta gttaggccac cacttcaaga actctgtagc accgcctaca   11100
tacctcgctc tgctaatcct gttaccagtg gctgctgcca gtggcgataa gtcgtgtctt   11160
accgggttgg actcaagacg atagttaccg gataaggcgc agcggtcggg ctgaacgggg   11220
ggttcgtgca cacagcccag cttggagcga acgacctaca ccgaactgag atacctacag   11280
cgtgagctat gagaaagcgc cacgcttccc gaagggagaa aggcggacag gtatccggta   11340
agcggcaggg tcggaacagg agagcgcacg agggagcttc caggggggaaa cgcctggtat   11400 ctttatagtc ctgtcgggtt tcgccacctc tgacttgagc gtcgatttt gtgatgctcg   11460 tcaggggggc ggagcctatg gaaaaacgcc agcaacgcgg cctttttacg gttcctggcc   11520
ttttgctggc cttttgctca catgttcttt cctgcgttat cccctgattc tgtggataac   11580
cgtattaccg cctttgagtg agctgatacc gctcgccgca gccgaacgac cgagcgcagc   11640
gagtcagtga gcgaggaagc ggaagagcgc ccaatacgca aaccgcctct ccccgcgcgt   11700
tggccgattc attaatgcag ctggcacgac aggtttcccg actggaaagc gggcagtgag   11760
cgcaacgcaa ttaatgtgag ttagctcact cattaggcac cccaggcttt acactttatg   11820
cttccggctc gtatgttgtg tggaattgtg agcggataac aatttcacac aggaaacagc   11880
tatgaccatg attacgccaa gcgcgcaatt aaccctcact aaagggaaca aaagctggag   11940
ctgcaagc                                                             11948
```

COMPOSITIONS AND METHODS FOR MITOCHONDRIAL GENOME EDITING

CROSS-REFERENCES TO RELATED APPLICATIONS

This application is a U.S. National Phase Application of PCT Application No. PCT/US2017/036821, filed Jun. 9, 2017, which claims the benefit of U.S. Provisional Application No. 62/348,262, filed Jun. 10, 2016, the contents of which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48440-598001WO_ST25.TXT, created Jun. 8, 2017, 175,122 bytes in size, machine format IBM-PC, MS-Windows operating system, is hereby incorporated by reference.

BACKGROUND OF THE INVENTION

Mitochondria are essential organelles that generate the bulk of cellular energy in the form of ATP from the oxidation of carbohydrates and fats. To carry out this central role in bioenergetics, mitochondria require their own genome, a 16.6 kilobase (kb) circular double-stranded molecule that encodes 37 genes. Each human cell carries hundreds to thousands of copies of mitochondria DNA (mtDNA). In mitochondrial encephalopmyopathies, cells typically contain a mixture of both pathogenic and normal mtDNA molecules, a state termed heteroplasmy. There are over 600 known mtDNA mutations associated with such mtDNA diseases, which have diverse clinical features, including maternal inheritance, defects in the central and peripheral nervous systems, muscle defects, and exercise intolerance. Due to the inability to transform mitochondrial DNA, there are no approved clinical therapies for the treatment of mitochondrial diseases. Provided herein are solutions to these and other problems in the art.

BRIEF SUMMARY OF THE INVENTION

In a first aspect, there is provided a composition including a delivery vehicle and a protein including a mitochondrial localization amino acid sequence covalently attached to an RNA-guided DNA endonuclease enzyme, where the protein is bound to the delivery vehicle.

In another aspect, there is provided a protein including a mitochondrial localization amino acid sequence covalently attached to Cpf1 or a Class II CRISPR endonuclease or a Cas9 variant.

In another aspect, there is provided a nucleic acid including a mitochondrial import sequence and a single-guide RNA (sgRNA) sequence.

In another aspect, there is provided a method of altering expression of at least one mitochondrial nucleic acid sequence, the method including introducing into an eukaryotic cell a nucleic acid as disclosed herein.

In another aspect, there is provided a method of treating a mitochondrial disorder in a subject in need thereof, the method including administering to the subject an effective amount of a composition disclosed herein and an effective amount of a nucleic acid disclosed herein.

In another aspect, there is provided a method of treating a mitochondrial disorder in a subject in need thereof, the method including administering to the subject an effective amount of a protein disclosed herein or a nucleic acid disclosed herein and an effective amount of another nucleic acid disclosed herein.

In another aspect, there is provided a kit including a nucleic acid disclosed herein, and a protein including a mitochondrial localization amino acid sequence covalently attached to an RNA-guided DNA endonuclease enzyme or a nucleic acid sequence encoding the protein.

BRIEF DESCRIPTION OF THE DRAWINGS

(FIG. 1A) Lentiviral vector expression system for mitochondrial localizing sgRNA (mito-sgRNA) and mito-Cas9-P2A-TagRFP. (FIG. 1B) Western blot of mitoCas9-Flag fractionation, "N" nuclear, "M" mitochondria, cytoplasmic "C". (FIG. 1C) Confocal microscopy of HeLa cells transduced with the vector from (A). MitoCas9-Flag co-localizes with the mitochondrial Tom20 protein, while TagRFP is dispersed throughout the cytoplasm and nucleus. (FIG. 1D) Plasmid map of construct disclosed herein. See Table 8 for specific sequence information forming FIG. 1D. The plasmid uses the SFFV promoter to express Cox8-Cas9 (mitoCas9)-P2A-TagRFP and the U6 promoter to express the CRISPR RNA with unique mitochondrial localization loops.

FIGS. 2A-2B. Mitochondrial localization loops. (FIG. 2A) Sequence and structure for five mitoloops. (FIG. 2B) General designs mitoloop-sgRNA chimeras. Target: a guide sequence having sufficient complementarity with a target polynucleotide sequence; repeat/anti-repeat: a tracr mate sequence having sufficient complementarity with tracrRNA sequence; mitoloop(s): mitochondrial import sequence(s).

(FIG. 3A) Image of Hela cell transfected with 488-labeled mito-loop sgRNA and stained with mitochondrial marker Tom20. (FIG. 3B) Magnified images of boxed regions in (FIG. 3A). Microscopy image shows Hela cells transduced with mtCas9 by lentivirus were subsequently transfected by Lipofectamine with Cy5-labeled F-loop sgRNA. Tom20 is used as mitochondrial marker. Partial co-localization of the F-loop sgRNA with mitochondria is observed in boxed region. Panel of images showed high magnification of boxed region in dual and single channels.

FIGS. 4A-4C. (FIG. 4A) A schematic of dual promoter lentiviral construct that expresses MTS-Cas9-3×FLAG-P2A-TagRFP from the SFFV promoter and the mito-sgRNA from the U6 promoter. (FIG. 4B) Western blot of nuclear, mitochondrial and cytoplasmic fractions showing enrichment of the mitoCas9-Flag protein in the mitochondrial fraction. Lamin A/C is a nuclear marker, β-tubulin represents the cytosol, and heat shock protein 60 (HSP60) is a mitochondrial protein. (FIG. 4C) Photomicrographs depicting Hela cells transfected with the mtCas9 construct indicated in FIG. 4A. The MTS is the Cox8 mitochondrial localization signal. Tom20 is an endogenous protein localized in the mitochondrial outer membrane and is stained with an anti-Tom20 fluorescent antibody. Mitochondrial-localizing Cas9 (mtCas9) contains a C-terminal FLAG tag and is stained with a fluorescent anti-FLAG antibody. Scale bar represents 10 µm.

(FIG. 5A) Reverse transcription of mito-sgRNA in RNA extract using RT primer with the addition of a stem loop. (FIG. 5B) The resulting cDNA is amplified using indicated primers (half arrows). (FIG. 5C) An agarose gel of the qPCR products from schematic B from nuclear or mitochondrial fraction of RNA extracts. Hela (H) are untransduced wild-type controls; L represents cells transduced with LDF mito-sgRNA (expected product 95 bp) and ZDF represent zDF mito-sgRNA (expected product 115 bp).

(FIG. 6A) Schematic of construct targeting mitoAsCpf1 to mitochondria using COX VIII targeting signal (represented as Mito in this scheme). There is a 3×HA tag at the 3' end of AsCpf1 and TagRFP is a marker of transfection. (FIG. 6B) Plasmid map of the construct in FIG. 6A. (FIG. 6C) Immunofluorescence micrographs of Hela cells transfected with mitoAsCpf1 construct in FIG. 6A. Tom20 is used as a marker of mitochondria and the 3×HA is used to determine localization of mitoAsCpf1. TagRFP expression is not shown. Scale bar represents 10 µm.

(FIG. 9A) Graph shows mtDNA per cell normalized to mock control. The sgRNA-ctrl has no mitoloops attached to the sgRNA. (FIG. 9B) Data table of FIG. 9A with the mean and standard deviation listed. The addition of G5S, RNaseP (RNP) and MRP loops show decreased copies of mtDNA relative to mock controls.

(FIG. 10A) Graph shows mtDNA content per nuclei normalized to mock control. The GSS, RNaseP, MRP, and zDF (D and F loops placed in the tetraloop and stemloop 2, respectively) mitoloops show decreased levels of mtDNA relative to mock control. (FIG. 10B) Data table of FIG. 10A showing mean and upper and lower limits of fold change.

TABLE 10

Primers

ND 1-internal (ND 1-int) Fwd:
CCCTAAAACCCGCCACATCT (SEQ ID NO: 119)

ND 1-internal Rev:
GAGCGATGGTGAGAGCTAAGGT (SEQ ID NO: 120)

ND 1-5' Fwd:
AACATACCCATGGCCAACCT (SEQ ID NO: 121)

ND 1-5' Rev:
AGCGAAGGGTTGTAGTAGCCC (SEQ ID NO: 122)

HBB Fwd:
GAAGAGCCAAGGACAGGTAC (SEQ ID NO: 123)

HBB Rev:
CAACTTCATCCACGTTCACC (SEQ ID NO: 124)

Figure 11:
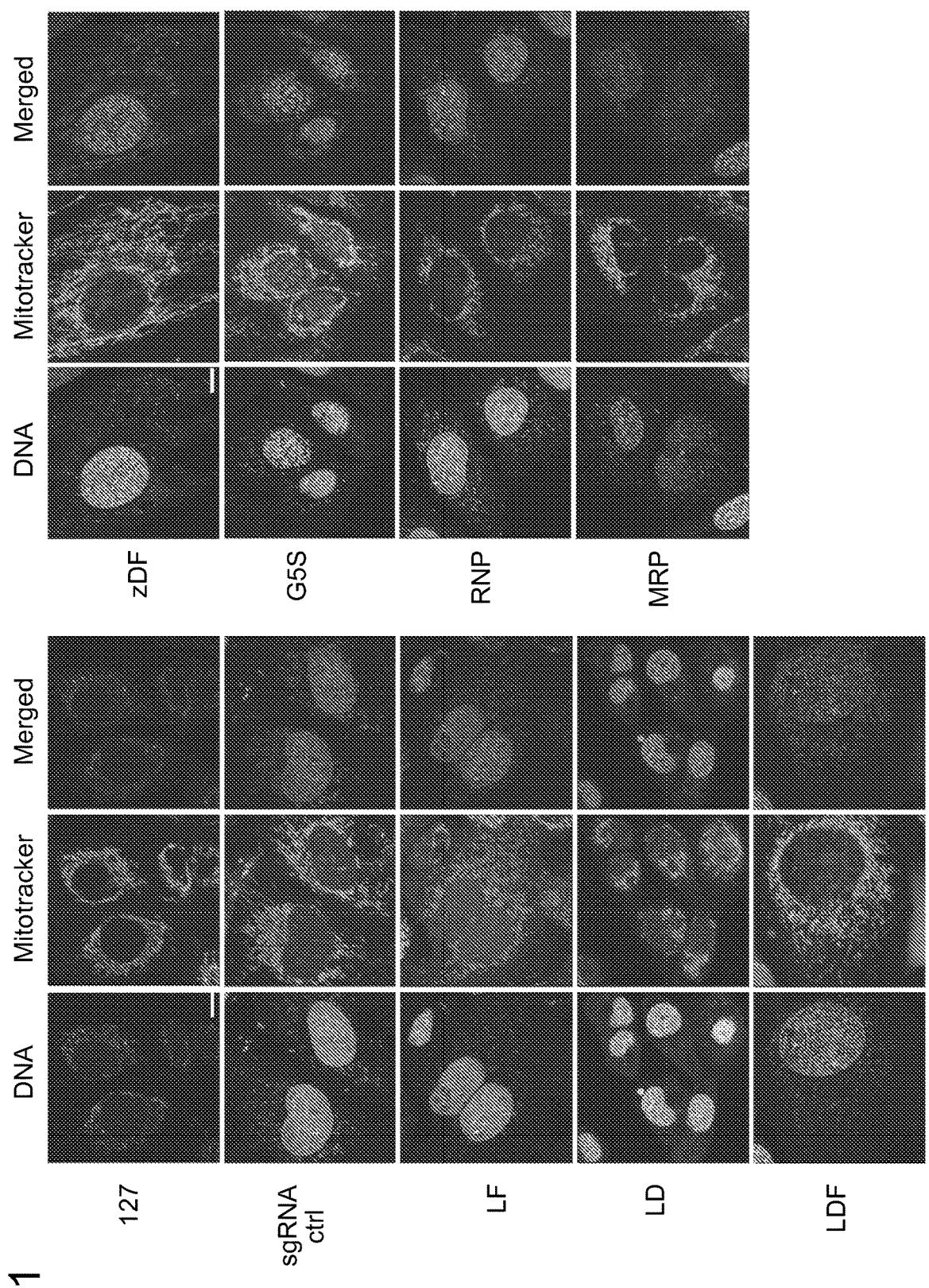

FIG. 11. Staining of mitochondrial DNA and morphology in cytochrome b deletion cybrids with mtCas9 and various sgRNA-mitoloops. Cells were incubated with Picogreen to stain both nuclear and mitochondrial DNA. Fluorescence micrographs show live cell imaging with DNA labeled by Picogreen (first column) and Mitotracker Red (second column) for mitochondrial morphology. The mtDNA puncta appears fewer in cybrids with the LD, zDF, G5 S, RNaseP and MRP sgRNA-mitoloops. The decreased labeling of mtDNA is consistent with the quantitative PCR results. Scale bar is 10 µm.

DETAILED DESCRIPTION OF THE INVENTION

I. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. In other words, the term "nucleotide analog" as used herein generally refers to a purine or pyrimidine nucleotide that differs structurally from A, T, G, C, or U, but is sufficiently similar to substitute for such "normal" nucleotides in a nucleic acid molecule. As used herein, the term "nucleotide analog" encompasses altered bases, different (or unusual) sugars, altered phosphate backbones, or any combination of these alterations. Examples of such analogues include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analogue nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Nucleotide analogues used herein also include nucleotides having modified 2' position of the ribose ring. For example, the 2' position of the ribose ring is substituted by O-methyl, O-alkyl, O-allyl, S-alkyl, S-allyl, or halo group. Mixtures of naturally occurring nucleic acids and analogues can be made; alternatively, mixtures of different nucleic acid analogues, and mixtures of naturally occurring nucleic acids and analogues may be made. In embodiments, the internucleotide linkages in DNA are phosphodiester, phosphodiester derivatives, or a combination of both.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As used herein, the term "conjugate" refers to the association between atoms or molecules. The association can be direct or indirect. For example, a conjugate between a first moiety (e.g., nucleic acid moiety) and a second moiety (peptide moiety) provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first moiety (e.g., polyamine moiety) is non-covalently attached to the second moiety (peptide moiety) through a non-covalent chemical reaction between a component of the first moiety (e.g., polyamine moiety) and a component of the second moiety (peptide moiety). In other embodiments, the first moiety (e.g., polyamine moiety) includes one or more reactive moieties, e.g., a covalent reactive moiety, as described herein (e.g., alkyne, azide, maleimide or thiol reactive moiety). In other embodiments, the first moiety (e.g., polyamine moiety) includes a linker with one or more reactive moieties, e.g., a covalent reactive moiety, as described herein (e.g., alkyne, azide, maleimide or thiol reactive moiety). In other embodiments, the second moiety (peptide moiety) includes one or more reactive moieties, e.g., a covalent reactive moiety, as described herein (e.g., alkyne, azide, maleimide or thiol reactive moiety). In other embodiments, the second moiety (peptide moiety) includes a linker with one or more reactive moieties, e.g., a covalent reactive moiety, as described herein (e.g., alkyne, azide, maleimide or thiol reactive moiety).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self 17 hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

Figure 5A:
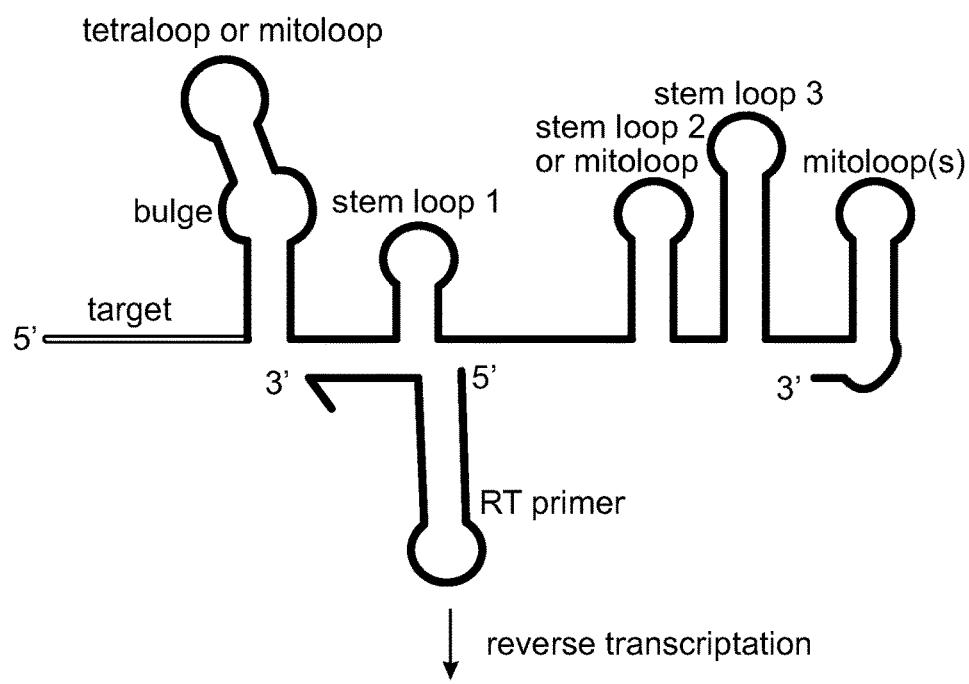
FIGS. 5A-5C. These figures illustrate the qPCR of sgRNA.
Figure 5B:
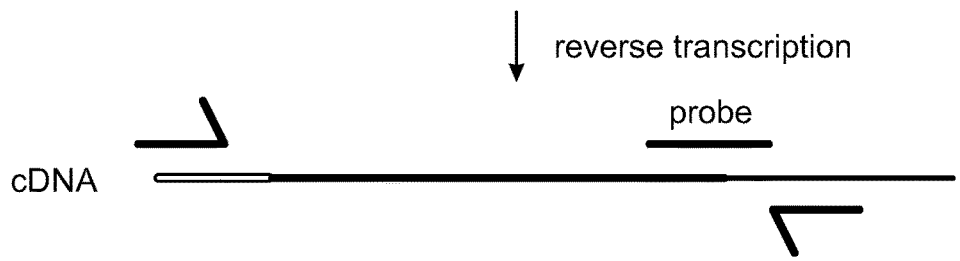
Figure 5C:
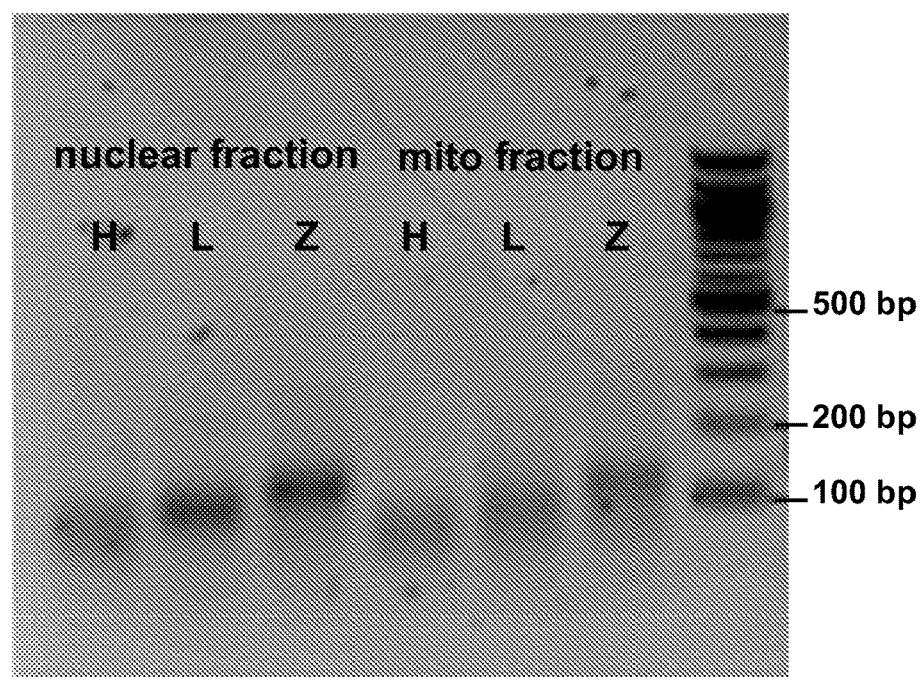

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 Molecular Cloning: A Laboratory Manual, 18.1-18.88. In illustrative embodiments, sgRNA can be detected by a specificalized stem-loop primers. The multiple stem loop structures in SpCas9 RNA provide significant thermostability during reverse transcription (RT) and PCR. To detect the mito-loop sgRNA targets by qPCR, the qPCR method for amplifying miRNA towards sgRNA was adapted. The concept is illustrated in FIGS. 5A-5C. A 44 nucleotide stem loop is attached to the 5' end of the RT primer (FIG. 5A). After reverse transcription, the cDNA is amplified using primers that overlap the target/spacer domain and the stem loop of the RT primer, denoted by the half arrows. A Taqman PCR probe overlaps both portions of the sgRNA and the stem loop (FIG. 5B). FIG. 5C shows the amplified product of the cDNA after qPCR from a nuclear and mitochondrial fractionation of samples that are untransduced with mitoloops (H) or transduced with LDF (labeled L) or zDF (labeled Z) mito-sgRNA. Exemplary primers are listed in the table below.

| | |
|---|---|
| RT primer | 5'-GTCGTATCCAGTGCGAATACCTCGGACCCTGCAC TGGATACGACCGGACTAGCCTT-3' |
| | (SEQ ID NO: 109) |
| qPCR_R | 5'-TACCTCGGACCCTGCACTGG-3' |
| | (SEQ ID NO: 110) |
| qPCR_14787_F | 5'-GGTTAGTTTTATTAGGGTTTTAGAGC-3' |
| | (SEQ ID NO: 111) |
| TaqMan probe | 5'-AGCAAGTTAAAATAAGGCTAGTCCGGTCGT-3' |
| | (SEQ ID NO: 112) |

Sequence in bold represents addition of stemloop.

The term "mitochondrial localization sequence" or "mitochondria targeting signal" and the like refer, in the usual and customary sense, to a short peptide sequence (about 3-70 amino acids long) that directs a newly synthesized proteins to the mitochondria within a cell. It is usually found at the N-terminus and consists of an alternating pattern of hydrophobic and positively charged amino acids to form what is called an amphipathic helix. Mitochondrial localization sequences can contain additional signals that subsequently target the protein to different regions of the mitochondria, such as the mitochondrial matrix. One exemplary mitochondrial localization sequence is the mitochondrial localization sequence derived from Cox8.

The term "Cox8" and the like refer, in the usual and customary sense, to cytochrome c oxidase subunit VIII. As used herein, the term refers to both biomolecules having the sequence of Cox8 and truncated and substituted versions thereof, including proteins and nucleic acids encoding the proteins, and to a sequence that performs the function of the cytochrome c oxidase subunit VIII, which function, as known in the art, is coupling of the transfer of electrons from cytochrome c to molecule oxygen, as the terminal step of the respiratory chain. The sequence of Cox8 (GenBank J04823.1) follows:

(SEQ ID NO: 54)
GGCTACGGCTGACCGTTTTTTGTGGTGTACTCCGTGCCATC<u>ATGTCCGT</u>

<u>CCTGACGCCGCTGCTGCTGCGGGGCTTGACAGGCTCGGCCCGGCGGCTC</u>

<u>CCAGTGCCGCGCGCCAAGATCCATTCGTTGCCGCCGGAGGGGAAGCTTG</u>

GGATCATGGAATTGGCCGTTGGGCTTACCTCCTGCTTCGTGACCTTCCT

CCTGCCAGCGGGCTGGATCCTGTCACACCTGGAGACCTACAGGAGGCCA

GAGTGAAGGGGTCCGTTCTGTCCCTCACACTGTGACCTGACCAGCCCCA

CCGGCCCATCCTGGTCATGTTACTGCATTTGTGGCCGGCCTCCCCTGGA

-continued

TCATGTCATTCAATTCCAGTCACCTCTTCTGCAATCATGACCTCTTGAT

GTCTCCATGGTGACCTCCTTGGGGGTCACTGACCCTGCTTGGTGGGGTC

CCCCTTGTAACAATAAATCTATTTAAACTTT

[Underlined sequence: the mitochondrial localization sequence of Cox8]

In embodiments, a mitochondrial localization sequence derived from Cox8 includes the amino acid sequence: MSVLTPLLLRGLTGSARRLPVPRAKIHSL (SEQ ID NO: 1). In the embodiments, the mitochondrial localization sequence derived from Cox8 includes an amino acid sequence that is about 50%, 55%, 60%, 65%, 70%, 75%, 80%, 85%, 90% or 95% identity to SEQ ID NO:1.

In embodiments, a mitochondrial localization sequence derived from Cox8 includes the nucleic acid sequence: ATGTCCGTCCTGACGCCGCTGCTGCTGCGGG GCTTGACAGGCTCGGCCCGGCGGCTCCC AGTGCCGCGCGCCAAGATCCATTCGTTG (SEQ ID NO: 2). In embodiments, the mitochondrial localization sequence derived from Cox8 includes a nucleic acid sequence that is about 50%, 55%, 60%, 65%, 70%, 75%, 80%, 85%, 90% or 95% identity to SEQ ID NO:2.

A "nuclear localization sequence" or "nuclear localization signal (NLS)" is a peptide that directs proteins to the nucleus. In embodiments, the NLS includes five basic, positively charged amino acids. The NLS may be located anywhere on the peptide chain.

A "mitochondrial import sequence" or "mitochondrial RNA import sequence" refers to an RNA sequence (e.g. small RNAs) capable of directing importation of exogenous RNA to mitochondria. The mitochondrial import sequence may be isolated from or derived from the mitochondrial transcriptome. Exemplary mitochondrial import sequences include, but are not limited to, the 5S ribosomal RNA, RNaseP ("RNP") and MRP RNA components and a modified γ domain of 5S rRNA, including D loop, F loop, MRP loop, RNP loop, γ 5 s loop including the sequence indicated in Table 1 below (see also FIG. 2A). Detailed description of small RNAs as mitochondrial import sequences can be found in Schneider et al., Annu Rev Biochem., 2011, 80:1033-53; Wang et al., Cell, 2010, 142(3):456-67; Comte et al., Nucelic Acids Res, 2013, 41(1):418-33; Tonin et al., J Biol Chem, 2014, 289(19): 13323-34; Smironov et al., RNA, 2008, 14(4):749-59; and Zelenka et al., J Bioenerg Biomembr, 2014, 46(2):147-56, contents of each of which are incorporated herein as entireties.

TABLE 1

| mitochondrial import sequence | Sequence |
|---|---|
| D loop | GCGCAATCGGTAGCGC (SEQ ID NO: 3) |
| F loop | GAGCCCCCTACAGGGCTC (SEQ ID NO: 4) |
| MRP | AGAAGCGTATCCCGCTGAGC (SEQ ID NO: 5) |
| RNP loop | TCTCCCTGAGCTTCAGGGAG (SEQ ID NO: 6) |

TABLE 1-continued

| mitochondrial import sequence | Sequence |
|---|---|
| γ 5s loop | GGCCTGGTTAGTACTTGGATGGGAGACCGCCAAGGAATACCGGGTG (SEQ ID NO: 7) |

In embodiments, the mitochondrial import sequence includes a nucelic acid sequence that is about 50%, 55%, 60%, 65%, 70%, 75%, 80%, 85%, 90%, 91%, 92%, 93%, 94%, 95%, 96%, 97%, 98%, 99% or 100% identity to SEQ ID NO: 3, 4, 5, 6 or 7.

For specific proteins described herein (e.g., Cas9, Cpf1, and the like), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

Thus, a "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the Uni-Prot reference number Q99ZW2 or a variant or homolog having substantial identity thereto. Cas9 refers to the protein also known in the art as "nickase". In embodiments, Cas9 is an RNA-guided DNA endonuclease enzyme that binds a CRISPR (clustered regularly interspaced short palindromic repeats) nucleic acid sequence. In embodiments, the CRISPR nucleic acid sequence is a prokaryotic nucleic acid sequence. In embodiments, the Cas9 nuclease from *Streptococcus pyogenes* is targeted to genomic DNA by a synthetic guide RNA consisting of a 20-nt guide sequence and a scaffold. The guide sequence base-pairs with the DNA target, directly upstream of a requisite 5'-NGG protospacer adjacent motif (PAM), and Cas9 mediates a double-stranded break (DSB) about 3-base pair upstream of the PAM. In embodiments, the CRISPR nuclease from *Streptococcus aureus* is targeted to genomic DNA by a synthetic guide RNA consisting of a 21-23-nt guide sequence and a scaffold. The guide sequence base-pairs with the DNA target, directly upstream of a requisite 5'-NNGRRT protospacer adjacent motif (PAM), and Cas9 mediates a double-stranded break (DSB) about 3-base pair upstream of the PAM.

The term "Cas9 variant" refers to proteins that have at least 80%, 85%, 90%, 95%, 96%, 97%, 98%, 99% or 100% amino acid sequence identity across the whole sequence or a functional portion of the sequence (e.g. a 50, 100, 150 or 200 continuous amino acid portion) compared to wild-type Cas9 protein and have one or more mutations that increase its binding specificity to PAM compared to wild-type Cas9 protein. Exemplary Cas9 variants are listed in the Table 2 below.

TABLE 2

| Cas9 Variants | PAM domains | References |
|---|---|---|
| Strep pyogenes (Sp) Cas9 | NGG | Hsu et al. 2014 Cell |
| Staph aureus (Sa) Cas9 | NNGRRT or NNGRR NNGGGT, NNGAAT, NNGAGT (Zetsche) | Ran et al. 2015 Nature |
| SpCas9 VQR mutant (D1135V, R1335Q, T1337R) | NGAG > NGAT = NGAA > NGAC NGCG | Kleinstiver et al. 2015 Nature |
| SpCas9 VRER mutant (D1135V/ G1218R/R1335E/ T1337R) | NGCG | Kleinstiver et al. 2015 Nature |
| SpCas9 D1135E | NGG, greater fidelity, less cutting at NAG and NGA sites | Kleinstiver et al. 2015 Nature |
| eSpCas9 1.1 mutant (K848A/ K1003A/R1060A) | NGG | Slaymaker et al. Science 2015 |
| SpCas9 HF1 (Q695A, Q926A, N497A, R661A) | NGG | Kleinstiver et al. 2016 Nature |
| AsCpf1 | TTTN (5' of sgRNA) | Zetsche et al. 2015 Cell |

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) may generated in four sequential steps. First, two non-coding RNAs, the pre-crRNA array and tracrRNA, may be transcribed from the CRISPR locus. Second, tracrRNA may hybridize to the direct repeats of pre-crRNA, which is then processed into mature crRNAs containing individual spacer sequences. Third, the mature crRNA:tracrRNA complex may direct Cas9 to the DNA target consisting of the protospacer and the corresponding PAM via heteroduplex formation between the spacer region of the crRNA and the protospacer DNA. Finally, Cas9 may mediate cleavage of target DNA upstream of PAM to create a DSB within the protospacer.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The terms "single guide RNA," "single guide RNA sequence," "chimeric RNA," "chimeric guide RNA," "guide RNA", and "synthetic guide RNA" are used interchangeably and refer to the polynucleotide sequence including the crRNA sequence and optionally the tracrRNA sequence. The crRNA sequence includes a guide sequence (i.e., "guide" or "spacer") and a tracr mate sequence (i.e., direct repeat(s)"). The term "guide sequence" refers to the sequence that specifies the target site.

In general, a guide sequence is any polynucleotide sequence having sufficient complementarity with a target polynucleotide sequence to hybridize with the target sequence (i.e., a mitochondrial DNA target sequence) and direct sequence-specific binding of a CRISPR complex to the target sequence (i.e., the mitochondrial DNA target sequence). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any mitochondrial DNA (mtDNA) target sequence. The term "mitochondrial DNA (mtDNA) target sequence" refers, in the usual and customary sense, to a nucleic acid sequence within the mitochondrial genome to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A guide sequence (spacer) may comprise any polynucleotide, such as DNA or RNA polynucleotides. In embodiments, a guide sequence (spacer) includes a nucleic acid sequence of one of SEQ ID Nos: 55-105. A target sequence may comprise any polynucleotide, such as DNA or RNA polynucleotides. In embodiments, an mtDNA target sequence includes one or more point mutations, one or more deletions, or any combination thereof. In embodiments, an mtDNA target sequence includes a nucleic acid sequence of one of SEQ ID Nos:8-22 or a fragment thereof. In embodiments, the mtDNA target sequence includes a nucleic acid sequence having at least 80%, 85%, 90%, 95%, 96%, 97%, 98%, 99% or 100% sequence identity to one of SEQ ID Nos:8-22 or a fragment thereof.

TABLE 3

| mtDNA targets | mtDNA mutation sequence | target/spacer RNA |
|---|---|---|
| 14787 cytochrome b (cyt b) deletion 4 bp (TTAA) | CCAATGACCCCAATACGCAAAA TTAACCCCCTAATAAAACTAA_ _CCACTCATTCATCGACCTCCC CACCCCATCCAACATCTCCGC (SEQ ID NO: 8) | 1. GAGTGGTTAGTTTTATTAGG (SEQ ID NO: 55)<br>2. AATGAGTGGTTAGTTTTATTA (SEQ ID NO: 56) |
| 3243A > G | CAGGGTTTGTTAAGATGGCAg GCCCGGTAATCGCATAAAACTT AA (SEQ ID NO: 9) | 1. CAGGGTTTGTTAAGATGGCA (SEQ ID NO: 57)<br>2. ACAGGGTTTGTTAAGATGGC (SEQ ID NO: 58) |
| 3271T > C | CCCGGTAATCGCATAAAACTTA AAACcTTACAGTCAGAGGTTCA ATTCCTCTTCTT (SEQ ID NO: 10) | 1. GAATTGAACCTCTGACTGTA (SEQ ID NO: 59)<br>2. ACTTAAAACCTTACAGTCAG (SEQ ID NO: 60) |
| 8344A > G | GCATTAACCTTTTAAGTTAAAG ATTAAGAGAgCCAACACCTCTC TACAGTGAAATGCCCCAACTA (SEQ ID NO: 11) | 1. CTTTTAAGTTAAAGATTAAG (SEQ ID NO: 61)<br>2. TTTAAGTTAAAGATTAAGAG (SEQ ID NO: 62) |
| 8356T > C | CCTTTTAAGTTAAAGATTAAGA GAACCAACACCTCTcTACAGTG AAATGCCCCAACTAAATAC (SEQ ID NO: 12) | 1. TGGGGCATTTCACTGTAGAG (SEQ ID NO: 63)<br>2. TAGTTGGGGCATTTCACTGT (SEQ ID NO: 64) |
| 8993T > G | CCATCAGCCTACTCATTCAACC AATAGCCCgGGCCGTACGCCTA ACCGCTAACATTACTGCAG (SEQ ID NO: 13) | 1. AGGCGTACGGCCCGGGCTAT (SEQ ID NO: 65)<br>2. TACTCATTCAACCAATAGCC (SEQ ID NO: 66)<br>3. AGCGGTTAGGCGTACGGCCC (SEQ ID NO: 67)<br>4. GGCGTACGGCCCGGGCTATTGG (SEQ ID NO: 68) |
| 8993T > C | CCATCAGCCTACTCATTCAACC AATAGCCCcGGCCGTACGCCTA ACCGCTAACATTACTGCAG (SEQ ID NO: 14) | 1. AGGCGTACGGCCGGGGCTAT (SEQ ID NO: 69)<br>2. TTAGCGGTTAGGCGTACGGC (SEQ ID NO: 70)<br>3. AGCGGTTAGGCGTACGGCCG (SEQ ID NO: 71)<br>4. GCGTACGGCCGGGGCTATTGG (SEQ ID NO: 72) |
| 3460G > A | GGGCTACTACAACCCTTCGCTG ACaCCATAAAACTCTTCACCAA AGAGCCCCT (SEQ ID NO: 15) | 1. GAGTTTTATGGTGTCAGCGA (SEQ ID NO: 73)<br>2. GAAGAGTTTTATGGTGTCAGCG (SEQ ID NO: 74)<br>3. GTGAAGAGTTTTATGGTGTCAGC (SEQ ID NO: 75)<br>4. TGGTGTCAGCGAAGGGTTGTAGT (SEQ ID NO: 76)<br>5. GTGAAGAGTTTTATGGTGTC (SEQ ID NO: 77) |
| 11778G > A | GCCTAGCAAACTCAAACTACGA ACGCACTCACAGTCaCATCATA ATCCTCTCTCAAGGACTTCAAA CTCTACTCCC (SEQ ID NO: 16) | 1. GAGAGAGGATTATGATGTGACT (SEQ ID NO: 78)<br>2. CACATCATAATCCTCTCTCA (SEQ ID NO: 79)<br>3. GATTATGATGTGACTGTGAG (SEQ ID NO: 80)<br>4. GAGGATTATGATGTGACTG (SEQ ID NO: 81) |
| 14484T > C | GCCATCGCTGTAGTATATCCAA AGACAACCAcCATTCCCCCTAA ATAAATTAAAAAAACTATTAAA CC (SEQ ID NO: 17) | 1. TTTAATTTATTTAGGGGGAA (SEQ ID NO: 82)<br>2. AATTTATTTAGGGGGAATGG (SEQ ID NO: 83)<br>3. GGGGGAATGGTGGTTGTCTT (SEQ ID NO: 84)<br>4. TAGGGGGAATGGTGGTTGTCT (SEQ ID NO: 85)<br>5. ATTTATTTAGGGGGAATGGTGGT (SEQ ID NO: 86)<br>6. GGGGGAATGGTGGTTGTCTTTGG (SEQ ID NO: 87)<br>7. TTTAATTTATTTAGGGGGAATGG (SEQ ID NO: 88) |

TABLE 3-continued

| mtDNA targets | mtDNA mutation sequence | target/spacer RNA |
|---|---|---|
| 14709T > C | ATTCTCGCACGGACTACAACCA CGACCAATGATAcGAAAAACCA TCGTTGTATTTCAACTACAAGA (SEQ ID NO: 18) | 1. ACGATGGTTTTTCGTATCAT (SEQ ID NO: 89)<br>2. GTATCATTGGTCGTGGTTGTAGT (SEQ ID NO: 90)<br>3. TCGTATCATTGGTCGTGGTTGTA (SEQ ID NO: 91)<br>4. GTTTTTCGTATCATTGGTCG (SEQ ID NO: 92) |
| 1555A > G | CCCCTACGCATTTATATAGAGG AGACAAGTCGTAACATGGTAAG (SEQ ID NO: 19) | 1. CCCCTACGCATTTATATAGA (SEQ ID NO: 93)<br>2. AGAGGAGACAAGTCGTAACA (SEQ ID NO: 94)<br>3. TGTCTCCTCTATATAAATGCGT (SEQ ID NO: 95)<br>4. TATAGAGGAGACAAGTCGTAACA (SEQ ID NO: 96) |
| 10158T > C | GACTACCACAACTCAACGGCTA CATAGAAAAAcCCACCCCTTAC GAGTGCGGCTTCGACCC (SEQ ID NO: 20) | 1. AAACCCACCCCTTACGAGTG (SEQ ID NO: 97)<br>2. AAGCCGCACTCGTAAGGGGT (SEQ ID NO: 98)<br>3. CATAGAAAAACCCACCCCTT (SEQ ID NO: 99) |
| 10191T > C | CCCCTTACGAGTGCGGCTTCGA CCCTATAcCCCCCGCCCGCGTC CCTTTCTCCATAAAATTCTTCT TAG (SEQ ID NO: 21) | 1. GGACGCGGGCGGGGGGTATA (SEQ ID NO: 100)<br>2. GAGAAAGGGACGCGGGCGGG (SEQ ID NO: 101)<br>3. GAAAGGGACGCGGGCGGGGGTA (SEQ ID NO: 102) |
| 6930G > A | GAAATGATCTGCTGCAGTGCTC TGAGCCCTAaGATTCATCTTTC TTTTCACCGTAGGTGGCCTGAC TGGC (SEQ ID NO: 22) | 1. GAAAAGAAAGATGAATCTT (SEQ ID NO: 103)<br>2. AAGATGAATCTTAGGGCTC (SEQ ID NO: 104)<br>3. GATGAATCTTAGGGCTCAG (SEQ ID NO: 105) |

In general, a tracr mate sequence includes any sequence that has sufficient complementarity with a tracr sequence (i.e., a tracrRNA sequence) to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin.

Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. Where the tracrRNA sequence is less than 100 (99 or less) nucleotides in length the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length.

In embodiments, the tracrRNA sequence for S. pyogenes is:
5'-gttggaaccattcaaaacagcatagcaagttaaaataaggctagtccgttat-caacttgaaaaagtggcaccgagtcggtgcttttt-3' (SEQ ID NO: 23). In embodiments, the tracrRNA sequence may have 80%, 85%, 90%, 91%, 92%, 93%, 94%, 95%, 96%, 97%, 98%, 99% or 100% sequence identity to SEQ ID NO: 23.

In embodiments, the crRNA with or without tracrRNA sequence for exemplary Class II CRISPR endonucleases may include:

TABLE 4

| crRNA ± tracrRNA of RNA-mediated endonuclease | |
|---|---|
| SpCas9 | GTTTTAGAGCTAGAAATAGCAAGTTAAAATAAGGCTAGTC CGTTATCAACTTGAAAAAGTGGCACCGAGTCGGTGC (SEQ ID NO: 106) |
| SaCas9 | GTTTTAGTACTCTGGAAACAGAATCTACTAAAACAAGGCA AAATGCCGTGTTTATCTCGTCAACTTGTTGGCGAGA (SEQ ID NO: 107) |
| Cpf1 | TAATTTCTACTCTTGTAGAT (SEQ ID NO: 108) |

The term "transfecting," "transfection" and the like refer, in the usual and customary sense, to the process of introducing nucleic acids into cells.

The compositions described herein can be purified. Purified compositions are at least about 60% by weight (dry weight) the compound of interest. Preferably, the preparation is at least about 75%, more preferably at least about 90%, and most preferably at least about 99% or higher by weight the compound of interest. Purity is measured by any appropriate standard method, for example, by High-performance liquid chromatography, polyacrylamide gel electrophoresis.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

A "pharmaceutical composition" is a formulation containing the nucleic acids described herein in a form suitable for administration to a subject. In embodiments, the pharmaceutical composition is in bulk or in unit dosage form. The unit dosage form is any of a variety of forms, including, for example, a capsule, an IV bag, a tablet, a single pump on an aerosol inhaler or a vial.

The quantity of active ingredient (e.g., a formulation of the disclosed nucleic acid) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In embodiments, the active nucleic acid is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. A thorough discussion of pharmaceutically acceptable excipients is available in REMINGTON'S PHARMACEUTICAL SCIENCES (Mack Pub. Co., N.J. 1991). Pharmaceutically acceptable excipients in therapeutic compositions may contain liquids such as water, saline, glycerol and ethanol. Additionally, auxiliary substances, such as wetting or emulsifying agents, pH buffering substances, and the like, may be present in such vehicles.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical composition of the invention can be administered to a subject in many of the well-known methods currently used for chemotherapeutic treatment. For example, for treatment of cancers, a composition of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The terms "subject," "individual," and "patient" are used interchangeably herein to refer to a vertebrate, preferably a mammal, more preferably a human. The mammal can be e.g., a human or appropriate non-human mammal, such as primate, mouse, rat, dog, cat, cow, horse, goat, camel, sheep or a pig. The subject can also be a bird or fowl. Tissues, cells and their progeny of a biological entity obtained in vivo or cultured in vitro are also encompassed. As used herein, a "subject in need thereof" or "a patient" may be a subject having a mitochondria disease.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal).

As used herein, "mitochondrial disorders" related to disorders which are due to abnormal mitochondria such as for example, a mitochondrial genetic mutation, enzyme pathways etc. Examples of disorders include and are not limited to: loss of motor control, muscle weakness and pain, gastrointestinal disorders and swallowing difficulties, poor growth, cardiac disease, liver disease, diabetes, respiratory complications, seizures, visual/hearing problems, lactic acidosis, developmental delays and susceptibility to infection. The mitochondrial abnormalities give rise to "mitochondrial diseases" which include, but not limited to: AD: Alzheimer's Disease; ADPD: Alzheimer's Disease and Parkinsons's Disease; AMDF: Ataxia, Myoclonus and Deafness CIPO: Chronic Intestinal Pseudoobstruction with myopathy and Opthalmoplegia; CPEO: Chronic Progressive External Opthalmoplegia; DEAF: Maternally inherited DEAFness or aminoglycoside-induced DEAFness; DEMCHO: Dementia and Chorea; DMDF: Diabetes Mellitus & DeaFness; Exercise Intolerance; ESOC: Epilepsy, Strokes, Optic atrophy, & Cognitive decline; FBSN: Familial Bilateral Striatal Necrosis; FICP: Fatal Infantile Cardiomyopathy Plus, a MELAS-associated cardiomyopathy; GER: Gastrointestinal Reflux; KSS Kearns Sayre Syndrome LDYT: Leber's hereditary optic neuropathy and DYsTonia; LHON: Leber Hereditary Optic Neuropathy; LIMM: Lethal Infantile Mitochondrial Myopathy; MDM: Myopathy and Diabetes Mellitus; MELAS: Mitochondrial Encephalomyopathy, Lactic Acidosis, and Stroke-like episodes; MEPR: Myoclonic Epilepsy and Psychomotor Regression; MERME: MERRF/MELAS overlap disease; MERRF: Myoclonic Epilepsy and Ragged Red Muscle Fibers; MHCM: Maternally Inherited Hypertrophic CardioMyopathy; MICM: Maternally Inherited Cardiomyopathy; MILS: Maternally Inherited Leigh Syndrome; Mitochondrial Encephalocardiomyopathy; Mitochondrial Encephalomyopathy; MM: Mitochondrial Myopathy; MMC: Maternal Myopathy and Cardiomyopathy; Multisystem Mitochondrial Disorder (myopathy, encephalopathy, blindness, hearing loss, peripheral neuropathy); NARP: Neurogenic muscle weakness, Ataxia, and Retinitis Pigmentosa; alternate phenotype at this locus is reported as Leigh Disease; NIDDM: Non-Insulin Dependent Diabetes Mellitus; PEM: Progressive Encephalopathy; PME: Progressive Myoclonus Epilepsy; RTT: Rett Syndrome; SIDS: Sudden Infant Death Syndrome.

In embodiments, a mitochondrial disorder is selected from the group consisting of Myoclonic Epilepsy with Ragged Red Fibers (MERRF); Mitochondrial Myopathy, Encephalopathy, Lactidosis, and Stroke (MELAS); Maternally Inherited Diabetes and Deafness (MIDD); Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (CoQ10) Deficiency; Complex I Deficiency; Complex II Deficiency; Complex III Deficiency; Complex IV Deficiency; Complex V Deficiency; other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; hearing and balance impairments; or other neurological disorders; epilepsy; genetic diseases; Huntington's Disease; mood disorders; nucleoside reverse transcriptase inhibitors (NRTI) treatment; HIV-associated neuropathy; schizophrenia; bipolar disorder; age-associated diseases; cerebral vascular diseases; macular degeneration; diabetes; and cancer.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

II. Compositions

In a first aspect, there is provided a composition including a delivery vehicle and a protein including a mitochondrial localization amino acid sequence covalently attached to an RNA-guided DNA endonuclease enzyme, wherein the protein is bound to the delivery vehicle. The term "delivery vehicle" or "carrier" refers to any support structure that brings about the transfer of a component of genetic material or a protein. Genetic material includes but is not limited to DNA, RNA or fragments thereof and proteins or polypeptides comprise amino acids and include but are not limited to antigens, antibodies, ligands, receptors or fragments thereof. Delivery vehicles include but are not limited to vectors such as viruses (examples include but are not limited to retroviruses, adenoviruses, adeno-associated viruses, pseudotyped viruses, replication competent viruses, herpes simplex virus), virus capsids, liposomes or liposomal vesicles, lipoplexes, polyplexes, dendrimers, macrophages, artificial chromosomes, nanoparticles, polymers and also hybrid particles, examples of which include virosomes. Delivery vehicles may have multiple surfaces and compartments for attachment and storage of components. These include but are not limited to outer surfaces and inner compartments.

In embodiments, the delivery vehicle is a nanoparticle or a lipid particle or a viral vector. Any nanoparticles known for protein or nucleic acid delivery can be used for the invention described herein. Nanoparticles are particles between 1 and 100 nanometers in size. Recent dramatic advances in nanotechnology have led to the development of a variety of nanoparticles (NPs) that provide valuable tools. Numerous nanomaterials such as polymers, liposomes, protein based NPs and inorganic NPs have been developed and a variety of particles are currently being evaluated in clinical studies with promising initial results; and some liposomal NPs are approved by the FDA. One of the major advantages of using these NPs is that they offer targeted tissue/site delivery. Their small size allows NPs to escape through blood vessels at the target site through the leaky vascular structure (Enhanced permeability and retention effect). In addition to this passive mechanism, a variety of targeting moieties can be attached to NPs to confer active targeting capability. Exemplary nanoparticles that can be used for delivering compositions described herein include, but are not limited to, solid nanoparticles (e.g., metals such as silver, gold, iron, titanium), non-metal, lipid-based solids (e.g., liposome), polymers (e.g., polyethylenimene, dendrimer), suspensions of nanoparticles, or combinations thereof (e.g., polyethylenimene-liposome, dendrisome). Any compositions described herein (such as Mito-Cas9, mito-Cpf1, or other mito-RNA guided nucleases (mito-RGN)) may be delivered in nanopoarticle complexes in the form of protein, DNA, or mRNA. Additional information about nanoparticles that can be used by the compositions described herein can be found in Coelho et al., N Engl J Med 2013; 369:819-29, Tabernero et al., Cancer Discovery, April 2013, Vol. 3, No. 4, pages 363-470, Zhang et al., WO2015089419 A2, and Zuris J A et al., Nat Biotechnol. 2015; 33(1):73-80, each of which is incorporated herein by reference.

In embodiments, the vector is a replication-incompetent viral vector. For example, the replication-incompetent viral vector is a replication-incompetent DNA viral vector (including, but is not limited to, adenoviruses, adeno-associated viruses). For example, the replication-incompetent viral vector is a replication-incompetent RNA viral vector (including, but is not limited to, replication defective retroviruses, lentiviruses, and rabies viruses).

In embodiments, the delivery vehicle is a lipid particle—a particle having lipid as a component, usch as liposomes or liposomal vesicles or lipoplexes. Liposomes, also known as vesicles, are generally composed of phospholipids and other lipid components such as cholesterol. They can function as carriers whose essential structural feature is a bipolar lipid membrane which envelops an aqueous core volume in which pharmacological agents are solubilized and therefore encapsulated. Various lipid formulations and methods for their preparation have been described for the delivery of pharmaceutically active agents to a host. For example, Geho and Lau in U.S. Pat. No. 4,603,044 describe a targeted liposomal delivery system for delivery of a drug to the hepatobiliary receptors of the liver. The system is composed of a drug or diagnostic agent encapsulated in or associated with lipid membrane structures in the form of vesicles or liposomes, and a molecule having a fatty substituent attached to the vesicle wall and a target substituent which is a biliary attracted chemical, such as a substituted iminodiacetate complex. The system is particularly useful for the delivery of insulin and serotonin in the treatment of Types I and II diabetes, respectively. Several cationic lipid reagents have become commercially available for transfecting eukaryotic cells. These examples include Lipofectin® (DOTMA: DOPE) (Invitrogen, Carlsbad, Calif.), LipofectAmine™ (DOSPA:DOPE)(Invitrogen), LipofectAmine2000™ (Invitrogen), LipofectAmine 3000™ (Invitrogen), Lipofectamine RNAiMax™ (Invitrogen), Lipofectamme LTX™ (Thermo Fisher Scientific), Fugene®, Transfectam® (DOGS), Effectene®, DC-Chol. US Patent Publication No. 20050019923 involves cationic dendrimers for delivering bioactive molecules, such as polynucleotide molecules, peptides and polypeptides and/or pharmaceutical agents, to a mammalian body, given the low toxicity and targeting specificity. Other derivatives of cationic dendrimer mentioned in Bioactive Polymers, US published application 20080267903, may also be suitable delivery vehicles for mitoCas9 gene therapy.

Various polymeric formulations of biologically active agents and methods for their preparation have been described. U.S. Pat. Nos. 3,773,919, 3,991,776, 4,076,779, 4,093,709, 4,118,470, 4,131,648, 4,138,344, 4,293,539 and 4,675,189, inter alia, disclose the preparation and use of biocompatible, biodegradable polymers, such as poly (lactic acid), poly(glycolic acid), copolymers of glycolic and lactic acids, poly (o-hydroxycarboxy lie acid), polylactones, polyacetals, polyorthoesters and polyorthocarbonates, for the encapsulation of drugs and medicaments. These polymers mechanically entrap the active constituents and later provide controlled release of the active ingredient via polymer dissolution or degradation. Certain condensation polymers formed from divinyl ethers and polyols are described in Polymer Letters, 18,293 (1980). Polymers have proven to be successful controlled-release drug delivery devices.

More information about liposomal constructs or polymeric constructs that can be used for the present invention can be found at Schwendener R A et al., Ther Adv Vaccines. 2014 November; 2(6): 159-182; Li Y et al., J Gene 2011, Med 13: 60-72; Pichon C et al., Methods Mol Biol 2013 969: 247-274; McNamara M A et al., J Immunol Res. 2015; 2015: 794528; Sayour E. J. et al., *Journal for Immunotherapy of Cancer.* 2015; 3, article 13; Bettinger T. et al, *Current Opinion in Molecular Therapeutics.* 2001; 3(2):116-124; Lu D. et al., *Cancer Gene Therapy.* 1994; 1(4):245-252; Wasungu L. et al., *Journal of Controlled Release.* 2006; 116(2):255-264; Little S. et al., *Proceedings of the National Academy of Sciences of the United States of America.* 2004; 101(26):9534-9539; Phua K. et al., *Journal of Controlled Release.* 2013; 166(3):227-233; Su X et al., *Molecular Pharmaceutics* 0.2011; 8(3):774-787; Phua K. K. L. et al., Nanoscale. 2014; 6(14):7715-7729; Phua K. K. L. et al., Scientific Reports.2014; 4, article 5128.

In embodiments, the protein is encapsulated within said delivery vehicle. Encapsulation can be carried out by any methods known in the art.

In embodiments, the mitochondrial localization amino acid sequence is N-terminal to the RNA-guided DNA endonuclease enzyme.

In embodiments, the mitochondrial localization amino acid sequence is the mitochondrial localization amino acid sequence of cytochrome c oxidase subunit VIII (Cox8) sequence.

In embodiments, the RNA-guided DNA endonuclease enzyme is Cas9 or Cpf1 or a Class II CRISPR endonuclease.

In embodiments, the RNA-guided DNA endonuclease enzyme is Cas9 (aka Strep *pyogenes* Cas9), containing the amino acid sequence of SEQ ID NO: 24 or an amino acid sequence having at least 80%, 85%, 90%, 95%, 96%, 97%, 98%, 99% or 100% identity to SEQ ID NO: 24 (or appropriate portion thereof).

```
                                            (SEQ ID NO: 24)
DKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKEDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD
```

In embodiments, the RNA-guided DNA endonuclease enzyme is Cpf1 (aka AsCpf1), containing the amino acid sequence of SEQ ID NO: 25 or an amino acid sequence having at least 80%, 85%, 90%, 95%, 96%, 97%, 98%, 99% or 100% identity to SEQ ID NO: 25 (or appropriate portion thereof).

```
                                            (SEQ ID NO: 25)
TQFEGFTNLYQVSKTLRFELIPQGKTLKHIQEQGFIEEDKARNDHYKELK

PIIDRIYKTYADQCLQLVQLDWENLSAAIDSYRKEKTEETRNALIEEQAT

YRNAIHDYFIGRTDNLTDAINKRHAEIYKGLFKAELFNGKVLKQLGTVTT

TEHENALLRSFDKFTTYFSGEYENRKNVFSAEDISTAIPHRIVQDNFPKF

KENCHIFTRLITAVPSLREHFENVKKAIGIFVSTSIEEVFSFPFYNQLLT

QTQIDLYNQLLGGISREAGTEKIKGLNEVLNLAIQKNDETAHIIASLPHR

FIPLFKQILSDRNTLSFILEEFKSDEEVIQSFCKYKTLLRNENVLETAEA

LFNELNSIDLTHIFISHKKLETISSALCDHWDTLRNALYERRISELTGKI

TKSAKEKVQRSLKHEDINLQEIISAAGKELSEAFKQKTSEILSHAHAALD

QPLPTTLKKQEEKEILKSQLDSLLGLYHLLDWFAVDESNEVDPEFSARLT

GIKLEMEPSLSFYNKARNYATKKPYSVEKFKLNFQMPTLASGWDVNKEKN

NGAILFVKNGLYYLGIMPKQKGRYKALSFEPTEKTSEGFDKMYYDYFPDA

AKMIPKCSTQLKAVTAHFQTHTTPILLSNNFIEPLEITKEIYDLNNPEKE

PKKFQTAYAKKTGDQKGYREALCKWIDFTRDFLSKYTKTTSIDLSSLRPS

SQYKDLGEYYAELNPLLYHISFQRIAEKEIMDAVETGKLYLFQIYNKDFA

KGHHGKPNLHTLYWTGLFSPENLAKTSIKLNGQAELFYRPKSRMKRMAHR

LGEKMLNKKLKDQKTPIPDTLYQELYDYVNHRLSHDLSDEARALLPNVIT

KEVSHEIIKDRRFTSDKFFFHVPITLNYQAANSPSKFNQRVNAYLKEHPE

TPIIGIDRGERNLIYITVIDSTGKILEQRSLNTIQQFDYQKKLDNREKER

VAARQAWSVVGTIKDLKQGYLSQVIHEIVDLMIHYQAVVVLENLNFGFKS

KRTGIAEKAVYQQFEKMLIDKLNCLVLKDYPAEKVGGVLNPYQLTDQFTS

FAKMGTQSGFLFYVPAPYTSKIDPLTGFVDPFVWKTIKNHESRKHFLEGF

DFLHYDVKTGDFILHFKMNRNLSFQRGLPGFMPAWDIVFEKNETQFDAKG

TPFIAGKRIVPVIENHRFTGRYRDLYPANELIALLEEKGIVFRDGSNILP

KLLENDDSHAIDTMVALIRSVLQMRNSNAATGEDYINSPVRDLNGVCFDS

RFQNPEWPMDADANGAYHIALKGQLLLNHLKESKDLKLQNGISNQDWLAY

IQELRN.
```

In embodiments, the RNA-guided DNA endonuclease enzyme is a Class II CRISPR endonuclease. A Class II CRISPR endonuclease can be identified via a method known in the art. Type II CRISPR-Cas systems are defined by the presence of a single subunit crRNA effector module. The Cpf1 enzyme belongs to a putative type V CRISPR-Cas system. Both type II and type V systems are included in Class II of the CRISPR-Cas system. Type II system are specific to bacteria whereas type V system is present in at least one archeon, see Makarova Nat Rev Microbiol 2015.

In embodiments, the RNA-guided DNA endonuclease enzyme has no nuclear localization sequence.

In embodiments, the Cas9 is a Cas9 variant, wherein the Cas9 variant has one or more mutations that increase its binding specificity to PAM compared to wild type Cas9. Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in Table 2, and the skilled person will be able to identify further PAM sequences for use with a given CRISPR enzyme. The binding specificity of Cas9 or Cas9 variants to PAM can be determined by any method known in the art, for example, methods described in the references in Table 2 above.

In embodiments, the RNA-guided DNA endonuclease enzyme is Staph *aureus* Cas9, containing the amino acid sequence of SEQ ID NO: 26 or an amino acid sequence having at least 80%, 85%, 90%, 95%, 96%, 97%, 98%, 99% or 100% identity to SEQ ID NO: 26 (or appropriate portion thereof).

(SEQ ID NO: 26)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTREQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQIIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF

NYEVDHIIPRSVSFDNSFNNKVLVKQEENSKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRELINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYREDVYLDNGVYKFVTVKNLDVIKKENYYEVNSKCYEEAK

KLKKISNQAEFIASFYNNDLIKINGELYRVIGVNNDLLNRIEVNMIDITY

REYLENMNDKRPPRIIKTIASKTQSIKKYSTDILGNLYEVKSKKHPQIIK

KG

In embodiments, the RNA-guided DNA endonuclease enzyme is SpCas9 VQR mutant, containing the amino acid sequence of SEQ ID NO: 27 or an amino acid sequence having at least 80%, 85%, 90%, 95%, 96%, 97%, 98%, 99% or 100% identity to SEQ ID NO: 27 (or appropriate portion thereof).

(SEQ ID NO: 27)
DKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLILTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFVSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKQYRSTKEVLDATLIHQS

ITGLYETRIDLSQLGGD

[Bold and underlined residues indicate the mutations D1135V, R1335Q and T1337R]

In embodiments, the RNA-guided DNA endonuclease enzyme is SpCas9 VRER mutant, containing the amino acid sequence of SEQ ID NO: 28 or an amino acid sequence having at least 80%, 85%, 90%, 95%, 96%, 97%, 98%, 99% or 100% identity to SEQ ID NO: 28 (or appropriate portion thereof).

(SEQ ID NO: 28)
DKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFVSPTVAYSVLVVAKVEK

GKSKKLKSVKELLGITIMERSSFEKNPIDFLEAKGYKEVKKDLIIKLPKY

SLFELENGRKRMLASARELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKEYRSTKEVLDATLIHQS

ITGLYETRIDLSQLGGD

[Bold and underlined residues indicate the mutations D1135V, G1218R, R1335E and T1337R]

In embodiments, the RNA-guided DNA endonuclease enzyme is SpCas9 D1135E mutant, containing the amino acid sequence of SEQ ID NO: 29 or an amino acid sequence having at least 80%, 85%, 90%, 95%, 96%, 97%, 98%, 99% or 100% identity to SEQ ID NO: 29 (or appropriate portion thereof).

(SEQ ID NO: 29)
DKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKN

LSDAILLSDILRVNTEITKAPLSASMIKRYDEHHQDLTLLKALVRQQLP

EKYKEIFFDQSKNGYAGYIDGGASQEEFYKFIKPILEKMDGTEELLVKL

NREDLLRKQRTFDNGSIPHQIHLGELHAILRRQEDFYPFLKDNREKIEK

ILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFL

SGEQKKAIVDLLFKTNRKVTVKQLKEDYFKKIECFDSVEISGVEDRFNA

SLGTYHDLLKIIKDKDFLDNEENEDILEDIVLILTLFEDREMIEERLKT

YAHLFDDKVMKQLKRRRYTGWGRLSRKLINGIRDKQSGKTILDFLKSDG

FANRNFMQLIHDDSLTFKEDIQKAQVSGQGDSLHEHIANLAGSPAIKKG

ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLKDDSIDNKVLTRSDKNRGKSDNVPSEEVVKKMKNYW

RQLLNAKLITQRKFDNLTKAERGGLSELDKAGFIKRQLVETRQITKHVA

QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFESPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGD

[Bold and underlined residue indicates the mutation D1135E]

In embodiments, the RNA-guided DNA endonuclease enzyme is eSpCas9 1.1 mutant, containing the amino acid sequence of SEQ ID NO: 30 or an amino acid sequence having at least 80%, 85%, 90%, 95%, 96%, 97%, 98%, 99% or 100% identity to SEQ ID NO: 30 (or appropriate portion thereof).

(SEQ ID NO: 30)
DKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKN

LSDAILLSDILRVNTEITKAPLSASMIKRYDEHHQDLTLLKALVRQQLP

EKYKEIFFDQSKNGYAGYIDGGASQEEFYKFIKPILEKMDGTEELLVKL

NREDLLRKQRTFDNGSIPHQIHLGELHAILRRQEDFYPFLKDNREKIEK

ILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFL

SGEQKKAIVDLLFKTNRKVTVKQLKEDYFKKIECFDSVEISGVEDRFNA

-continued

```
SLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDG

FANRNFMQLIHDDSLIFKEDIQKAQVSGQGDSLHEHIANLAGSPAIKKG

ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLADDSIDNKVLTRSDKNRGKSDNVPSEEVVKKMKNYW

RQLLNAKLITQRKFDNLTKAERGGLSELDKAGFIKRQLVETRQITKHVA

QILDSRMNTKYDENDKLIREVKVITLKSKLVSDFRKDFQFYKVREINNY

HHAHDAYLNAVVGTALIKKYPALESEFVYGDYKVYDVRKMIAKSEQEIG

KATAKYFFYSNIMNFFKTEITLANGEIRKAPLIETNGETGEIVWDKGRD

FATVRKVLSMPQVNIVKKTEVQTGGESKESILPKRNSDKLIARKKDWDP

KKYGGFDSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGD

[Bold and underlined residues indicate the mutations K848A/K1003A/R1060A]
```

In embodiments, the RNA-guided DNA endonuclease enzyme is SpCas9 HF1 mutant, containing the amino acid sequence of SEQ ID NO: 31 or an amino acid sequence having at least 80%, 85%, 90%, 95%, 96%, 97%, 98%, 99% or 100% identity to SEQ ID NO: 31 (or appropriate portion thereof).

```
                                    (SEQ ID NO: 31)
DKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFH

RLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSL

GLTPNFKSNFDLAEDAKLQLSKDTYDDDLDNLLAQIGDQYADLFLAAKN

LSDAILLSDILRVNTEITKAPLSASMIKRYDEHHQDLTLLKALVRQQLP

EKYKEIFFDQSKNGYAGYIDGGASQEEFYKFIKPILEKMDGTEELLVKL

NREDLLRKQRTFDNGSIPHQIHLGELHAILRRQEDFYPFLKDNREKIEK

ILTFRIPYYVGPLARGNSRFAWMTRKSEETITPWNFEEVVDKGASAQSF

IERMTAFDKNLPNEKVLPKHSLLYEYFTVYNELTKVKYVTEGMRKPAFL

SGEQKKAIVDLLFKTNRKVTVKQLKEDYFKKIECFDSVEISGVEDRFNA

SLGTYHDLLKIIKDKDFLDNEENEDILEDIVLTLTLFEDREMIEERLKT

YAHLFDDKVMKQLKRRRYTGWGALSRKLINGIRDKQSGKTILDFLKSDG

FANRNFMALIHDDSLTFKEDIQKAQVSGQGDSLHEHIANLAGSPAIKKG

ILQTVKVVDELVKVMGRHKPENIVIEMARENQTTQKGQKNSRERMKRIE

EGIKELGSQILKEHPVENTQLQNEKLYLYYLQNGRDMYVDQELDINRLS

DYDVDHIVPQSFLKDDSIDNKVLTRSDKNRGKSDNVPSEEVVKKMKNYW

RQLLNAKLITQRKFDNLTKAERGGLSELDKAGFIKRQLVETRAITKHVA

QILDSRMNTKYDENDKLIREVKVITLKSKLVSDFRKDFQFYKVREINNY

HHAHDAYLNAVVGTALIKKYPKLESEFVYGDYKVYDVRKMIAKSEQEIG

KATAKYFFYSNIMNFFKTEITLANGEIRKRPLIETNGETGEIVWDKGRD

FATVRKVLSMPQVNIVKKTEVQTGGFSKESILPKRNSDKLIARKKDWDP

KKYGGFDSPTVAYSVLVVAKVEKGKSKKLKSVKELLGITIMERSSFEKN

PIDFLEAKGYKEVKKDLIIKLPKYSLFELENGRKRMLASAGELQKGNEL

ALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAF

KYFDTTIDRKRYTSTKEVLDATLIHQSITGLYETRIDLSQLGGD

[Bold and underlined residues indicate the mutations Q695A, Q926A, N497A and R661A]
```

In embodiments, the composition described herein includes a delivery vehicle (e.g., a nanoparticle, a lipid particle or a viral vector) and a protein that comprises a mitochondrial localization amino acid sequence covalently attached to Cas9, where the protein is bound to the delivery vehicle, the mitochondrial localization amino acid sequence includes an amino acid sequence of SEQ ID NO: 1 and the Cas9 protein includes an amino acid sequence of SEQ ID NO: 24.

In embodiments, the composition described herein includes a delivery vehicle (e.g., a nanoparticle, a lipid particle or a viral vector) and a protein that contains a mitochondrial localization amino acid sequence covalently attached to Cpf1, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cpf1 protein includes an amino acid sequence having at least 80%, 85%, 90%, 95%, 96%, 97%, 98%, 99% or 100% identity to SEQ ID NO: 24.

In embodiments, the composition described herein includes a delivery vehicle (e.g., a nanoparticle, a lipid particle or a viral vector) and a protein that contains a mitochondrial localization amino acid sequence covalently attached to Cpf1, where the protein is bound to the delivery vehicle, the mitochondrial localization amino acid sequence includes an amino acid sequence of SEQ ID NO: 1 and the Cpf1 protein includes an amino acid sequence of SEQ ID NO: 25.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 25.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence of SEQ ID NO: 1 and the Cas9 variant protein includes an amino acid sequence of SEQ ID NO: 26.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 26.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence of SEQ ID NO: 1 and the Cas9 variant protein includes an amino acid sequence of SEQ ID NO: 27.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 27.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence of SEQ ID NO: 1 and the Cas9 variant protein includes an amino acid sequence of SEQ ID NO: 28.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 28.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence of SEQ ID NO: 1 and the Cas9 variant protein includes an amino acid sequence of SEQ ID NO: 29.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 29.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence of SEQ ID NO: 1 and the Cas9 variant protein includes an amino acid sequence of SEQ ID NO: 30.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 30.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence of SEQ ID NO: 1 and the Cas9 variant protein includes an amino acid sequence of SEQ ID NO: 31.

In embodiments, the composition described herein includes a delivery vehicle (e.g., a nanoparticle, a lipid particle or a viral vector) and a protein that contains a mitochondrial localization amino acid sequence covalently attached to a Cas9 variant, where the protein is bound to the delivery vehicle, the mitochondrial localization amino acid sequence includes an amino acid sequence having at least 80%, 85%, 90%, 95%, 96%, 97%, 98%, 99% or 100% identity to SEQ ID NO: 1 and the Cas9 variant protein includes an amino acid sequence having at least 80%, 85%, 90%, 95%, 96%, 97%, 98%, 99% or 100% identity to SEQ ID NO: 31.

In another aspect, there is provided a composition including a delivery vehicle and a nucleic acid encoding a protein as disclosed herein. In embodiments, the composition includes a delivery vehicle and a nucleic acid encoding a protein according to any aspect or embodiment disclosed above.

In embodiments, the composition includes a delivery vehicle and a nucleic acid encoding a protein that includes a mitochondrial localization amino acid sequence (e.g., SEQ ID NO:1) covalently attached to an RNA-guided DNA endonuclease enzyme (e.g., Cas9, Cpf1, or a Class II CRISPR endonuclease), where the nucleic acid is bound to the delivery vehicle.

In embodiments, a nucleic acid encoding a mitochondrial localization amino acid sequence includes the nucleic acid sequence of SEQ ID NO: 2 or a nucleic acid having at least 80%, 85%, 90%, 95%, 96%, 97%, 98%, 99% or 100% identity to SEQ ID NO: 2.

In embodiments, a nucleic acid encoding Cas9 includes the nucleic acid sequence of SEQ ID NO: 33 or a nucleic acid having at least 80%, 85%, 90%, 95%, 96%, 97%, 98%, 99% or 100% identity to SEQ ID NO: 32.

```
                                            (SEQ ID NO: 32)
gacaagaagt acagcatcgg cctggacatc ggcaccaact ctgtgggctg ggccgtgatc accgacgagt acaaggtgcc cagcaagaaa ttcaaggtgc tgggcaacac cgaccggcac agcatcaaga agaacctgat cggagccctg ctgttcgaca gcggcgaaac agccgaggcc acccggctga agagaaccgc cagaagaaga tacaccagac ggaagaaccg gatctgctat ctgcaagaga tcttcagcaa cgagatggcc aaggtggacg acagcttctt ccacagactg gaagagtcct tcctggtgga agaggataag aagcacgagc ggcaccccat cttcggcaac atcgtggacg aggtggccta ccacgagaag taccccacca tctaccacct gagaaagaaa ctggtggaca gcaccgacaa ggccgacctg cggctgatct atctggccct ggcccacatg atcaagttcc ggggccactt cctgatcgag ggcgacctga accccgacaa cagcgacgtg gacaagctgt tcatccagct ggtgcagacc tacaaccagc tgttcgagga aaaccccatc aacgccagcg gcgtggacgc caaggccatc ctgtctgcca gactgagcaa gagcagacgg ctggaaaatc tgatcgccca gctgcccggc gagaagaaga tggcctgtt cggaaacctg attgccctga gcctgggcct gaccccaac ttcaagagca acttcgacct ggccgaggat gccaaactgc agctgagcaa ggacacctac gacgacgacc tggacaacct gctggcccag atcggcgacc agtacgccga cctgtttctg gccgccaaga acctgtccga cgccatcctg ctgagcgaca tcctgagagt gaacaccgag atcaccaagg cccccctgag cgcctctatg atcaagagat acgacgagca ccaccaggac ctgaccctgc tgaaagctct cgtgcggcag cagctgcctg agaagtacaa agagattttc ttcgaccaga gcaagaacgg ctacgccggc tacattgacg gcggagccag ccaggaagag ttctacaagt tcatcaagcc catcctggaa aagatggacg gcaccgagga actgctcgtg aagctgaaca gagaggacct gctgcggaag cagcggacct tcgacaacgg cagcatcccc caccagatcc acctgggaga gctgcacgcc attctgcggc ggcaggaaga
```

-continued
```
ttttttaccca ttcctgaagg acaaccggga aaagatcgag aagatcctga ccttccgcat cccctactac gtgggccctc tggccagggg aaacagcaga ttcgcctgga tgaccagaaa gagcgaggaa accatcaccc cctggaactt cgaggaagtg gtggacaagg gcgcttccgc ccagagcttc atcgagcgga tgaccaactt cgataagaac ctgcccaacg agaaggtgct gcccaagcac agcctgctgt acgagtactt caccgtgtat aacgagctga ccaaagtgaa atacgtgacc gagggaatga gaaagcccgc cttcctgagc ggcgagcaga aaaaggccat cgtggacctg ctgttcaaga ccaaccggaa agtgaccgtg aagcagctga agaggacta cttcaagaaa atcgagtgct tcgactccgt ggaaatctcc ggcgtggaag atcggttcaa cgcctccctg ggcacatacc acgatctgct gaaaattatc aaggacaagg acttcctgga caatgaggaa aacgaggaca ttctggaaga tatcgtgctg accctgacac tgtttgagga cagagagatg atcgaggaac ggctgaaaac ctatgcccac ctgttcgacg acaaagtgat gaagcagctg aagcggcgga gatacaccgg ctggggcagg ctgagccgga agctgatcaa cggcatccgg gacaagcagt ccggcaagac aatcctggat ttcctgaagt ccgacggctt cgccaacaga aacttcatgc agctgatcca cgacgacagc ctgaccttta aagaggacat ccagaaagcc caggtgtccg gccagggcga tagcctgcac gagcacattg ccaatctggc cggcagcccc gccattaaga agggcatcct gcagacagtg aaggtggtgg acgagctcgt gaaagtgatg ggccggcaca gcccgagaa catcgtgatc gaaatggcca gagagaacca gaccacccag aagggacaga agaacagccg cgagagaatg aagcggatcg aagagggcat caaagagctg ggcagccaga tcctgaaaga acacccgtg gaaaacaccc agctgcagaa cgagaagctg tacctgtact acctgcagaa tgggcgggat atgtacgtgg accaggaact ggacatcaac cggctgtccg actacgatgt ggaccatatc gtgcctcaga gctttctgaa ggacgactcc atcgacaaca aggtgctgac cagaagcgac aagaaccggg gcaagagcga caacgtgccc tccgaagagg tcgtgaagaa gatgaagaac tactggcggc agctgctgaa cgccaagctg attcccaga gaaagttcga caatctgacc aaggccgaga gaggcggcct gagcgaactg gataaggccg gcttcatcaa gagacagctg gtggaaaccc ggcagatcac aaagcacgtg gcacagatcc tggactcccg gatgaacact aagtacgacg agaatgacaa gctgatccgg gaagtgaaag tgatcaccct gaagtccaag ctggtgtccg atttccggaa ggatttccag ttttacaaag
```

-continued

```
tgcgcgagat caacaactac caccacgccc acgacgccta
cctgaacgcc gtcgtgggaa ccgccctgat caaaaagtac
cctaagctgg aaagcgagtt cgtgtacggc gactacaagg
tgtacgacgt gcggaagatg atcgccaaga gcgagcagga
aatcggcaag gctaccgcca agtacttctt ctacagcaac
atcatgaact ttttcaagac cgagattacc ctggccaacg
gcgagatccg gaagcggcct ctgatcgaga caaacggcga
aaccggggag atcgtgtggg ataagggccg ggattttgcc
accgtgcgga aagtgctgag catgccccaa gtgaatatcg
tgaaaaagac cgaggtgcag acaggcggct tcagcaaaga
gtctatcctg cccaagagga acagcgataa gctgatcgcc
agaaagaagg actgggaccc taagaagtac ggcggcttcg
acagccccac cgtggcctat tctgtgctgg tggtggccaa
agtggaaaag ggcaagtcca agaaactgaa gagtgtgaaa
gagctgctgg ggatcaccat catggaaaga agcagcttcg
agaagaatcc catcgacttt ctggaagcca agggctacaa
agaagtgaaa aaggacctga tcatcaagct gcctaagtac
tccctgttcg agctggaaaa cggccggaag agaatgctgg
cctctgccgg cgaactgcag aagggaaacg aactggccct
gccctccaaa tatgtgaact tcctgtacct ggccagccac
tatgagaagc tgaagggctc ccccgaggat aatgagcaga
aacagctgtt tgtggaacag cacaagcact acctggacga
gatcatcgag cagatcagcg agttctccaa gagagtgatc
ctggccgacg ctaatctgga caaagtgctg tccgcctaca
acaagcaccg ggataagccc atcagagagc aggccgagaa
tatcatccac ctgtttaccc tgaccaatct gggagcccct
gccgccttca agtactttga caccaccatc gaccggaaga
ggtacaccag caccaaagag gtgctggacg ccaccctgat
ccaccagagc atcaccgccc tgtacgagac acggatcgac
ctgtctcagc tgggaggcga c
```

In embodiments, a nucleic acid encoding Cpf1 includes the nucleic acid sequence of SEQ ID NO: 33 or a nucleic acid having at least 80%, 85%, 90%, 95%, 96%, 97%, 98%, 99% or 100% identity to SEQ ID NO: 33.

```
                                        (SEQ ID NO: 33)
ACACAGTTCGAGGGCTTTACCAACCTGTATCAGGTGAGCAAGACACTGCG

GTTTGAGCTGATCCCACAGGGCAAGACCCTGAAGCACATCCAGGAGCAGG

GCTTCATCGAGGAGGACAAGGCCCGCAATGATCACTACAAGGAGCTGAAG

CCCATCATCGATCGGATCTACAAGACCTATGCCGACCAGTGCCTGCAGCT

GGTGCAGCTGGATTGGGAGAACCTGAGCGCCGCCATCGACTCCTATAGAA

AGGAGAAAACCGAGGAGACAAGGAACGCCCTGATCGAGGAGCAGGCCACA

TATCGCAATGCCATCCACGACTACTTCATCGGCCGGACAGACAACCTGAC

CGATGCCATCAATAAGAGACACGCCGAGATCTACAAGGGCCTGTTCAAGG

CCGAGCTGTTTAATGGCAAGGTGCTGAAGCAGCTGGGCACCGTGACCACA

ACCGAGCACGAGAACGCCCTGCTGCGGAGCTTCGACAAGTTTACAACCTA

CTTCTCCGGCTTTTATGAGAACAGGAAGAACGTGTTCAGCGCCGAGGATA

TCAGCACAGCCATCCCACACCGCATCGTGCAGGACAACTTCCCCAAGTTT

AAGGAGAATTGTCACATCTTCACACGCCTGATCACCGCCGTGCCCAGCCT

GCGGGAGCACTTTGAGAACGTGAAGAAGGCCATCGGCATCTTCGTGAGCA

CCTCCATCGAGGAGGTGTTTTCCTTCCCTTTTTATAACCAGCTGCTGACA

CAGACCCAGATCGACCTGTATAACCAGCTGCTGGGAGGAATCTCTCGGGA

GGCAGGCACCGAGAAGATCAAGGGCCTGAACGAGGTGCTGAATCTGGCCA

TCCAGAAGAATGATGAGACAGCCCACATCATCGCCTCCCTGCCACACAGA

TTCATCCCCCTGTTTAAGCAGATCCTGTCCGATAGGAACACCCTGTCTTT

CATCCTGGAGGAGTTTAAGAGCGACGAGGAAGTGATCCAGTCCTTCTGCA

AGTACAAGACACTGCTGAGAAACGAGAACGTGCTGGAGACAGCCGAGGCC

CTGTTTAACGAGCTGAACAGCATCGACCTGACACACATCTTCATCAGCCA

CAAGAAGCTGGAGACAATCAGCAGCGCCCTGTGCGACCACTGGGATACAC

TGAGGAATGCCCTGTATGAGCGGAGAATCTCCGAGCTGACAGGCAAGATC

ACCAAGTCTGCCAAGGAGAAGGTGCAGCGCAGCCTGAAGCACGAGGATAT

CAACCTGCAGGAGATCATCTCTGCCGCAGGCAAGGAGCTGAGCGAGGCCT

TCAAGCAGAAAACCAGCGAGATCCTGTCCCACGCACACGCCGCCCTGGAT

CAGCCACTGCCTACAACCCTGAAGAAGCAGGAGGAGAAGGAGATCCTGAA

GTCTCAGCTGGACAGCCTGCTGGGCCTGTACCACCTGCTGGACTGGTTTG

CCGTGGATGAGTCCAACGAGGTGGACCCCGAGTTCTCTGCCCGGCTGACC

GGCATCAAGCTGGAGATGGAGCCTTCTCTGAGCTTCTACAACAAGGCCAG

AAATTATGCCACCAAGAAGCCCTACTCCGTGGAGAAGTTCAAGCTGAACT

TTCAGATGCCTACACTGGCCTCTGGCTGGGACGTGAATAAGGAGAAGAAC

AATGGCGCCATCCTGTTTGTGAAGAACGGCCTGTACTATCTGGGCATCAT

GCCAAAGCAGAAGGGCAGGTATAAGGCCCTGAGCTTCGAGCCCACAGAGA

AAACCAGCGAGGGCTTTGATAAGATGTACTATGACTACTTCCCTGATGCC

GCCAAGATGATCCCAAAGTGCAGCACCCAGCTGAAGGCCGTGACAGCCCA

CTTTCAGACCCACACAACCCCCATCCTGCTGTCCAACAATTTCATCGAGC

CTCTGGAGATCACAAAGGAGATCTACGACCTGAACAATCCTGAGAAGGAG

CCAAAGAAGTTTCAGACAGCCTACGCCAAGAAAACCGGCGACCAGAAGGG

CTACAGAGAGGCCCTGTGCAAGTGGATCGACTTCACAAGGGATTTTCTGT

CCAAGTATACCAAGACAACCTCTATCGATCTGTCTAGCCTGCGGCCATCC

TCTCAGTATAAGGACCTGGGCGAGTACTATGCCGAGCTGAATCCCCTGCT

GTACCACATCAGCTTCCAGAGAATCGCCGAGAAGGAGATCATGGATGCCG

TGGAGACAGGCAAGCTGTACCTGTTCCAGATCTATAACAAGGACTTTGCC

AAGGGCCACCACGGCAAGCCTAATCTGCACACACTGTATTGGACCGGCCT

GTTTTCTCCAGAGAACCTGGCCAAGACAAGCATCAAGCTGAATGGCCAGG
```

CCGAGCTGTTCTACCGCCCTAAGTCCAGGATGAAGAGGATGGCACACCGG

CTGGGAGAGAAGATGCTGAACAAGAAGCTGAAGGATCAGAAAACCCCAAT

CCCCGACACCCTGTACCAGGAGCTGTACGACTATGTGAATCACAGACTGT

CCCACGACCTGTCTGATGAGGCCAGGGCCCTGCTGCCCAACGTGATCACC

AAGGAGGTGTCTCACGAGATCATCAAGGATAGGCGCTTTACCAGCGACAA

GTTCTTTTTCCACGTGCCTATCACACTGAACTATCAGGCCGCCAATTCCC

CATCTAAGTTCAACCAGAGGGTGAATGCCTACCTGAAGGAGCACCCCGAG

ACACCTATCATCGGCATCGATCGGGGCGAGAGAAACCTGATCTATATCAC

AGTGATCGACTCCACCGGCAAGATCCTGGAGCAGCGGAGCCTGAACACCA

TCCAGCAGTTTGATTACCAGAAGAAGCTGGACAACAGGGAGAAGGAGAGG

GTGGCAGCAAGGCAGGCCTGGTCTGTGGTGGGCACAATCAAGGATCTGAA

GCAGGGCTATCTGAGCCAGGTCATCCACGAGATCGTGGACCTGATGATCC

ACTACCAGGCCGTGGTGGTGCTGGAGAACCTGAATTTCGGCTTTAAGAGC

AAGAGGACCGGCATCGCCGAGAAGGCCGTGTACCAGCAGTTCGAGAAGAT

GCTGATCGATAAGCTGAATTGCCTGGTGCTGAAGGACTATCCAGCAGAGA

AAGTGGGAGGCGTGCTGAACCCATACCAGCTGACAGACCAGTTCACCTCC

TTTGCCAAGATGGGCACCCAGTCTGGCTTCCTGTTTTACGTGCCTGCCCC

ATATACATCTAAGATCGATCCCCTGACCGGCTTCGTGGACCCCTTCGTGT

GGAAAACCATCAAGAATCACGAGAGCCGCAAGCACTTCCTGGAGGGCTTC

GACTTTCTGCACTACGACGTGAAAACCGGCGACTTCATCCTGCACTTTAA

GATGAACAGAAATCTGTCCTTCCAGAGGGGCCTGCCCGGCTTTATGCCTG

CATGGGATATCGTGTTCGAGAAGAACGAGACACAGTTTGACGCCAAGGGC

ACCCCTTTCATCGCCGGCAAGAGAATCGTGCCAGTGATCGAGAATCACAG

ATTCACCGGCAGATACCGGGACCTGTATCCTGCCAACGAGCTGATCGCCC

TGCTGGAGGAGAAGGGCATCGTGTTCAGGGATGGCTCCAACATCCTGCCA

AAGCTGCTGGAGAATGACGATTCTCACGCCATCGACACCATGGTGGCCCT

GATCCGCAGCGTGCTGCAGATGCGGAACTCCAATGCCGCCACAGGCGAGG

ACTATATCAACAGCCCCGTGCGCGATCTGAATGGCGTGTGCTTCGACTCC

CGGTTTCAGAACCCAGAGTGGCCCATGGACGCCGATGCCAATGGCGCCTA

CCACATCGCCCTGAAGGGCCAGCTGCTGCTGAATCACCTGAAGGAGAGCA

AGGATCTGAAGCTGCAGAACGGCATCTCCAATCAGGACTGGCTGGCCTAC

ATCCAGGAGCTGCGCAACAAAAGGCCGGCGGCCACGAAAAAGGCCGGCCA

GGCAAAAAAGAAAAAG

In embodiments, a nucleic acid encoding a Cas9 variant (SaCas9) includes the nucleic acid sequence of SEQ ID NO: 34 or a nucleic acid having at least 80%, 85%, 90%, 95%, 96%, 97%, 98%, 99% or 100% identity to SEQ ID NO: 34.

(SEQ ID NO: 34)
aagcggaactacatcctgggcctggacatcggcatcaccagcgtgggcta cggcatcatcgactacgagacacgggacgtgatcgatgccggcgtgcggc tgttcaaagaggccaacgtggaaaacaacgagggcaggcggagcaagaga ggcgccagaaggctgaagcggcggaggcggcatagaatccagagagtgaa gaagctgctgttcgactacaacctgctgaccgaccacagcgagctgagcg gcatcaaccctacgaggccagagtgaagggcctgagccagaagctgagc gaggaagagttctctgccgccctgctgcacctggccaagagaagaggcgt gcacaacgtgaacgaggtggaagaggacaccggcaacgagctgtccacca gagagcagatcagccggaacagcaaggccctggaagagaaatacgtggcc gaactgcagctggaacggctgaagaaagacggcgaagtgcggggcagcat caacagattcaagaccagcgactacgtgaaagaagccaaacagctgctga aggtgcagaaggcctaccaccagctggaccagagcttcatcgacacctac atcgacctgctggaaacccggcggacctactatgagggacctggcgaggg cagccccttcggctggaaggacatcaaagaatggtacgagatgctgatgg gccactgcacctacttccccgaggaactgcggagcgtgaagtacgcctac aacgccgacctgtacaacgccctgaacgacctgaacaatctcgtgatcac cagggacgagaacgagaagctggaatattacgagaagttccagatcatcg agaacgtgttcaagcagaagaagaagcccacctgaagcagatcgccaaa gaaatcctcgtgaacgaagaggatattaagggctacagagtgaccagcac cggcaagcccgagttcaccaacctgaaggtgtaccacgacatcaaggaca ttaccgcccggaaagagattattgagaacgccgagctgctggatcagatt gccaagatcctgaccatctaccagagcagcgaggacatccaggaagaact gaccaatctgaactccgagctgacccaggaagagatcgagcagatctcta atctgaagggctataccggcacccacaacctgagcctgaaggccatcaac ctgatcctggacgagctgtggcacaccaacgacaaccagatcgctatctt caaccggctgaagctggtgcccaagaaggtggacctgtcccagcagaaag atccccaccacctggtggacgacttcatcctgagccccgtcgtgaag agaagcttcatccagagcatcaaagtgatcaacgccatcatcaagaagta cggcctgcccaacgacatcattatcgagctggcccgcgagaagaactcca aggacgcccagaaaatgatcaacgagatgcagaagcggaaccggcagacc aacgagcggatcgaggaaatcatccggaccaccggcaaagagaacgccaa gtacctgatcgagaagatcaagctgcacgacatgcaggaaggcaagtgcc tgtacagcctggaagccatccctctggaagatctgctgaacaacccttc aactatgaggtggaccacatcatccccagaagcgtgtccttcgacaacag cttcaacaacaaggtgctcgtgaagcaggaagaaaacagcaagaagggca accggacccattccagtacctgagcagcagcgacagcaagatcagctac gaaaccttcaagaagcacatcctgaatctggccaagggcaagggcagaat cagcaagaccaagaaagagtatctgctggaagaacgggacatcaacaggt tctccgtgcagaaagacttcatcaaccggaacctggtggataccagatac gccaccagaggcctgatgaacctgctgcggagctacttcagagtgaacaa cctggacgtgaaagtgaagtccatcaatggcggcttcaccagctttctgc ggcggaagtggaagtttaagaaagagcggaacaaggggtacaagcaccac gccgaggacgccctgatcattgccaacgccgatttcatcttcaaagagtg gaagaaactggacaaggccaaaaaagtgatggaaaaccagatgttcgagg aaaagcaggccgagagcatgcccgagatcgaaaccgagcaggagtacaaa
gagatcttcatccccccaccagatcaagcacattaaggacttcaagga
ctacaagtacagccaccgggtggacaagaagcctaatagagagctgatta
acgacaccctgtactccacccggaaggacgacaagggcaacaccctgatc
gtgaacaatctgaacggcctgtacgacaaggacaatgacaagctgaaaaa
gctgatcaacaagagccccgaaaagctgctgatgtaccaccacgaccccc
agacctaccagaaactgaagctgattatggaacagtacggcgacgagaag
aatcccctgtacaagtactacgaggaaaccgggaactacctgaccaagta
ctccaaaaaggacaacggccccgtgatcaagaagattaagtattacggca
acaaactgaacgcccatctggacatcaccgacgactaccccaacagcaga
aacaaggtcgtgaagctgtccctgaagccctacagattcgacgtgtacct
ggacaatggcgtgtacaagttcgtgaccgtgaagaatctggatgtgatca
aaaagaaaactactacgaagtgaatagcaagtgctatgaggaagctaag
aagctgaagaagatcagcaaccaggccgagtttatcgcctccttctacaa
caacgatctgatcaagatcaacggcgagctgtatagagtgatcggcgtga
acaacgacctgctgaaccggatcgaagtgaacatgatcgacatcacctac
cgcgagtacctggaaaacatgaacgacaagaggccccccaggatcattaa
gacaatcgcctccaagacccagagcattaagaagtacagcacagacattc
tgggcaacctgtatgaagtgaaatctaagaagcaccctcagatcatcaaa
aagggc In embodiments, a nucleic acid encoding a Cas9 variant (SpCas9 VQR) includes the nucleic acid sequence of SEQ ID NO: 35 or a nucleic acid having at least 80%, 85%, 90%, 95%, 96%, 97%, 98%, 99% or 100% identity to SEQ ID NO: 35.

(SEQ ID NO: 35)
gataaaaagtattctattggtttagacatcggcactaattccgttggatg
ggctgtcataaccgatgaatacaaagtaccttcaaagaaatttaaggtgt
tggggaacacagaccgtcattcgattaaaaagaatcttatcggtgccctc
ctattcgatagtggcgaaacggcagaggcgactcgcctgaaacgaaccgc
tcggagaaggtatacacgtcgcaagaaccgaatatgttacttacaagaaa
ttttagcaatgagatggccaaagttgacgattctttctttcaccgtttg
gaagagtccttccttgtcgaagaggacaagaaacatgaacggcacccat
ctttggaaacatagtagatgaggtggcatatcatgaaaagtacccaacga
tttatcacctcagaaaaagctagttgactcaactgataaagcggacctg
aggttaatctacttggctcttgcccatatgataaagttccgtgggcactt
tctcattgagggtgatctaaatccggacaactcggatgtcgacaaactgt
tcatccagttagtacaaacctataatcagttgtttgaagagaaccctata
aatgcaagtggcgtggatgcgaaggctattcttagcccgcctctctaa
atcccgacggctagaaaacctgatcgcacaattacccggagagaagaaa
atgggttgttcggtaaccttatagcgctctcactaggcctgacaccaaat
tttaagtcgaacttcgacttagctgaagatgccaaattgcagcttagtaa
ggacacgtacgatgacgatctcgacaatctactggcacaaattggagatc
agtatgcggacttattttttggctgccaaaaaccttagcgatgcaatcctc
ctatctgacatactgagagttaatactgagattaccaaggcgccgttatc
cgcttcaatgatcaaaaggtacgatgaacatcaccaagacttgacacttc
tcaaggccctagtccgtcagcaactgcctgagaaatataaggaaatattc
tttgatcagtcgaaaaacgggtacgcaggttatattgacggcggagcgag
tcaagaggaattctacaagtttatcaaacccatattagagaagatggatg
ggacggaagagttgcttgtaaaactcaatcgcgaagatctactgcgaaag
cagcggactttcgacaacggtagcattccacatcaaatccacttaggcga
attgcatgctatacttagaaggcaggaggattttttatccgttcctcaaag
acaatcgtgaaaagattgagaaaatcctaacctttcgcataccttactat
gtgggacccctggcccgagggaactctcggttcgcatggatgacaagaaa
gtccgaagaaacgattactccatggaattttgaggaagttgtcgataaag
gtgcgtcagctcaatcgttcatcgagaggatgaccaactttgacaagaat
ttaccgaacgaaaagtattgcctaagcacagtttactttacgagtattt
cacagtgtacaatgaactcacgaaagttaagtatgtcactgagggcatgc
gtaaacccgcctttctaagcggagaacagaagaaagcaatagtagatctg
ttattcaagaccaaccgcaaagtgacagttaagcaattgaaagaggacta
ctttaagaaaattgaatgcttcgattctgtcgagatctccggggtagaag
atcgatttaatgcgtcacttggtacgtatcatgacctcctaaagataatt
aaagataaggacttcctggataacgaagagaatgaagatatcttagaaga
tatagtgttgactcttacctcttttgaagatcgggaaatgattgaggaaa
gactaaaaacatacgctcacctgttcgacgataaggttatgaaacagtta
aagaggcgtcgctatacgggctggggacgattgtcgcggaaaacttatcaa
cgggataagagacaagcaaagtggtaaaactattctcgatttctaaaga
gcgacggcttcgccaataggaactttatgcagctgatccatgatgactct
ttaaccttcaaagaggatatacaaaaggcacaggtttccggacaagggga
ctcattgcacgaacatattgcgaatcttgctggttcgccagccatcaaaa
agggcatactccagacagtcaaagtagtggatgagctagttaaggtcatg
ggacgtcacaaaccggaaaacattgtaatcgagatggcacgcgaaaatca
aacgactcagaaggggcaaaaaaacagtcgagagcggatgaagagaatag
aagagggtattaaagaactgggcagccagatcttaaaggagcatcctgtg
gaaaatacccaattgcagaacgagaaactttacctctattacctacaaaa
tggaagggacatgtatgttgatcaggaactggacataaaccgtttatctg
attacgacgtcgatcacattgtaccccaatccttttttgaaggacgattca
atcgacaataaagtgcttacacgctcggataagaaccgagggaaaagtga
caatgttccaagcgaggaagtcgtaaagaaaatgaagaactattggcggc
agctcctaaatgcgaaactgataacgcaaagaaagttcgataacttaact
aaagctgagaggggtggcttgtctgaacttgacaaggccggatttattaa
acgtcagctcgtggaaacccgccaaatcacaaagcatgttgcacagatac

```
tagattcccgaatgaatacgaaatacgacgagaacgataagctgattcgg
gaagtcaaagtaatcactttaaagtcaaaattggtgtcggacttcagaaa
ggattttcaattctataaagttagggagataaataactaccaccatgcgc
acgacgcttatcttaatgccgtcgtagggaccgcactcattaagaaatac
ccgaagctagaaagtgagtttgtgtatggtgattacaaagtttatgacgt
ccgtaagatgatcgcgaaaagcgaacaggagataggcaaggctacagcca
aatacttcttttattctaacattatgaatttctttaagacggaaatcact
ctggcaaacggagagatacgcaaacgacctttaattgaaccaatgggga
gacaggtgaaatcgtatgggataagggccgggacttcgcgacggtgagaa
aagttttgtccatgccccaagtcaacatagtaaagaaaactgaggtgcag
accggagggttttcaaaggaatcgattcttccaaaaaggaatagtgataa
gctcatcgctcgtaaaaaggactgggacccgaaaaagtacggtggcttcg
tgagccctacagttgcctattctgtcctagtagtggcaaaagttgagaag
ggaaaatccaagaaactgaagtcagtcaaagaattattggggataacgat
tatggagcgctcgtctttttgaaaagaaccccatcgacttccttgaggcga
aaggttacaaggaagtaaaaaaggatctcataattaaactaccaaagtat
agtctgtttgagttagaaaatggccgaaaacggatgttggctagcgccgg
agagcttcaaaaggggaacgaactcgcactaccgtctaaatacgtgaatt
tcctgtatttagcgtcccattacgagaagttgaaaggttcacctgaagat
aacgaacagaagcaacttttttgttgagcagcacaaacattatctcgacga
aatcatagagcaaatttcggaattcagtaagagagtcatcctagctgatg
ccaatctggacaaagtattaagcgcatacaacaagcacagggataaaccc
atacgtgagcaggcggaaaatattatccatttgtttactcttaccaacct
cggcgctccagccgcattcaagtattttgacacaacgatagatcgcaaac
agtacagatctaccaaggaggtgctagacgcgacactgattcaccaatcc
atcacgggattatatgaaactcggatagatttgtcacagcttgggggtga
c
```

In embodiments, a nucleic acid encoding a Cas9 variant (SpCas9 VRER) includes the nucleic acid sequence of SEQ ID NO: 36 or a nucleic acid having at least 80%, 85%, 90%, 95%, 96%, 97%, 98%, 99% or 100% identity to SEQ ID NO: 36.

```
                                            (SEQ ID NO: 36)
gataaaaagtattctattggtttagacatcggcactaattccgttggatg
ggctgtcataaccgatgaatacaaagtaccttcaaagaaatttaaggtgt
tggggaacacagaccgtcattcgattaaaaagaatcttatcggtgccctc
ctattcgatagtggcgaaacggcagaggcgactcgcctgaaacgaaccgc
tcggagaaggtatacacgtcgcaagaaccgaatatgttacttacaagaaa
tttttagcaatgagatggccaaagttgacgattctttctttcaccgtttg
gaagagtccttccttgtcgaagaggacaagaaacatgaacggcacccccat
cttttggaaacatagtagatgaggtggcatatcatgaaaagtacccaacga
tttatcacctcagaaaaaagctagttgactcaactgataaagcggacctg
aggttaatctacttggctcttgcccatatgataaagttccgtgggcactt
tctcattgagggtgatctaaatccggacaactcggatgtcgacaaactgt
tcatccagttagtacaaacctataatcagttgtttgaagagaaccctata
aatgcaagtggcgtggatgcgaaggctattcttagcgcccgcctctctaa
atcccgacggctagaaaacctgatcgcacaattacccggagagaagaaaa
atgggttgttcggtaaccttatagcgctctcactaggcctgacaccaaat
tttaagtcgaacttcgacttagctgaagatgccaaattgcagcttagtaa
ggacacgtacgatgacgatctcgacaatctactggcacaaattggagatc
agtatgcggacttattttttggctgccaaaaaccttagcgatgcaatcctc
ctatctgacatactgagagttaatactgagattaccaaggcgccgttatc
cgcttcaatgatcaaaaggtacgatgaacatcaccaagacttgacacttc
tcaaggccctagtccgtcagcaactgcctgagaaatataaggaaatattc
tttgatcagtcgaaaaacgggtacgcaggttatattgacggcggagcgag
tcaagaggaattctacaagtttatcaaacccatattagagaagatggatg
ggacggaagagttgcttgtaaaactcaatcgcgaagatctactgcgaaag
cagcggactttcgacaacggtagcattccacatcaaatccacttaggcga
attgcatgctatacttagaaggcaggaggattttttatccgttcctcaaag
acaatcgtgaaaagattgagaaaatcctaaccttttcgcataccttactat
gtgggacccctggcccgagggaactctcggttcgcatggatgacaagaaa
gtccgaagaaacgattactccatggaattttgaggaagttgtcgataaag
gtgcgtcagctcaatcgttcatcgagaggatgaccaactttgacaagaat
ttaccgaacgaaaaagtattgcctaagcacagtttactttacgagtattt
cacagtgtacaatgaactcacgaaagttaagtatgtcactgagggcatgc
gtaaacccgccttttctaagcggagaacagaagaaagcaatagtagatctg
ttattcaagaccaaccgcaaagtgacagttaagcaattgaaagaggacta
ctttaagaaaattgaatgcttcgattctgtcgagatctccggggtagaag
atcgatttaatgcgtcacttggtacgtatcatgacctcctaaagataatt
aaagataaggacttcctggataacgaagagaatgaagatatcttagaaga
tatagtgttgactcttaccctcttttgaagatcgggaaatgattgaggaaa
gactaaaaacatacgctcacctgttcgacgataaggttatgaaacagtta
aagaggcgtcgctatacgggctggggacgattgtcgcggaaacttatcaa
cgggataagagacaagcaaagtggtaaaactattctcgatttttctaaaga
gcgacggcttcgccaataggaactttatgcagctgatccatgatgactct
ttaaccttcaaagaggatatacaaaaggcacaggtttccggacaagggga
ctcattgcacgaacatattgcgaatcttgctggttcgccagccatcaaaa
agggcatactccagacagtcaaagtagtggatgagctagttaaggtcatg
ggacgtcacaaaccggaaaacattgtaatcgagatggcacgcgaaaatca
aacgactcagaaggggcaaaaaaacagtcgagagcggatgaagagaatag
aagagggtattaaagaactgggcagccagatcttaaaggagcatcctgtg
gaaaatacccaattgcagaacgagaaactttacctctattacctacaaaa
``` tggaagggacatgtatgttgatcaggaactggacataaaccgtttatctg
attacgacgtcgatcacattgtacccaatcttttgaaggacgattca
atcgacaataaagtgcttacacgctcggataagaaccgagggaaagtga
caatgttccaagcgaggaagtcgtaaagaaaatgaagaactattggcggc
agctcctaaatgcgaaactgataacgcaaagaaagttcgataacttaact
aaagctgagaggggtggcttgtctgaacttgacaaggccggatttattaa
acgtcagctcgtggaaaccgccaaatcacaaagcatgttgcacagatac
tagattcccgaatgaatacgaaatacgacgagaacgataagctgattcgg
gaagtcaaagtaatcactttaaagtcaaaattggtgtcggacttcagaaa
ggattttcaattctataaagttagggagataaataactaccaccatgcgc
acgacgcttatcttaatgccgtcgtagggaccgcactcattaagaaatac
ccgaagctagaaagtgagtttgtgtatggtgattacaaagtttatgacgt
ccgtaagatgatcgcgaaaagcgaacaggagataggcaaggctacagcca
aatacttcttttattctaacattatgaatttctttaagacggaaatcact
ctggcaaacggagagatacgcaaacgaccttaattgaaaccaatgggga
gacaggtgaaatcgtatgggataagggccgggacttcgcgacggtgagaa
aagtttgtccatgccccaagtcaacatagtaaagaaaactgaggtgcag
accggagggttttcaaaggaatcgattcttccaaaaaggaatagtgataa
gctcatcgctcgtaaaaaggactgggacccgaaaaagtacggtggcttcg
tgagccctacagttgcctattctgtcctagtagtggcaaaagttgagaag
ggaaaatccaagaaactgaagtcagtcaaagaattattggggataacgat
tatgggagcgctcgtcttttgaaaagaaccccatcgacttccttgaggcga
aaggttacaaggaagtaaaaaaggatctcataattaaactaccaaagtat
agtctgtttgagttagaaaatggccgaaaacggatgttggctagcgccag
agagcttcaaaaggggaacgaactcgcactaccgtctaaatacgtgaatt
tcctgtatttagcgtcccattacgagaagttgaaaggttcacctgaagat
aacgaacagaagcaacttttttgttgagcagcacaaacattatctcgacga
aatcatagagcaaatttcggaattcagtaagagagtcatcctagctgatg
ccaatctggacaaagtattaagcgcatacaacaagcacagggataaaccc
atacgtgagcaggcggaaaatattatccatttgtttactcttaccaacct
cggcgctccagccgcattcaagtattttgacacaacgatagatcgcaaag
agtacagatctaccaaggaggtgctagacgcgacactgattcaccaatcc
atcacgggattatatgaaactcggatagatttgtcacagcttgggggtga
c In embodiments, a nucleic acid encoding a Cas9 variant (SpCas9 D1135E) includes the nucleic acid sequence of SEQ ID NO: 37 or a nucleic acid having at least 80%, 85%, 90%, 95%, 96%, 97%, 98%, 99% or 100% identity to SEQ ID NO: 37.

(SEQ ID NO: 37)
gataaaaagtattctattggtttagacatcggcactaattccgttggatg
ggctgtcataaccgatgaatacaaagtaccttcaaagaaatttaaggtgt
tggggaacacagaccgtcattcgattaaaaagaatcttatcggtgccctc
ctattcgatagtggcgaaacggcagaggcgactcgcctgaaacgaaccgc
tcggagaaggtatacacgtcgcaagaaccgaatatgttacttacaagaaa
ttttagcaatgagatggccaaagttgacgattctttctttcaccgtttg
gaagagtccttccttgtcgaagaggacaagaaacatgaacggcaccccat
ctttggaaacatagtagatgaggtggcatatcatgaaaagtacccaacga
tttatcacctcagaaaaagctagttgactcaactgataaagcggacctg
aggttaatctacttggctcttgcccatatgataaagttccgtgggcactt
tctcattgagggtgatctaaatccggacaactcggatgtcgacaaactgt
tcatccagttagtacaaacctataatcagttgtttgaagagaaccctata
aatgcaagtggcgtggatgcgaaggctattcttagcgcccgcctctctaa
atcccgacggctagaaaaacctgatcgcacaattacccggagagaagaaa
atgggttgttcggtaaccttatagcgctctcactaggcctgacaccaaat
tttaagtcgaacttcgacttagctgaagatgccaaattgcagcttagtaa
ggacacgtacgatgacgatctcgacaatctactggcacaaattggagatc
agtatgcggacttatttttggctgccaaaaaccttagcgatgcaatcctc
ctatctgacatactgagagttaatactgagattaccaaggcgccgttatc
cgcttcaatgatcaaaaggtacgatgaacatcaccaagacttgacacttc
tcaaggccctagtccgtcagcaactgcctgagaaatataaggaaatattc
tttgatcagtcgaaaaacgggtacgcaggttatattgacggcggagcgag
tcaagaggaattctacaagtttatcaaacccatattagagaagatggatg
ggacggaagagttgcttgtaaaactcaatcgcgaagatctactgcgaaag
cagcggactttcgacaacggtagcattccacatcaaatccacttaggcga
attgcatgctatacttagaaggcaggaggattttatccgttcctcaaag
acaatcgtgaaaagattgagaaaatcctaaccttcgcataccttactat
gtgggacccctggcccgagggaactctcggttcgcatggatgacaagaaa
gtccgaagaaacgattactccatggaattttgaggaagttgtcgataaag
gtgcgtcagctcaatcgttcatcgagaggatgaccaactttgacaagaat
ttaccgaacgaaaaagtattgcctaagcacagtttactttacgagtattt
cacagtgtacaatgaactcacgaaagttaagtatgtcactgagggcatgc
gtaaacccgcctttctaagcggagaacagaagaaagcaatagtagatctg
ttattcaagaccaaccgcaaagtgacagttaagcaattgaaagaggacta
ctttaagaaaattgaatgcttcgattctgtcgagatctccggggtagaag
atcgatttaatgcgtcacttggtacgtatcatgacctcctaaagataatt
aaagataaggacttcctggataacgaagagaatgaagatatcttagaaga
tatagtgttgactcttacccctctttgaagatcgggaaatgattgaggaaa
gactaaaaacatacgctcacctgttcgacgataaggttatgaaacagtta
aagaggcgtcgctatacgggctggggacgattgtcgcggaaacttatcaa

```
cgggataagagacaagcaaagtggtaaaactattctcgattttctaaaga
gcgacggcttcgccaataggaactttatgcagctgatccatgatgactct
ttaaccttcaaagaggatatacaaaaggcacaggtttccggacaagggga
ctcattgcacgaacatattgcgaatcttgctggttcgccagccatcaaaa
agggcatactccagacagtcaaagtagtggatgagctagttaaggtcatg
ggacgtcacaaaccggaaaacattgtaatcgagatggcacgcgaaaatca
aacgactcagaaggggcaaaaaaacagtcgagagcggatgaagagaatag
aagagggtattaaagaactgggcagccagatcttaaaggagcatcctgtg
gaaaatacccaattgcagaacgagaaactttacctctattacctacaaaa
tggaagggacatgtatgttgatcaggaactggacataaaccgtttatctg
attacgacgtcgatcacattgtaccccaatccttttttgaaggacgattca
atcgacaataaagtgcttacacgctcggataagaaccgagggaaaagtga
caatgttccaagcgaggaagtcgtaaagaaaatgaagaactattggcggc
agctcctaaatgcgaaactgataacgcaaagaaagttcgataacttaact
aaagctgagaggggtggcttgtctgaacttgacaaggccggatttattaa
acgtcagctcgtggaaacccgccaaatcacaaagcatgttgcacagatac
tagattcccgaatgaatacgaaatacgacgagaacgataagctgattcgg
gaagtcaaagtaatcactttaaagtcaaaattggtgtcggacttcagaaa
ggattttcaattctataaagttagggagataaataactaccaccatgcgc
acgacgcttatcttaatgccgtcgtagggaccgcactcattaagaaatac
ccgaagctagaaagtgagtttgtgtatggtgattacaaagtttatgacgt
ccgtaagatgatcgcgaaaagcgaacaggagataggcaaggctacagcca
aatacttcttttattctaacattatgaatttctttaagacggaaatcact
ctggcaaacggagagatacgcaaacgacctttaattgaaccaatgggga
gacaggtgaaatcgtatgggataagggccgggacttcgcgacggtgagaa
aagtttttgtccatgccccaagtcaacatagtaaagaaaactgaggtgcag
accggagggttttcaaaggaatcgattcttccaaaaaggaatagtgataa
gctcatcgctcgtaaaaaggactgggacccgaaaaagtacggtggcttcg
agagccctacagttgcctattctgtcctagtagtggcaaaagttgagaag
ggaaaatccaagaaactgaagtcagtcaaagaattattggggataacgat
tatggagcgctcgtcttttgaaaagaaccccatcgacttccttgaggcga
aaggttacaaggaagtaaaaaaggatctcataattaaactaccaaagtat
agtctgtttgagttagaaaatggccgaaaacggatgttggctagcgccgg
agagcttcaaaaggggaacgaactcgcactaccgtctaaatacgtgaatt
tcctgtatttagcgtcccattacgagaagttgaaaggttcacctgaagat
aacgaacagaagcaactttttgttgagcagcacaaacattatctcgacga
aatcatagagcaaatttcggaattcagtaagagagtcatcctagctgatg
ccaatctggacaaagtattaagcgcatacaacaagcacagggataaaccc
atacgtgagcaggcggaaaatattatccatttgtttactcttaccaacct
cggcgctccagccgcattcaagtattttgacacaacgatagatcgcaaac
```

```
gatacacttctaccaaggaggtgctagacgcgacactgattcaccaatcc
atcacgggattatatgaaactcggatagatttgtcacagcttgggggtga
c
```

In embodiments, a nucleic acid encoding a Cas9 variant (eSpCas9 1.1 mutant) includes the nucleic acid sequence of SEQ ID NO: 38 or a nucleic acid having at least 80%, 85%, 90%, 95%, 96%, 97%, 98%, 99% or 100% identity to SEQ ID NO: 38.

(SEQ ID NO: 38)
```
GACAAGAAGTACAGCATCGGCCTGGACATCGGCACCAACTCTGTGGGCTG
GGCCGTGATCACCGACGAGTACAAGGTGCCCAGCAAGAAATTCAAGGTGC
TGGGCAACACCGACCGGCACAGCATCAAGAAGAACCTGATCGGAGCCCTG
CTGTTCGACAGCGGCGAAACAGCCGAGGCCACCCGGCTGAAGAGAACCGC
CAGAAGAAGATACACCAGACGGAAGAACCGGATCTGCTATCTGCAAGAGA
TCTTCAGCAACGAGATGGCCAAGGTGGACGACAGCTTCTTCCACAGACTG
GAAGAGTCCTTCCTGGTGGAAGAGGATAAGAAGCACGAGCGGCACCCCAT
CTTCGGCAACATCGTGGACGAGGTGGCCTACCACGAGAAGTACCCCACCA
TCTACCACCTGAGAAAGAAACTGGTGGACAGCACCGACAAGGCCGACCTG
CGGCTGATCTATCTGGCCCTGGCCCACATGATCAAGTTCCGGGGCCACTT
CCTGATCGAGGGCGACCTGAACCCCGACAACAGCGACGTGGACAAGCTGT
TCATCCAGCTGGTGCAGACCTACAACCAGCTGTTCGAGGAAAACCCCATC
AACGCCAGCGGCGTGGACGCCAAGGCCATCCTGTCTGCCAGACTGAGCAA
GAGCAGACGGCTGGAAAATCTGATCGCCCAGCTGCCCGGCGAGAAGAAGA
ATGGCCTGTTCGGAAACCTGATTGCCCTGAGCCTGGGCCTGACCCCCAAC
TTCAAGAGCAACTTCGACCTGGCCGAGGATGCCAAACTGCAGCTGAGCAA
GGACACCTACGACGACGACCTGGACAACCTGCTGGCCCAGATCGGCGACC
AGTACGCCGACCTGTTTCTGGCCGCCAAGAACCTGTCCGACGCCATCCTG
CTGAGCGACATCCTGAGAGTGAACACCGAGATCACCAAGGCCCCCCTGAG
CGCCTCTATGATCAAGAGATACGACGAGCACCACCAGGACCTGACCCTGC
TGAAAGCTCTCGTGCGGCAGCAGCTGCCTGAGAAGTACAAAGAGATTTTC
TTCGACCAGAGCAAGAACGGCTACGCCGGCTACATTGACGGCGGAGCCAG
CCAGGAAGAGTTCTACAAGTTCATCAAGCCCATCCTGGAAAAGATGGACG
GCACCGAGGAACTGCTCGTGAAGCTGAACAGAGAGGACCTGCTGCGGAAG
CAGCGGACCTTCGACAACGGCAGCATCCCCCACCAGATCCACCTGGGAGA
GCTGCACGCCATTCTGCGGCGGCAGGAAGATTTTTACCCATTCCTGAAGG
ACAACCGGGAAAAGATCGAGAAGATCCTGACCTTCCGCATCCCCTACTAC
GTGGGCCCTCTGGCCAGGGGAAACAGCAGATTCGCCTGGATGACCAGAAA
GAGCGAGGAAACCATCACCCCCTGGAACTTCGAGGAAGTGGTGGACAAGG
GCGCTTCCGCCCAGAGCTTCATCGAGCGGATGACCAACTTCGATAAGAAC
CTGCCCAACGAGAAGGTGCTGCCCAAGCACAGCCTGCTGTACGAGTACTT
CACCGTGTATAACGAGCTGACCAAAGTGAAATACGTGACCGAGGGAATGA
GAAAGCCCGCCTTCCTGAGCGGCGAGCAGAAAAAGGCCATCGTGGACCTG
```

```
CTGTTCAAGACCAACCGGAAAGTGACCGTGAAGCAGCTGAAAGAGGACTA

CTTCAAGAAAATCGAGTGCTTCGACTCCGTGGAAATCTCCGGCGTGGAAG

ATCGGTTCAACGCCTCCCTGGGCACATACCACGATCTGCTGAAAATTATC

AAGGACAAGGACTTCCTGGACAATGAGGAAAACGAGGACATTCTGGAAGA

TATCGTGCTGACCCTGACACTGTTTGAGGACAGAGAGATGATCGAGGAAC

GGCTGAAAACCTATGCCCACCTGTTCGACGACAAAGTGATGAAGCAGCTG

AAGCGGCGGAGATACACCGGCTGGGGCAGGCTGAGCCGGAAGCTGATCAA

CGGCATCCGGGACAAGCAGTCCGGCAAGACAATCCTGGATTTCCTGAAGT

CCGACGGCTTCGCCAACAGAAACTTCATGCAGCTGATCCACGACGACAGC

CTGACCTTTAAAGAGGACATCCAGAAAGCCCAGGTGTCCGGCCAGGGCGA

TAGCCTGCACGAGCACATTGCCAATCTGGCCGGCAGCCCCGCCATTAAGA

AGGGCATCCTGCAGACAGTGAAGGTGGTGGACGAGCTCGTGAAAGTGATG

GGCCGGCACAAGCCCGAGAACATCGTGATCGAAATGGCCAGAGAGAACCA

GACCACCCAGAAGGGACAGAAGAACAGCCGCGAGAGAATGAAGCGGATCG

AAGAGGGCATCAAAGAGCTGGGCAGCCAGATCCTGAAAGAACACCCCGTG

GAAAACACCCAGCTGCAGAACGAGAAGCTGTACCTGTACTACCTGCAGAA

TGGGCGGGATATGTACGTGGACCAGGAACTGGACATCAACCGGCTGTCCG

ACTACGATGTGGACCATATCGTGCCTCAGAGCTTTCTGGCGGACGACTCC

ATCGACAACAAGGTGCTGACCAGAAGCGACAAGAACCGGGGCAAGAGCGA

CAACGTGCCCTCCGAAGAGGTCGTGAAGAAGATGAAGAACTACTGGCGGC

AGCTGCTGAACGCCAAGCTGATTACCCAGAGAAAGTTCGACAATCTGACC

AAGGCCGAGAGAGGCGGCCTGAGCGAACTGGATAAGGCCGGCTTCATCAA

GAGACAGCTGGTGGAAACCCGGCAGATCACAAAGCACGTGGCACAGATCC

TGGACTCCCGGATGAACACTAAGTACGACGAGAATGACAAGCTGATCCGG

GAAGTGAAAGTGATCACCCTGAAGTCCAAGCTGGTGTCCGATTTCCGGAA

GGATTTCCAGTTTTACAAAGTGCGCGAGATCAACAACTACCACCACGCCC

ACGACGCCTACCTGAACGCCGTCGTGGGAACCGCCCTGATCAAAAAGTAC

CCTGCGCTGGAAAGCGAGTTCGTGTACGGCGACTACAAGGTGTACGACGT

GCGGAAGATGATCGCCAAGAGCGAGCAGGAAATCGGCAAGGCTACCGCCA

AGTACTTCTTCTACAGCAACATCATGAACTTTTTCAAGACCGAGATTACC

CTGGCCAACGGCGAGATCCGGAAGGCGCCTCTGATCGAGACAAACGGCGA

AACCGGGGAGATCGTGTGGGATAAGGGCCGGGATTTTGCCACCGTGCGGA

AAGTGCTGAGCATGCCCCAAGTGAATATCGTGAAAAAGACCGAGGTGCAG

ACAGGCGGCTTCAGCAAAGAGTCTATCCTGCCCAAGAGGAACAGCGATAA

GCTGATCGCCAGAAAGAAGGACTGGGACCCTAAGAAGTACGGCGGCTTCG

ACAGCCCCACCGTGGCCTATTCTGTGCTGGTGGTGGCCAAAGTGGAAAAG

GGCAAGTCCAAGAAACTGAAGAGTGTGAAAGAGCTGCTGGGGATCACCAT

CATGGAAAGAAGCAGCTTCGAGAAGAATCCCATCGACTTTCTGGAAGCCA

AGGGCTACAAAGAAGTGAAAAAGGACCTGATCATCAAGCTGCCTAAGTAC

TCCCTGTTCGAGCTGGAAAACGGCCGGAAGAGAATGCTGGCCTCTGCCGG

CGAACTGCAGAAGGGAAACGAACTGGCCCTGCCCTCCAAATATGTGAACT

TCCTGTACCTGGCCAGCCACTATGAGAAGCTGAAGGGCTCCCCCGAGGAT

AATGAGCAGAAACAGCTGTTTGTGGAACAGCACAAGCACTACCTGGACGA

GATCATCGAGCAGATCAGCGAGTTCTCCAAGAGAGTGATCCTGGCCGACG

CTAATCTGGACAAAGTGCTGTCCGCCTACAACAAGCACCGGGATAAGCCC

ATCAGAGAGCAGGCCGAGAATATCATCCACCTGTTTACCCTGACCAATCT

GGGAGCCCCTGCCGCCTTCAAGTACTTTGACACCACCATCGACCGGAAGA

GGTACACCAGCACCAAAGAGGTGCTGGACGCCACCCTGATCCACCAGAGC

ATCACCGGCCTGTACGAGACACGGATCGACCTGTCTCAGCTGGGAGGCGA

CAAAAGGCCGGCGGCCACGAAAAAGGCCGGCCAGGCAAAAAAGAAAAAG
```

In embodiments, a nucleic acid encoding a Cas9 variant (SpCas9 HF1) includes the nucleic acid sequence of SEQ ID NO: 39 or a nucleic acid having at least 80%, 85%, 90%, 95%, 96%, 97%, 98%, 99% or 100% identity to SEQ ID NO: 39.

```
                                        (SEQ ID NO: 39)
GATAAAAAGTATTCTATTGGTTTAGACATCGGCACTAATTCCGTTGGATG

GGCTGTCATAACCGATGAATACAAAGTACCTTCAAAGAAATTTAAGGTGT

TGGGGAACACAGACCGTCATTCGATTAAAAAGAATCTTATCGGTGCCCTC

CTATTCGATAGTGGCGAAACGGCAGAGGCGACTCGCCTGAAACGAACCGC

TCGGAGAAGGTATACACGTCGCAAGAACCGAATATGTTACTTACAAGAAA

TTTTTAGCAATGAGATGGCCAAAGTTGACGATTCTTTCTTTCACCGTTTG

GAAGAGTCCTTCCTTGTCGAAGAGGACAAGAAACATGAACGGCACCCCAT

CTTTGGAAACATAGTAGATGAGGTGGCATATCATGAAAAGTACCCAACGA

TTTATCACCTCAGAAAAAAGCTAGTTGACTCAACTGATAAAGCGGACCTG

AGGTTAATCTACTTGGCTCTTGCCCATATGATAAAGTTCCGTGGGCACTT

TCTCATTGAGGGTGATCTAAATCCGGACAACTCGGATGTCGACAAACTGT

TCATCCAGTTAGTACAAACCTATAATCAGTTGTTTGAAGAGAACCCTATA

AATGCAAGTGGCGTGGATGCGAAGGCTATTCTTAGCGCCCGCCTCTCTAA

ATCCCGACGGCTAGAAAACCTGATCGCACAATTACCCGGAGAGAAGAAAA

ATGGGTTGTTCGGTAACCTTATAGCGCTCTCACTAGGCCTGACACCAAAT

TTTAAGTCGAACTTCGACTTAGCTGAAGATGCCAAATTGCAGCTTAGTAA

GGACACGTACGATGACGATCTCGACAATCTACTGGCACAAATTGGAGATC

AGTATGCGGACTTATTTTTGGCTGCCAAAAACCTTAGCGATGCAATCCTC

CTATCTGACATACTGAGAGTTAATACTGAGATTACCAAGGCGCCGTTATC

CGCTTCAATGATCAAAAGGTACGATGAACATCACCAAGACTTGACACTTC

TCAAGGCCCTAGTCCGTCAGCAACTGCCTGAGAAATATAAGGAAATATTC

TTTGATCAGTCGAAAAACGGGTACGCAGGTTATATTGACGGCGGAGCGAG

TCAAGAGGAATTCTACAAGTTTATCAAACCCATATTAGAGAAGATGGATG

GGACGGAAGAGTTGCTTGTAAAACTCAATCGCGAAGATCTACTGCGAAAG

CAGCGGACTTTCGACAACGGTAGCATTCCACATCAAATCCACTTAGGCGA

ATTGCATGCTATACTTAGAAGGCAGGAGGATTTTTATCCGTTCCTCAAAG
```

```
ACAATCGTGAAAAGATTGAGAAAATCCTAACCTTTCGCATACCTTACTAT

GTGGGACCCCTGGCCCGAGGGAACTCTCGGTTCGCATGGATGACAAGAAA

GTCCGAAGAAACGATTACTCCCTGGAATTTTGAGGAAGTTGTCGATAAAG

GTGCGTCAGCTCAATCGTTCATCGAGAGGATGACCGCCTTTGACAAGAAT

TTACCGAACGAAAAGTATTGCCTAAGCACAGTTTACTTTACGAGTATTT

CACAGTGTACAATGAACTCACGAAAGTTAAGTATGTCACTGAGGGCATGC

GTAAACCCGCCTTTCTAAGCGGAGAACAGAAGAAAGCAATAGTAGATCTG

TTATTCAAGACCAACCGCAAAGTGACAGTTAAGCAATTGAAAGAGGACTA

CTTTAAGAAAATTGAATGCTTCGATTCTGTCGAGATCTCCGGGGTAGAAG

ATCGATTTAATGCGTCACTTGGTACGTATCATGACCTCCTAAAGATAATT

AAAGATAAGGACTTCCTGGATAACGAAGAGAATGAAGATATCTTAGAAGA

TATAGTGTTGACTCTTACCCTCTTTGAAGATCGGGAAATGATTGAGGAAA

GACTAAAAACATACGCTCACCTGTTCGACGATAAGGTTATGAAACAGTTA

AAGAGGCGTCGCTATACGGGCTGGGGAGCCTTGTCGCGGAAACTTATCAA

CGGGATAAGAGACAAGCAAAGTGGTAAAACTATTCTCGATTTTCTAAAGA

GCGACGGCTTCGCCAATAGGAACTTTATGGCCCTGATCCATGATGACTCT

TTAACCTTCAAAGAGGATATACAAAAGGCACAGGTTTCCGGACAAGGGGA

CTCATTGCACGAACATATTGCGAATCTTGCTGGTTCGCCAGCCATCAAAA

AGGGCATACTCCAGACAGTCAAAGTAGTGGATGAGCTAGTTAAGGTCATG

GGACGTCACAAACCGGAAAACATTGTAATCGAGATGGCACGCGAAAATCA

AACGACTCAGAAGGGGCAAAAAAACAGTCGAGAGCGGATGAAGAGAATAG

AAGAGGGTATTAAAGAACTGGGCAGCCAGATCTTAAAGGAGCATCCTGTG

GAAAATACCCAATTGCAGAACGAGAAACTTTACCTCTATTACCTACAAAA

TGGAAGGGACATGTATGTTGATCAGGAACTGGACATAAACCGTTTATCTG

ATTACGACGTCGATCACATTGTACCCCAATCCTTTTTGAAGGACGATTCA

ATCGACAATAAAGTGCTTACACGCTCGGATAAGAACCGAGGGAAAAGTGA

CAATGTTCCAAGCGAGGAAGTCGTAAAGAAAATGAAGAACTATTGGCGGC

AGCTCCTAAATGCGAAACTGATAACGCAAAGAAAGTTCGATAACTTAACT

AAAGCTGAGAGGGGTGGCTTGTCTGAACTTGACAAGGCCGGATTTATTAA

ACGTCAGCTCGTGGAAACCCGCGCCATCACAAAGCATGTTGCCCAGATAC

TAGATTCCCGAATGAATACGAAATACGACGAGAACGATAAGCTGATTCGG

GAAGTCAAAGTAATCACTTTAAAGTCAAAATTGGTGTCGGACTTCAGAAA

GGATTTTCAATTCTATAAAGTTAGGGAGATAAATAACTACCACCATGCGC

ACGACGCTTATCTTAATGCCGTCGTAGGGACCGCACTCATTAAGAAATAC

CCGAAGCTAGAAAGTGAGTTTGTGTATGGTGATTACAAAGTTTATGACGT

CCGTAAGATGATCGCGAAAAGCGAACAGGAGATAGGCAAGGCTACAGCCA

AATACTTCTTTTATTCTAACATTATGAATTTCTTTAAGACGGAAATCACT

CTGGCAAACGGAGAGATACGCAAACGACCTTTAATTGAAACCAATGGGGA

GACAGGTGAAATCGTATGGGATAAGGGCCGGGACTTCGCGACGGTGAGAA

AAGTTTTGTCCATGCCCCAAGTCAACATAGTAAAGAAAACTGAGGTGCAG

ACCGGAGGGTTTTCAAAGGAATCGATTCTTCCAAAAAGGAATAGTGATAA

GCTCATCGCTCGTAAAAAGGACTGGGACCCGAAAAAGTACGGTGGCTTCG

ATAGCCCTACAGTTGCCTATTCTGTCCTAGTAGTGGCAAAAGTTGAGAAG

GGAAAATCCAAGAAACTGAAGTCAGTCAAAGAATTATTGGGGATAACGAT

TATGGAGCGCTCGTCTTTTGAAAAGAACCCCATCGACTTCCTTGAGGCGA

AAGGTTACAAGGAAGTAAAAAAGGATCTCATAATTAAACTACCAAAGTAT

AGTCTGTTTGAGTTAGAAAATGGCCGAAAACGGATGTTGGCTAGCGCCGG

AGAGCTTCAAAAGGGGAACGAACTCGCACTACCGTCTAAATACGTGAATT

TCCTGTATTTAGCGTCCCATTACGAGAAGTTGAAAGGTTCACCTGAAGAT

AACGAACAGAAGCAACTTTTTGTTGAGCAGCACAAACATTATCTCGACGA

AATCATAGAGCAAATTTCGGAATTCAGTAAGAGAGTCATCCTAGCTGATG

CCAATCTGGACAAAGTATTAAGCGCATACAACAAGCACAGGGATAAACCC

ATACGTGAGCAGGCGGAAAATATTATCCATTTGTTTACTCTTACCAACCT

CGGCGCTCCAGCCGCATTCAAGTATTTTGACACAACGATAGATCGCAAAC

GATACACTTCTACCAAGGAGGTGCTAGACGCGACACTGATTCACCAATCC

ATCACGGGATTATATGAAACTCGGATAGATTTGTCACAGCTTGGGGGTGA

C
```

In embodiments, the composition described herein includes a delivery vehicle (e.g., a nanoparticle, a lipid particle or a viral vector) and a nucleic acid encoding a protein that includes a mitochondrial localization amino acid sequence covalently attached to Cas9, where the nucleic acid is bound to the delivery vehicle, the nucleic acid encoding the mitochondrial localization amino acid sequence includes SEQ ID NO: 2, and the nucleic acid encoding the Cas9 protein includes SEQ ID NO: 32.

In embodiments, the composition described herein includes a delivery vehicle (e.g., a nanoparticle, a lipid particle or a viral vector) and a nucleic acid encoding a protein that includes a mitochondrial localization amino acid sequence covalently attached to Cas9, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 protein includes a nucleic acid sequence having at least 80%, 85%, 90%, 95%, 96%, 97%, 98%, 99% or 100% identity to SEQ ID NO: 32.

In embodiments, the composition described herein includes a delivery vehicle (e.g., a nanoparticle, a lipid particle or a viral vector) and a nucleic acid encoding a protein that includes a mitochondrial localization amino acid sequence covalently attached to Cas9, where the nucleic acid is bound to the delivery vehicle, the nucleic acid encoding the mitochondrial localization amino acid sequence includes SEQ ID NO: 2, and the nucleic acid encoding the Cas9 protein includes SEQ ID NO: 33.

In embodiments, the composition described herein includes a delivery vehicle (e.g., a nanoparticle, a lipid particle or a viral vector) and a nucleic acid encoding a protein that includes a mitochondrial localization amino acid sequence covalently attached to Cas9, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 protein includes a nucleic acid sequence having at least 80%, 85%, 90%, 95%, 96%, 97%, 98%, 99% or 100% identity to SEQ ID NO: 33.

In embodiments, the composition described herein includes a delivery vehicle (e.g., a nanoparticle, a lipid particle or a viral vector) and a nucleic acid encoding a protein that includes a mitochondrial localization amino acid sequence covalently attached to Cpf1, where the nucleic acid is bound to the delivery vehicle, the nucleic acid encoding the mitochondrial localization amino acid sequence includes SEQ ID NO: 2, and the nucleic acid encoding the Cpf1 protein includes SEQ ID NO: 34.

In embodiments, the composition described herein includes a delivery vehicle (e.g., a nanoparticle, a lipid particle or a viral vector) and a nucleic acid encoding a protein that includes a mitochondrial localization amino acid sequence covalently attached to Cpf1, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cpf1 protein includes a nucleic acid sequence having at least 80%, 85%, 90%, 95%, 96%, 97%, 98%, 99% or 100% identity to SEQ ID NO: 34.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes SEQ ID NO: 2, and the nucleic acid encoding the Cas9 variant protein includes SEQ ID NO: 35.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 variant protein includes a nucleic acid sequence having at least 80%, 85%, 90%, 95%, 96%, 97%, 98%, 99% or 100% identity to SEQ ID NO: 35.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes SEQ ID NO: 2, and the nucleic acid encoding the Cas9 variant protein includes SEQ ID NO: 36.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 variant protein includes a nucleic acid sequence having at least 80%, 85%, 90%, 95%, 96%, 97%, 98%, 99% or 100% identity to SEQ ID NO: 36.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes SEQ ID NO: 2, and the nucleic acid encoding the Cas9 variant protein includes SEQ ID NO: 37.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 variant protein includes a nucleic acid sequence having at least 80%, 85%, 90%, 95%, 96%, 97%, 98%, 99% or 100% identity to SEQ ID NO: 37.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes SEQ ID NO: 2, and the nucleic acid encoding the Cas9 variant protein includes SEQ ID NO: 38.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 variant protein includes a nucleic acid sequence having at least 80%, 85%, 90%, 95%, 96%, 97%, 98%, 99% or 100% identity to SEQ ID NO: 38.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes SEQ ID NO: 2, and the nucleic acid encoding the Cas9 variant protein includes SEQ ID NO: 39.

In embodiments, the composition described herein includes a delivery vehicle (e.g., a nanoparticle, a lipid particle or a viral vector) and a nucleic acid encoding a protein that includes a mitochondrial localization amino acid sequence covalently attached to a Cas9 variant, where the nucleic acid is bound to the delivery vehicle, the nucleic acid encoding the mitochondrial localization amino acid sequence includes a nucleic acid sequence having at least 80%, 85%, 90%, 95%, 96%, 97%, 98%, 99% or 100% identity to SEQ ID NO: 2, and the nucleic acid encoding the Cas9 variant protein includes a nucleic acid sequence having at least 80%, 85%, 90%, 95%, 96%, 97%, 98%, 99% or 100% identity to SEQ ID NO: 39.

In another aspect, there is provided a protein including a mitochondrial localization amino acid sequence covalently attached to Cpf1 or a Class II CRISPR endonuclease or a Cas9 variant.

In embodiments, the protein includes a mitochondrial localization amino acid sequence covalently attached to Cpf1.

In embodiments, the protein includes a mitochondrial localization amino acid sequence covalently attached to a Class II CRISPR endonuclease.

In embodiments, the protein includes a mitochondrial localization amino acid sequence covalently attached to a Cas9 variant.

In embodiments, the protein described herein includes a mitochondrial localization amino acid sequence including SEQ ID NO: 1 and Cpf1 protein including SEQ ID NO: 25.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and Cpf1 protein including an amino acid sequence having at least 80%, 85%, 90%, 95%, 96%, 97%, 98%, 99% or 100% identity to SEQ ID NO: 25.

In embodiments, the protein described herein includes a mitochondrial localization amino acid sequence including SEQ ID NO: 1 and a Cas9 variant protein including SEQ ID NO: 26.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and a Cas9 variant protein including an amino acid sequence having at least 80%, 85%, 90%, 95%, 96%, 97%, 98%, 99% or 100% identity to SEQ ID NO: 26.

In embodiments, the protein described herein includes a mitochondrial localization amino acid sequence including SEQ ID NO: 1 and a Cas9 variant protein including SEQ ID NO: 27.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and a Cas9 variant protein including an amino acid sequence having at least 80%, 85%, 90%, 95%, 96%, 97%, 98%, 99% or 100% identity to SEQ ID NO: 27.

In embodiments, the protein described herein includes a mitochondrial localization amino acid sequence including SEQ ID NO: 1 and a Cas9 variant protein including SEQ ID NO: 28.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and a Cas9 variant protein including an amino acid sequence having at least 80%, 85%, 90%, 95%, 96%, 97%, 98%, 99% or 100% identity to SEQ ID NO: 28.

In embodiments, the protein described herein includes a mitochondrial localization amino acid sequence including SEQ ID NO: 1 and a Cas9 variant protein including SEQ ID NO: 29.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and a Cas9 variant protein including an amino acid sequence having at least 80%, 85%, 90%, 95%, 96%, 97%, 98%, 99% or 100% identity to SEQ ID NO: 29.

In embodiments, the protein described herein includes a mitochondrial localization amino acid sequence including SEQ ID NO: 1 and a Cas9 variant protein including SEQ ID NO: 30.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and a Cas9 variant protein including an amino acid sequence having at least 80%, 85%, 90%, 95%, 96%, 97%, 98%, 99% or 100% identity to SEQ ID NO: 30.

In embodiments, the protein described herein includes a mitochondrial localization amino acid sequence including SEQ ID NO: 1 and a Cas9 variant protein including SEQ ID NO: 31.

In embodiments, the protein described herein includes a mitochondrial localization amino acid sequence including an amino acid sequence having at least 80%, 85%, 90%, 95%, 96%, 97%, 98%, 99% or 100% identity to SEQ ID NO: 1 and a Cas9 variant protein including an amino acid sequence having at least 80%, 85%, 90%, 95%, 96%, 97%, 98%, 99% or 100% identity to SEQ ID NO: 31.

In another aspect, there is provided a nucleic acid encoding a protein as disclosed hereinabove. In embodiments, the nucleic acid encodes a protein including a mitochondrial localization amino acid sequence covalently attached to Cpf1 or a Class II CRISPR endonuclease or a Cas9 variant.

In embodiments, the nucleic acid described herein encodes a protein including a mitochondrial localization amino acid sequence covalently attached to Cpf1.

In embodiments, the nucleic acid described herein encodes a protein including a mitochondrial localization amino acid sequence covalently attached to a Class II CRISPR endonuclease.

In embodiments, the nucleic acid described herein encodes a protein including a mitochondrial localization amino acid sequence covalently attached to a Cas9 variant.

In embodiments, the nucleic acid described herein includes a nucleic acid including SEQ ID NO: 2 and a nucleic acid including SEQ ID NO: 32.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 32.

In embodiments, the nucleic acid described herein includes a nucleic acid including SEQ ID NO: 2 and a nucleic acid including SEQ ID NO: 33.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 33.

In embodiments, the nucleic acid described herein includes a nucleic acid including SEQ ID NO: 2 and a nucleic acid including SEQ ID NO: 34.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 34.

In embodiments, the nucleic acid described herein includes a nucleic acid including SEQ ID NO: 2 and a nucleic acid including SEQ ID NO: 35.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 35.

In embodiments, the nucleic acid described herein includes a nucleic acid including SEQ ID NO: 2 and a nucleic acid including SEQ ID NO: 36.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 36.

In embodiments, the nucleic acid described herein includes a nucleic acid including SEQ ID NO: 2 and a nucleic acid including SEQ ID NO: 37.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 37.

In embodiments, the nucleic acid described herein includes a nucleic acid including SEQ ID NO: 2 and a nucleic acid including SEQ ID NO: 38.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 38.

In embodiments, the nucleic acid described herein includes a nucleic acid including SEQ ID NO: 2 and a nucleic acid including SEQ ID NO: 39.

In embodiments, the nucleic acid described herein includes a nucleic acid including a nucleic acid having at least 80%, 85%, 90%, 95%, 96%, 97%, 98%, 99% or 100% identity to SEQ ID NO: 2 and a nucleic acid including a nucleic acid having at least 80%, 85%, 90%, 95%, 96%, 97%, 98%, 99% or 100% identity to SEQ ID NO: 39.

In another aspect, there is provided a nucleic acid including a mitochondrial import sequence and a single-guide RNA (sgRNA) sequence.

In embodiments, the mitochondrial import sequence includes a D loop, an F loop, an MRP loop, an RNP loop, a γ 5 s loop, or any combination thereof.

In embodiments, the mitochondrial import sequence includes SEQ ID NO: 3 or a nucleic acid having at least 80%, 85%, 90%, 95%, 96%, 97%, 98%, 99% or 100% identity to SEQ ID NO: 3. In embodiments, the mitochondrial import sequence includes SEQ ID NO: 4 or a nucleic acid having at least 80%, 85%, 90%, 95%, 96%, 97%, 98%, 99% or 100% identity to SEQ ID NO: 4. In embodiments, the mitochondrial import sequence includes SEQ ID NO: 5 or a nucleic acid having at least 80%, 85%, 90%, 95%, 96%, 97%, 98%, 99% or 100% identity to SEQ ID NO: 5. In embodiments, the mitochondrial import sequence includes SEQ ID NO: 6 or a nucleic acid having at least 80%, 85%, 90%, 95%, 96%, 97%, 98%, 99% or 100% identity to SEQ ID NO: 6. In embodiments, the mitochondrial import sequence includes SEQ ID NO: 7 or a nucleic acid having at least 80%, 85%, 90%, 95%, 96%, 97%, 98%, 99% or 100% identity to SEQ ID NO: 7. In embodiments, the mitochondrial import sequence includes any combination of SEQ ID NOs: 3-7 or any combination of the nucleic acid sequences having at least 80%, 85%, 90%, 95%, 96%, 97%, 98%, 99% or 100% identity to any one of SEQ ID Nos 3-7.

In embodiments, the sgRNA sequence includes a guide sequence (i.e., a nucleic acid sequence that is complementary to a mitochondrial DNA (mtDNA) target sequence). In embodiments, the mtDNA target sequence includes at least one mutation or deletion. In embodiments, the mtDNA target sequence is 8-100 nucleotides in length.

In embodiments, the mtDNA target sequence may optionally have a minimum length of one of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In embodiments, the mtDNA target sequence may optionally have a maximum length of one of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In embodiments, the mtDNA target sequence may optionally have a length of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

Where the mtDNA target sequence is less than 100 (99 or less) nucleotides in length, the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 114, 13, 12, 11, 10, 9 or 8 nucleotides in length. In embodiments, the mtDNA target sequence is less than 90 nucleotides in length. In embodiments, the mtDNA target sequence is less than 80 nucleotides in length. In embodiments, the mtDNA target sequence is less than 70 nucleotides in length. In embodiments, the mtDNA target sequence is less than 60 nucleotides in length. In embodiments, the mtDNA target sequence is less than 50 nucleotides in length. In embodiments, the mtDNA target sequence is less than 40 nucleotides in length. In embodiments, the mtDNA target sequence is less than 30 nucleotides in length. In embodiments, the mtDNA target sequence is less than 20 nucleotides in length. In embodiments, the mtDNA target sequence is less than 10 nucleotides in length.

In embodiments, the mtDNA target sequence is between 10 and 99 nucleotides in length. In embodiments, the mtDNA target sequence is between 10 and 80 nucleotides in length. In embodiments, the mtDNA target sequence is between 10 and 70 nucleotides in length. In embodiments, the mtDNA target sequence is between 10 and 60 nucleotides in length. In embodiments, the mtDNA target sequence is between 10 and 50 nucleotides in length. In embodiments, the mtDNA target sequence is between 10 and 40 nucleotides in length. In embodiments, the mtDNA target sequence is between 10 and 30 nucleotides in length. In embodiments, the mtDNA target sequence is between 10 and 25 nucleotides in length. In embodiments, mtDNA target sequence is between 16 and 24 nucleotides in length.

Exemplary mt DNA target sequence may includes, but is not limited to, a fragment of any one of SEQ ID Nos: 8-22.

In embodiments, the sgRNA sequence comprises a trans-activating crRNA (tracrRNA) sequence. In embodiments, the sgRNA sequence includes a crRNA sequence (i.e., a guide sequence and a tracr mate sequence). In embodiments, the sgRNA sequence includes a tracrRNA sequence and a crRNA sequence.

Exemplary nucleic acid sequences including a mitochondrial import sequence and a sgRNA sequence include, but are not limited to, SEQ ID Nos: 40-48. In embodiments, an extra "G" may be added in front of sgRNAs that do not start with a G nucleotide in order to obtain efficient expression from U6 promoter.

TABLE 5

| Mito-sgRNA | Sequence | SEQ ID NO |
|---|---|---|
| sgRNA-D | GTTTTAGAGCTAGAAATAGCAAGTTAAAAT AAGGCTAGTCCGTTATCAACTTGAAAAAGT GGCACCGAGTCGGTGCgggaGCGCAATCGG TAGCGCttcccTTTTT | 40 |
| sgRNA-F | GTTTTAGAGCTAGAAATAGCAAGTTAAAAT AAGGCTAGTCCGTTATCAACTTGAAAAAGT GGCACCGAGTCGGTGCgggaGAGCCCCTACAG GGCTCttcccTTTTT | 41 |
| sgRNA-DF | GTTTTAGAGCTAGAAATAGCAAGTTAAAAT AAGGCTAGTCCGTTATCAACTTGAAAAAGT GGCACCGAGTCGGTGCgggaGCGCAATCGGTAG CGCGAGCCCCTACAGGGCTCttcccTTTTT | 42 |
| sgRNA-zDF | GTTTTAGAGCTAGGCCGCGCAATCGGTAG CGCGGCCTAGCAAGTTAAAATAAGGCTAG TCCGTTATCAACTTGGCCGAGCCCCCTAC AGGGCTCGGCCAAGTGGCACCGAGTCGGT GCTTTTT | 43 |
| sgRNA-RNP (RNase P) | GTTTTAGAGCTAGAAATAGCAAGTTAAAAT AAGGCTAGTCCGTTATCAACTTGAAAAAGT GGCACCGAGTCGGTGCgggaTCTCCCTGAG CTTCAGGGAGttcccTTTTT | 44 |
| sgRNA-MRP | GTTTTAGAGCTAGAAATAGCAAGTTAAAAT AAGGCTAGTCCGTTATCAACTTGAAAAAGT GGCACCGAGTCGGTGCgggaAGAAGCGTAT CCCGCTGAGCttcccTTTTT | 45 |
| sgRNA-g5s (gamma 5s) | GTTTTAGAGCTAGAAATAGCAAGTTAAAAT AAGGCTAGTCCGTTATCAACTTGAAAAAGT GGCACCGAGTCGGTGCgggaGGCCTGGTTA GTACTTGGATGGGAGACCGCCAAGGAAT ACCGGGTGttcccTTTTT | 46 |
| Cpf1 sgRNA | TAATTTCTACTCTTGTAGATNNNNNNNNNN NNNNNNNNNNNN | 47 |
| saCas9 sgRNA | NNNNNNNNNNNNNNNNNNNNNNNGTTTTA GTACTCTGGAAACAGAATCTACTAAAACAA GGCAAAATGCCGTGTTTATCTCGTCAACTT GTTGGCGAGA | 48 |

Capital: crRNA and tracrRNA
Capital and bold: mitochondrial import sequence
Non-capital: stem for structural stability of mitoloops In embodiments, the sgRNA sequence may include a nuclear-encoded and mitochondrial-localizing tRNA sequence. A transfer RNA (abbreviated tRNA and archaically referred to as sRNA, for soluble RNA) is an adaptor molecule composed of RNA, typically 76 to 90 nucleotides in length, that serves as the physical link between the mRNA and the amino acid sequence of proteins. It does this by carrying an amino acid to the protein synthetic machinery of a cell (ribosome) as directed by a three-nucleotide sequence (codon) in a messenger RNA (mRNA). As such, tRNAs are a necessary component of translation, the biological synthesis of new proteins according to the genetic code. a nuclear-encoded and mitochondrial-localizing tRNA sequence refers to a tRNA has tRNA genes in its nuclear genome, but it is later transported into mitochondria to function after it is transcribed and matured.

Exemplary nuclear-encoded and mitochondrial-localizing tRNA sequences may include, but are not limited to, any one of SEQ ID Nos: 49-53.

TABLE 6

| 5' addition of tRNA to Cpf1 sgRNA | Sequence | SEQ ID NO |
|---|---|---|
| Rat tRNA CUG1 Gln | GGTCCCATGGTGTAATGGTTAGCACTCTGG ACTCTGAATCCAGCGATCCGAGTTCAAATC TCGGTGGGACCTCCA | 49 |
| Rat tRNA CUG2 Gln | GGTCCCATGGTGTAATGGTGAGCACTCTGG ACTCTGAATCCAGCGATCCGAGTTCAAATC TCGGTGGGACCTCCA | 50 |
| Rat tRNA UUG1 Gln | GGTCCCATGGTGTAATGGTTAGCACTCTGG ACTTTGAATCCAGCGATCCGAGTTCAAATC TCGGTGGGACCTCCA | 51 |
| Rat tRNA UUG2 Gln | GGTCCCATGGTGTAATGGTGAGCACTCTGG ACTTTGAATCCAGCGATCCGAGTTCAAATC TCGGTGGGACCTCCA | 52 |
| human tRNA CUG Gln | ggttccatggtgtaatggtgagcactctgg actctgaatccagcgatccgagttcgagtc tcggtggaacctCCA | 53 |

In embodiments, the nucleic acid described herein is bound to a delivery vehicle. In embodiments, the delivery vehicle is a nanoparticle, a lipid particle or a viral vector.

In embodiments, the nucleic acid is DNA. In embodiments, the nucleic acid is RNA. In embodiments, the RNA includes one or more modified nucleotides or nucleotide analogues.

In another aspect, there is provided a complex that includes a protein including a mitochondrial localization amino acid sequence described herein (e.g., SEQ ID NO: 1) covalently attached to an RNA-guided DNA endonuclease enzyme described herein (e.g., Cas9, Cpf1, a Class II CRISPR endonuclease or a Cas9 variant) and a nucleic acid including one or more mitochondrial import sequences described herein (e.g., SEQ ID Nos: 3-7) and a sgRNA sequence described herein, where the protein binds to the nucleic acid.

In another aspect, there is provided a vector including any nucleic acid disclosed herein. In embodiments, the vector includes a nucleic acid according to any embodiments set forth above, or a combination thereof.

In embodiments, the vector includes a nucleic acid encoding a protein that includes a mitochondrial localization amino acid sequence covalently attached to an RNA-guided DNA endonuclease enzyme (e.g., Cas9, Cpf1, a Class II CRISPR endonuclease or a Cas9 variant).

In embodiments, the vector includes a nucleic acid including SEQ ID NO: 2 and a nucleic acid including any one of SEQ ID NOs: 32-39.

In embodiments, the vector includes a nucleic acid including a nucleic acid sequence having at least 80%, 85%, 90%, 95%, 96%, 97%, 98%, 99% or 100% identity to SEQ ID NO: 2 and a nucleic acid including a nucleic acid sequence having at least 80%, 85%, 90%, 95%, 96%, 97%, 98%, 99% or 100% identity to any one of SEQ ID NOs: 32-39.

In embodiments, the vector includes a nucleic acid including one or more (e.g., 1, 2, 3, 4 or more) mitochondrial import sequences and a sgRNA sequence.

In embodiments, the vector includes a nucleic acid including at least one (e.g., 1, 2, 3, 4 or more) mitochondrial import sequence of any one of SEQ ID Nos: 3-7 and a sgRNA sequence.

In embodiments, the vector is a replication incompetent viral vector. In embodiments, the replication incompetent viral vector is a replication incompetent lentiviral, adeno-associated viral, or adenoviral vector.

In another aspect, there is provided a pharmaceutical composition including a composition disclosed herein, a protein disclosed herein, a nucleic acid disclosed herein, a vector disclosed herein, and a pharmaceutically acceptable excipient.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylase or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component.

The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

III. Methods

In another aspect, there is provided a method of altering expression of at least one mitochondrial nucleic acid sequence, the method including introducing into an eukaryotic cell a nucleic acid as disclosed herein, where the nucleic acid includes a mitochondrial import sequence and a single-guide RNA (sgRNA) sequence.

In embodiments, the mitochondrial import sequence includes a D loop, an F loop, an MRP loop, an RNP loop, a γ 5 s loop, or any combination thereof. In embodiments, the mitochondrial import sequence includes SEQ ID NO: 3 or a nucleic acid having at least 80%, 85%, 90%, 95%, 96%, 97%, 98%, 99% or 100% identity to SEQ ID NO: 3. In embodiments, the mitochondrial import sequence includes SEQ ID NO: 4 or a nucleic acid having at least 80%, 85%, 90%, 95%, 96%, 97%, 98%, 99% or 100% identity to SEQ ID NO: 4. In embodiments, the mitochondrial import sequence includes SEQ ID NO: 5 or a nucleic acid having at least 80%, 85%, 90%, 95%, 96%, 97%, 98%, 99% or 100% identity to SEQ ID NO: 5. In embodiments, the mitochondrial import sequence includes SEQ ID NO: 6 or a nucleic acid having at least 80%, 85%, 90%, 95%, 96%, 97%, 98%, 99% or 100% identity to SEQ ID NO: 6. In embodiments, the mitochondrial import sequence includes SEQ ID NO: 7 or a nucleic acid having at least 80%, 85%, 90%, 95%, 96%, 97%, 98%, 99% or 100% identity to SEQ ID NO: 7. In embodiments, the mitochondrial import sequence includes any combination of SEQ ID NOs: 3-7 or any combination of the nucleic acid sequences having at least 80%, 85%, 90%, 95%, 96%, 97%, 98%, 99% or 100% identity to any one of SEQ ID Nos 3-7.

In embodiments, the sgRNA sequence includes a guide sequence (i.e., a nucleic acid sequence that is complementary to a mitochondrial DNA (mtDNA) target sequence). In embodiments, the mtDNA target sequence includes at least one mutation or deletion. In embodiments, the mtDNA target sequence is 8-100 nucleotides in length.

Exemplary mt DNA target sequence may include, but is not limited to, a fragment (e.g., 10-30 nucleotides) of any one of SEQ ID Nos: 8-22.

Exemplary guide sequence may include, but is not limited to, any one of SEQ ID Nos: 55-105.

In embodiments, the sgRNA sequence comprises a trans-activating crRNA (tracrRNA) sequence. In embodiments, the sgRNA sequence includes a crRNA sequence (i.e., a guide sequence and a tracr mate sequence). In embodiments, the sgRNA sequence includes a tracrRNA sequence and a crRNA sequence. Exemplary crRNA sequence with or without a tracrRNA sequence includes, but is not limited to, any one of SEQ ID NOs: 106-108.

Exemplary nucleic acid sequences including a mitochondrial import sequence and a sgRNA sequence include, but are not limited to, SEQ ID Nos: 40-48.

In embodiments, the sgRNA sequence may include a nuclear-encoded and mitochondrial-localizing tRNA sequence. Exemplary nuclear-encoded and mitochondrial-localizing tRNA sequences may include, but are not limited to, any one of SEQ ID Nos: 49-53.

In embodiments, the method further includes introducing into the eukaryotic cell a composition as disclosed herein, a protein as disclosed herein, or another nucleic acid disclosed herein. For example, the composition includes a delivery vehicle (e.g., a nanoparticle, a lipid particle or a viral vector) and a protein including a mitochondrial localization amino acid sequence covalently attached to an RNA-guided DNA endonuclease enzyme (e.g., Cas9, Cpf1, a Class II CRISPR endonuclease or a Cas9 variant), where the protein is bound to the delivery vehicle. For example, the protein includes a mitochondrial localization amino acid sequence covalently attached to an RNA-guided DNA endonuclease enzyme (e.g., Cas9, Cpf1, a Class II CRISPR endonuclease or a Cas9 variant). For example, another nucleic acid includes a nucleic acid encoding a protein including a mitochondrial localization amino acid sequence covalently attached to an RNA-guided DNA endonuclease enzyme (e.g., Cas9, Cpf1, a Class II CRISPR endonuclease or a Cas9 variant).

In embodiments, the eukaryotic cell is an oocyte. In embodiments, the eukaryotic cell is part of a fertilized embryo.

In embodiments, the mitochondrial nucleic acid sequence comprises at least one mutation or deletion. Exemplary mitochondrial nucleic acid sequences including at least one mutation or deletion include, but are not limited to, any one of SEQ ID Nos: 8-22.

Altering expression refers to an increase of expression of a wild type mitochondrial nucleic acid sequence, a decrease of expression of a mutant mitochondrial nucleic acid sequence or a combination thereof. In embodiments, altering expression of at least one mitochondrial nucleic acid sequence refers to a decrease (i.e., downregulation) of at least one mutant mitochondrial nucleic acid sequence.

Levels of expression may be quantitated for absolute comparison, or relative comparisons may be made.

In some embodiments upregulation of expression may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

In some embodiments downregulation of expression may be considered to be present when the level of expression in the test sample is at least 1.1 times lower than that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times lower than that of the reference level.

Expression levels may be determined by one of a number of known in vitro assay techniques, such as PCR based assays, in situ hybridization assays, flow cytometry assays, immunological or immunohistochemical assays.

In embodiments, the method may further comprise a step of determining expression level (pre-treated level) of at least one mitochondrial nucleic acid sequence before introducing the nucleic acid into the eukaryotic cell. In embodiments, the method may further comprise another step of determining expression level (post-treated level) of the same at least one mitochondrial nucleic acid sequence after introducing the nucleic acid into the eukaryotic cell. In embodiments, the method may further comprise a step of comparing the difference of the pre-treated level and the post-treated level in order to determine if the expression of the at least one mitochondrial nucleic acid sequence of interest has been altered.

In another aspect, there is provided a method of treating a mitochondrial disorder in a subject in need thereof, the method including administering to the subject an effective amount of a composition disclosed herein and an effective amount of a nucleic acid disclosed herein. For example, the composition includes a delivery vehicle (e.g., a nanoparticle, a lipid particle or a viral vector) and a protein including a mitochondrial localization amino acid sequence covalently attached to an RNA-guided DNA endonuclease enzyme (e.g., Cas9, Cpf1, a Class II CRISPR endonuclease or a Cas9 variant), where the protein is bound to the delivery vehicle. For example, the nucleic acid includes a mitochondrial import sequence and a single-guide RNA (sgRNA) sequence.

In another aspect, there is provided a method of treating a mitochondrial disorder in a subject in need thereof, the method including administering to the subject an effective amount of a protein disclosed herein and an effective amount of a nucleic acid disclosed herein. For example, the protein includes a mitochondrial localization amino acid sequence covalently attached to an RNA-guided DNA endonuclease enzyme (e.g., Cas9, Cpf1, a Class II CRISPR endonuclease or a Cas9 variant). For example, the nucleic acid includes a mitochondrial import sequence and a single-guide RNA (sgRNA) sequence.

In another aspect, there is provided a method of treating a mitochondrial disorder in a subject in need thereof, the method including administering to the subject an effective amount of a first nucleic acid disclosed herein and an effective amount of second nucleic acid disclosed herein. For example, the first nucleic acid includes a nucleic acid encoding a protein including a mitochondrial localization amino acid sequence covalently attached to an RNA-guided DNA endonuclease enzyme (e.g., Cas9, Cpf1, a Class II CRISPR endonuclease or a Cas9 variant). For example, the second nucleic acid includes a mitochondrial import sequence and a single-guide RNA (sgRNA) sequence.

Further to aspect or embodiments disclosed herein providing a method of treating a mitochondrial disorder in a subject in need thereof, in embodiments the mitochondrial disorder is selected from the group consisting of Myoclonic Epilepsy with Ragged Red Fibers (MERRF); Mitochondrial Myopathy, Encephalopathy, Lactacidosis, and Stroke (MELAS); Maternally Inherited Diabetes and Deafness (MIDD); Leber's Hereditary Optic Neuropathy (LHON); chronic progressive external ophthalmoplegia (CPEO); Leigh Disease; Kearns-Sayre Syndrome (KSS); Friedreich's Ataxia (FRDA); Co-Enzyme Q10 (CoQ10) Deficiency; Complex I Deficiency; Complex II Deficiency; Complex III Deficiency; Complex IV Deficiency; Complex V Deficiency; other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; hearing and balance impairments; or other neurological disorders; epilepsy; genetic diseases; Huntington's Disease; mood disorders; nucleoside reverse transcriptase inhibitors (NRTI) treatment; HIV-associated neuropathy; schizophrenia; bipolar disorder; age-associated diseases; cerebral vascular diseases; macular degeneration; diabetes; and cancer.

IV. Kits

In another aspect, there is provided a kit including a first nucleic acid disclosed herein, and a protein described herein that includes a mitochondrial localization amino acid sequence covalently attached to an RNA-guided DNA endonuclease enzyme or a second nucleic acid sequence encoding the protein. For example, the first nucleic acid includes a mitochondrial import sequence and a single-guide RNA (sgRNA) sequence.

In embodiments, the mitochondrial localization amino acid sequence is N-terminal to the RNA-guided DNA endonuclease enzyme. In embodiments, the mitochondrial localization amino acid sequence is a cytochrome c oxidase subunit VIII (Coxa) sequence. In embodiments, the RNA-guided DNA endonuclease enzyme is Cas9 or Cpf1 or a Class II CRISPR endonuclease. In embodiments, the RNA-guided DNA endonuclease enzyme has no nuclear localization sequence. In embodiments, the Cas9 is a mutant Cas9, wherein the mutant Cas9 has one or more mutations that increase its binding specificity to PAM compared to wild type Cas9.

In embodiments, the first nucleic acid sequence forms part of a first viral vector nucleic acid sequence. In embodiments, the second nucleic acid sequence forms part of a second viral vector nucleic acid sequence. In embodiments, the first viral vector and the second viral vector are the same. In embodiments, the first viral vector is different from the second viral vector.

V. Examples

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1. Selective Elimination of Leber's Hereditary Optic Neuropathy (LHON)-Associated Mitochondrial DNA Mutations in Patient-Derived Induced Pluripotent Stem Cells Using a Novel Mitochondria-Targeted CRISPR System Significance:

Mitochondria are essential organelles that generate the bulk of cellular energy in the form of ATP from the oxidation of carbohydrates and fats. To carry out this central role in bioenergetics, mitochondria require their own genome, a 16.6 kilobase (kb) circular double-stranded molecule that encodes 37 genes. Each human cell carries hundreds to thousands of copies of mitochondria DNA (mtDNA). In mitochondrial encephalopmyopathies, cells typically contain a mixture of both pathogenic and normal mtDNA molecules, a state termed heteroplasmy. There are over 600 known mtDNA mutations associated such mtDNA diseases, which have diverse clinical features, including maternal inheritance (because mtDNA is inherited strictly from the mother), defects in the central and peripheral nervous systems, muscle defects, and exercise intolerance. Due to the inability to transform mitochondrial DNA, there are no approved clinical therapies for the treatment of mitochondrial diseases.

Leber's hereditary optic neuropathy (LHON) is one of the most common mitochondrial diseases that manifests in the eye. Greater than 95% of LHON patients are characterized by one of three mtDNA point mutations, although dozens of other mtDNA mutations have also been linked to this disease. LHON causes acute bilateral central vision loss affecting preferentially males between the second and third decades of life. Visual loss is often permanent with poor prognosis. Although the pathogenic mtDNA mutations associated with LHON were first identified in complex I subunits more than four decades ago, the pathologic mechanisms of LHON remain incomplete as a result of limitations in cellular and animal models. Most in vitro models of LHON utilize trans-mitochondrial cytoplasmic hybrid, or 'cybrids', which are derived from an immortalized osteosarcoma cell line to model the sensitivity of neurons towards mitochondrial bioenergetic defects. Thus, results from cybrid studies have not correlated well with the clinical severity of LHON patients. This may be in part due to the predominant reliance on the glycolytic pathway by tumor cells for ATP production and thereby circumventing oxidative phosphorylation deficiencies due to complex I mutations.

Because LHON and other mtDNA diseases begin from heteroplasmic mutations, proof-of-principle attempts have been made to remove the pathogenic mtDNA, thereby shifting the ratio of normal to pathogenic mtDNA. It has been shown that modified transcription activator-like effector nucleases (TALENs) and zinc finger nucleases (ZFNs) that localize into mitochondrion can shift mtDNA heteroplasmy to favor normal mtDNA. Because a high mutational load is required for respiratory dysfunction, a shift in heteroplasmy can restore mitochondrial function to cells carrying mtDNA mutations. While other gene editing methods TALENs and ZFNs are useful biological tools for gene manipulation, each requires protein engineering that can be tedious and inefficient. In contrast, the RNA-guided CRISPR/Cas9 gene editing system requires the design of a short gene-specific single guide RNA (sgRNA) and is amenable for targeting multiple genes simultaneously by multiplexing sgRNAs. In this study we have engineered the CRISPR RNA and Cas9 protein components for trafficking into the mitochondria matrix in order to induce genome editing of mitochondrial DNA. This mtDNA-specific genome editing system could be programmed to target any mutant mtDNA target sequence and could offer new strategy for treating diseases caused by mtDNA mutations.

Accordingly, the system described herein offers a novel approach for correcting mtDNA disorders, for which there are no effective treatments. In particular, there are provided reagents and method for engineering the CRISPR gene editing technology for mitochondrial localization and selective targeting of LHON-associated mtDNA mutations as a therapy for disease (e.g., mtDNA disease).

The microbial RNA-mediated adaptive immune system CRISPR, clustered regularly interspaced short palindromic repeats, has become a powerful gene editing tool in eukaryotic cells since the discovery of its mechanism[36]. There are five classes of CRISPR-Cas system, but Class II CRISPR-Cas9 is most widely used because it requires only one endonuclease protein, Cas9, to generate double-strand breaks in the DNA. The Cas9 protein utilizes a synthetic short guide RNA (sgRNA) to direct its DNA cleavage. The sgRNA is composed of a spacer region that is complementary to the DNA target, a CRISPR RNA and a trans-CRISPR RNA duplex. The target specificity is generated from the spacer domain, and the site of cleavage is determined by a proto-spacer adjacent motif (PAM) upstream of the PAM site.

Innovation:

There are provided reagents and methods useful for engineering the CRISPR gene editing technology for mitochondrial localization and selective targeting of LHON-associated mtDNA mutations as a potential therapy for mitochondrial disease. By utilizing the CRISPR/Cas9 system to target mtDNA, our approach offers four distinct advantages over other similar mtDNA endonuclease technologies. First, the mitoCRISPR system can be easily tailored for any particular mtDNA mutation. Although LHON is primarily caused by three pathogenic mtDNA mutations, there are more than 600 mtDNA mutations linked to mitochondrial diseases according to current records from MITOMAP [43]. Targeting any of these mutations with mitoCRISPR would require the same mitoCas9 enzyme with a unique mito-sgRNA that is complementary to the mtDNA mutation sequence. This is much more versatile than comparable approaches using mitoTALENS or mitoZFNS, which each require two protein arms that must be uniquely engineered to recognize any particular mtDNA mutation. Second, in the design of mitoTALENs and mitoZFNs, one arm is designed to specifically bind to the mutant mtDNA sequence while the other arm must bind to the adjacent wild-type sequence; thus, one protein arm will always bind to both mutant and wild-type mtDNA genomes in a heteroplasmic environment, potentially leading to the steric inhibition of wild-type mtDNA transcription and replication. In contrast, because mitoCRISPR requires only a single mito-sgRNA to target the mutant mtDNA sequence, there should be minimal interference to wild-type mtDNA genomes. Third, while mitoZFNs and their larger mitoTALEN counterparts require two adeno-associated virus (AAV) for expression (one vector for each arm), the mitoCRISPR system can be expressed from a single vector. Fourth, mitoCRISPR offers the ability to simultaneously target multiple mtDNA mutations by multiplexing sgRNA expression. This strategy benefits LHON patients carrying primary and secondary mutations. A similar approach with mitoTALENs or mitoZFNs would demand four mitoTALEN or mitoZFN proteins (two arms per target site), which would require extensive protein engineering and multiple expression vectors.

Accordingly, one goal is to engineer the CRISPR technology for targeting heteroplasmic mtDNA mutations in LHON-derived iPSC as a means to establish a robust cellular model for therapeutically reversing this disease. Genome editing technologies such as CRISPR, TALENs, and ZFNs, enable the treatment of genetic or acquired diseases by altering defective or pathogenic genes. However, there are several challenges that hinder the clinical translation of these technologies for nuclear gene therapy. These hurdles include the ability to avoid off target effects, the poor targeting of heterochromatic DNA, the extreme inefficiencies of template-directed homologous DNA recombination (HDR) for gene replacement, and the random nature of non-homologous end joining (NHEJ) for inducing targeted mutagenesis. In contrast to nuclear genome editing, our strategy for targeting mtDNA avoids all of these challenges. First, mtDNA is not wrapped in chromatin and is thus more accessible to targeted endonucleases than most nuclear DNA. Second, at less than 16 kb long, the mitochondria genome is approximately 200,000 times shorter than the nuclear genome, so there is minimal risk of off-target mtDNA cleavage. Third, because mitoCas9 localizes efficiently to the mitochondria with no detectable nuclear localization (FIG. 1B), it is unlikely that any off-target genome editing will occur in the nucleus. Finally, unlike nuclear gene editing applications, which rely on NHEJ for site-directed mutagenesis or HDR for gene replacement therapy, mitoCRISPR is predicated on the selective cleavage and destruction of the mutant mtDNA target sequence. Degradation of double-stranded breaks in mtDNA is the predominant pathway for purging mutations due to the limited repair mechanisms in mitochondria. Thus, the application of mitoCRISPR gene editing may circumvent many of the challenges associated with nuclear gene editing.

Figure 1A:
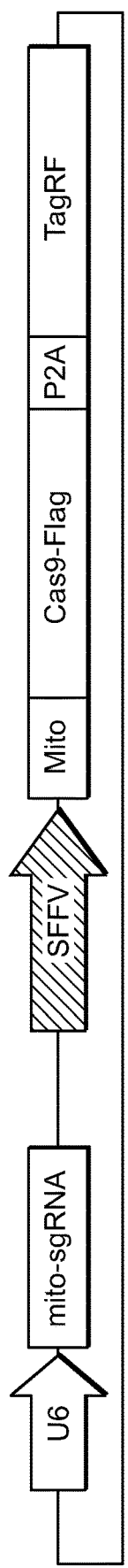
FIGS. 1A-1D. Mito-Cas9 localizes to mitochondria.

In embodiments, there are provided reagents and methods useful to adapt CRISPR gene editing towards mitochondria: We have successfully targeted the *S. pyogenes* Cas9 protein into the mitochondrial matrix by removing the nuclear localization signals and adding an N-terminal mitochondrial targeting sequence derived from the cytochrome c oxidase subunit VIII (Coxa). We have generated a lentiviral vector with mitoCas9-Flag protein driven by the SFFV promoter and a U6 RNA polymerase III promoter that drives expression of the mitochondrial-localizing sgRNA (mito-sgRNA) (FIG. 1A). Confocal analysis shows highly co-localized signal between mitoCas9-Flag protein with mitochondrial outer membrane marker Tom20 (FIG. 1C). Mitochondrial fractionation also demonstrates an enrichment of Cas9-flag in the mitochondrial fraction (FIG. 1B) relative to the nucleus or cytosol. FIGS. 5A and 5B further demonstrate that engineered mitoCas9 is successfully localized at mitochondrial matrix according to the Mander's coefficient for the degree of co-localization of mitoCas9 with mitochondria (see Table 7 below).

TABLE 7

Figure 3A:
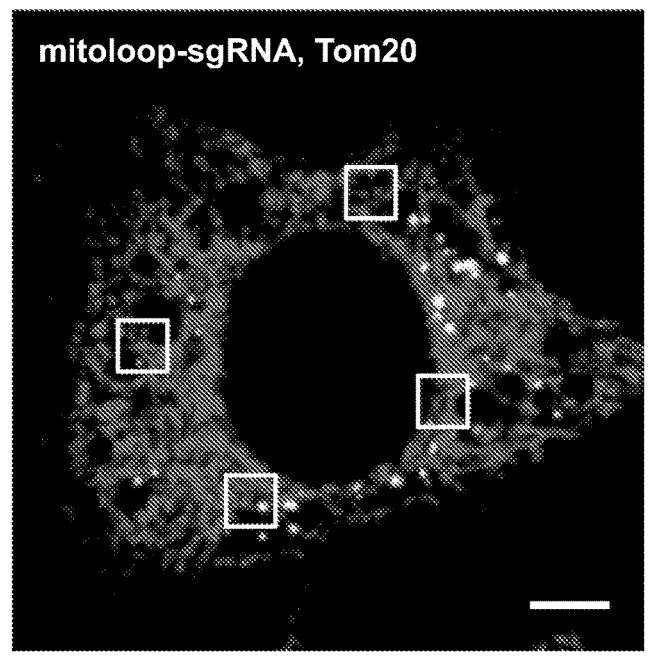
FIGS. 3A-3B. Mitoloop-sgRNA chimera exhibits some co-localization with mitochondria.
Figure 3B:
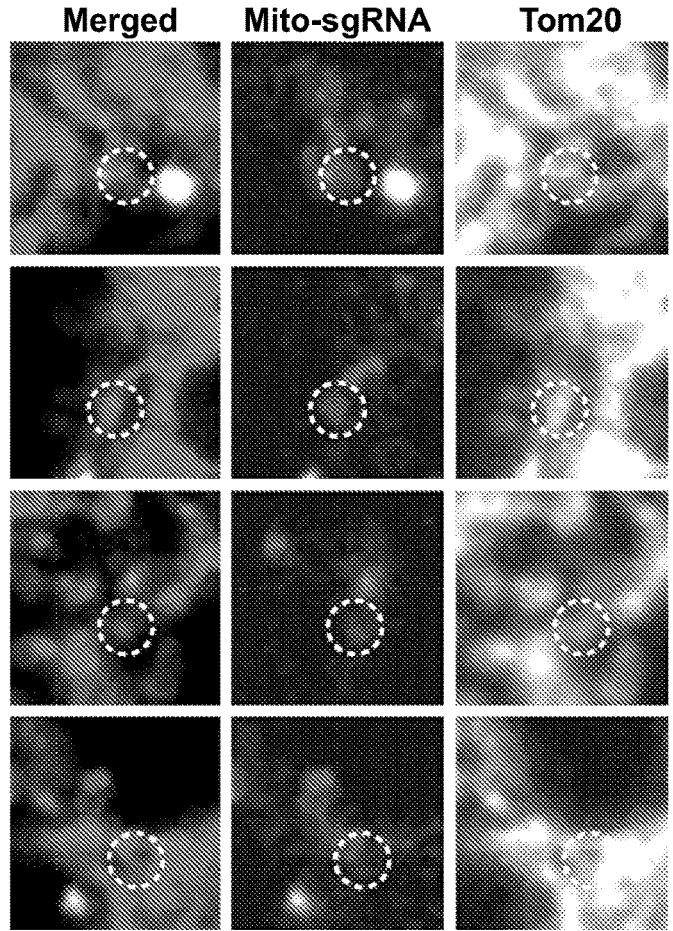

M1 (fraction of Flag signal co-localized with mitochondria):
0.8 ± 0.02 (mean ± SEM), n = 15 images
M2 (fraction of mitochondria with Flag signal): 0.64 ± 0.03
(mean ± SEM), n = 15 images In embodiments, there are provided reagents and methods useful to create sgRNAs that efficiently localize into the mitochondrial matrix: We are developing strategies for directing the mitochondrial import of the sgRNA using rationale design. Mechanisms for RNA import in mammalian mitochondria have not been well characterized, but several small RNAs have been isolated from the mitochondrial transcriptome, including the 5S ribosomal RNA, RNaseP and MRP RNA components (reviewed in [46]). Importantly, the delivery of exogenous mRNA or tRNA into mitochondria has been demonstrated by attaching these hairpin loops to the exogenous RNA [47, 48]. Additionally, a modified γ domain of 5S rRNA exhibits enhanced import of RNA into the mitochondria [49]. We will verify the efficacy of these mitochondrial localization loops (mitoloop) for mitochondrial import of the sgRNA (FIG. 2A). We have designed insertion sites of various mitoloops at positions in the sgRNA that have minimal interactions with Cas9, as seen in FIG. 2B. In particular, we have selected the tetraloop and the stem loop 2 to be replaced by mitoloops as mutations in these regions bear no impact on Cas9 binding or activity [50]. Fluorescently labeled sgRNA with various mitoloops have been transfected into mammalian cells. We observe a small degree of colocalization between 488-labeled mito-sgRNA chimera and the mitochondrial marker Tom20 (FIG. 3A). However, with the low efficiency of co-localization by lipofectamine transfection, we have employed a new strategy using lentiviral delivery of the mito-sgRNA driven by a U6 promoter, similar to the construct in FIG. 1A. With constitutive over-expression of the mito-sgRNA chimera, we anticipate greater import of the sgRNA into mitochondria to allow for sufficient mitoCas9 cleavage activity. We have constructed stable cell lines of all the lentiviral expression vectors carrying various permutations of the mito-sgRNA. We will be comparing the efficiency of sgRNA import for each mitoloop using quantitative reverse-transcription PCR (qRT-PCR) of mitoplasts. Mitochondrial outer member is selectively dissolved to form mitoplast as a means to reduce cytoplasmic RNA contamination in our assay.

In embodiments, there are provided reagents and methods to evaluate and optimize mito-sgRNA specificity for mutant mtDNA target: There are over 600 mutations in mtDNA associated with devastating encephalomyopathies, and most of these mutations are single point mutations. We are optimizing the specificity of mitoCRISPR mtDNA editing by examining the minimum length of sgRNA to maximize on-target DNA recognition. Truncation of the complementarity region of the sgRNA to 17-18 nt can significantly reduce off-target cleavage with minimal effects on on-target recognition [51]. To examine the specificity of mitoCRISPR towards mtDNA targets, we will develop a nuclear assay with dual chemiluminescence to assess cleavage activity at the wild-type or mutant mtDNA target in the nucleus with nuclear Cas9. Small regions of the mtDNA with wild-type sequence or a single point mutation will be cloned in frame with a chemiluminescence reporter plasmid, which will be transfected into Hela cells. Cleavage of the target should result in insertions/deletions (indels) that disrupt the downstream translation of the reporter or degradation of the linearized reporter plasmid by cellular exonucleases, both of which will result in a loss of signal. Various sgRNA lengths will be tested for DNA recognition specificity. Furthermore, the PAM domain is a critical region in Cas9-mediated DNA melting and RNA-DNA heteroduplex formation. We will test several Cas9 mutants with expanded repertoire of PAM recognition sites and determine if utilizing mutations that create a new PAM domain will enhance the specificity of CRISPR technology for targeting single point mutations in mtDNA.

In embodiments, there are provided reagents and method to restore mitochondrial function in LHON iPSC with mitoCRISPR: After we have determined the mitoloop design with highest import efficiency and the sgRNA with the highest specificity, we will apply the mitoCRISPR technology to patient-derived iPSC. Rescue of metabolic defects will be assessed using similar assays used to characterize the parental fibroblast and reprogrammed iPSC. It would include measuring changes in heteroplasmy levels, mtDNA copy number normalized to nuclear content, oxygen consumption, ATP levels, complex I activity, mitochondrial number and morphology. Improvements in cell growth and ROS levels will also be determined. This study is the first demonstration of mitoCRISPR as a gene therapy tool for mtDNA disorders and may serve as a therapeutic approach for stem cell transplantation.

EXPERIMENTAL

Creation of Lentiviral Construct (Plasmid Map Will be Attached).

Addgene vector 57826 was modified by removing both the 5' and 3' nuclear localization signal (NLS) of Cas9 protein. The cytochrome c oxidase subunit 8 (COX8) signal was inserted in frame with Cas9 protein at the 5' terminus as a mitochondrial targeting signal. A 3× flag tag was added in the 3' end of Cas9 as a marker for protein localization. There is a U6 promoter within the vector for expression of guide RNA. We replaced the 2 kb dummy sequence downstream of the U6 promoter with the mito-loop sgRNA constructs. The vector is renamed pL_mitoCRISPR.

Therapy Implications.

The system described herein can also utilize the mitoloop to deliver a normal copy of tRNA into mitochondria for functional rescue. This approach/system is most applicable to mtDNA diseases such MELAS (myopathy, encephalopathy, lactic acidosis, stroke-like episodes), MERRF (myoclonic epilepsy, myopathy), and MIDD (maternally inherited diabetes and deafness). However, we can also potentially rescue mtDNA diseases by delivering functional mRNA, codon-optimized for mitochondrial translation, to the mitochondria via the mitoloop. These strategies are tested in available cybrid models. Cellular function and mitochondrial respiration are quantified to determine therapeutic efficacy and efficiency of mitoloop delivery.

Cpf1.

With the recent discovery of Cpf1 as another CRISPR system in Class II, type V, the system described herein also targets Cpf1 into the mitochondria using a similar strategy as Cas9 by fusing a COX8 signal to the 5' of the Cpf1 protein. We utilize the advantages of a shorter guide RNA and ability to modify the 5' end of the guide RNA to test tRNA-mediated delivery of the sgRNA. There have been several reports that nuclear tRNA Glutamine can be imported into the mitochondria. We plan to fuse previously reported tRNA glutamine with CUG and UUG anticodon to the 5' of the Cpf1 sgRNA and determine efficiency of sgRNA delivery into mitochondria. The sequences of the tRNA have been listed in the attached Excel file.

Development of qPCR Strategy for Detecting sgRNA.

From predicted folding algorithms (e.g., M-Fold and NuPack) and our own empirical results, we have observed the single-stranded sgRNA is highly structured, with particularly strong thermodynamic stability of the sgRNA Stem-loop 2 and Stem-loop 3. Thus, when we tested RT primers which are complementary or downstream of these stem-loop regions, we observed a partial or complete inhibition of the reverse transcription reaction, owing to the unfavorable thermodynamic stability of the folded sgRNA. Thus, we have designed a new RT primer that contains a 12-nt 3'-end sequence which is complementary to a single-stranded region of the sgRNA between Stem-loops 1 and 2 (FIG. 5). Due to the short length of the resulting complementary DNA (cDNA), which limits our ability to detect it by quantitative polymerase chain reaction (qPCR), we extended the length of the resulting cDNA by adding a 44-nt stem-loop sequence to the 5'-end of the RT primer. Thus, the complete RT primer is 56-nt long. To detect the PCR amplicon for quantification, we designed a TaqMan probe that spans regions unique to the sgRNA sequence and the RT primer stem-loop. Without this design, we would be unable to detect the sgRNA by qRT-PCR, which would preclude us from confirming its localization to mitochondria.

TABLE 8 pL_mitoCRISPR plasmid map, Genbank file format. See FIG. 1D.

```
LOCUS           Exported 11948 bp ds-DNA circular SYN 13-SEP.-2015
DEFINITION      synthetic circular DNA
ACCESSION       .
VERSION         .
KEYWORDS        pL_mitoCRISPR
SOURCE          synthetic DNA construct
  ORGANISM      recombinant plasmid
REFERENCE       1 (bases 1 to 11948)
  AUTHORS       Trial User
  TITLE         Direct Submission
  JOURNAL       Exported Jan. 25, 2016 from SnapGene 3.0.3
                http://www.snapgene.com
FEATURES             Location/Qualifiers
     source          1 . . . 11948
                     /organism = "recombinant plasmid"
                     /mol_type = "other DNA"

promoter        5 . . . 231
                     /note = "RSV promoter"
                     /note = "Rous sarcoma virus enhancer/promoter"

LTR             232 . . . 412
                     /note = "5' LTR (truncated)"
                     /note = "truncated 5' long terminal repeat (LTR) from HIV-1"

misc_feature    459 . . . 584
                     /note = "HIV-1 Psi"
                     /note = "packaging signal of human immunodeficiency virus
                     type 1"

misc_feature    1077 . . . 1310
                     /note = "RRE"
                     /note = "The Rev response element (RRE) of HIV-1 allows for
                     Rev-dependent mRNA export from the nucleus to the
                     cytoplasm."

promoter        1717 . . . 1965
                     /note = "U6 promoter"
                     /note = "RNA polymerase III promoter for human U6 snRNA"

misc_feature    1962 . . . 2103 misc_feature    1962 . . . 1991
                     /label = sgRNA Target Spacer
                     /note = "sgRNA Target Spacer"

misc_feature    1967 . . . 1972
                     /label = BsmBI
                     /note = "BsmBI"
                     /note = "Name: BsmBI; Pattern: cgtctc; Number_of_matches:
                     2; cut_0_on_positive_strand:
                     1961^1962; cut_0_on_negative_strand: 1965^1966; inhibited_ by:
                     3': N4-methylcytosine 5': 5-methylcytosine; site_type:
                     other; restriction site"

misc_feature    1981 . . . 1986
                     /label = BsmBI
                     /note = "BsmBI"
                     /note = "Name: BsmBI; Pattern: cgtctc; Number_of_matches:
                     2; cut_0_on_positive_strand:
                     3846^3847; cut_0_on_negative_strand: 3850^3851; inhibited_by:
                     3': N4-methylcytosine 5': 5-methylcytosine; site_type:
                     other; restriction site"

misc_signal     1988 . . . 2063
                     /label = CRISPR RNA
                     /note = "CRISPR RNA"

misc_feature    2064 . . . 2099
                     /label = Mitochondrial Localization Loop Spacer
                     /note = "Mitochondrial Localization Loop Spacer"

misc_feature    complement(2072 . . . 2078)
                     /label = AarI
                     /note = "AarI"
```

TABLE 8-continued pL_mitoCRISPR plasmid map, Genbank file format. See FIG. 1D.

```
misc_feature    2085 . . . 2091
                /label = AarI
                /note = "AarI"

misc_feature    2144 . . . 2261
                /note = "cPPT/CTS"
                /note = "central polypurine tract and central termination
                sequence of HIV-1"

misc_feature    2732 . . . 2737
                /note = "kozak"

misc_signal     2738 . . . 2824
                /note = "Cox8"

CDS             2831 . . . 6931
                /codon_start = 1
                /product = "Cas9 (Csn1) endonuclease from the Streptococcus
                pyogenes Type II CRISPR/Cas system"
                /note = "Cas9"
                /note = "generates RNA-guided double strand breaks in DNA"
                /translation = "DKKYSIGLDIGTNSVGWAVITDEYKVPSKKFKVLGNTDRHSIKKN
                LIGALLFDSGETAEATRLKRTARRRYTRRKNRICYLQEIFSNEMAKVDDSFFHRLEESF
                LVEEDKKHERHPIFGNIVDEVAYHEKYPTIYHLRKKLVDSTDKADLRLIYLALAHMIKF
                RGHFLIEGDLNPDNSDVDKLFIQLVQTYNQLFEENPINASGVDAKAILSARLSKSRRLE
                NLIAQLPGEKKNGLFGNLIALSLGLIPNFKSNFDLAEDAKLQLSKDTYDDDLDNLLAQI
                GDQYADLFLAAKNLSDAILLSDILRVNTEITKAPLSASMIKRYDEHHQDLTLLKALVRQ
                QLPEKYKEIFFDQSKNGYAGYIDGGASQEEFYKFIKPILEKMDGTEELLVKLNREDLLR
                KQRTFDNGSIPHQIHLGELHAILRRQEDFYPFLKDNREKIEKILTFRIPYYVGPLARGN
                SRFAWMTRKSEETITPWNFEEVVDKGASAQSFIERMTNFDKNLPNEKVLPKHSLLYEYF
                TVYNELTKVKYVTEGMRKPAFLSGEQKKAIVDLLFKTNRKVTVKQLKEDYFKKIECFDS
                VEISGVEDRFNASLGTYHDLLKIIKDKDFLDNEENEDILEDIVLTLTLFEDREMIEERL
                KTYAHLFDDKVMKQLKRRRYTGWGRLSRKLINGIRDKQSGKTILDFLKSDGFANRNFMQ
                LIHDDSLTFKEDIQKAQVSGQGDSLHEHIANLAGSPAIKKGILQTVKVVDELVKVMGRH
                KPENIVIEMARENQTTQKGQKNSRERMKRIEEGIKELGSQILKEHPVENTQLQNEKLYL
                YYLQNGRDMYVDQELDINRLSDYDVDHIVPQSFLKDDSIDNKVLTRSDKNRGKSDNVPS
                EEVVKKMKNYWRQLLNAKLITQRKFDNLTKAERGGLSELDKAGFIKRQLVETRQITKHV
                AQILDSRMNTKYDENDKLIREVKVITLKSKLVSDFRKDFQFYKVREINNYHHAHDAYLN
                AVVGTALIKKYPKLESEFVYGDYKVYDVRKMIAKSEQEIGKATAKYFFYSNIMNFFKTE
                ITLANGEIRKRPLIETNGETGEIVWDKGRDFATVRKVLSMPQVNIVKKTEVQTGGFSKE
                SILPKRNSDKLIARKKDWDPKKYGGFDSPTVAYSVLVVAKVEKGKSKKLKSVKELLGIT
                IMERSSFEKNPIDFLEAKGYKEVKKDLIIKLPKYSLFELENGRKRMLASAGELQKGNEL
                ALPSKYVNFLYLASHYEKLKGSPEDNEQKQLFVEQHKHYLDEIIEQISEFSKRVILADA
                NLDKVLSAYNKHRDKPIREQAENITHLFTLTNLGAPAAFKYFDTTIDRKRYTSTKEVLD
                ATLIHQSITGLYETRIDLSQLGGD" (SEQ ID NO: 24)

misc_feature    6939 . . . 7010
                /note = "3XFlag_ETKsite"

CDS             7019 . . . 7075
                /codon_start = 1
                /product = "2A peptide from porcine teschovirus-1
                polyprotein"
                /note = "P2A"
                /note = "Eukaryotic ribosomes fail to insert a peptide bond
                between the Gly and Pro residues, yielding separate
                polypeptides."
                /translation = "ATNFSLLKQAGDVEENPGP"

CDS             7076 . . . 7789
                /codon_start = 1
                /product = "monomeric derivative of red fluorescent protein
                from Entacmaea quadricolor (Merzlyak et al., 2007)"
                /note = "TagRFP"
                /note = "mammalian codon-optimized"
                /translation = "MVSKGEELIKENMHMKLYMEGTVNNHHFKCTSEGEGKPYEGTQTM
                RIKVVEGGPLPFAFDILATSFMYGSRTFINHTQGIPDFFKQSFPEGFTWERVTTYEDGG
                VLTATQDTSLQDGCLIYNVKIRGVNFPSNGPVMQKKTLGWEANTEMLYPADGGLEGRSD
                MALKLVGGGHLICNEKTTYRSKKPAKNLKMPGVYYVDHRLERIKEADKETYVEQHEVAV
                ARYCDLPSKLGHKLN"

misc_feature    7805 . . . 8393
                /note = "WPRE"
                /note = "woodchuck hepatitis virus posttranscriptional
                regulatory element"
```

TABLE 8-continued pL_mitoCRISPR plasmid map, Genbank file format. See FIG. 1D.

```
CDS             complement(8276 . . . 8287)
                /codon_start = 1
                /product = "Factor Xa recognition and cleavage site"
                /note = "Factor Xa site"
                /translation = "IEGR"

LTR             8465 . . . 8698
                /note = "3' LTR (Delta-U3)"
                /note = "self-inactivating 3' long terminal repeat (LTR) from
                HIV-1"

polyA_signal    8776 . . . 8897
                /note = "SV40 poly(A) signal"
                /note = "SV40 polyadenylation signal"

rep_origin      8937 . . . 9072
                /note = "SV40 ori"
                /note = "SV40 origin of replication"

promoter        complement(9093 . . . 9111)
                /note = "T7 promoter"
                /note = "promoter for bacteriophage T7 RNA polymerase"

primer_bind     complement(9121 . . . 9137)
                /note = "M13 fwd"
                /note = "common sequencing primer, one of multiple similar
                variants"

rep_origin      9279 . . . 9734
                /direction = RIGHT
                /note = "f1 ori"
                /note = "f1 bacteriophage origin of replication; arrow
                indicates direction of (+) strand synthesis"

promoter        9760 . . . 9864
                /gene = "bla"
                /note = "AmpR promoter"

CDS             9865 . . . 10725
                /codon_ start = 1
                /gene = "bla"
                /product = "beta-lactamase"
                /note = "AmpR"
                /note = "confers resistance to ampicillin, carbenicillin, and
                related antibiotics"
                /translation = "MSIQHFRVALIPFFAAFCLPVFAHPETLVKVKDAEDQLGARVGYI
                ELDLNSGKILESFRPEERFPMMSTFKVLLCGAVLSRIDAGQEQLGRRIHYSQNDLVEYS
                PVTEKHLTDGMTVRELCSAAITMSDNTAANLLLTTIGGPKELTAFLHNMGDHVTRLDRW
                EPELNEAIPNDERDTTMPVAMATTLRKLLTGELLTLASRQQLIDWMEADKVAGPLLRSA
                LPAGWFIADKSGAGERGSRGIIAALGPDGKPSRIVVIYTTGSQATMDERNRQIAEIGAS
                LIKHW"

rep_origin      10896 . . . 11484
                /direction = RIGHT
                /note = "ori"
                /note = "high-copy-number ColE1/pMB1/pBR322/pUC origin of
                replication"

protein_bind    11772 . . . 11793
                /bound_moiety = "E. coli catabolite activator protein"
                /note = "CAP binding site"
                /note = "CAP binding activates transcription in the presence
                of cAMP."

promoter        11808 . . . 11838
                /note = "lac promoter"
                /note = "promoter for the E. coli lac operon"

protein_bind    11846 . . . 11862
                /bound_moiety = "lac repressor encoded by lacI"
                /note = "lac operator"
                /note = "The lac repressor binds to the lac operator to
                inhibit transcription in E. coli. This inhibition can be
                relieved by adding lactose or
                isopropyl-beta-D-thiogalactopyranoside (IPTG)."
```

TABLE 8-continued pL_mitoCRISPR plasmid map, Genbank file format. See FIG. 1D.

```
     primer_bind    11870 . . . 11886
                    /note = "M13 rev"
                    /note = "common sequencing primer, one of multiple similar
                    variants"

promoter       11907 . . . 11925
                    /note = "T3 promoter"
                    /note = "promoter for bacteriophage T3 RNA polymerase"

ORIGIN
         1    ttaatgtagt cttatgcaat actcttgtag tcttgcaaca tggtaacgat gagttagcaa
        61    catgccttac aaggagagaa aaagcaccgt gcatgccgat tggtggaagt aaggtggtac
       121    gatcgtgcct tattaggaag gcaacagacg ggtctgacat ggattggacg aaccactgaa
       181    ttgccgcatt gcagagatat tgtatttaag tgcctagctc gatacataaa cgggtctctc
       241    tggttagacc agatctgagc ctgggagctc tctggctaac tagggaaccc actgcttaag
       301    cctcaataaa gcttgccttg agtgcttcaa gtagtgtgtg cccgtctgtt gtgtgactct
       361    ggtaactaga gatccctcag accctttag tcagtgtgga aaatctctag cagtggcgcc
       421    cgaacaggga cttgaaagcg aaagggaaac cagaggagct ctctcgacgc aggactcggc
       481    ttgctgaagc gcgcacggca agaggcgagg gcggcgact ggtgagtacg ccaaaaattt
       541    tgactagcgg aggctagaag gagagagatg ggtgcgagag cgtcagtatt aagcggggga
       601    gaattagatc gcgatgggaa aaaattcggt taaggccagg gggaagaaa aaatataaat
       661    taaaacatat agtatgggca agcagggagc tagaacgatt cgcagttaat cctggcctgt
       721    tagaaacatc agaaggctgt agacaaatac tgggacagct acaaccatcc cttcagacag
       781    gatcagaaga acttagatca ttatataata cagtagcaac cctctattgt gtgcatcaaa
       841    ggatagagat aaaagacacc aaggaagctt tagacaagat agaggaagag caaaacaaaa
       901    gtaagaccac cgcacagcaa gcggccgctg atcttcagac ctggaggagg agatatgagg
       961    gacaattgga gaagtgaatt atataaatat aaagtagtaa aaattgaacc attaggagta
      1021    gcacccacca aggcaaagag aagagtggtg cagagagaaa aaagagcagt gggaatagga
      1081    gctttgttcc ttgggttctt gggagcagca ggaagcacta tgggcgcagc gtcaatgacg
      1141    ctgacggtac aggccagaca attattgtct ggtatagtgc agcagcagaa caatttgctg
      1201    agggctattg aggcgcaaca gcatctgttg caactcacag tctggggcat caagcagctc
      1261    caggcaagaa tcctggctgt ggaaagatac ctaaaggatc aacagctcct ggggatttgg
      1321    ggttgctctg gaaaactcat ttgcaccact gctgtgcctt ggaatgctag ttggagtaat
      1381    aaatctctgg aacagatttg gaatcacacg acctggatgg agtgggacag agaaattaac
      1441    aattacacaa gcttaataca ctccttaatt gaagaatcgc aaaaccagca agaaaagaat
      1501    gaacaagaat tattggaatt agataaatgg gcaagtttgt ggaattggtt taacataaca
      1561    aattggctgt ggtatataaa attattcata atgatagtag gaggcttggt aggtttaaga
      1621    atagttttg ctgtactttc tatagtgaat agagttaggc agggatattc accattatcg
      1681    tttcagaccc acctcccaac cccgagggga cccagagggg gcctatttcc catgattcct
      1741    tcatatttgc atatacgata caaggctgtt agagagataa ttagaattaa tttgactgta
      1801    aacacaaaga tattagtaca aaatacgtga cgtagaaagt aataatttct tgggtagttt
      1861    gcagttttaa aattatgttt taaaatggac tatcatatgc ttaccgtaac ttgaaagtat
      1921    ttcgatttct tggctttata tatcttgtgg aaaggacgaa acaccggaga cggcggccgc
      1981    cgtctctgtt ttagagctag aaatagcaag ttaaaataag gctagtccgt tatcaacttg
      2041    aaaaagtggc accgagtcgg tgccaccggc cgcaggtggg atcccacctg ccatggtttt
      2101    ttgaattcta gatcttgaga caaatgcag tattcatcca caattttaaa agaaaagggg
      2161    ggattggggg gtacagtgca ggggaaagaa tagtagacat aatagcaaca gacatacaaa
      2221    ctaaagaatt acaaaaacaa attacaaaaa ttcaaaattt tcgggttttat tacagggaca
      2281    gcagagatcc actttggcgc cggctcgagc gagctgcagt aacgccattt tgcaaggcat
      2341    ggaaaatac caaaccaaga atagagaagt tcagatcaag ggcgggtaca tgaaaatagc
      2401    taacgttggg ccaaacagga tatctgcggt gagcgggttc ggcccggcc cggggccaag
      2461    aacagatggt caccgcagtt tcggcccgg cccgaggcca agaacagatg gtccccagat
      2521    atgcccaac cctcagcagt ttcttaagac ccatcagatg tttccaggct cccccaagga
      2581    cctgaaatga ccctgcgcct tatttgaatt aaccaatcag cctgcttctc gcttctgttc
      2641    gcgcgcttct gcttcccgag ctctataaaa gagctcacaa cccctcactc ggcgcgccag
      2701    tcctccgaca gactgagtcg gatcaactag tgccaccatg tccgtcctga cgccgctgct
      2761    gctgcgggc ttgacaggct cggcccggcg ctcccagtg ccgcgcgcca agatccattc
      2821    gttggatccg gacaagaagt acagcatcgg cctggacatc ggcaccaact ctgtgggctg
      2881    ggccgtgatc accgacgagt acaaggtgcc cagcaagaaa ttcaaggtgc tgggcaacac
      2941    cgaccggcac agcatcaaga agaacctgat cggagccctg ctgttcgaca gcggcgaaac
      3001    agccgaggcc acccggctga agagaaccgc cagaagaaga tacaccgac ggaagaaccg
      3061    gatctgctat ctgcaagaga tcttcagcaa cgagatggcc aaggtggacg acagcttctt
      3121    ccacagactg gaagagtcct tcctggtgga agaggataag aagcacgagc ggcaccccat
      3181    cttcggcaac atcgtggacg aggtggccta ccacgaaaag taccccacca tctaccacct
      3241    gagaaagaaa ctggtggaca gcaccgacaa ggccgacctg cggctgatct atctggccct
      3301    ggcccacatg atcaagttcc ggggccactt cctgatcgag ggcgacctga accccgacaa
      3361    cagcgacgtg gacaagctgt tcatccagct ggtgcagacc tacaaccagc tgttcgagga
      3421    aaaccccatc aaccgccacg gcgtggacgc caaggccatc ctgtctgcca gactgagcaa
      3481    gagcagacgg ctggaaaatc tgatcgccca gctgcccggc gagaagaaga atggcctgtt
      3541    cggaaacctg attgccctga gcctgggcct gaccccaac ttcaagagca acttcgacct
      3601    ggccgaggat gccaaactgc agctgagcaa ggacacctac gacgacgacc tggacaacct
      3661    gctgcccag atcggcgacc agtacgccga cctgtttctg gccgccaaga acctgtccga
      3721    cgccatcctg ctgagcgaca tcctgagagt gaacaccgag atcaccaagg ccccccctgag
      3781    cgcctctatg atcaagagat acgacgagca ccaccaggac ctgaccctgc tgaaagctct
      3841    cgtgcggcag cagctgcctg agaagtacaa agagatttc ttcgaccaga gcaagaacgg
      3901    ctacgccggc tacattgacg gcggagccag ccaggaagag ttctacaagt tcatcaagcc
      3961    catcctggaa aagatggacg gcaccgagga actgctcgtg aagctgaaca gagaggacct
```

TABLE 8-continued pL_mitoCRISPR plasmid map, Genbank file format. See FIG. 1D.

```
4021    gctgcggaag cagcggacct tcgacaacgg cagcatcccc caccagatcc acctgggaga
4081    gctgcacgcc attctgcggc ggcaggaaga ttttaccca ttcctgaagg acaaccggga
4141    aaagatccag aagatcctga ccttccgcat ccctactac gtggggcctc tggccagggg
4201    aaacagcaga ttcgcctgga tgaccagaaa gagcgaggaa accatcaccc cctggaactt
4261    cgaggaagtg gtggacaagg gcgcttccgc ccagagcttc atcgagcgga tgaccaactt
4321    cgataagaac ctgcccaacg agaaggtgct gcccaagcac agcctgctgt acgagtactt
4381    caccgtgtat aacgagctga ccaaagtgaa atacgtgacc gagggaatga gaaagcccgc
4441    cttcctgagc ggcgagcaga aaaaggccat cgtggacctg ctgttcaaga ccaaccggaa
4501    agtgaccgtg aagcagctga agaggacta cttcaagaaa atcgagtgct tcgactccgt
4561    ggaaatctcc ggcgtggaag atcggttcaa cgcctccctg ggcacatacc acgatctgct
4621    gaaaattatc aaggacaagg acttcctgga caatgaggaa aacgaggaca ttctggaaga
4681    tatcgtgctg accctgacac tgtttgagga cagagagatg atcgaggaac ggctgaaaac
4741    ctatgcccac ctgttcgacg acaaagtgat gaagcagctg aagcggcgga gatacaccgg
4801    ctggggcagg ctgagccgga agctgatcaa cggcatccgg acaagcagt ccggcaagac
4861    aatcctggat ttcctgaagt ccgacggctt cgccaacaga aacttcatgc agctgatcca
4921    cgacgacagc ctgacctta aagaggacat ccagaaagcc caggtgtccg gccagggcga
4981    tagcctgcac gagcacattg ccaatctggc cggcagcccc gccattaaga agggcatcct
5041    gcagacagtg aaggtggtgg acgagctcgt gaaagtgatg ggccggcaca gcccgagaa
5101    catcgtgatc gaaatggcca gagagaacca gaccaccag aagggacaga agaacagccg
5161    cgagagaatg aagcggatcg aagagggcat caaagagctg ggcagccaga tcctgaaaga
5221    acacccgtg gaaaacaccc agctgcagaa cgagaagctg tacctgtact acctgcagaa
5281    tgggcgggat atgtacgtgg accaggaact ggacatcaac cggctgtccg actacgatgt
5341    ggaccatatc gtgcctcaga gctttctgaa ggacgactcc atcgacaaca aggtgctgac
5401    cagaagcgac aagaaccggg gcaagagcga caacgtgccc tccgaagagg tcgtgaagaa
5461    gatgaagaac tactggcggc agctgctgaa cgccaagctg attcccaga gaaagttcga
5521    caatctgacc aaggccgaga gaggcggcct gagcgaactg gataaggccg gcttcatcaa
5581    gagacagctg gtggaaaccc ggcagatcac aaagcacgtg gcacagatcc tggactcccg
5641    gatgaacact aagtacgacg agaatgacaa gctgatccgg gaagtgaaag tgatcaccct
5701    gaagtccaag ctggtgtccg atttccggaa ggatttccag ttttacaaag tgcgcgagat
5761    caacaactac caccacgccc acgacgccta cctgaacgcc gtcgtgggaa ccgccctgat
5821    caaaaagtac cctaagctgg aaagcgagtt cgtgtacggc gactacaagg tgtacgacgt
5881    gcggaagatg atcgccaaga gcagcagga aatcggcaag gctaccgcca agtacttctt
5941    ctacagcaac atcatgaact ttttcaagac cgagattacc ctggccaacg cgagatccg
6001    gaagcggcct ctgatcgaga caaacgcga aacggggag atcgtgtggg ataagggccg
6061    ggattttgcc accgtgcgga aagtgctgag catgccccaa gtgaatatcg tgaaaaagac
6121    cgaggtgcag acaggcggct tcagcaaaga gtctatcctg cccaagaga acagcgataa
6181    gctgatcgcc agaaagaagg actgggaccc taagaagtac ggcggcttcg acagcccac
6241    cgtggcctat tctgtgctgg tggtggccaa agtggaaaag ggcaagtcca gaaactgaa
6301    gagtgtgaaa gagctgctgg ggatcaccat catggaaga agcagcttcg agaagaatcc
6361    catcgacttt ctggaagcca agggctacaa agaagtgaaa aaggacctga tcatcaagct
6421    gcctaagtac tccctgttcg agctggaaaa cggccggaag gaatgctgag cctctgccgg
6481    cgaactgcag aagggaaacg aactggccct gcctccaaa tatgtgaact tctgtaccct
6541    ggccagccac tatgagaagc tgaagggctc ccccgaggat aatgagcaga acagctgtt
6601    tgtggaacag cacaagcact acctggacga gatcatcgag cagatcagcg agttctccaa
6661    gagagtgatc ctggccgacg ctaatctgga caaagtgctg tccgcctaca acaagcaccg
6721    ggataagccc atcagagagc aggccgagaa tatcatccac ctgtttaccc tgaccaatct
6781    gggagcccct gccgccttca gtactttga caccaccatc gaccggaaga ggtacaccag
6841    caccaaagag gtgctgagcg ccaccctgat ccaccagagc atcaccggcc tgtacgagac
6901    acggatcgac ctgtctcagc tgggaggcga cgctagcgac tataaggacc acgacggaga
6961    ctacaaggat catgatattg attacaaaga cgatgacgat aagcctagcg cagcggcgc
7021    caccaacttc agcctgctga gcaggccgg cgacgtggag gagaaccccg gccccatggt
7081    gtctaagggc gaagagctga ttaaggagaa catgcacatg aagctgtata tggagggcac
7141    cgtgaacaac caccacttca gtgcacatc cgagggcgaa ggcaagcct acgagggcac
7201    ccagaccatg agaatcaagg tggtcgaggg cggccctctc cccttcgcct tcgacatcct
7261    ggctaccagc ttcatgtacg gcagcagaac cttcatcaac cacccagg gcatccccga
7321    cttctttaag cagtccttcc ctgagggctt cacatgggag agagtcacca tacgaagga
7381    cggggggcgtg ctgaccgtca cccaggacac gaccggctcgc tcatctacaa
7441    cgtcaagatc agaggggtga acttcccatc caacggccct gtgatgcaga agaaaacact
7501    cggctgggag gccaacaccg agatgctgta ccccgctgac ggcggcctgg aaggcagaag
7561    cgacatggcc ctgaagctcg tgggcggggg ccacctgatc tgcaacttca gaccacata
7621    cagatccaag aaacccgcta agaacctgaa gatgcccggc gtctactatg tggaccacag
7681    actggaaaga atcaaggagg ccgacaaaga gacctacgtc gagcagcacg aggtggctgt
7741    ggccagatac tgcgacctcc ctagcaaact ggggcacaaa cttaattgaa cgcgttaagt
7801    cgacaatcaa cctctggatt acaaaatttg tgaaagattg actggtattc ttaactatgt
7861    tgctcctttt acgctatgtg gatacgctgc tttatgcct ttgtatcatg ctattgcttc
7921    ccgtatggct ttcattttct cctccttgta taatcctggt tgctgtctc tttatgagga
7981    gttgtggccc gttgtcaggc aacgtggcgt ggtgtgcact gtgtttgctg acgcaacccc
8041    cactggttgg ggcattgcca ccacctgtca gctcctttcc gggactttcg ctttcccct
8101    ccctattgcc acggcggaac tcatcgccgc ctgccttgc cgctgctgac caggggctcg
8161    gctgttgggc actgacaatt ccgtggtgtt gtcggggaaa tcatcgtcct ttccttggct
8221    gctcgcctgt gttgccacct ggattctgcg cgggacgtcc ttctgctacg tcccttcggc
8281    cctcaatcca gcggaccttc cttcccgcgg cctgctgccg gctctgcggc ctcttccgcg
8341    tcttcgcctt cgccctcaga cgagtcggat ctccctttgg gccgcctccc cgcctgact
8401    ttaagaccaa tgacttacaa ggcagctgta gatcttagcc acttttaaa agaaaagggg
8461    ggactggaag gctaattca ctcccaacga agacaagatc tgcttttgtc ttgtactggg
8521    tctctctggt tagaccagat ctgagcctgg gagctctctg ctaactagg gaacccactg
8581    cttaagcctc aataaagctt gccttgagtg cttcaagtag tgtgtgcccg tctgttgtgt
8641    gactctggta actagagatc cctcagaccc tttagtcag tgtggaaaat ctctagcagt
```

TABLE 8-continued pL_mitoCRISPR plasmid map, Genbank file format. See FIG. 1D.

```
8701       acgtatagta gttcatgtca tcttattatt cagtatttat aacttgcaaa gaaatgaata
8761       tcagagagtg agaggaactt gtttattgca gcttataatg gttacaaata aagcaatagc
8821       atcacaaatt tcacaaataa agcatttttt tcactgcatt ctagttgtgg tttgtccaaa
8881       ctcatcaatg tatcttatca tgtctggctc tagctatccc gccctaact ccgcccatcc
8941       cgcccctaac tccgcccagt tccgcccatt ctccgcccca tggctgacta atttttttta
9001       tttatgcaga ggccgaggcc gcctcggcct ctgagctatt ccagaagtag tgaggaggct
9061       tttttggagg cctagggacg tacccaattc gccctatagt gagtcgtatt acgcgcgctc
9121       actggccgtc gttttacaac gtcgtgactg ggaaaaccct ggcgttaccc aacttaatcg
9181       ccttgcagca catcccccctt tcgccagctg gcgtaatagc gaagaggccc gcaccgatcg
9241       cccttcccaa cagttgcgca gcctgaatgg cgaatgggac gcgccctgta gcggcgcatt
9301       aagcgcggcg ggtgtggtgg ttacgcgcag cgtgaccgct acacttgcca gcgccctagc
9361       gcccgctcct ttcgctttct tcccttcctt tctcgccacg ttcgccggct ttccccgtca
9421       agctctaaat cgggggctcc ctttagggtt ccgatttagt gctttacggc acctcgaccc
9481       caaaaaactt gattagggtg atggttcacg tagtgggcca tcgccctgat agacggtttt
9541       tcgccctttg acgttggagt ccacgttctt taatagtgga ctcttgttcc aaactggaac
9601       aacactcaac cctatctcgg tctattcttt tgatttataa gggattttgc cgatttcggc
9661       ctattggtta aaaaatgagc tgatttaaca aaaatttaac gcgaatttta acaaaatatt
9721       aacgcttaca atttaggtgg cactttttcgg ggaaatgtgc gcggaacccc tatttgttta
9781       tttttctaaa tacattcaaa tatgtatccg ctcatgagac aataaccctg ataaatgctt
9841       caataatatt gaaaaaggaa gagtatgagt attcaacatt tccgtgtcgc ccttattccc
9901       tttttttgcgg catttttgcct tcctgttttt gctcacccag aaacgctggt gaaagtaaaa
9961       gatgctgaag atcagttggg tgcacgagtg ggttacatcg aactggatct caacagcggt
10021      aagatccttg agagtttttcg ccccgaagaa cgttttccaa tgatgagcac ttttaaagtt
10081      ctgctatgtg gcgcggtatt atcccgtatt gacgccgggc aagagcaact cggtcgccgc
10141      atacactatt ctcagaatga cttggttgag tactcaccag tcacagaaaa gcatcttacg
10201      gatggcatga cagtaagaga attatgcagt gctgccataa ccatgagtga taacactgcg
10261      gccaacttac ttctgacaac gatcggagga ccgaaggagc taaccgcttt tttgcacaac
10321      atgggggatc atgtaactcg ccttgatcgt tgggaaccgg agctgaatga agccatacca
10381      aacgacgagc gtgacaccac gatgcctgta gcaatggcaa caacgttgcg caaactatta
10441      actggcgaac tacttactct agcttcccgg caacaattaa tagactggat ggaggcggat
10501      aaagttgcag gaccacttct gcgctcggcc cttccggctg gctggtttat tgctgataaa
10561      tctggagccg gtgagcgtgg gtctcgcggt atcattgcag cactggggcc agatggtaag
10621      ccctcccgta tcgtagttat ctacacgacg gggagtcagg caactatgga tgaacgaaat
10681      agacagatcg ctgagatagg tgcctcactg attaagcatt ggtaactgtc agaccaagtt
10741      tactcatata tactttagat tgatttaaaa cttcatttttt aatttaaaag gatctaggtg
10801      aagatccttt ttgataatct catgaccaaa atcccttaac gtgagttttc gttccactga
10861      gcgtcagacc ccgtagaaaa gatcaaagga tcttcttgag atccttttttt tctgcgcgta
10921      atctgctgct tgcaaacaaa aaaaccaccg ctaccagcgg tggtttgttt gccggatcaa
10981      gagctaccaa ctctttttcc gaaggtaact ggcttcagca gagcgcagat accaaatact
11041      gttcttctag gtagccgta gttaggccac cacttcaaga actctgtagc accgcctaca
11101      tacctcgctc tgctaatcct gttaccagtg gctgctgcca gtggcgataa gtcgtgtctt
11161      accgggttgg actcaagacg atagttaccg gataaggcgc agcggtcggg ctgaacgggg
11221      ggttcgtgca cacagcccag cttggagcga acgacctaca ccgaactgag atacctacag
11281      cgtgagctat gagaaagcgc cacgcttccc gaagggagaa aggcggacag gtatccggta
11341      agcggcaggg tcggaacagg agagcgcacg agggagcttc caggggggaaa cgcctggtat
11401      ctttatagtc ctgtcgggtt tcgccacctc tgacttgagc gtcgatttttt gtgatgctcg
11461      tcaggggggc ggagcctatg gaaaaacgcc agcaacgcgg cctttttacg gttcctggcc
11521      ttttgctggc cttttgctca catgttcttt cctgcgttat cccctgattc tgtggataac
11581      cgtattaccg cctttgagtg agctgatacc gctcgccgca gccgaacgac cgagcgcagc
11641      gagtcagtga gcgaggaagc ggaagagcgc ccaatacgca aaccgcctct ccccgcgcgt
11701      tggccgattc attaatgcag ctggcacgac aggtttcccg actggaaagc gggcagtgag
11761      cgcaacgcaa ttaatgtgag ttagctcact cattaggcac cccaggcttt acactttatg
11821      cttccggctc gtatgttgtg tggaattgtg agcggataac aatttcacac aggaaacagc
11881      tatgaccatg attacgccaa gcgcgcaatt aaccctcact aaagggaaca aaagctggag
11941      ctgcaagc   (SEQ ID NO: 125)
//
```

References (Example 1)

[1] Huoponen, K., et al., A new mtDNA mutation associated with Leber hereditary optic neuroretinopathy. American Journal of Human Genetics, 1991. 48(6): p. 1147-53.: [2] Wallace, D. C., et al., Mitochondrial DNA mutation associated with Leber's hereditary optic neuropathy. Science, 1988. 242(4884): p. 1427-30.: [3] Yu-Wai-Man, P., P. G. Griffiths, and P. F. Chinnery, Mitochondrial optic neuropathies—disease mechanisms and therapeutic strategies. Prog Retin Eye Res, 2011. 30(2): p. 81-114.: [4] Pan, B. X., et al., Mathematically modeling the involvement of axons in Leber's hereditary optic neuropathy. Invest Ophthalmol Vis Sci, 2012. 53(12): p. 7608-17.: [5]. oilkonda, R. D. and J. Guy, Leber's Hereditary Optic Neuropathy-Gene Therapy: From Benchtop to Bedside. J Ophthalmol, 2011. 2011: p. 179412.: [6] Erickson, R. P., Leber's optic atrophy, a possible example of maternal inheritance. Am J Hum Genet, 1972. 24(3): p. 348-9.: [7] Carelli, V., F. N. Ross-Cisneros, and A. A. Sadun, Mitochondrial dysfunction as a cause of optic neuropathies. Prog Retin Eye Res, 2004. 23(1): p. 53-89.: [8] Huoponen, K., Leber hereditary optic neuropathy: clinical and molecular genetic findings. Neurogenetics, 2001. 3(3): p. 119-25.: [9] Bu, X. D. and J. I. Rotter, X chromosome-linked and mitochondrial gene control of Leber hereditary optic neuropathy: evidence from segregation analysis for dependence on X chromosome inactivation. Proc Natl Acad Sci USA, 1991. 88(18): p. 8198-202.: [10] Ji, Y., et al., Evaluation of the X-linked modifier loci for Leber hereditary optic neuropathy with the G11778A mutation in Chinese. Mol Vis, 2010. 16: p. 416-24.: [11] Hudson, G., et al., Identification of an X-chromosomal locus and haplotype modulating the phenotype of a mitochondrial DNA disorder. Am J Hum Genet, 2005. 77(6): p. 1086-91.: [12] Chen, J. D. and M. J. Denton, X-chromosomal gene in Leber hereditary optic neuroretinopathy. Am J Hum Genet, 1991. 49(3): p. 692-3.: [13] Oostra, R. J., et al., No evidence for 'skewed' inactivation of the X-chromosome as cause of Leber's hereditary optic neuropathy in female carriers. Hum Genet, 1996. 97(4): p. 500-5.: [14] Giordano, C., et al., Oestrogens ameliorate mitochondrial dysfunction in Leber's hereditary optic neuropathy. Brain, 2011. 134(Pt 1): p. 220-34.: [15] Pisano, A., et al., Targeting estrogen receptor beta as preventive therapeutic strategy for Leber's hereditary optic neuropathy. Hum Mol Genet, 2015. 24(24): p. 6921-31.: [16] Bristow, E. A., et al., The distribution of mitochondrial activity in relation to optic nerve structure. Arch Ophthalmol, 2002. 120(6): p. 791-6.: [17] Sadun, A. A., et al., Leber's hereditary optic neuropathy differentially affects smaller axons in the optic nerve. Trans Am Ophthalmol Soc, 2000. 98: p. 223-32; discussion 232-5.: [18] King, M. P. and G. Attardi, Human cells lacking mtDNA: repopulation with exogenous mitochondria by complementation. Science, 1989. 246(4929): p. 500-3.: [19] Schoeler, S., et al., Glutathione depletion in antioxidant defense of differentiated NT2-LHON cybrids. Neurobiol Dis, 2007. 25(3): p. 536-44.: [20] Zanna, C., et al., Caspase-independent death of Leber's hereditary optic neuropathy cybrids is driven by energetic failure and mediated by AIF and Endonuclease G. Apoptosis, 2005. 10(5): p. 997-1007.: [21] Baracca, A., et al., Severe impairment of complex I-driven adenosine triphosphate synthesis in Leber hereditary optic neuropathy cybrids. Arch Neurol, 2005. 62(5): p. 730-6.: [22] Kirches, E., LHON: Mitochondrial Mutations and More. Current Genomics, 2011. 12(1): p. 44-54.: [23] Sadun, A. A., et al., Extensive investigation of a large Brazilian pedigree of 11778/haplogroup J Leber hereditary optic neuropathy. Am J Ophthalmol, 2003. 136(2): p. 231-8.: [24] Sadun, A. A., et al., Effect of EPI-743 on the clinical course of the mitochondrial disease Leber hereditary optic neuropathy. Arch Neurol, 2012. 69(3): p. 331-8.: [25] Meyerson, C., G. Van Stavern, and C. McClelland, Leber hereditary optic neuropathy: current perspectives. Clin Ophthalmol, 2015. 9: p. 1165-76.: [26] Koilkonda, R. D., et al., Safety and effects of the vector for the Leber hereditary optic neuropathy gene therapy clinical trial. JAMA Ophthalmol, 2014. 132(4): p. 409-20.: [27] Lightowlers, R. N., R. W. Taylor, and D. M. Turnbull, Mutations causing mitochondrial disease: What is new and what challenges remain? Science, 2015. 349(6255): p. 1494-9.: [28] Alexeyev, M., et al., The maintenance of mitochondrial DNA integrity—critical analysis and update. Cold Spring Harb Perspect Biol, 2013. 5(5): p. a012641.: [29] Bacman, S. R., et al., Specific elimination of mutant mitochondrial genomes in patient-derived cells by mito-TALENs. Nat Med, 2013. 19(9): p. 1111-3.: [30] Gammage, P. A., et al., Mitochondrially targeted ZFNs for selective degradation of pathogenic mitochondrial genomes bearing large-scale deletions or point mutations. EMBO Mol Med, 2014. 6(4): p. 458-66.: [31] Hashimoto, M., et al., Mito-TALEN: A General Approach to Reduce Mutant mtDNA Loads and Restore Oxidative Phosphorylation Function in Mitochondrial Diseases. Mol Ther, 2015. 23(10): p. 1592-9.: [32] Reddy, P., et al., Selective elimination of mitochondrial mutations in the germline by genome editing. Cell, 2015. 161(3): p. 459-69.: [33] Tachibana, M., et al., Mitochondrial gene replacement in primate offspring and embryonic stem cells. Nature, 2009. 461(7262): p. 367-72.: [34] Ma, H., et al., Metabolic rescue in pluripotent cells from patients with mtDNA disease. Nature, 2015. 524(7564): p. 234-8.: [35] Deuse, T., et al., SCNT-derived ESCs with mismatched mitochondria trigger an immune response in allogeneic hosts. Cell Stem Cell, 2015. 16(1): p. 33-8.: [36] Jinek, M., et al., A programmable dual-RNA-guided DNA endonuclease in adaptive bacterial immunity. Science, 2012. 337 (6096): p. 816-21.: [37] Vierbuchen, T., et al., Direct conversion of fibroblasts to functional neurons by defined factors. Nature, 2010. 463(7284): p. 1035-41.: [38] Zhang, Y., et al., Rapid single-step induction of functional neurons from human pluripotent stem cells. Neuron, 2013. 78(5): p. 785-98.: [39] Tanaka, T., et al., Generation of retinal ganglion cells with functional axons from human induced pluripotent stem cells. Sci Rep, 2015. 5: p. 8344.: [40] Folmes, C. D., et al., Disease-causing mitochondrial heteroplasmy segregated within induced pluripotent stem cell clones derived from a patient with MELAS. Stem Cells, 2013. 31(7): p. 1298-308.: [41] Schwartz, S. D., et al., Human embryonic stem cell-derived retinal pigment epithelium in patients with age-related macular degeneration and Stargardt's macular dystrophy: follow-up of two open-label phase 1/2 studies. Lancet, 2015. 385(9967): p. 509-16.: [42] Song, W. K., et al., Treatment of macular degeneration using embryonic stem cell-derived retinal pigment epithelium: preliminary results in Asian patients. Stem Cell Reports, 2015. 4(5): p. 860-72.: [43] Brandon, M. C., et al., MITOMAP: a human mitochondrial genome database—2004 update. Nucleic Acids Res, 2005. 33(Database issue): p. D611-3.: [44] Howell, N., et al., A heteroplasmic LHON family: tissue distribution and transmission of the 11778 mutation. Am J Hum Genet, 1994. 55(1): p. 203-6.: [45] Phillips, N. R., M. L. Sprouse, and R. K. Roby, Simultaneous quantification of mitochondrial DNA copy number and deletion ratio: a multiplex real-time PCR assay. Sci Rep, 2014. 4: p. 3887.: [46] Schneider, A., Mitochondrial tRNA import and its consequences for mitochondrial translation. Annu Rev Biochem, 2011. 80: p. 1033-53.: [47] Wang, G., et al., PNPASE regulates RNA import into mitochondria. Cell, 2010. 142(3): p. 456-67.: [48] Comte, C., et al., Mitochondrial targeting of recombinant RNAs modulates the level of a heteroplasmic mutation in human mitochondrial DNA associated with Kearns Sayre Syndrome. Nucleic Acids Res, 2013. 41(1): p. 418-33.: [49] Zelenka, J., et al., Import of desired nucleic acid sequences using addressing motif of mitochondrial ribosomal 5S-rRNA for fluorescent in vivo hybridization of mitochondrial DNA and RNA. J Bioenerg Biomembr, 2014. 46(2): p. 147-56.: [50] Konermann, S., et al., Genome-scale transcriptional activation by an engineered CRISPR-Cas9 complex. Nature, 2014.: [51] Fu, Y., et al., Improving CRISPR-Cas nuclease specificity using truncated guide RNAs. Nat Biotechnol, 2014. 32(3): p. 279-84.

Example 2. Mitochondrial DNA Manipulation Using CRISPR/Cas9 Genome Editing Technology Specific Aims:

The CRISPR single-guide RNA (sgRNA) and Cas9 protein are engineered for trafficking into the mitochondrial matrix for genome editing of mitochondrial DNA (mtDNA). Our overarching goal is to develop novel therapeutic strategies to treat and potentially cure mitochondrial diseases resulting from pathogenic mtDNA mutations that exist in heteroplasmy.

Aim 1: To create sgRNAs that efficiently localize into the mitochondrial matrix.

Aim 2: To evaluate and optimize mito-sgRNA specificity for mutant mtDNA target.

Aim 3: To restore oxidative phosphorylation in cybrid cells with mitoCRISPR.

Significance:

Mitochondria are unique organelles that are the powerhouse of the cell and carry its own genomic content. Mitochondrial DNA (mtDNA) is a double-stranded circular molecule that encodes 37 genes, 24 of which are necessary for mtDNA translation (2 ribosomal RNAs, 22 transfer RNAs) and 13 subunits of the respiratory chain (complex I, III, IV and V) critical for producing energy in the form of ATP. MtDNA is present in hundreds to thousands of copies inside the cell and nucleotide polymorphisms produce a state of heteroplasmy. Random genetic drift during cell division can result in some cells or tissues containing higher loads of pathogenic mtDNA. Once a critical mutation threshold has been reached, cells exhibit a bioenergetic defect due to dysfunction of the respiratory chain. Many mitochondrial diseases lead to devastating disorders of encephalomyopathies wherein tissues with high metabolic demands, such as musculoskeletal and neuronal tissues, are severely affected.

Strategies aimed at eliminating mutant mtDNA have shown to be effective in shifting heteroplasmy towards lower mutation load and rescuing cellular metabolic defects, thus establishing the proof-of-principle of the propose strategy(1). There are limited DNA repair mechanisms in mammalian mitochondria, and given the high redundancy of mitochondrial genome in the cell, clearance of mtDNA is a predominant mechanism in protecting the fidelity of mtDNA in mammalian cells(2, 3). As a result, targeting of restriction endonucleases or homing endonucleases, such as transcription activator-like effector nucleases (TALENs) and zinc-finger nucleases (ZFNs), to mitochondria with high levels of heteroplasmy resulted in successful depletion of mutant mtDNA and rescue of metabolic defects(2, 4-8). Furthermore, these gene editing modalities have been utilized for inducing heteroplasmic shift in the germline of murine models and human oocytes with minimal adverse effects on cell development or animal fitness suggesting that the strategy is a viable clinical therapy(9). However, the generalizability of these tools for clinical therapy is limited. Usage of restriction endonucleases requires a specific mutation that creates a compatible restriction site, and thus it is not a generalizable technique for the vast amount of characterized mtDNA mutations. Homing endonucleases such as TALENs and ZFNs require mitochondrial import of large bulky protein motifs for sequence recognition and often result in insufficient expression and poor localization in mitochondria. Although mitochondrial replacement by means of spindle-chromosomal complex transfer in oocytes(10) or somatic cell nuclear transfer in pluripotent stem cells(11) has shown promise, recent studies showed that mismatched mitochondria in nuclear-transfer-derived embryonic stem cells (NT-ESCs) can trigger an adaptive immune response and cause immune rejection of the graft(12).

Innovation:

The system described herein adapts the CRISPR genome editing technology towards manipulating mtDNA. Our goal is to engineer this technology for targeting heteroplasmic mtDNA mutations in cybrid models of mitochondrial diseases. The development of mitoCRISPR, as we have termed it, would offer greater versatility and specificity over other mitochondrial-localizing genome editing platforms (e.g., mito-ZFN, mito-TALEN, etc.), since mitoCRISPR could be tailored to target any of the >200 documented mtDNA mutations with sequence-specific sgRNAs.

Results:

We have successfully targeted the *S. pyogenes* Cas9 protein into the mitochondrial matrix by removing the nuclear localization signals and adding an N-terminal mitochondrial targeting sequence derived from the cytochrome c oxidase subunit VIII (Coxa). We have generated a lentiviral vector with mitoCas9-Flag protein driven by the SFFV promoter and a U6 RNA polymerase III promoter that drives expression of the mitochondrial-localizing sgRNA (mito-sgRNA) (FIG. 1A). Confocal analysis shows highly co-localized signal between mitoCas9-Flag protein with mitochondrial outer membrane marker Tom20 (FIG. 1C).

Figure 1B:
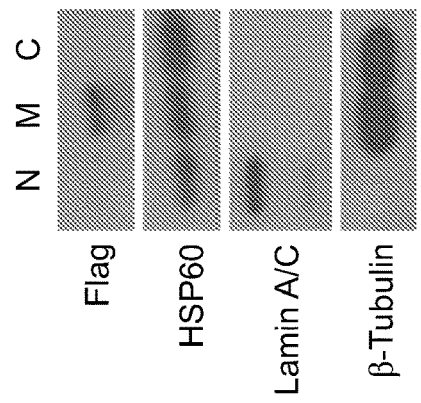
Figure 1C:
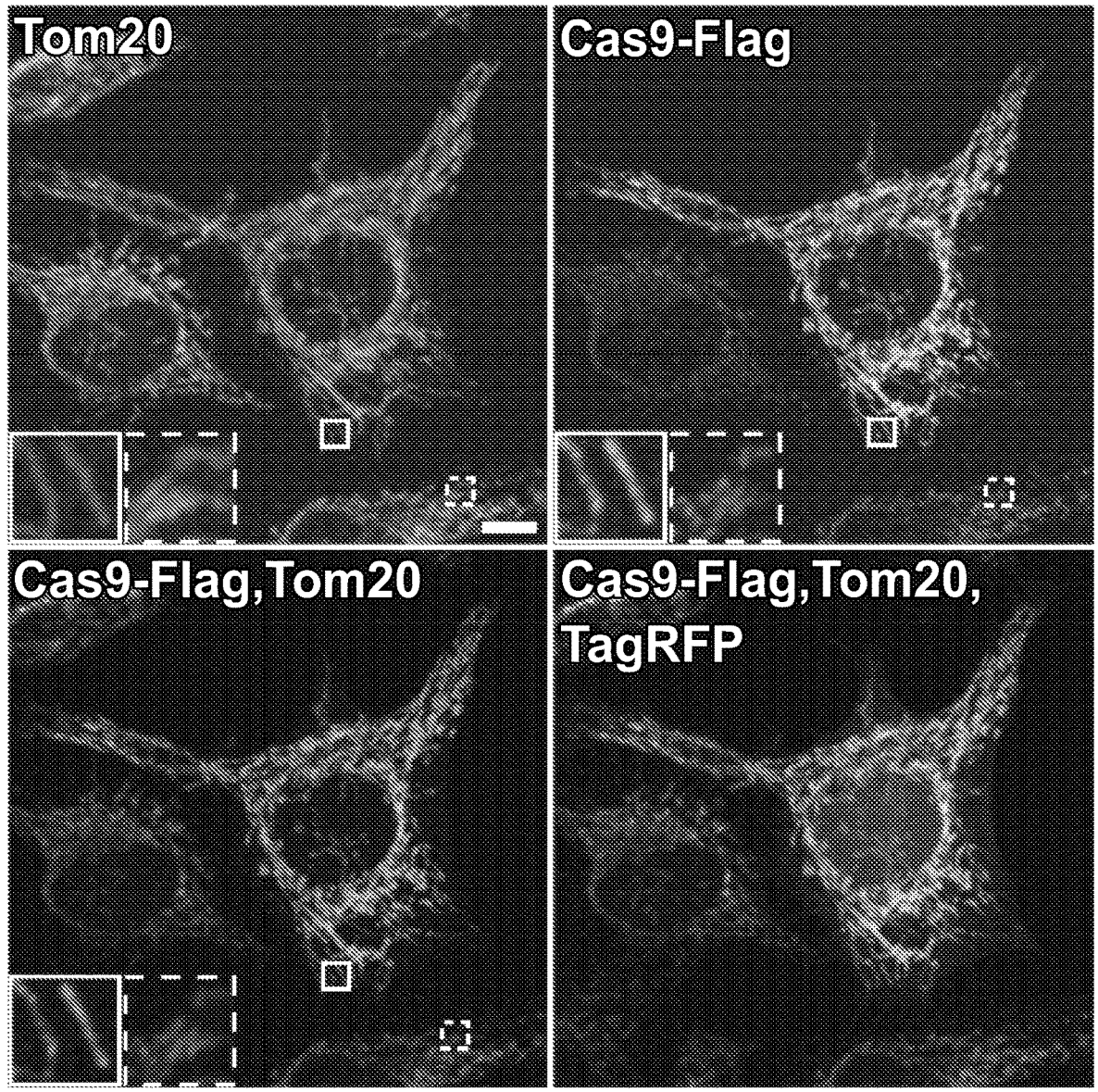
Figure 1D:
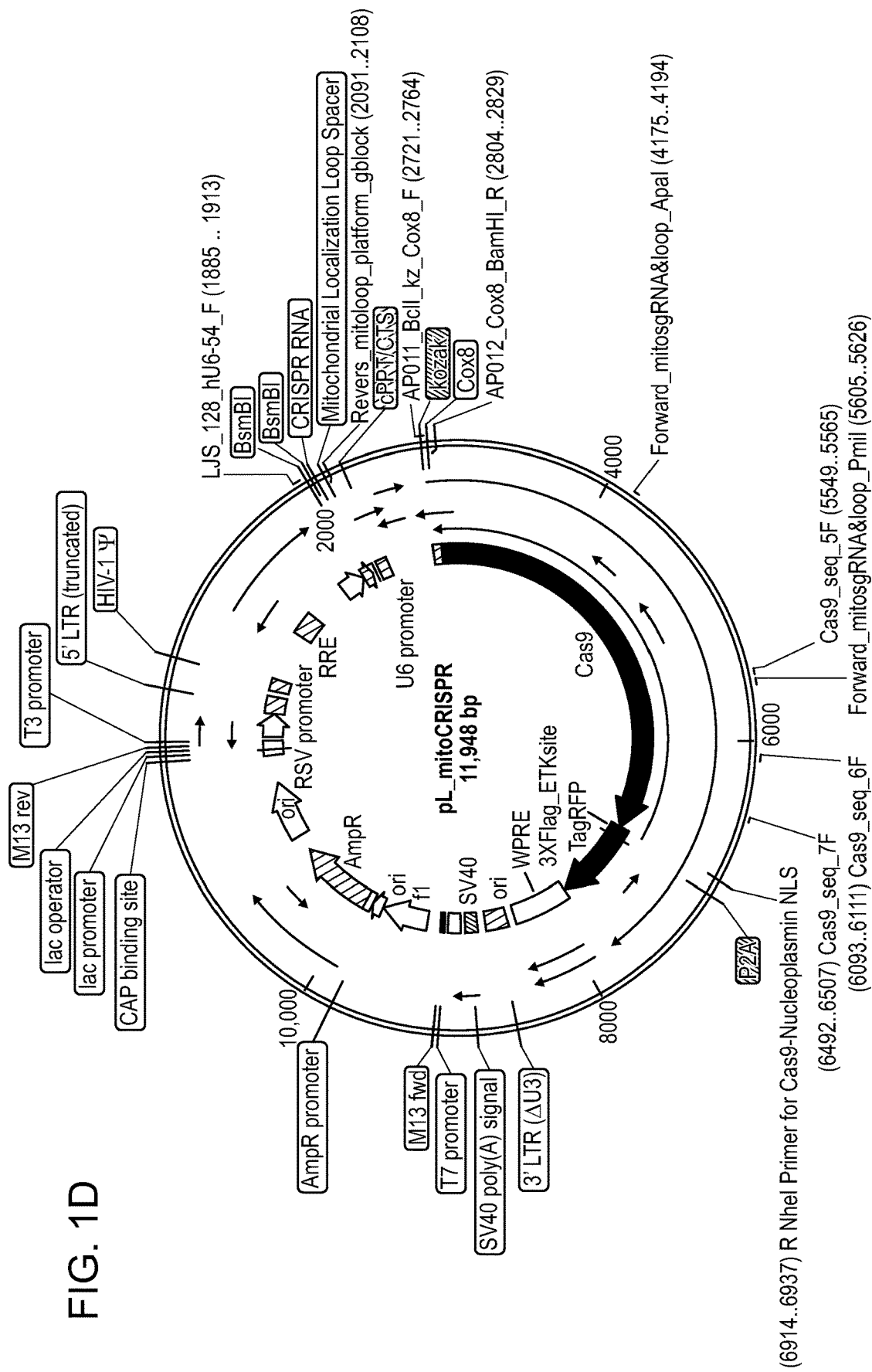

Mitochondrial fractionation also demonstrates an enrichment of Cas9-flag in the mitochondrial fraction (FIG. 1B). Given the new discovery that Cpf1 is another Class II (type V) CRISPR protein with similar genome editing efficiency in mammalian cells relative to Cas9(13), we are now constructing mitoCpf1 using a similar strategy.

To create sgRNAs that efficiently localize into the mitochondrial matrix: We are developing strategies for directing the mitochondrial import of the sgRNA using rationale design. Mechanisms for RNA import in mammalian mitochondria have not been defined, but several small RNAs have been isolated from the mitochondrial transcriptome, including the 5S ribosomal RNA, RNaseP and MRP RNA components (reviewed in (14)). Importantly, the delivery of exogenous mRNA or tRNA into mitochondria has been demonstrated by attaching these hairpin loops to the exogenous RNA (15-17). Additionally, a modified γ domain of 5S rRNA exhibits enhanced import of RNA into the mitochondria (18, 19). We will verify the efficacy of these mitochondrial localization loops (mitoloop) for mitochondrial import of the sgRNA (FIG. 2A). We have designed insertion sites of various mitoloops at positions in the sgRNA that have minimal interactions with Cas9, as seen in FIG. 2B. In particular, we have selected the tetraloop and the stem loop 2 to be replaced by mitoloops as mutations in these regions bear no impact on Cas9 binding or activity(20). The import of sgRNA into the mitochondria will be verified by imaging analysis and quantitative reverse transcription PCR (qRT-PCR). Fluorescently labeled sgRNA with various mitoloops will be introduced to mammalian cells via transfection or electroporation techniques. Co-localization analysis will be performed between the sgRNA signal and a mitochondrial marker as a measure of sgRNA import efficiency. Furthermore, we will quantify sgRNA content in purified mitoplast, formed by selective dissolution of mitochondrial outer membrane, by qRT-PCR.

To evaluate and optimize mito-sgRNA specificity for mutant mtDNA target: There are over 200 mutations in mtDNA associated with devastating encephalomyopathies, and most of these mutations are single point mutations. We are optimizing the specificity of CRISPR genome editing by examining the minimum length of sgRNA to maximize on-target DNA recognition. Truncation of the complementarity region of the sgRNA to 17-18 nt can significantly reduce off target cleavage with minimal effects on on-target recognition (25). To examine the specificity of CRISPR towards mtDNA targets, we will develop a nuclear assay with dual chemiluminescence or fluorescence to assess cleavage activity at the wildtype or mutant DNA target in the nucleus with nuclear Cas9. Small regions of the mtDNA with wildtype sequence or a single point mutation will be fused in frame with a chemiluminescence reporter. Cleavage of the target should result in insertions/deletions (indels) that may disrupt the downstream translation of the reporter and result in a loss of signal. Various sgRNA lengths will be tested for DNA recognition specificity. Furthermore, the protospacer adjacent motif (PAM) domain is critical region in Cas9-mediated DNA melting and RNA-DNA heteroduplex formation. Several mutation variants of Cas9 have been generated with expanded repertoire of PAM recognition sites. We will determine if utilizing mutations that create a new PAM domain will enhance the specificity of CRISPR technology for targeting single point mutations in mtDNA.

To restore oxidative phosphorylation in cybrid cells with mitoCRISPR: After we have determined the mitoloop design with highest import efficiency, we will apply the mitoCRISPR technology with mito-sgRNA in cellular models of mitochondrial diseases. Cytoplasmic hybrids (cybrids) have become an invaluable resource for studying the mechanisms and testing therapies for mitochondrial diseases due to the inability to transform mtDNA. Cybrids are derived from enucleated fibroblasts from patients that carry mitochondria with heteroplasmic or homoplasmic mutations. These cells are subsequently fused with an immortalized osteosarcoma cell line that has been depleted of mitochondria. We have obtained homoplasmic cybrid cell lines that carry individual mtDNA mutations in complex I, III, IV, and IV and a heteroplasmic cybrid for the MERRF mutation to test gene editing by mitoCRISPR. Cybrids will be transduced by lentiviral vector carrying the mito-sgRNA with the appropriate mitoloop and mitoCas9. Depletion of mutant mtDNA will be assessed by quantitative PCR and possibly by digital droplet PCR (ddPCR) for greater sensitivity. Sequencing of mtDNA will be required to verify the efficiency of target cleavage. Mitochondrial respiration will be measured to assess functional rescue of decreasing mutation load.

In order to engineer the CRISPR/Cas9 system to operate on the mtDNA genome, targeting of the protein component (Cas9) and the RNA component (sgRNA) into the mitochondrial matrix is desirable. An exemplary construct to achieve this end is set forth in FIG. 2.

References (Example 2)

[1] Lightowlers R N, Taylor R W, Turnbull D M. Mutations causing mitochondrial disease: What is new and what challenges remain? Science. 2015; 349(6255):1494-9. Epub 2015/09/26. doi: 10.1126/science.aac7516. PubMed PMID: 26404827.; [2] Alexeyev M, Shokolenko I, Wilson W, LeDoux S. The maintenance of mitochondrial DNA integrity—critical analysis and update. Cold Spring Harb Perspect Biol. 2013; 5(5):a012641. doi: 10.1101/cshperspect.a012641. PubMed PMID: 23637283; PubMed Central PMCID: PMCPMC3632056.; [3] Kazak L, Reyes A, Holt I J. Minimizing the damage: repair pathways keep mitochondrial DNA intact. Nat Rev Mol Cell Biol. 2012; 13(10):659-71. doi: 10.1038/nrm3439. PubMed PMID: 22992591.; [4] Bacman S R, Williams S L, Pinto M, Peralta S, Moraes C T. Specific elimination of mutant mitochondrial genomes in patient-derived cells by mitoTALENs. Nat Med. 2013; 19(9):1111-3. Epub 2013/08/06. doi: 10.1038/nm.3261. PubMed PMID: 23913125; PubMed Central PMCID: PMC4153471.; [5] Bayona-Bafaluy M P, Blits B, Battersby B J, Shoubridge E A, Moraes C T. Rapid directional shift of mitochondrial DNA heteroplasmy in animal tissues by a mitochondrially targeted restriction endonuclease. Proc Natl Acad Sci USA. 2005; 102(40):14392-7. doi: 10.1073/pnas.0502896102. PubMed PMID: 16179392; PubMed Central PMCID: PMCPMC1242285.; [6] Gammage P A, Rorbach J, Vincent A I, Rebar E J, Minczuk M. Mitochondrially targeted ZFNs for selective degradation of pathogenic mitochondrial genomes bearing large-scale deletions or point mutations. EMBO Mol Med. 2014; 6(4):458-66. Epub 2014/02/26. doi: 10.1002/emmm.201303672. PubMed PMID: 24567072; PubMed Central PMCID: PMC3992073.; [7] Hashimoto M, Bacman S R, Peralta S, Falk M J, Chomyn A, Chan D C, et al. MitoTALEN: A General Approach to Reduce Mutant mtDNA Loads and Restore Oxidative Phosphorylation Function in Mitochondrial Diseases. Mol Ther. 2015; 23(10):1592-9. doi: 10.1038/mt.2015.126. PubMed PMID: 26159306.; [8] Minczuk M, Kolasinska-Zwierz P, Murphy M P, Papworth M A. Construction and testing of engineered zinc-finger proteins for sequence-specific modification of mtDNA. Nat Protoc. 2010; 5(2):342-56. Epub 2010/02/06. doi: 10.1038/nprot.2009.245. PubMed PMID: 20134433.; [9] Reddy P, Ocampo A, Suzuki K, Luo J, Bacman S R, Williams S L, et al. Selective elimination of mitochondrial mutations in the germline by genome editing. Cell. 2015; 161(3):459-69. Epub 2015/04/25. doi: 10.1016/j.cell.2015.03.051. PubMed PMID: 25910206.; [10] Tachibana M, Sparman M, Sritanaudomchai H, Ma H, Clepper L, Woodward J, et al. Mitochondrial gene replacement in primate offspring and embryonic stem cells. Nature. 2009; 461(7262):367-72. Epub 2009/08/28. doi: 10.1038/nature08368. PubMed PMID: 19710649; PubMed Central PMCID: PMC2774772.; [11] Ma H, Folmes C D, Wu J, Morey R, Mora-Castilla S, Ocampo A, et al. Metabolic rescue in pluripotent cells from patients with mtDNA disease. Nature. 2015; 524(7564):234-8. Epub 2015/07/16. doi: 10.1038/nature14546. PubMed PMID: 26176921.; [12] Deuse T, Wang D, Stubbendorff M, Itagaki R, Grabosch A, Greaves L C, et al. SCNT-derived ESCs with mismatched mitochondria trigger an immune response in allogeneic hosts. Cell stem cell. 2015; 16(1):33-8. Epub 2014/12/04. doi: 10.1016/j.stem.2014.11.003. PubMed PMID: 25465116.; [13] Zetsche B, Gootenberg J S, Abudayyeh 00, Slaymaker I M, Makarova K S, Essletzbichler P, et al. Cpf1 Is a Single RNA-Guided Endonuclease of a Class 2 CRISPR-Cas System. Cell. 2015; 163(3):759-71. Epub 2015/10/01. doi: 10.1016/j.cell.2015.09.038. PubMed PMID: 26422227; PubMed Central PMCID: PMC4638220.; [14] Schneider A. Mitochondrial tRNA import and its consequences for mitochondrial translation. Annu Rev Biochem. 2011; 80:1033-53. Epub 2011/03/23. doi: 10.1146/annurev-biochem-060109-092838. PubMed PMID: 21417719.; [15] Wang G, Chen H W, Oktay Y, Zhang J, Allen E L, Smith G M, et al. PNPASE regulates RNA import into mitochondria. Cell. 2010; 142(3):456-67. Epub 2010/08/10. doi: S0092-8674(10)00725-7 10.1016/j.cell.2010.06.035. PubMed PMID: 20691904; PubMed Central PMCID: PMC2921675.; [16] Comte C, Tonin Y, Heckel-Mager A M, Boucheham A, Smirnov A, Aure K, et al. Mitochondrial targeting of recombinant RNAs modulates the level of a heteroplasmic mutation in human mitochondrial DNA associated with Kearns Sayre Syndrome. Nucleic Acids Res. 2013; 41(1):418-33. doi: 10.1093/nar/gks965. PubMed PMID: 23087375; PubMed Central PMCID: PMCPMC3592399.; [17] Tonin Y, Heckel A M, Vysokikh M, Dovydenko I, Meschaninova M, Rotig A, et al. Modeling of antigenomic therapy of mitochondrial diseases by mitochondrially addressed RNA targeting a pathogenic point mutation in mitochondrial DNA. J Biol Chem. 2014; 289 (19):13323-34. doi: 10.1074/jbc.M113.528968. PubMed PMID: 24692550; PubMed Central PMCID: PMCPMC4036341.; [18] Smirnov A, Tarassov I, Mager-Heckel A M, Letzelter M, Martin R P, Krasheninnikov I A, et al. Two distinct structural elements of 5S rRNA are needed for its import into human mitochondria. RNA. 2008; 14(4):749-59. doi: 10.1261/rna.952208. PubMed PMID: 18314502; PubMed Central PMCID: PMCPMC2271358.;

[19] Zelenka J, Alan L, Jaburek M, Jezek P. Import of desired nucleic acid sequences using addressing motif of mitochondrial ribosomal 5 S-rRNA for fluorescent in vivo hybridization of mitochondrial DNA and RNA. J Bioenerg Biomembr. 2014; 46(2):147-56. doi: 10.1007/s10863-014-9543-2. PubMed PMID: 24562889.; [20] Konermann S, Brigham M D, Trevino A E, Joung J, Abudayyeh 00, Barcena C, et al. Genome-scale transcriptional activation by an engineered CRISPR-Cas9 complex. Nature. 2014. Epub 2014/12/11. doi: 10.1038/nature14136. PubMed PMID: 25494202.; [21] Zhou J, Satheesan S, Li H, Weinberg M S, Morris K V, Burnett J C, et al. Cell-specific RNA aptamer against human CCR5 specifically targets HIV-1 susceptible cells and inhibits HIV-1 infectivity. Chem Biol. 2015; 22(3):379-90. Epub 2015/03/11. doi: 10.1016/j.chembiol.2015.01.005. PubMed PMID: 25754473; PubMed Central PMCID: PMC4369413.; [22] Zhou J, Tiemann K, Chomchan P, Alluin J, Swiderski P, Burnett J, et al. Dual functional BAFF receptor aptamers inhibit ligand-induced proliferation and deliver siRNAs to NHL cells. Nucleic Acids Res. 2013; 41(7):4266-83. Epub 2013/03/09. doi: 10.1093/nar/gkt125. PubMed PMID: 23470998; PubMed Central PMCID: PMC3627597.; [23] Takahashi M, Burnett J C, Rossi J J. Aptamer-siRNA chimeras for HIV. Advances in experimental medicine and biology. 2015; 848:211-34. Epub 2015/03/12. doi: 10.1007/978-1-4939-2432-5_11. PubMed PMID: 25757623.; [24] Burnett J C, Rossi J J. RNA-based therapeutics: current progress and future prospects. Chem Biol. 2012; 19(1):60-71. Epub 2012/01/31. doi: S1074-5521(11)00459-5 [pii] 10.1016/j.chembiol.2011.12.008. PubMed PMID: 22284355; PubMed Central PMCID: PMC3269031.; [25] Fu Y, Sander J D, Reyon D, Cascio V M, Joung J K. Improving CRISPR-Cas nuclease specificity using truncated guide RNAs. Nat Biotechnol. 2014; 32(3):279-84. doi: 10.1038/nbt.2808. PubMed PMID: 24463574; PubMed Central PMCID: PMCPMC3988262.

Example 3. Exemplary Delivery Vehicle

We are currently testing electroporation of the Cas9 mRNA and sgRNA (Amaxa Electroporator for laboratory scale and MaxCyte for clinical/GMP scale); liposomal formulation of Cas9 mRNA and sgRNA (encoded from plasmid DNA, or as separate RNA molecules, or as plasmid DNA for mtCas9 and in vitro transcribed RNA for the sgRNA); and lentiviral delivery in a vector that expresses both the mtCas9 gene and the sgRNA. We have successfully used liposomes (Lipofectamine 2000) to deliver a plasmid that encodes mtCas9 together with in vitro transcribed sgRNA (FIG. 4). Nanoparticles or dendrimers are used for delivery of Cas9 or sgRNA.

Example 4. Methods

Cybrid Cell Culturing

Cybrids were maintained in DMEM media (ThermoFisher #12800082) containing 10% fetal bovine serum, 100 U/mL penicillin/streptomycin, high glucose (25 mM), 1 mM pyruvate, 4 mM L-Glutamine and uridine 50 µg/ml. The cytochrome b mutants carry with homoplasmic deletion of 4 nucleotides at position 14787. They were generated from 143B/206 osteosarcoma nuclear background and described previously (2). Cells were cultured in a 37° C. incubator with $CO_2$ maintained at 5%.

Stable Cell Lines

Lentiviral vectors were packaged in 293T cells and purified by ultracentrifugation as described previously (3). Hela and cybrids cells were transduced with bicistronic lentiviral vectors that expressed both mitoCRISPR and TagRFP. Spin transduction was performed at 300 g for 30 min in the presence of 4 µg/uL polybrene. Cells were transduced at a multiplicity of infection less than 0.5. Viral containing media were removed 6 hours post-transduction. Cells were subsequently sorted for TagRFP by flow cytometry activated cell sorting (FACS).

Mitoplast Isolation and Taqman Quantitative Reverse Transcription-PCR

The enrichment of sgRNA in mitochondria was assessed by quantifying the amount of sgRNA in purified mitoplasts relative to total cytoplasm. Mitochondria were isolated from cells by differential centrifugation and treated with digitonin 1 mg/mL on ice for 10 min with intermittent agitation to generate mitoplasts. Cytosolic RNA contamination was removed by treatment with RnaseA 100 µg/mL and micrococcal S7 nuclease 300 U (ThermoFisher) for 30 min at room temperature. Mitoplast and cytoplasmic RNA were extracted by Trizol. Primers and TaqMan probes used for sgRNA, mitochondrial housekeeping RNA cytochrome B (cytB), and cytoplasm housekeeping RNA beta actin (β-actin) are listed below. Data were first analyzed by ΔΔCt method relative to the "no mitoloop control" as well as either the cytB or bactin control RNAs. Data were then normalized to combine ΔΔCt for both housekeeping genes into a single numerical value by computing the Euclidean distance from the "no mitoloop control" (4, 5). Hence, the value of the "no mitoloop control" was set to 1.0.

TABLE 9

| Primers | Taqman Probe |
|---|---|
| Cyt B Fwd:<br>GCCTATATTACGGATCATTTCTCT<br>ACT (SEQ ID NO: 113) | CytB probe:<br>CCTGAAACATCGGCATTATCCTCC<br>TGCT (SEQ ID NO: 117) |
| Cyt B Rev:<br>GCCTATGAAGGCTGTTGCTATAGT<br>(SEQ ID NO: 114) | |
| β-actin Fwd:<br>ACCTGACTGACTACCTCATGAAG<br>ATCCTCACCGA<br>(SEQ ID NO: 115) | β -actin:<br>AGCGGGAAATCGTGCGTGACATTA<br>(SEQ ID NO: 118) |
| β -actin Rev:<br>GGAGCTGGAAGCAGCCGTGGCCA<br>TCTCTTGCTCGAA<br>(SEQ ID NO: 116) | |

Figure 6A:
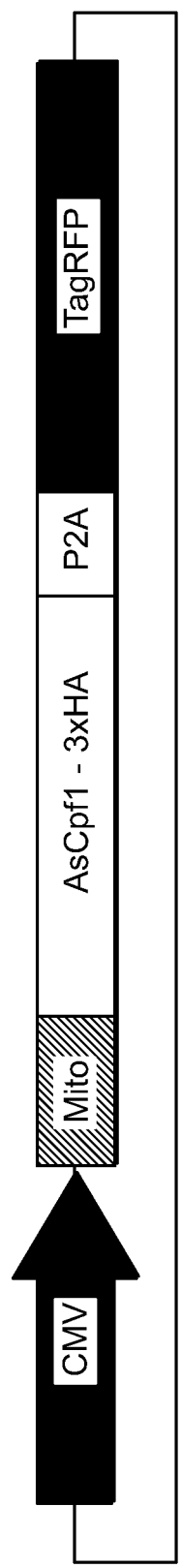
FIGS. 6A-6C. These figures illustrate the mitochondrial localization of mitoAsCpf1.
Figure 6B:
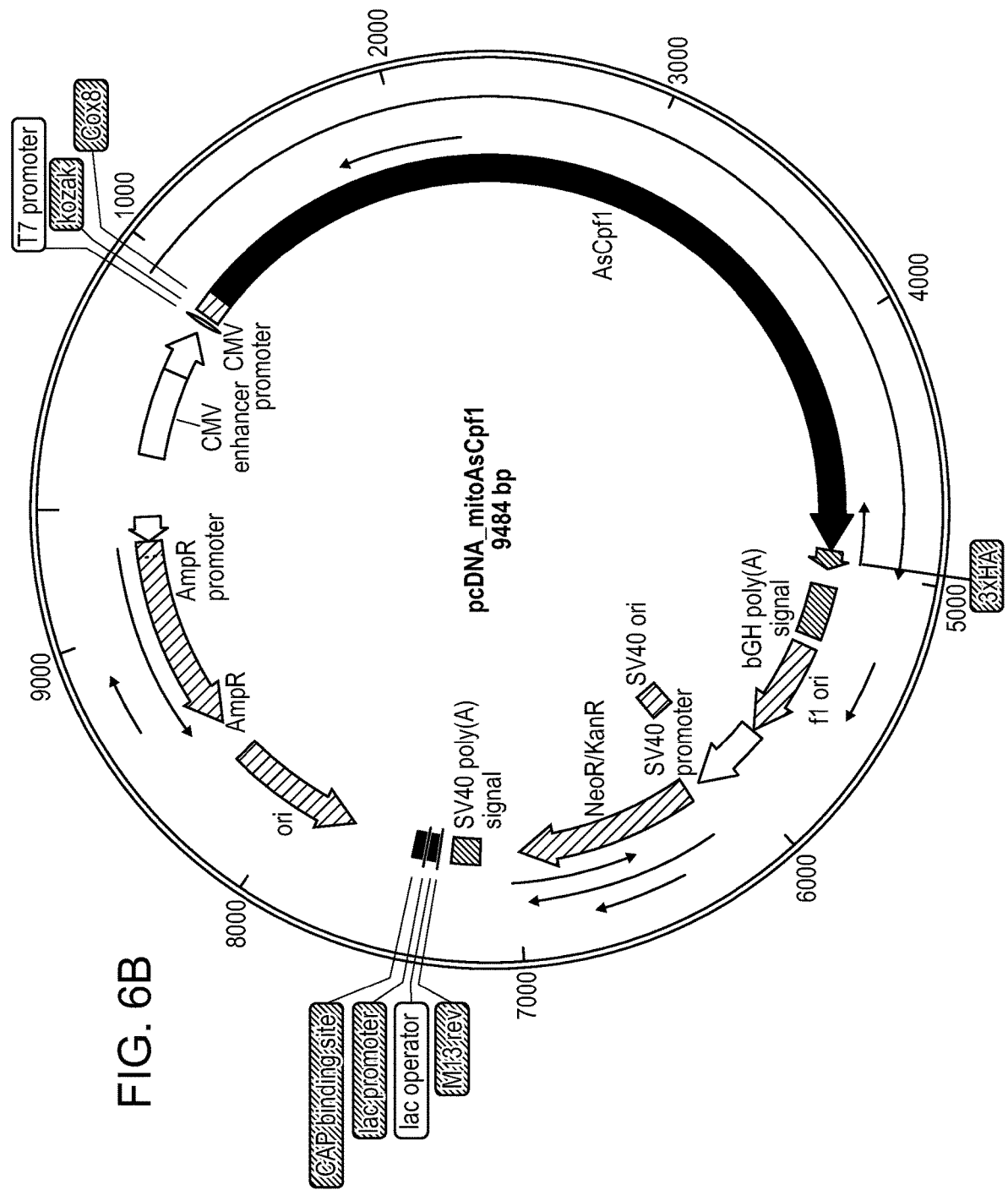
Figure 6C:
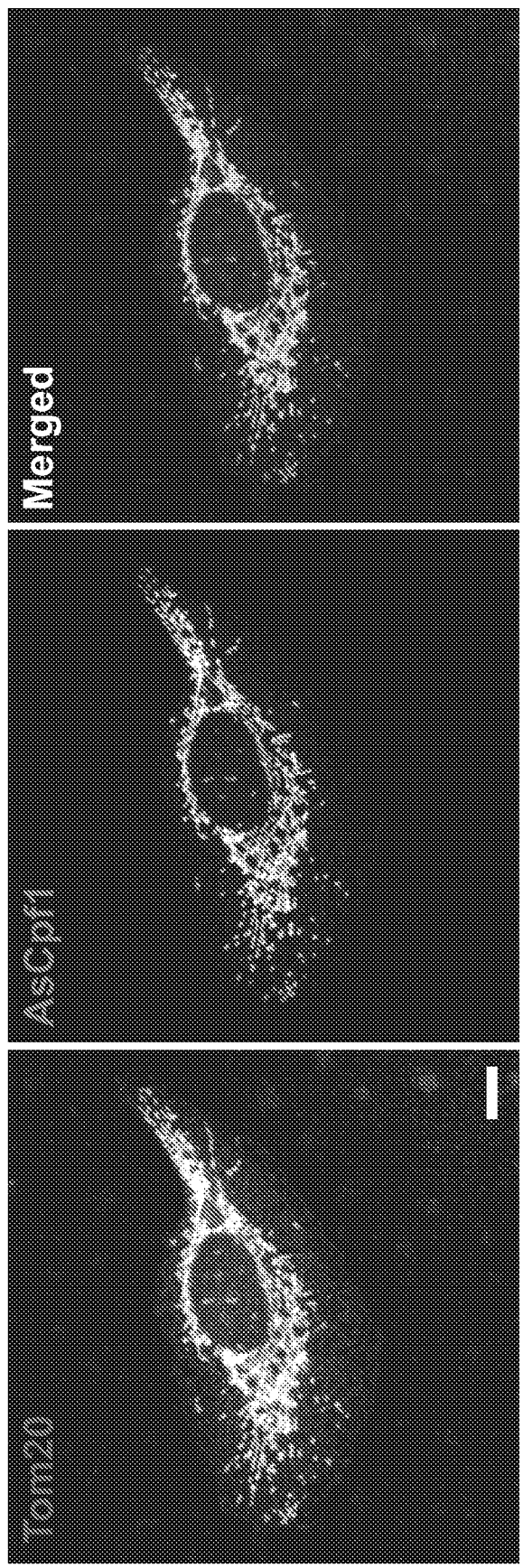

FIGS. 6A-6C show that CRISPR endonuclease AsCpf1 can be engineered to localize to the mitochondria, which is termed mitoAsCpf1. FIGS. 1A-1C and FIGS. 4A-4C had demonstrated this for an engineered version of spCas9 (mitoCas9), which is the most commonly used CRISPR endonuclease. Thus, the mitoCRISPR technology extends beyond Cas9-based CRISPR systems, and applies to other CRISPR systems.

Figure 7:
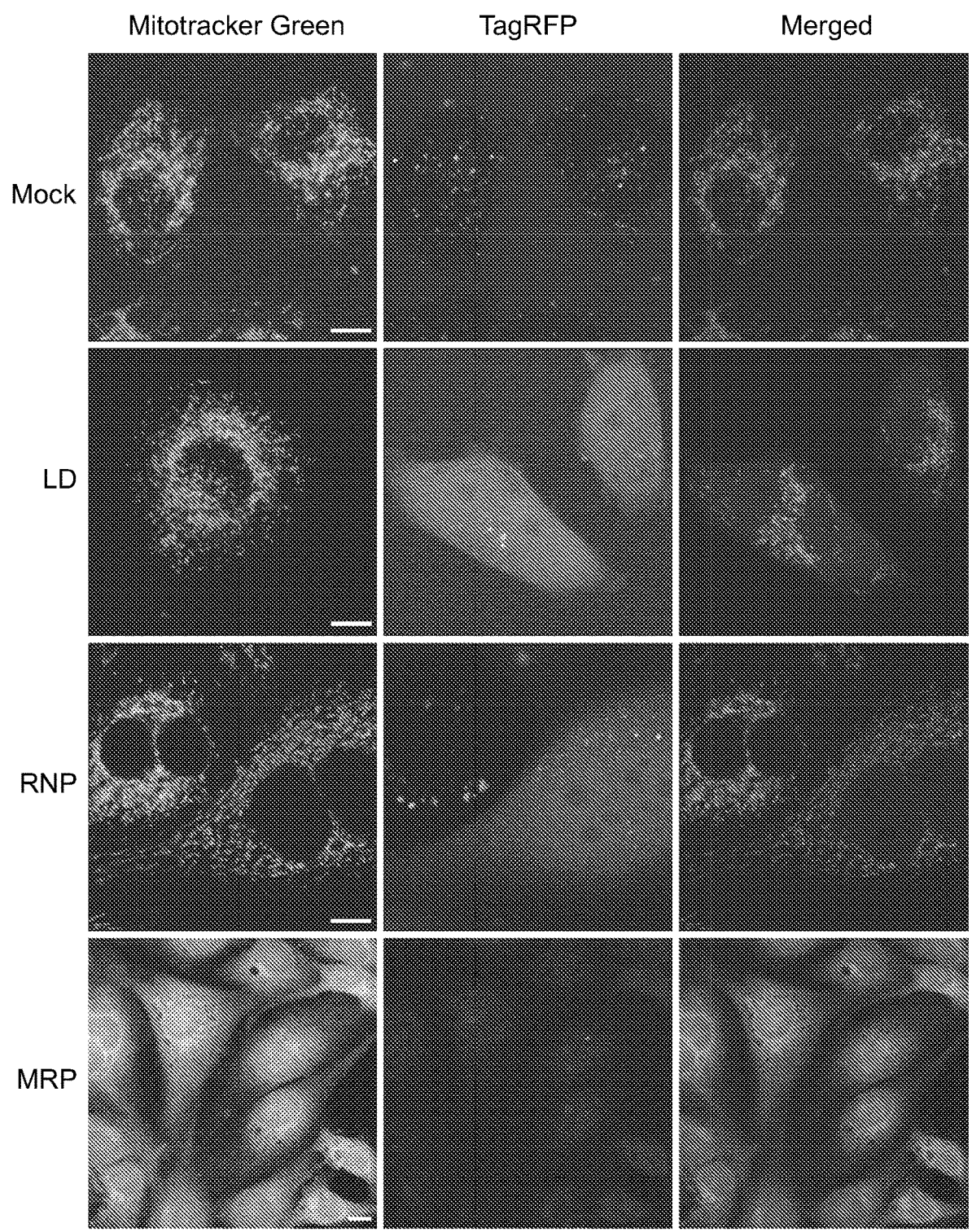
FIG. 7. Mitochondrial morphology in cytB deletion cybrids with constitutive expression of mitoCas9 and sgRNA mitoloops. Homoplasmic cybrids were transduced with pL_mitoCRISPR vectors (as in FIG. 1D), which express mitoCas9 and the indicated sgRNAs. The sgRNAs include no additional mitoloop (Mock) or sgRNA with LD, RNP, or MRP mitoloops added at the 3' end (as in FIGS. 2A-2B). The transduced cells were sorted by TagRFP, a marker of transduction. The spacer domain is specific for the 14787 cytochrome b deletion mutation. Mitotracker green is a mitochondrial dye that selectively accumulates in healthy mitochondria with intact membrane potential. Cybrids with the sgRNA-MRP loop exhibited depolarized mitochondria as indicated by the diffuse signal of Mitotracker Green. This suggests possible targeted effects on mtDNA thereby resulting in increased susceptibility to transient depolarization of mitochondrial membrane potential. Scale bar represents 10 µm.

FIG. 7 shows a functional assay for mitoCRISPR activity with mitoCas9 and engineered sgRNAs with different mitoloops. The functional readout is the mitochondrial morphology, which is visibly perturbed in the sgRNAs with mitoloops.

Figure 8:
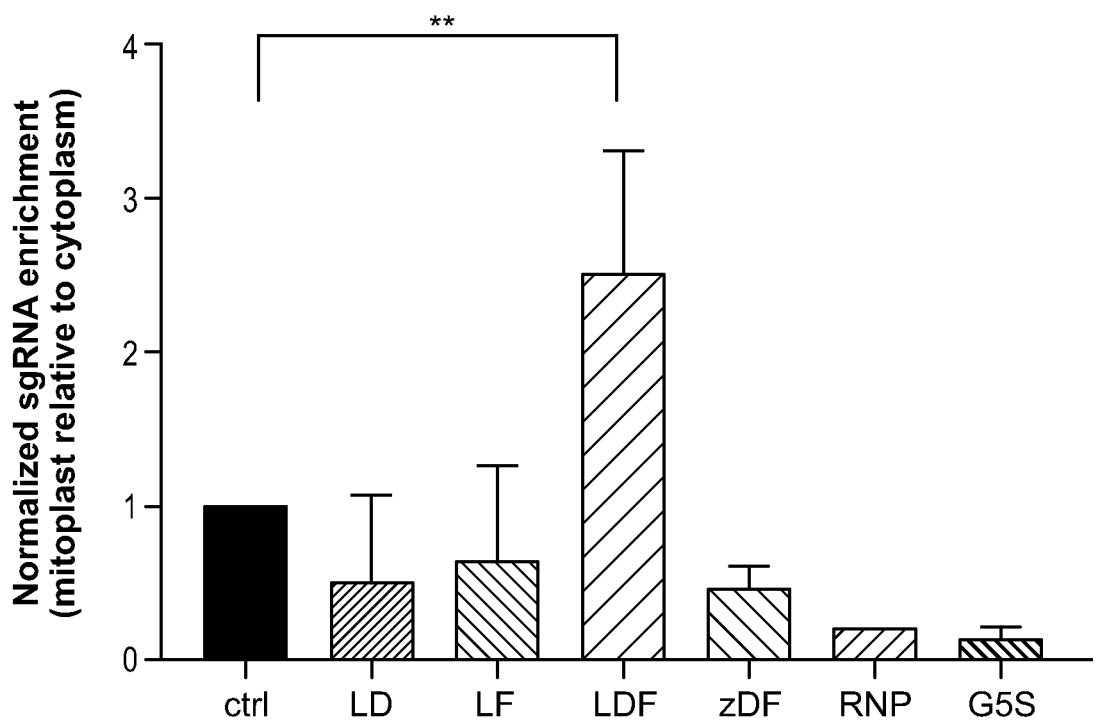
FIG. 8. Mitochondrial enrichment of sgRNA in Hela cells stably expressing mitoCRISPR with various mitoloops. The control cells have constitutive expression of mitoCas9 and sgRNA without mitoloop additions. The sgRNA RNA levels were measured relative to two housekeeping RNAs, B-actin for the cytoplasm and cytochrome b for the mitochondria and compared between mitoplast fraction and cytoplasmic fraction. Given the multivariable analysis using the ΔΔCt method, the Euclidean distance from the control was calculated to obtain a single numerical value for fold enrichment as described in the Methods. As seen in the graph, the attachment of the L-loop and D-loop in tandem (LDF) resulted in a significant enrichment of sgRNA in mitoplast relative to cytochrome b and β-actin. These data were consistent with previous observations of mitochondrial import for smaller, non-CRISPR nuclear-transcribed RNAs, in which the LDF double-loop was much more efficiently localized into mitochondria than either the LD or LF loops. Comparisons were made pairwise relative to control by one tailed t-test with Welch correction. ** p<0.01.
Figures 9A, 9B:
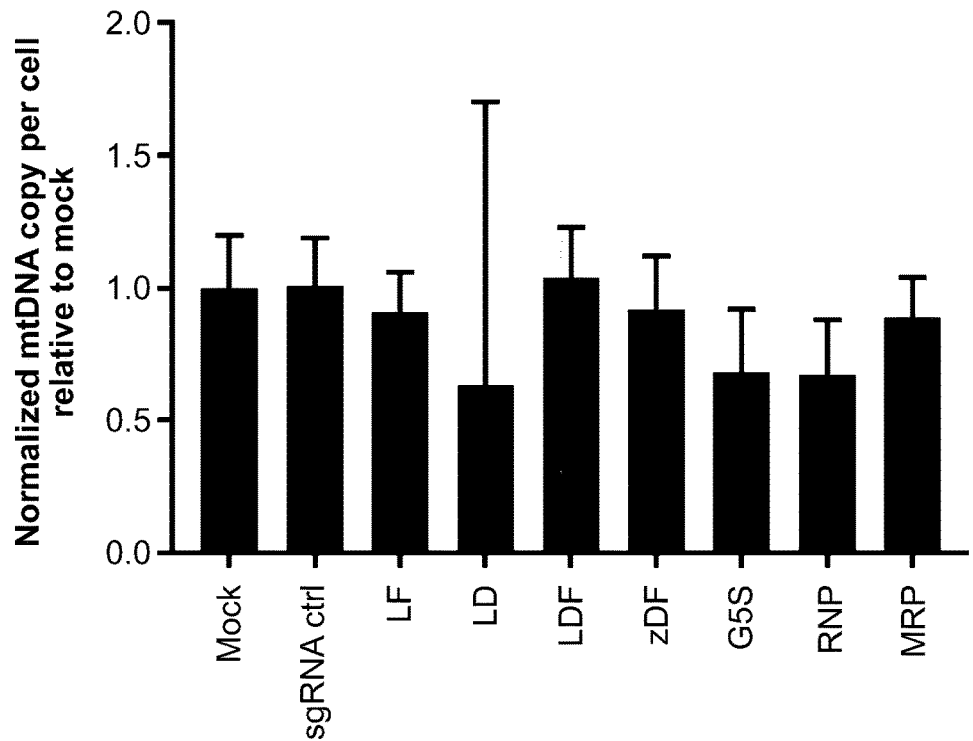
FIGS. 9A-9B. These figures illustrate the measurement of mtDNA copy number in cytochrome b deletion mutants by qPCR. Cybrids have constitutive expression of mtCas9 and various sgRNA-mitoloops. Mitochrondial DNA content was measured by extrapolating the copy numbers of cytochrome b and β-actin genes from standard curves.
Figures 10A, 10B:
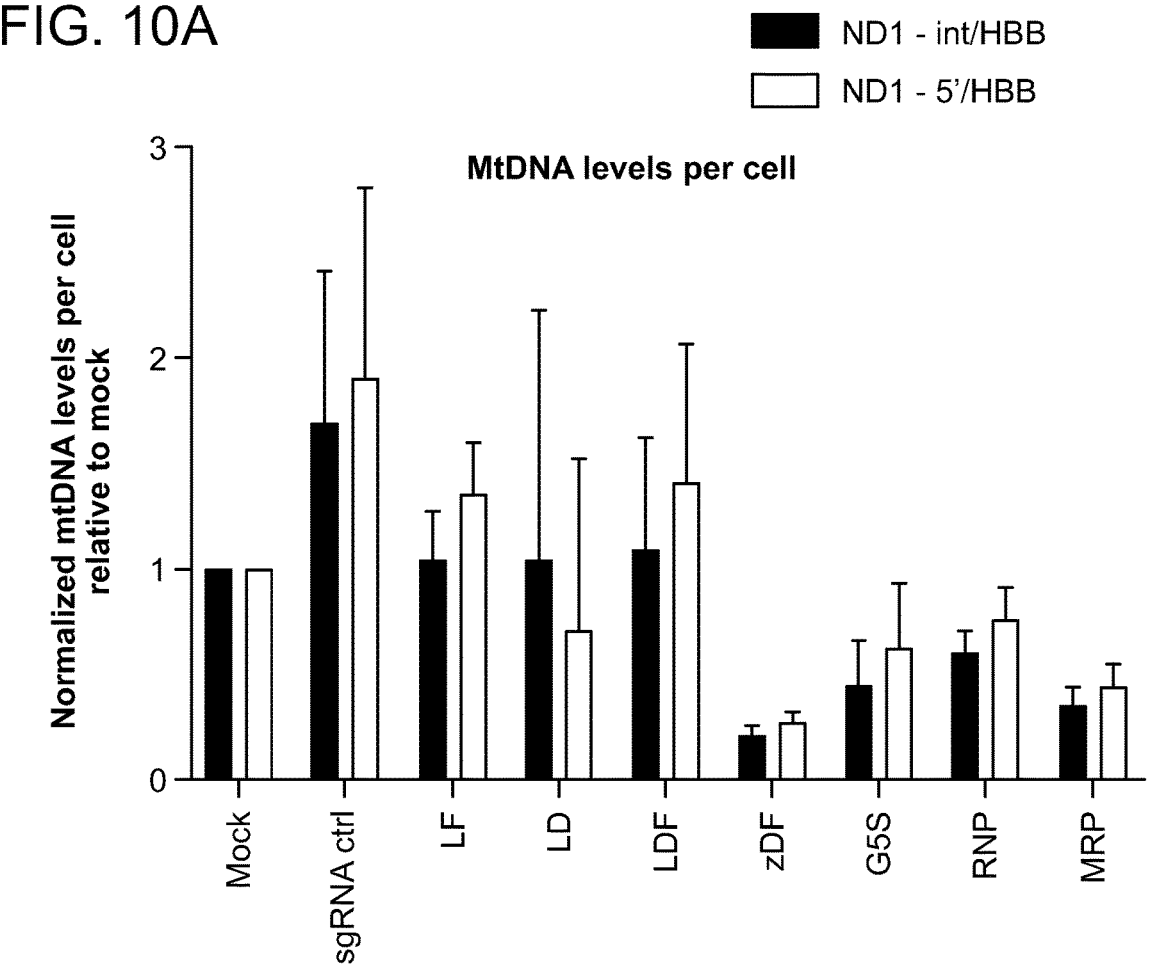
FIGS. 10A-10B. These figures illustrate the measurement of mtDNA copy number using a second set of mitochondrial and nuclear genes. The amount of mtDNA copy per cell is calculated by AACT method using two regions in the ND1 mitochondrial gene (e.g., ND1-int and ND1-5') and the nuclear HBB gene.

FIG. 8 shows the enrichment of sgRNAs into mitochondria. This experiment confirms that sgRNAs with mitoloops (in particular the LDF mitoloop) can be trafficked to mitochondria with increased efficiency. This is a novel demonstration. This data confirmed achieving mitoCRISPR using the sgRNA-mitoloop design.

References (Example 4)

[1] Kolesnikova O, et al. (2010) Selection of RNA aptamers imported into yeast and human mitochondria. RNA 16(5):926-941.; [2] Rana M, de Coo I, Diaz F, Smeets H, & Moraes C T (2000) An out-of-frame cytochrome b gene deletion from a patient with parkinsonism is associated with impaired complex III assembly and an increase in free radical production. Annals of neurology 48(5):774-781.; [3] Burnett J C, Miller-Jensen K, Shah P S, Arkin A P, & Schaffer D V (2009) Control of stochastic gene expression by host factors at the HIV promoter. PLoS pathogens 5(1):e1000260.; [4] Bergkvist A, et al. (2010) Gene expression profiling—Clusters of possibilities. Methods 50(4): 323-335.; [5] Wolf A R & Mootha V K (2014) Functional genomic analysis of human mitochondrial RNA processing. Cell Rep 7(3):918-931.

What is claimed is:

1. A composition comprising a nucleic acid comprising a mitochondrial import sequence and a single-guide RNA (sgRNA) sequence,
   wherein said mitochondrial import sequence comprises a D loop and a F loop,
   wherein said D loop is within a tetraloop or stemloop 2 and said F loop is 3' to stemloop 3 of a nucleic acid sequence within the sgRNA that is complementary to a mitochondrial DNA (mtDNA) target sequence.

2. The composition of claim 1, further comprising a delivery vehicle and a nucleic acid encoding a protein comprising a mitochondrial localization amino acid sequence and an RNA-guided DNA endonuclease enzyme.

3. The composition of claim 1, wherein said mtDNA target sequence comprises at least one mutation or deletion.

4. The composition of claim 3, wherein said mtDNA target sequence is 16-24 nucleotides in length.

5. The composition of claim 1, wherein said sgRNA sequence comprises one or both of a transactivating crRNA (tracrRNA) sequence and a crRNA sequence.

6. The composition of claim 1, wherein said sgRNA sequence comprises a nuclear-encoded and mitochondrial-localizing tRNA sequence.

7. The composition of claim 1, wherein said nucleic acid is bound to a delivery vehicle.

8. The composition of claim 7, wherein said delivery vehicle is a nanoparticle or a lipid particle.

9. A pharmaceutical composition comprising the composition of claim 1, and a pharmaceutically acceptable excipient.

10. A kit, comprising the composition of claim 1, and a protein comprising a mitochondrial localization amino acid sequence covalently attached to an RNA-guided DNA endonuclease enzyme or a nucleic acid sequence encoding said protein.

11. The composition of claim 1, further comprising a delivery vehicle and a protein comprising a mitochondrial localization amino acid sequence covalently attached to an RNA-guided DNA endonuclease enzyme, wherein said protein is bound to said delivery vehicle.

12. The composition of claim 11, wherein said delivery vehicle is a nanoparticle or a lipid particle or a viral vector.

13. The composition of claim 11, wherein said protein is encapsulated within said delivery vehicle.

14. The composition of claim 11, wherein said mitochondrial localization amino acid sequence is N-terminal to said RNA-guided DNA endonuclease enzyme.

15. The composition of claim 11, wherein said mitochondrial localization amino acid sequence is a cytochrome c oxidase subunit VIII (Cox8) sequence.

16. The composition of claim 11, wherein said RNA-guided DNA endonuclease enzyme is Cas9 or Cpf1 or a Class II CRISPR endonuclease.

17. The composition of claim 16, wherein said Cas9 is a Cas9 variant, wherein said Cas9 variant has one or more mutations that increase its binding specificity to PAM compared to wild type Cas9.

18. The composition of claim 11, wherein said RNA-guided DNA endonuclease enzyme has no nuclear localization sequence.

* * * * *